(12) United States Patent
Cauthen, III et al.

(10) Patent No.: US 7,615,076 B2
(45) Date of Patent: Nov. 10, 2009

(54) METHOD AND APPARATUS FOR THE TREATMENT OF THE INTERVERTEBRAL DISC ANNULUS

(75) Inventors: Joseph C. Cauthen, III, Gainesville, FL (US); Matthew M. Burns, Orono, MN (US); Lawrence W. Wales, Maplewood, MN (US); Brian L. Dukart, Brooklyn Park, MN (US); Bradley J. Wessman, Maple Grove, MN (US); Rodney L. Houfburg, Prior Lake, MN (US); Ishmael Bentley, Eagan, MN (US)

(73) Assignee: Anulex Technologies, Inc., Minnetonka, MN (US)

( * ) Notice: Subject to any disclaimer, the term of this patent is extended or adjusted under 35 U.S.C. 154(b) by 661 days.

(21) Appl. No.: 11/120,750

(22) Filed: May 3, 2005

(65) Prior Publication Data

US 2005/0283246 A1 Dec. 22, 2005

Related U.S. Application Data

(63) Continuation-in-part of application No. 10/352,981, filed on Jan. 29, 2003, which is a continuation-in-part of application No. 10/327,106, filed on Dec. 24, 2002, now Pat. No. 7,004,970, which is a continuation-in-part of application No. 10/133,339, filed on Apr. 29, 2002, now Pat. No. 7,052,516, which is a continuation-in-part of application No. 09/947,078, filed on Sep. 5, 2001, now Pat. No. 6,592,625, which is a continuation of application No. 09/484,706, filed on Jan. 18, 2000, now abandoned.

(60) Provisional application No. 60/160,710, filed on Oct. 20, 1999, provisional application No. 60/309,105, filed on Jul. 31, 2001.

(51) Int. Cl.
*A61F 2/44* (2006.01)
*A61B 17/58* (2006.01)
*A61B 17/04* (2006.01)
*A61B 17/08* (2006.01)
*A61B 17/88* (2006.01)
*A61B 19/00* (2006.01)

(52) U.S. Cl. .................. 623/17.11; 623/17.16; 606/232; 606/233; 606/215; 606/216; 606/60; 606/279; 606/99; 128/898

(58) Field of Classification Search ................. 606/279, 606/86 A, 914, 99, 60, 215, 216, 232, 233; 623/17.11, 17.16; 128/898
See application file for complete search history.

(56) References Cited

U.S. PATENT DOCUMENTS 1,995,970 A 3/1935 Dorough (Continued)

FOREIGN PATENT DOCUMENTS

EP 0 020 021 A2 12/1980

(Continued)

OTHER PUBLICATIONS

Copending U.S. Appl. No. 10/075,615, filed Feb. 15, 2002 by Cauthen.

(Continued)

*Primary Examiner*—Eduardo C Robert
*Assistant Examiner*—Ellen Rust
(74) *Attorney, Agent, or Firm*—Faegre & Benson LLP

(57) ABSTRACT

The present invention provides methods and devices for treating the annulus of an intervertebral disc. The methods and devices can employ an expandable treatment device which is deployed at least partially in the subannular space. Fixation devices and methods are also disclosed, which help to secure the treatment device in place.

21 Claims, 85 Drawing Sheets

U.S. PATENT DOCUMENTS

| | | |
|---|---|---|
| 2,609,347 A | 9/1952 | Wilson |
| 2,653,917 A | 9/1953 | Hammon |
| 2,659,935 A | 11/1953 | Hammon |
| 2,664,366 A | 12/1953 | Wilson |
| 2,664,367 A | 12/1953 | Wilson |
| 2,676,945 A | 4/1954 | Higgins |
| 2,683,136 A | 7/1954 | Higgins |
| 2,703,316 A | 3/1955 | Schneider |
| 2,758,987 A | 8/1956 | Salzberg |
| 2,846,407 A | 8/1958 | Wilson |
| 2,951,828 A | 9/1960 | Zeile |
| 3,531,561 A | 9/1970 | Trehu |
| 3,580,256 A | 5/1971 | Wilkinson |
| 3,874,388 A | 4/1975 | King et al. |
| 3,875,595 A | 4/1975 | Froning |
| 3,895,753 A | 7/1975 | Bone |
| 3,990,619 A | 11/1976 | Russell |
| 4,006,747 A | 2/1977 | Kronenthal et al. |
| 4,007,743 A | 2/1977 | Blake |
| 4,224,413 A | 9/1980 | Burbidge |
| 4,349,921 A | 9/1982 | Kuntz |
| 4,369,788 A | 1/1983 | Goald |
| 4,413,359 A | 11/1983 | Akiyama et al. |
| 4,502,161 A | 3/1985 | Wall |
| 4,512,338 A | 4/1985 | Balko et al. |
| 4,520,821 A | 6/1985 | Schmidt |
| 4,532,926 A | 8/1985 | O'Holla |
| 4,602,635 A | 7/1986 | Mulhollan et al. |
| 4,663,358 A | 5/1987 | Hyon et al. |
| 4,669,473 A | 6/1987 | Richards et al. |
| 4,678,459 A | 7/1987 | Onik et al. |
| 4,736,746 A | 4/1988 | Anderson |
| 4,743,260 A | 5/1988 | Burton |
| 4,744,364 A | 5/1988 | Kensey |
| 4,781,190 A | 11/1988 | Lee |
| 4,790,303 A * | 12/1988 | Steffee .................. 606/300 |
| 4,798,205 A | 1/1989 | Bonomo et al. |
| 4,834,757 A | 5/1989 | Brantigan |
| 4,837,285 A | 6/1989 | Berg et al. |
| 4,844,088 A | 7/1989 | Kambin |
| 4,863,477 A | 9/1989 | Monson |
| 4,884,572 A | 12/1989 | Bays et al. |
| 4,895,148 A | 1/1990 | Bays et al. |
| 4,904,261 A | 2/1990 | Dove et al. |
| 4,911,718 A | 3/1990 | Lee et al. |
| 4,917,704 A | 4/1990 | Frey et al. |
| 4,919,667 A | 4/1990 | Richmond |
| 4,946,378 A | 8/1990 | Hirayama et al. |
| 4,955,908 A | 9/1990 | Frey et al. |
| 4,976,715 A | 12/1990 | Bays et al. |
| 5,002,576 A | 3/1991 | Fuhrmann et al. |
| 5,035,716 A | 7/1991 | Downey |
| 5,041,129 A | 8/1991 | Hayhurst et al. |
| 5,047,055 A | 9/1991 | Bao |
| 5,053,046 A | 10/1991 | Janese |
| 5,059,193 A | 10/1991 | Kuslich |
| 5,059,206 A | 10/1991 | Winters |
| 5,062,344 A | 11/1991 | Gerker |
| 5,071,437 A | 12/1991 | Steffee |
| 5,085,661 A | 2/1992 | Moss |
| 5,100,422 A | 3/1992 | Berguer et al. |
| 5,108,420 A | 4/1992 | Marks |
| 5,116,357 A | 5/1992 | Eberbach |
| 5,122,155 A | 6/1992 | Eberbach |
| 5,123,913 A | 6/1992 | Wilk et al. |
| 5,123,926 A | 6/1992 | Pisharodi |
| 5,129,912 A | 7/1992 | Noda et al. |
| 5,141,515 A | 8/1992 | Eberbach |
| 5,171,259 A | 12/1992 | Inoue |
| 5,171,280 A | 12/1992 | Baumgartner |
| 5,171,281 A | 12/1992 | Parsons et al. |
| 5,176,691 A | 1/1993 | Pierce |
| 5,176,692 A | 1/1993 | Wilk et al. |
| 5,192,326 A | 3/1993 | Bao et al. |
| 5,207,695 A | 5/1993 | Trout |
| 5,222,962 A | 6/1993 | Burkhart |
| 5,222,974 A | 6/1993 | Kensey et al. |
| 5,242,439 A | 9/1993 | Larsen et al. |
| 5,254,133 A | 10/1993 | Seid |
| 5,269,791 A | 12/1993 | Mayzels et al. |
| 5,282,827 A | 2/1994 | Kensey et al. |
| 5,282,863 A | 2/1994 | Burton |
| 5,304,194 A | 4/1994 | Chee et al. |
| 5,306,311 A | 4/1994 | Stone et al. |
| 5,312,435 A | 5/1994 | Nash et al. |
| 5,320,629 A | 6/1994 | Noda et al. |
| 5,320,644 A | 6/1994 | Baumgartner |
| 5,342,394 A | 8/1994 | Matsuno et al. |
| 5,344,442 A | 9/1994 | Deac |
| 5,350,399 A | 9/1994 | Erlebacher |
| 5,354,736 A | 10/1994 | Bhatnagar |
| 5,370,660 A | 12/1994 | Weinstein et al. |
| 5,370,697 A | 12/1994 | Baumgartner |
| 5,374,268 A | 12/1994 | Sander |
| 5,383,477 A | 1/1995 | DeMatteis |
| 5,383,905 A | 1/1995 | Golds et al. |
| 5,391,182 A | 2/1995 | Chin |
| 5,397,326 A | 3/1995 | Mangum |
| 5,397,332 A | 3/1995 | Kammerer et al. |
| 5,397,991 A | 3/1995 | Rogers |
| 5,398,861 A | 3/1995 | Green |
| 5,405,352 A | 4/1995 | Weston |
| 5,405,360 A | 4/1995 | Tovey |
| 5,411,520 A | 5/1995 | Nash |
| 5,417,699 A | 5/1995 | Klein et al. |
| 5,425,772 A | 6/1995 | Brantigan |
| 5,425,773 A | 6/1995 | Boyd et al. |
| 5,429,598 A | 7/1995 | Waxman et al. |
| 5,437,631 A | 8/1995 | Janzen |
| 5,437,680 A | 8/1995 | Yoon |
| 5,456,720 A | 10/1995 | Schultz et al. |
| 5,464,407 A | 11/1995 | McGuire |
| 5,470,337 A | 11/1995 | Moss |
| 5,489,307 A | 2/1996 | Kuslich et al. |
| 5,492,697 A | 2/1996 | Boyan et al. |
| 5,496,348 A | 3/1996 | Bonutti |
| 5,507,755 A | 4/1996 | Gresl et al. |
| 5,514,180 A | 5/1996 | Heggeness et al. |
| 5,520,700 A | 5/1996 | Beyar et al. |
| 5,531,678 A | 7/1996 | Tomba et al. |
| 5,534,030 A | 7/1996 | Navarro et al. |
| 5,540,704 A | 7/1996 | Gordon et al. |
| 5,540,715 A | 7/1996 | Katsaros et al. |
| 5,545,229 A | 8/1996 | Parsons et al. |
| 5,556,428 A | 9/1996 | Shah |
| 5,562,684 A | 10/1996 | Kammerer |
| 5,562,738 A | 10/1996 | Boyd et al. |
| 5,569,252 A | 10/1996 | Justin et al. |
| 5,573,286 A | 11/1996 | Rogozinski |
| 5,582,616 A | 12/1996 | Bolduc et al. |
| 5,584,862 A | 12/1996 | Bonutti |
| 5,591,177 A | 1/1997 | Lehrer |
| 5,591,223 A | 1/1997 | Lock et al. |
| 5,593,425 A | 1/1997 | Bonutti et al. |
| 5,613,974 A | 3/1997 | Andreas et al. |
| 5,620,012 A | 4/1997 | Benderev et al. |
| 5,624,463 A | 4/1997 | Stone et al. |
| 5,626,612 A | 5/1997 | Bartlett et al. |
| 5,626,613 A | 5/1997 | Schmieding |
| 5,626,614 A | 5/1997 | Hart |
| 5,634,931 A | 6/1997 | Kugel |
| 5,643,319 A | 7/1997 | Green et al. |
| 5,645,084 A | 7/1997 | McKay |
| 5,658,343 A | 8/1997 | Hauselmann et al. |

| Patent No. | Kind | Date | Inventor |
|---|---|---|---|
| 5,662,681 | A | 9/1997 | Nash et al. |
| 5,662,683 | A | 9/1997 | Kay |
| 5,669,935 | A | 9/1997 | Rosenman et al. |
| 5,674,294 | A | 10/1997 | Bainville et al. |
| 5,674,296 | A | 10/1997 | Bryan et al. |
| 5,676,698 | A | 10/1997 | Janzen et al. |
| 5,676,701 | A | 10/1997 | Yuan et al. |
| 5,681,351 | A | 10/1997 | Jamiolkowski et al. |
| 5,683,417 | A | 11/1997 | Cooper |
| 5,683,465 | A | 11/1997 | Shinn et al. |
| 5,695,525 | A | 12/1997 | Mulhauser et al. |
| 5,697,950 | A | 12/1997 | Fucci et al. |
| 5,702,449 | A | 12/1997 | McKay |
| 5,702,450 | A | 12/1997 | Bisserie |
| 5,702,451 | A | 12/1997 | Biedermann et al. |
| 5,702,462 | A | 12/1997 | Oberlander |
| 5,704,943 | A | 1/1998 | Yoon et al. |
| 5,716,404 | A | 2/1998 | Vacanti et al. |
| 5,716,408 | A | 2/1998 | Eldridge et al. |
| 5,716,409 | A | 2/1998 | Debbas |
| 5,716,413 | A | 2/1998 | Walter et al. |
| 5,725,552 | A | 3/1998 | Kotula et al. |
| 5,725,577 | A | 3/1998 | Saxon |
| 5,728,109 | A | 3/1998 | Schulze et al. |
| 5,728,150 | A | 3/1998 | McDonald et al. |
| 5,730,744 | A | 3/1998 | Justin et al. |
| 5,735,875 | A | 4/1998 | Bonutti |
| 5,736,746 | A | 4/1998 | Furutoh |
| 5,743,917 | A | 4/1998 | Saxon |
| 5,746,755 | A | 5/1998 | Wood et al. |
| 5,752,964 | A | 5/1998 | Mericle |
| 5,759,189 | A | 6/1998 | Ferragamo et al. |
| 5,766,246 | A | 6/1998 | Mulhauser et al. |
| 5,769,864 | A | 6/1998 | Kugel |
| 5,769,893 | A | 6/1998 | Shah |
| 5,772,661 | A | 6/1998 | Michelson |
| 5,776,183 | A | 7/1998 | Kanesaka et al. |
| 5,782,860 | A | 7/1998 | Epstein et al. |
| 5,786,217 | A | 7/1998 | Tubo et al. |
| 5,792,152 | A | 8/1998 | Klein et al. |
| 5,797,929 | A | 8/1998 | Andreas et al. |
| 5,800,550 | A | 9/1998 | Sertich |
| 5,810,848 | A | 9/1998 | Hayhurst |
| 5,810,851 | A | 9/1998 | Yoon |
| 5,823,994 | A | 10/1998 | Sharkey et al. |
| 5,824,008 | A | 10/1998 | Bolduc et al. |
| 5,824,082 | A | 10/1998 | Brown |
| 5,824,094 | A | 10/1998 | Serhan et al. |
| 5,827,325 | A | 10/1998 | Landgrebe et al. |
| 5,827,328 | A | 10/1998 | Buttermann |
| 5,836,315 | A | 11/1998 | Benderev et al. |
| 5,842,477 | A | 12/1998 | Naughton et al. |
| 5,843,084 | A | 12/1998 | Hart et al. |
| 5,846,261 | A | 12/1998 | Kotula et al. |
| 5,853,422 | A | 12/1998 | Huebsch et al. |
| 5,855,614 | A | 1/1999 | Stevens et al. |
| 5,860,425 | A | 1/1999 | Benderev et al. |
| 5,860,977 | A | 1/1999 | Zucherman et al. |
| 5,861,004 | A | 1/1999 | Kensey |
| 5,865,845 | A | 2/1999 | Thalgott |
| 5,865,846 | A | 2/1999 | Bryan et al. |
| 5,868,762 | A | 2/1999 | Cragg et al. |
| 5,888,222 | A | 3/1999 | Coates |
| 5,888,226 | A | 3/1999 | Rogozinski |
| 5,893,592 | A | 4/1999 | Schulze et al. |
| 5,893,889 | A | 4/1999 | Harrington |
| 5,895,426 | A | 4/1999 | Scarborough et al. |
| 5,904,703 | A | 5/1999 | Gilson et al. |
| 5,919,235 | A | 7/1999 | Husson et al. |
| 5,922,026 | A | 7/1999 | Chin |
| 5,941,439 | A | 8/1999 | Kammerer et al. |
| 5,944,738 | A | 8/1999 | Amplatz et al. |
| 5,948,001 | A | 9/1999 | Larsen |
| 5,948,002 | A | 9/1999 | Bonutti |
| 5,954,716 | A | 9/1999 | Sharkey et al. |
| 5,957,939 | A | 9/1999 | Heaven et al. |
| 5,964,783 | A | 10/1999 | Grafton et al. |
| 5,972,000 | A | 10/1999 | Beyar et al. |
| 5,972,007 | A | 10/1999 | Sheffield et al. |
| 5,984,948 | A | 11/1999 | Hasson |
| 6,001,130 | A | 12/1999 | Bryan et al. |
| 6,007,567 | A | 12/1999 | Bonutti |
| 6,007,575 | A | 12/1999 | Samuels |
| 6,019,793 | A | 2/2000 | Perren et al. |
| 6,024,096 | A | 2/2000 | Buckberg |
| 6,024,754 | A | 2/2000 | Engelson |
| 6,024,758 | A | 2/2000 | Thal |
| 6,027,527 | A | 2/2000 | Asano et al. |
| 6,036,699 | A | 3/2000 | Andreas et al. |
| 6,039,761 | A | 3/2000 | Li et al. |
| 6,039,762 | A | 3/2000 | McKay |
| 6,045,561 | A | 4/2000 | Marshall et al. |
| 6,063,378 | A | 5/2000 | Nohara et al. |
| 6,066,146 | A | 5/2000 | Carroll et al. |
| 6,073,051 | A | 6/2000 | Sharkey et al. |
| 6,080,182 | A | 6/2000 | Shaw et al. |
| 6,093,205 | A | 7/2000 | McLeod et al. |
| 6,106,545 | A | 8/2000 | Egan |
| 6,113,609 | A | 9/2000 | Adams |
| 6,113,623 | A | 9/2000 | Sgro |
| 6,113,639 | A | 9/2000 | Ray et al. |
| 6,123,715 | A | 9/2000 | Amplatz |
| 6,143,006 | A | 11/2000 | Chan et al. |
| 6,146,380 | A | 11/2000 | Racz et al. |
| 6,146,422 | A | 11/2000 | Lawson |
| 6,162,203 | A | 12/2000 | Haago |
| 6,171,317 | B1 | 1/2001 | Jackson et al. |
| 6,171,329 | B1 | 1/2001 | Shaw et al. |
| 6,174,322 | B1 | 1/2001 | Schneidt |
| 6,176,863 | B1 | 1/2001 | Kugel et al. |
| 6,179,879 | B1 | 1/2001 | Robinson et al. |
| 6,190,401 | B1 | 2/2001 | Green et al. |
| 6,200,329 | B1 | 3/2001 | Fung et al. |
| 6,203,554 | B1 | 3/2001 | Roberts |
| 6,203,565 | B1 | 3/2001 | Bonutti |
| 6,206,895 | B1 | 3/2001 | Levinson |
| 6,221,092 | B1 | 4/2001 | Koike et al. |
| 6,221,109 | B1 | 4/2001 | Geistlich et al. |
| 6,231,615 | B1 | 5/2001 | Preissman |
| 6,245,080 | B1 | 6/2001 | Levinson |
| 6,248,131 | B1 | 6/2001 | Felt et al. |
| 6,267,772 | B1 | 7/2001 | Mulhauser et al. |
| 6,293,961 | B2 | 9/2001 | Schwartz et al. |
| 6,296,659 | B1 | 10/2001 | Foerster |
| 6,306,159 | B1 | 10/2001 | Schwartz et al. |
| 6,306,177 | B1 | 10/2001 | Felt et al. |
| 6,312,448 | B1 | 11/2001 | Bonutti |
| 6,319,263 | B1 | 11/2001 | Levinson |
| 6,332,894 | B1 | 12/2001 | Stalcup |
| 6,342,064 | B1 | 1/2002 | Koike et al. |
| 6,344,057 | B1 | 2/2002 | Rabbe et al. |
| 6,355,052 | B1 | 3/2002 | Neuss |
| 6,364,897 | B1 | 4/2002 | Bonutti |
| 6,371,984 | B1 | 4/2002 | Van Dyke et al. |
| 6,391,060 | B1 | 5/2002 | Ory et al. |
| 6,402,784 | B1 | 6/2002 | Wardlaw |
| 6,402,785 | B1 | 6/2002 | Zdeblick |
| 6,409,739 | B1 | 6/2002 | Nobles et al. |
| 6,419,676 | B1 | 7/2002 | Zucherman et al. |
| 6,419,702 | B1 | 7/2002 | Ferree |
| 6,419,703 | B1 | 7/2002 | Fallin et al. |
| 6,419,704 | B1 | 7/2002 | Ferree |
| 6,419,706 | B1 | 7/2002 | Graf |
| 6,423,065 | B2 | 7/2002 | Ferree |
| 6,425,924 | B1 | 7/2002 | Rousseau |
| 6,428,562 | B2 | 8/2002 | Bonutti |

| | | | | | | |
|---|---|---|---|---|---|---|
| 6,432,107 | B1 | 8/2002 | Ferree | 6,716,216 B1 | 4/2004 | Boucher et al. |
| 6,432,123 | B2 | 8/2002 | Schwartz et al. | 6,719,761 B1 | 4/2004 | Reiley et al. |
| 6,436,098 | B1 | 8/2002 | Michelson | 6,719,773 B1 | 4/2004 | Boucher et al. |
| 6,436,143 | B1 | 8/2002 | Ross et al. | 6,719,797 B1 | 4/2004 | Ferree |
| 6,454,804 | B1 | 9/2002 | Ferree | 6,723,058 B2 | 4/2004 | Li |
| 6,464,712 | B1 | 10/2002 | Epstein | 6,723,095 B2 | 4/2004 | Hammerslag |
| 6,482,235 | B1 | 11/2002 | Lambrecht et al. | 6,723,097 B2 | 4/2004 | Fraser et al. |
| 6,488,691 | B1 | 12/2002 | Carroll et al. | 6,723,107 B1 | 4/2004 | Skiba et al. |
| 6,491,724 | B1 | 12/2002 | Ferree | 6,723,133 B1 | 4/2004 | Pajotin |
| 6,494,883 | B1 | 12/2002 | Ferree | 6,723,335 B1 | 4/2004 | Moehlenbruck et al. |
| 6,500,132 | B1 | 12/2002 | Li | 6,726,696 B1 | 4/2004 | Houser |
| 6,500,184 | B1 | 12/2002 | Chan et al. | 6,726,721 B2 | 4/2004 | Stoy et al. |
| 6,506,204 | B2 | 1/2003 | Mazzocchi | 6,730,112 B2 | 5/2004 | Levinson |
| 6,508,839 | B1 | 1/2003 | Lambrecht et al. | 6,733,531 B1 | 5/2004 | Trieu |
| 6,511,488 | B1 | 1/2003 | Marshall et al. | 6,733,534 B2 | 5/2004 | Sherman |
| 6,511,498 | B1 | 1/2003 | Fumex | 6,736,815 B2 | 5/2004 | Ginn |
| 6,511,958 | B1 | 1/2003 | Atkinson et al. | 6,740,093 B2 | 5/2004 | Hochschuler et al. |
| 6,514,255 | B1 | 2/2003 | Ferree | 6,743,255 B2 | 6/2004 | Ferree |
| 6,514,514 | B1 | 2/2003 | Atkinson et al. | 6,752,831 B2 | 6/2004 | Sybert et al. |
| 6,533,799 | B1 | 3/2003 | Bouchier | 6,758,863 B2 | 7/2004 | Estes et al. |
| 6,533,817 | B1 | 3/2003 | Norton et al. | 6,761,720 B1 | 7/2004 | Senegas |
| 6,547,806 | B1 | 4/2003 | Ding | 6,764,514 B1 | 7/2004 | Li et al. |
| 6,558,386 | B1 | 5/2003 | Cragg | 6,767,037 B2 | 7/2004 | Wenstrom |
| 6,558,390 | B2 | 5/2003 | Cragg | 6,773,699 B2 | 8/2004 | Soltz et al. |
| 6,562,052 | B2 | 5/2003 | Nobles et al. | 6,783,546 B2 | 8/2004 | Zucherman |
| 6,569,187 | B1 | 5/2003 | Bonutti et al. | 6,805,695 B2 * | 10/2004 | Keith et al. ............... 623/17.11 |
| 6,569,442 | B2 | 5/2003 | Gan et al. | 6,805,697 B1 | 10/2004 | Helm et al. |
| 6,572,635 | B1 | 6/2003 | Bonutti | 6,805,715 B2 | 10/2004 | Reuter et al. |
| 6,572,653 | B1 | 6/2003 | Simonson | 6,812,211 B2 | 11/2004 | Slivka et al. |
| 6,575,979 | B1 | 6/2003 | Cragg | 6,821,276 B2 | 11/2004 | Lambrecht et al. |
| 6,576,017 | B2 | 6/2003 | Foley et al. | 6,824,562 B2 | 11/2004 | Mathis et al. |
| 6,579,291 | B1 | 6/2003 | Keith et al. | 6,827,716 B2 | 12/2004 | Ryan et al. |
| 6,592,608 | B2 | 7/2003 | Fisher et al. | 6,827,743 B2 | 12/2004 | Eisermann et al. |
| 6,592,609 | B1 | 7/2003 | Bonutti | 6,830,570 B1 | 12/2004 | Frey et al. |
| 6,596,012 | B2 | 7/2003 | Akerfeldt et al. | 6,833,006 B2 | 12/2004 | Foley et al. |
| 6,602,291 | B1 | 8/2003 | Ray et al. | 6,835,205 B2 | 12/2004 | Atkinson et al. |
| 6,605,096 | B1 | 8/2003 | Ritchart | 6,835,207 B2 | 12/2004 | Zacouto et al. |
| 6,607,541 | B1 | 8/2003 | Gardiner et al. | 6,835,208 B2 | 12/2004 | Marchosky |
| 6,610,006 | B1 | 8/2003 | Amid et al. | 6,841,150 B2 | 1/2005 | Halvorsen et al. |
| 6,610,071 | B1 | 8/2003 | Cohn et al. | 6,852,128 B2 | 2/2005 | Lange |
| 6,610,079 | B1 | 8/2003 | Li et al. | 6,860,895 B1 | 3/2005 | Akerfeldt et al. |
| 6,610,091 | B1 | 8/2003 | Reiley | 6,878,155 B2 | 4/2005 | Sharkey et al. |
| 6,610,666 | B1 | 8/2003 | Akerblom | 6,878,167 B2 | 4/2005 | Ferree |
| 6,613,044 | B2 | 9/2003 | Carl | 6,883,520 B2 | 4/2005 | Lambrecht et al. |
| 6,620,185 | B1 | 9/2003 | Harvie et al. | 6,893,462 B2 | 5/2005 | Buskirk et al. |
| 6,620,196 | B1 | 9/2003 | Trieu | 6,896,675 B2 | 5/2005 | Leung et al. |
| 6,623,492 | B1 | 9/2003 | Berube et al. | 6,913,622 B2 | 7/2005 | Gjunter |
| 6,623,508 | B2 | 9/2003 | Shaw et al. | 6,923,823 B1 | 8/2005 | Bartlett et al. |
| 6,626,899 | B2 | 9/2003 | Houser et al. | 6,932,833 B1 | 8/2005 | Sandoval et al. |
| 6,626,916 | B1 | 9/2003 | Yeung et al. | 6,936,070 B1 | 8/2005 | Muhanna |
| 6,635,073 | B2 | 10/2003 | Bonutti et al. | 6,936,072 B2 | 8/2005 | Lambrecht et al. |
| 6,645,247 | B2 | 11/2003 | Ferree | 6,960,215 B2 | 11/2005 | Olson, Jr. et al. |
| 6,648,918 | B2 | 11/2003 | Ferree | 6,964,674 B1 | 11/2005 | Matsuura et al. |
| 6,648,919 | B2 | 11/2003 | Ferree | 6,966,910 B2 | 11/2005 | Ritland |
| 6,648,920 | B2 | 11/2003 | Ferree | 6,966,931 B2 | 11/2005 | Huang |
| 6,652,585 | B2 | 11/2003 | Lange | 6,969,404 B2 | 11/2005 | Ferree |
| 6,656,182 | B1 | 12/2003 | Hayhurst | 6,972,027 B2 | 12/2005 | Fallin et al. |
| 6,669,687 | B1 | 12/2003 | Saadat | 6,974,479 B2 | 12/2005 | Trieu |
| 6,669,707 | B1 | 12/2003 | Swanstrom et al. | 6,980,862 B2 | 12/2005 | Fredricks et al. |
| 6,669,729 | B2 | 12/2003 | Chin | 7,004,970 B2 | 2/2006 | Cauthen |
| 6,673,088 | B1 | 1/2004 | Vargas et al. | 7,033,393 B2 | 4/2006 | Gainor |
| 6,676,665 | B2 | 1/2004 | Foley et al. | 7,037,334 B1 | 5/2006 | Hlavka et al. |
| 6,679,914 | B1 | 1/2004 | Gabbay | 7,128,073 B1 | 10/2006 | Van der Burg |
| 6,684,886 | B1 | 2/2004 | Alleyne | 7,445,634 B2 * | 11/2008 | Trieu ....................... 623/17.11 |
| 6,685,695 | B2 | 2/2004 | Ferree | 2002/0077701 A1 | 6/2002 | Kuslich |
| 6,692,506 | B1 | 2/2004 | Ory et al. | 2002/0147461 A1 | 10/2002 | Aldrich |
| 6,695,858 | B1 | 2/2004 | Dubrul et al. | 2003/0040796 A1 | 2/2003 | Ferree |
| 6,696,073 | B2 | 2/2004 | Boyce | 2003/0195514 A1 | 10/2003 | Trieu |
| 6,699,263 | B2 | 3/2004 | Cope | 2004/0039392 A1 | 2/2004 | Trieu |
| 6,706,068 | B2 | 3/2004 | Ferree | 2004/0054414 A1 | 3/2004 | Trieu |
| 6,712,836 | B1 | 3/2004 | Berg et al. | 2004/0092969 A1 | 5/2004 | Kumar |
| 6,712,837 | B2 | 3/2004 | Akerfeldt et al. | 2004/0097980 A1 | 5/2004 | Ferree |
| 6,712,853 | B2 | 3/2004 | Kuslich | 2004/0138703 A1 | 7/2004 | Alleyne |

| | | | |
|---|---|---|---|
| 2004/0210310 A1 | 10/2004 | Trieu | |
| 2004/0260397 A1 | 12/2004 | Lambrecht et al. | |
| 2005/0033440 A1 | 2/2005 | Lambrecht et al. | |
| 2005/0038519 A1 | 2/2005 | Lambrecht et al. | |
| 2005/0060038 A1 | 3/2005 | Lambrecht et al. | |
| 2006/0060038 A1 | 3/2006 | Sammartin | |
| 2006/0129156 A1 | 6/2006 | Cauthen | |
| 2006/0167553 A1 | 7/2006 | Cauthen | |
| 2006/0173545 A1 | 8/2006 | Cauthen | |
| 2006/0195193 A1 | 8/2006 | Bloemer | |
| 2006/0247776 A1 | 11/2006 | Kim | |
| 2006/0282167 A1 | 12/2006 | Lambrecht | |
| 2007/0067040 A1 | 3/2007 | Ferree | |
| 2007/0100349 A1 | 5/2007 | O'Neil | |
| 2008/0140188 A1* | 6/2008 | Rahdert et al. | 623/2.1 |

FOREIGN PATENT DOCUMENTS

| | | |
|---|---|---|
| EP | 0 025 706 A1 | 3/1981 |
| EP | 0 042 953 A2 | 1/1982 |
| EP | 0 049 978 A1 | 4/1982 |
| EP | 0 061 037 A1 | 9/1982 |
| EP | 0 062 832 A1 | 10/1982 |
| EP | 0 076 409 A1 | 4/1983 |
| EP | 0 110 316 A2 | 6/1984 |
| EP | 0 112 107 A2 | 6/1984 |
| EP | 0 121 246 A2 | 10/1984 |
| EP | 0 122 902 A2 | 10/1984 |
| EP | 0 126 570 A2 | 11/1984 |
| EP | 0 145 577 A2 | 6/1985 |
| EP | 0 193 784 A2 | 9/1986 |
| EP | 0 195 818 A1 | 10/1986 |

OTHER PUBLICATIONS

Copending U.S. Appl. No. 10/085,040, filed Mar. 1, 2002 by Cauthen.
Copending U.S. Appl. No. 10/352,981, filed Jan. 29, 2003 by Cauthen.
Copending U.S. Appl. No. 10/394,061, filed Mar. 24, 2003 by Cauthen.
Copending U.S. Appl. No. 10/394,266, filed Mar. 24, 2003 by Cauthen.
Copending U.S. Appl. No. 10/394,008, filed Mar. 24, 2003 by Cauthen.
Copending U.S. Appl. No. 10/392,733, filed Mar. 19, 2003 by Cauthen.
Copending U.S. Appl. No. 10/985,735, filed Nov. 10, 2004 by Cauthen.
Copending U.S. Appl. No. 11/235,764, filed Sep. 26, 2005 by Wales.
Copending U.S. Appl. No. 11/386,642, filed Mar. 23, 2006 by Cauthen et al.
Copending U.S. Appl. No. 11/398,583, filed Apr. 6, 2006 by Cauthen.
Copending U.S. Appl. No. 11/410,420, filed Apr. 25, 2006 by Cauthen.
Copending U.S. Appl. No. 11/313,738, filed Dec. 22, 2005 by Cauthen.
Copending U.S. Appl. No. 11/351,657, filed Feb. 10, 2006 by Cauthen.
Copending U.S. Appl. No. 11/355,426, filed Feb. 16, 2006 by Cauthen.
Copending U.S. Appl. No. 11/376,301, filed Mar. 16, 2006 by Cauthen.
Copending U.S. Appl. No. 11/350,843, filed Feb. 10, 2006 by Cauthen et al.
Copending U.S. Appl. No. 11/386,616, filed Mar. 23, 2006 by Cauthen et al.
Copending U.S. Appl. No. 11/512,251, filed Aug. 30, 2006 by Cauthen et al.
Copending U.S. Appl. No. 11/558,034, filed Nov. 9, 2006 by Cauthen.
Copending U.S. Appl. No. 11/841,513, filed Aug. 20, 2007 by Cauthen.
Copending U.S. Appl. No. 11/521,473, filed Sep. 15, 2006 by Cauthen.
Copending U.S. Appl. No. 11/556,878, filed Nov. 6, 2006 by Cauthen et al.
Copending U.S. Appl. No. 11/557,997, filed Nov. 9, 2006 by Cauthen et al.
Copending U.S. Appl. No. 11/559,457, filed Nov. 14, 2006 by Cauthen et al.
Copending U.S. Appl. No. 11/608,480, filed Dec. 8, 2006 by Cauthen et al.
Copending U.S. Appl. No. 11/622,631, filed Jan. 12, 2007 by Cauthen et al.
Copending U.S. Appl. No. 11/686,599, filed Mar. 15, 2007 by Cauthen et al.
Copending U.S. Appl. No. 11/527,903, filed Sep. 26, 2006 by Cauthen et al.
International Search Report for PCT/US06/16292 (PCT counterpart of this application) dated Apr. 28, 2006, Blaine R. Copenheaver.
Ahlgren, B.D., MD., et al., "Anular Incision Technique on the Strength and Multidirectional Flexibility of the Healing Intervertebral Disc," *Spine* 19(8):948-954 (1994).
Cauthen, Joseph, Draft Abstract entitled "Microsurgical Annular Reconstruction (Annuloplasty) Following Lumbar Microdiscectomy: Preliminary Report of a New Technique" from abstracts@neurosurgery.org. Sep. 4, 1998.
Mineiro, J., et al., "Dynamic Neutralization With Dynesys Review of 113 Cases with More than 1 Year Follow-Up," *Spineweek 2004*, Porto, Portugal May 30 to Jun. 5, 2004, Abstract B19, p. 181.
US 6,447,535, 09/2002, Jacobs et al. (withdrawn)

* cited by examiner

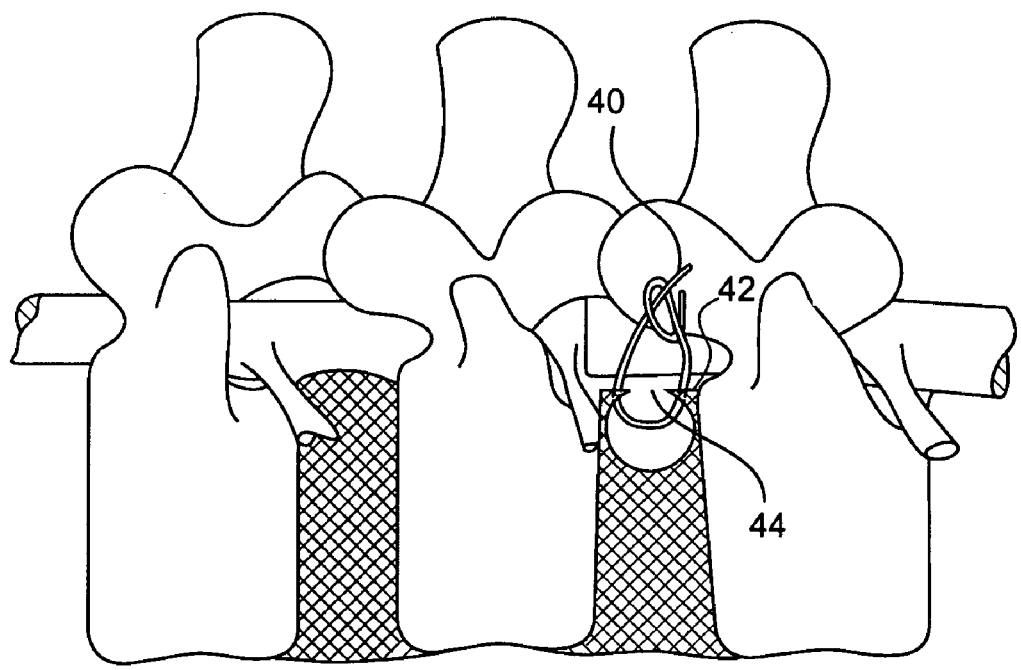
FIG. 1
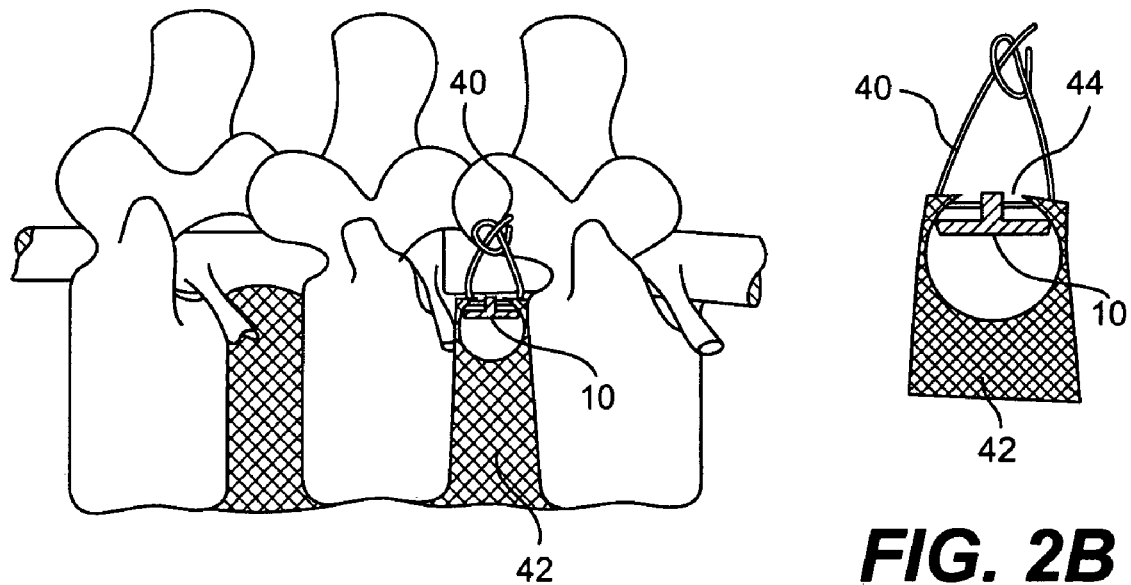
FIG. 2A
FIG. 2B

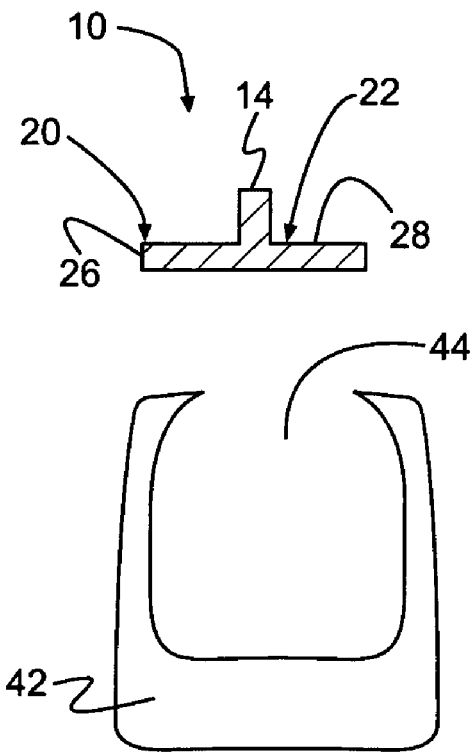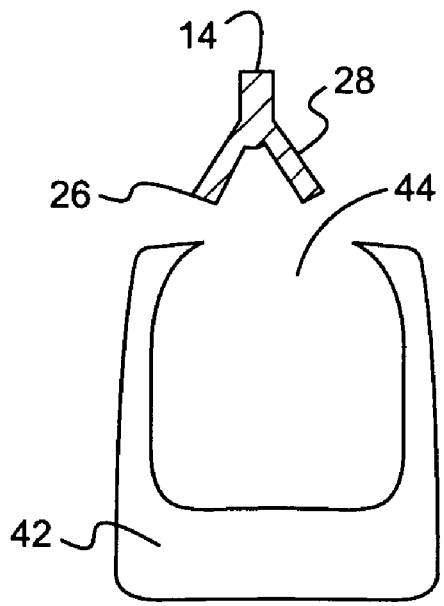
FIG. 3A FIG. 3B
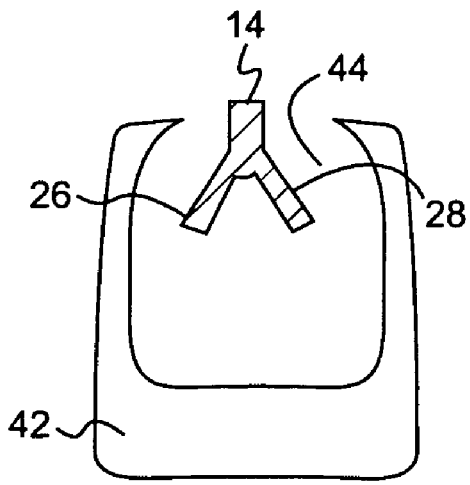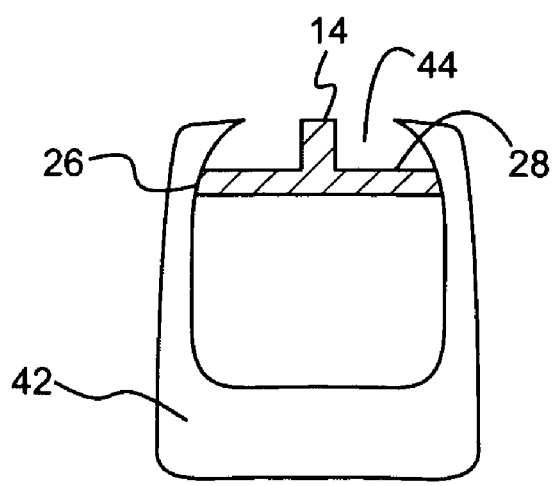
FIG. 3C FIG. 3D

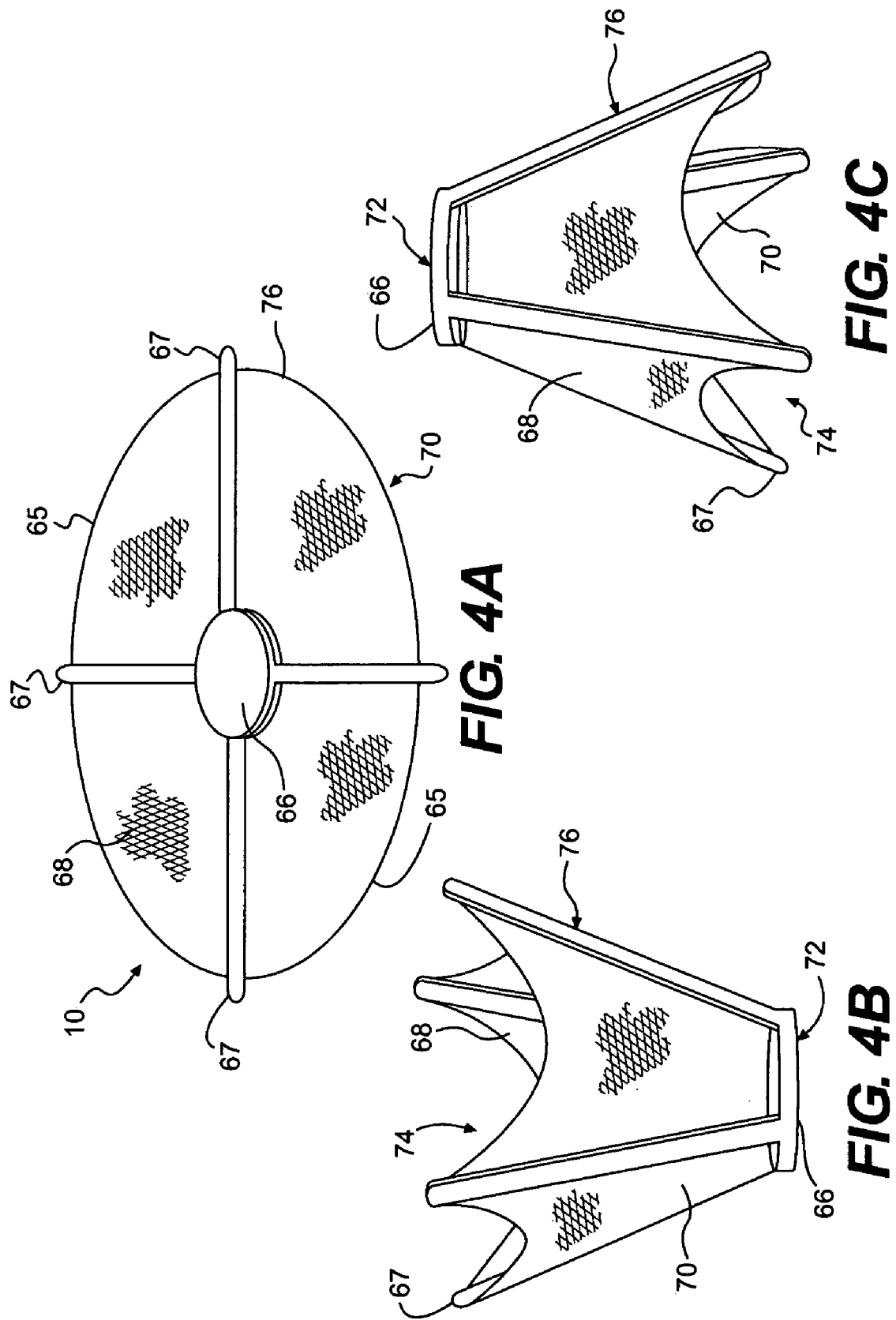

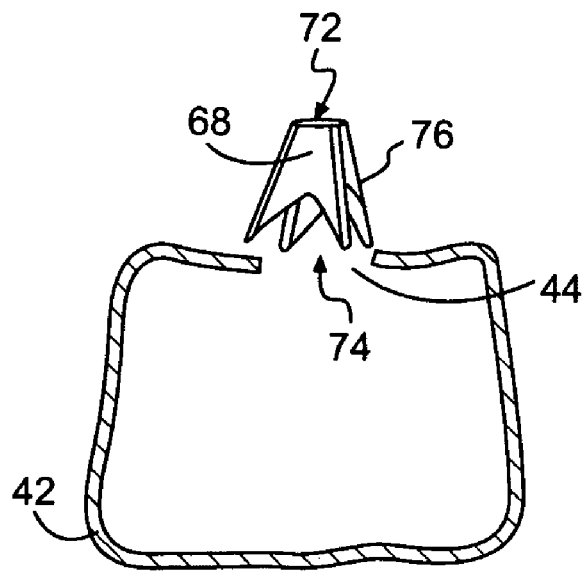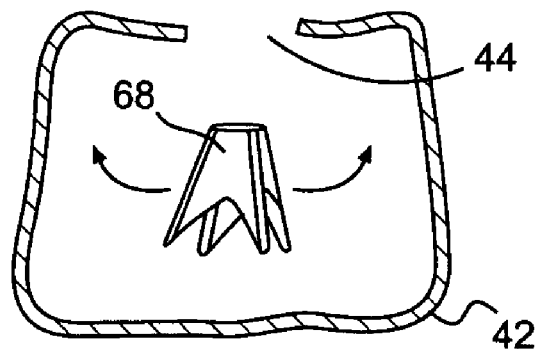
FIG. 6A  FIG. 6B
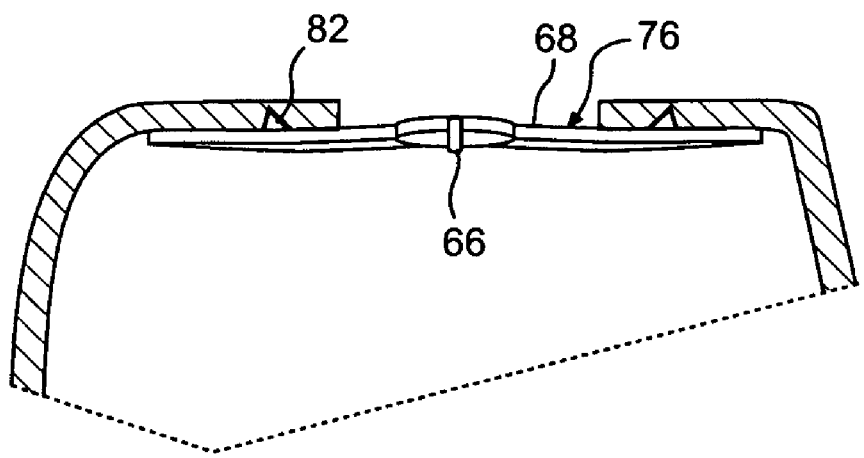
FIG. 6C

HERNIATED DISC

DISC, POST-DISCECTOMY

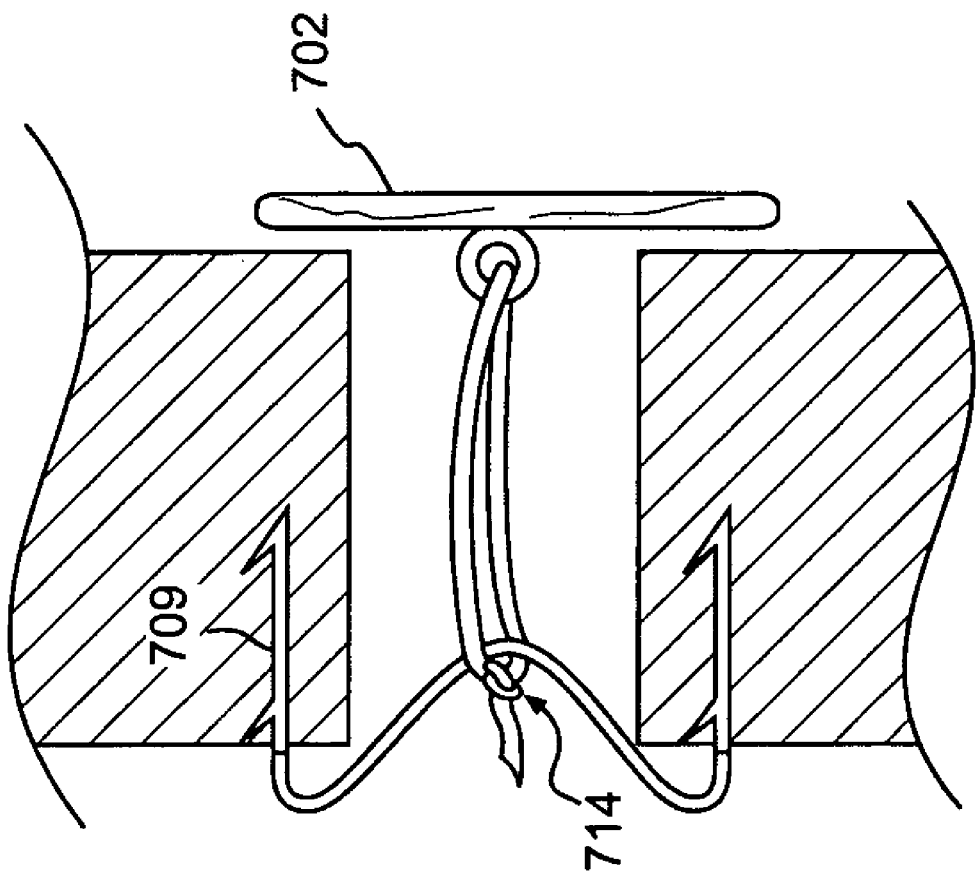
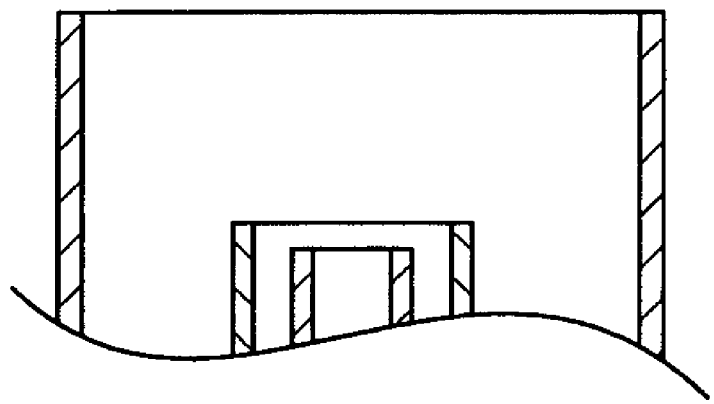
FIG. 14C

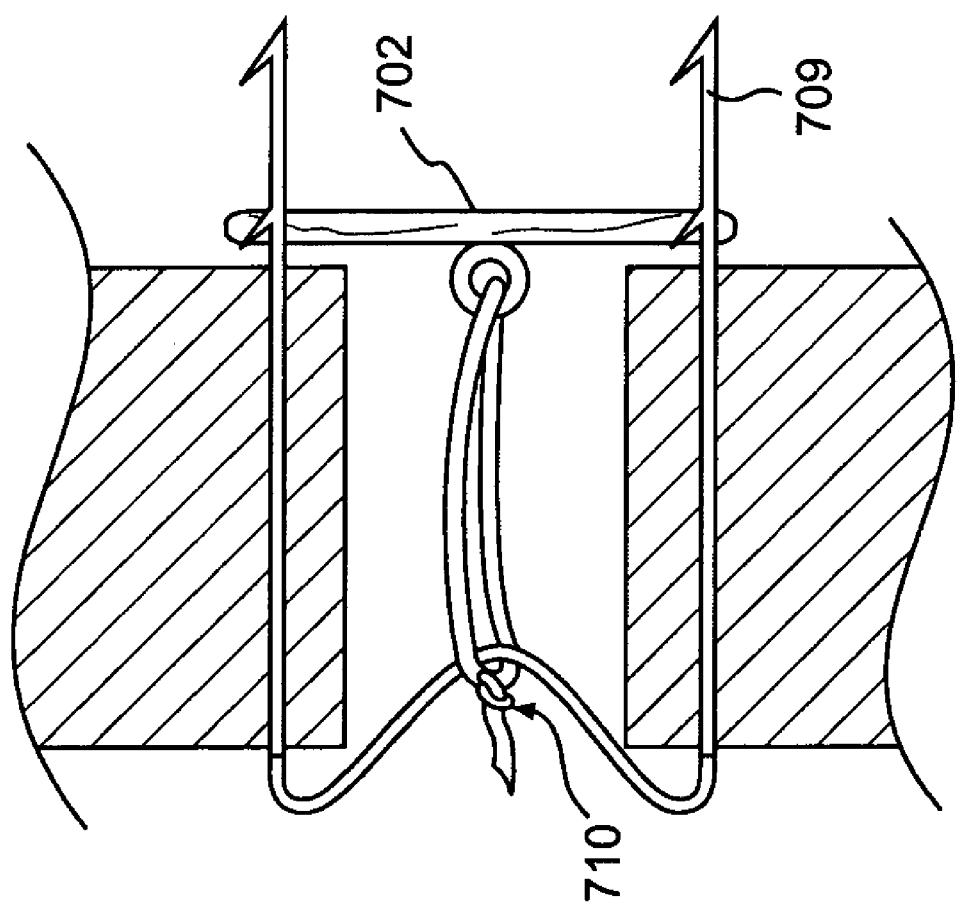
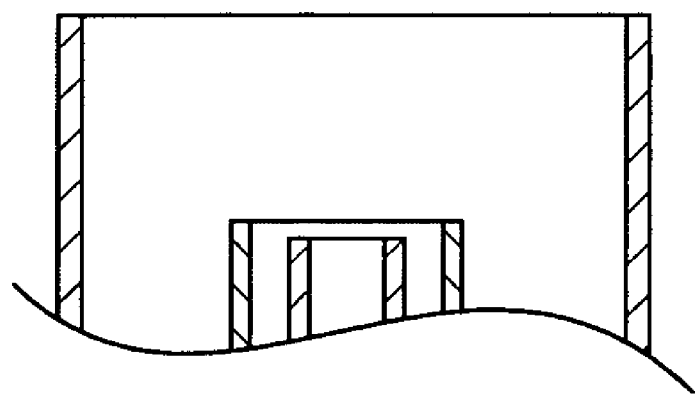
FIG. 16C

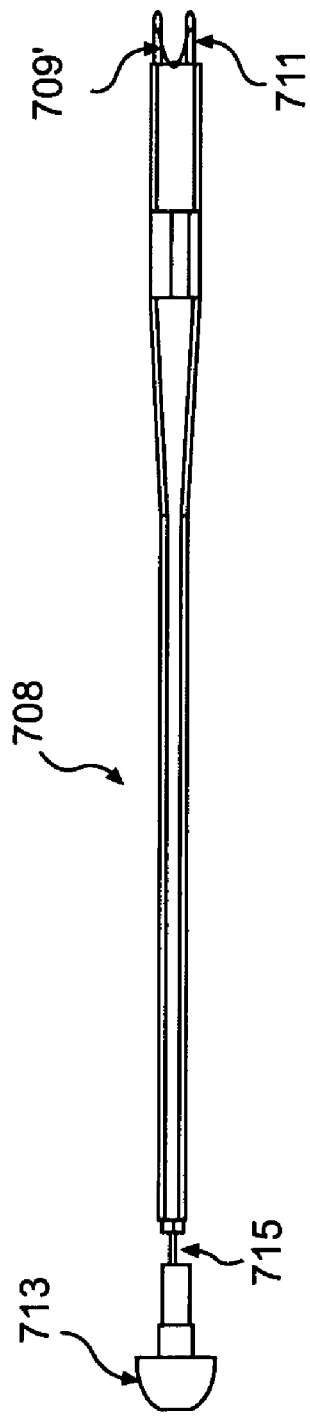
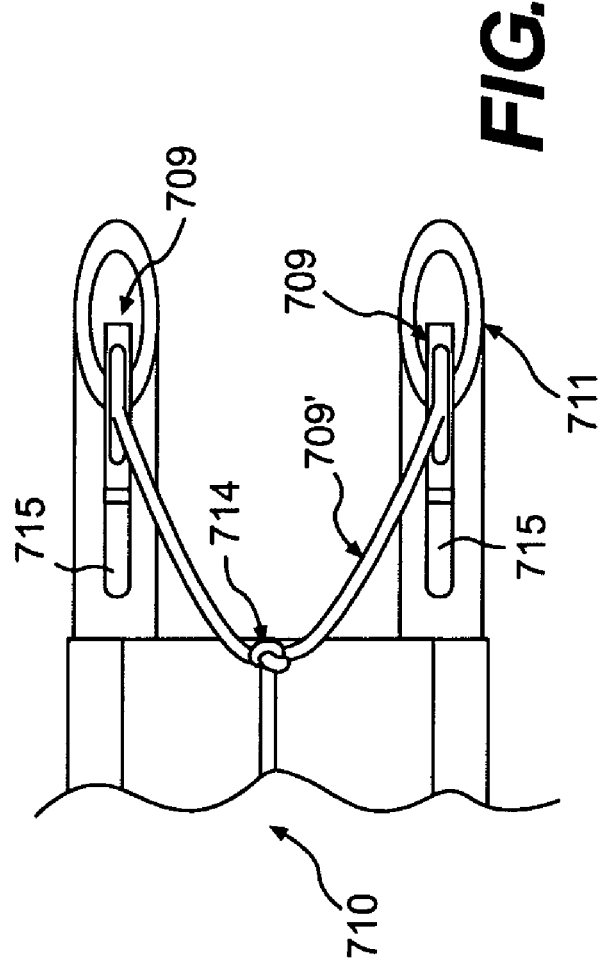
FIG. 24A
FIG. 24B

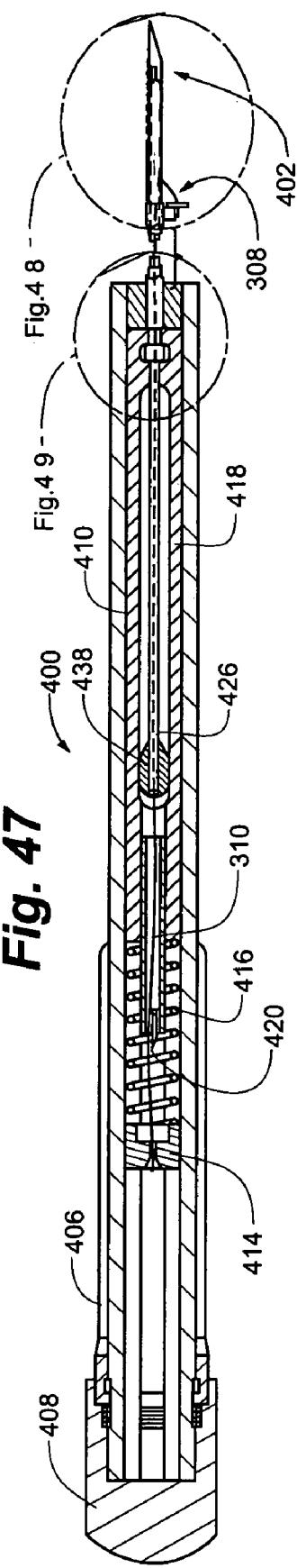
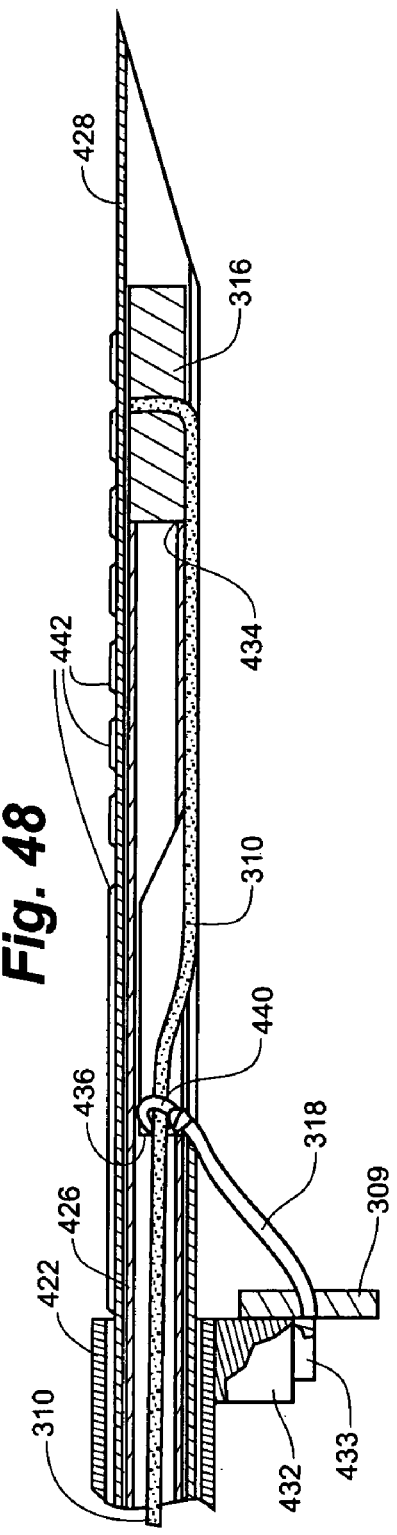
Fig. 47
Fig. 48

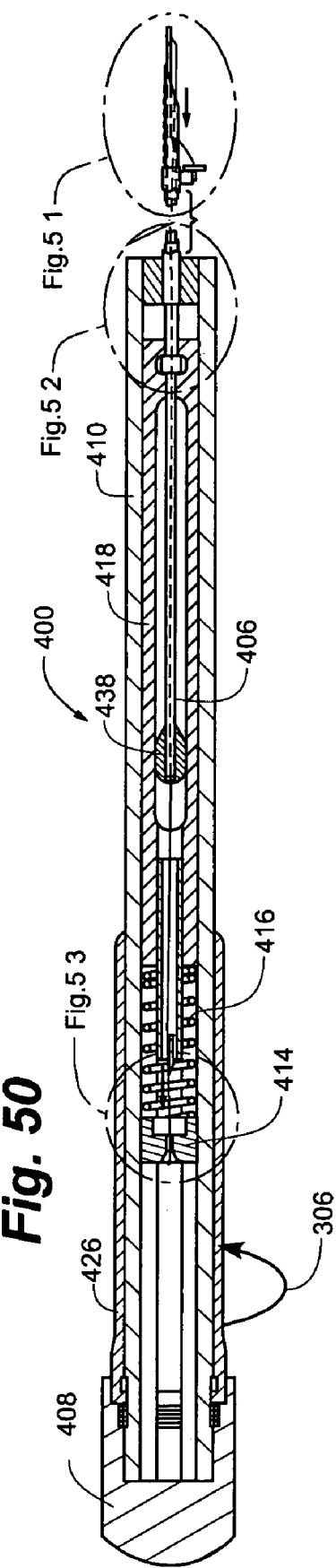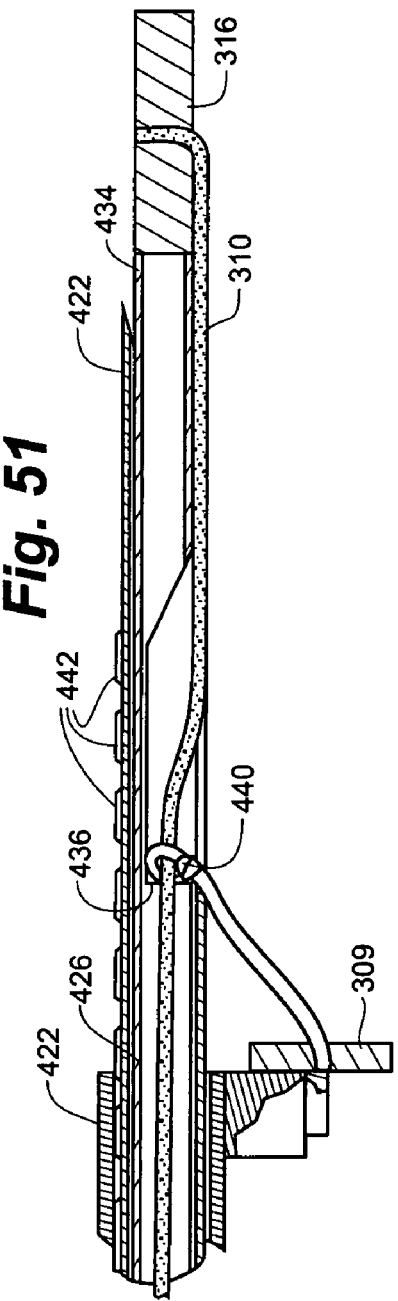

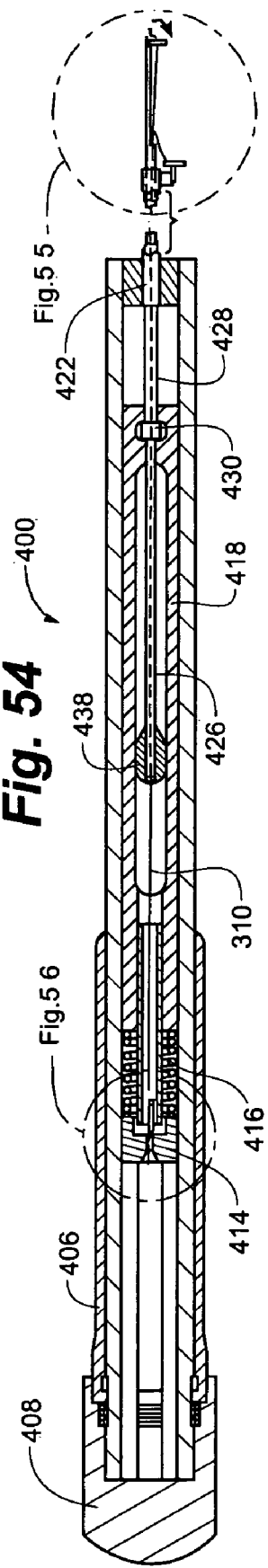

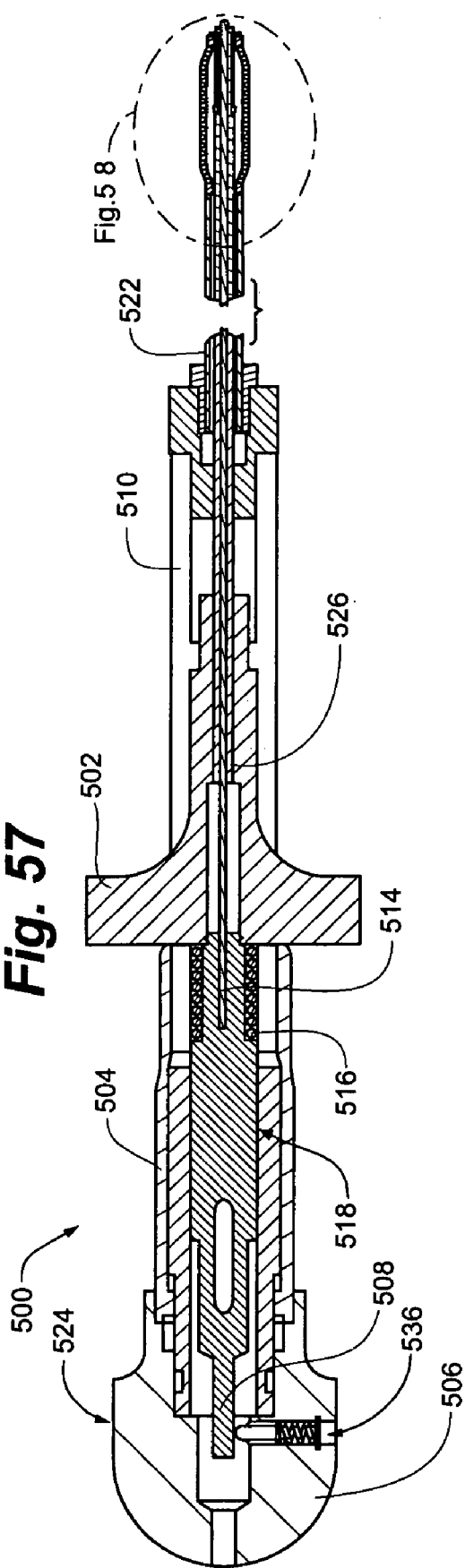
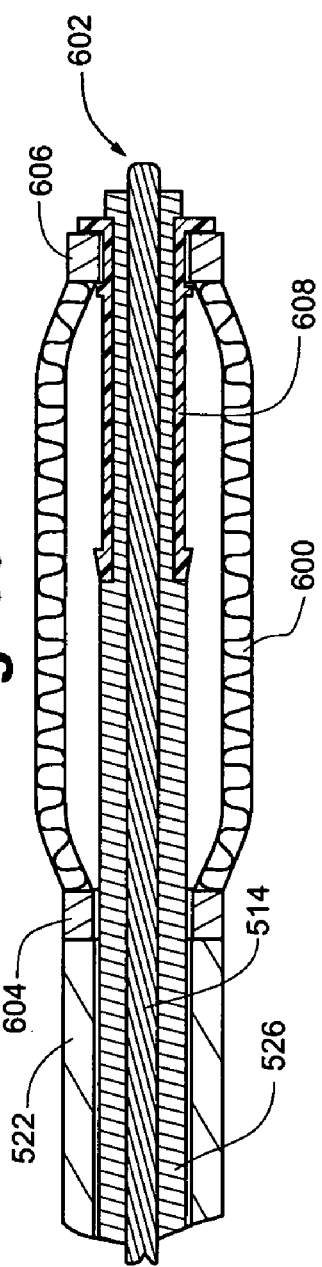

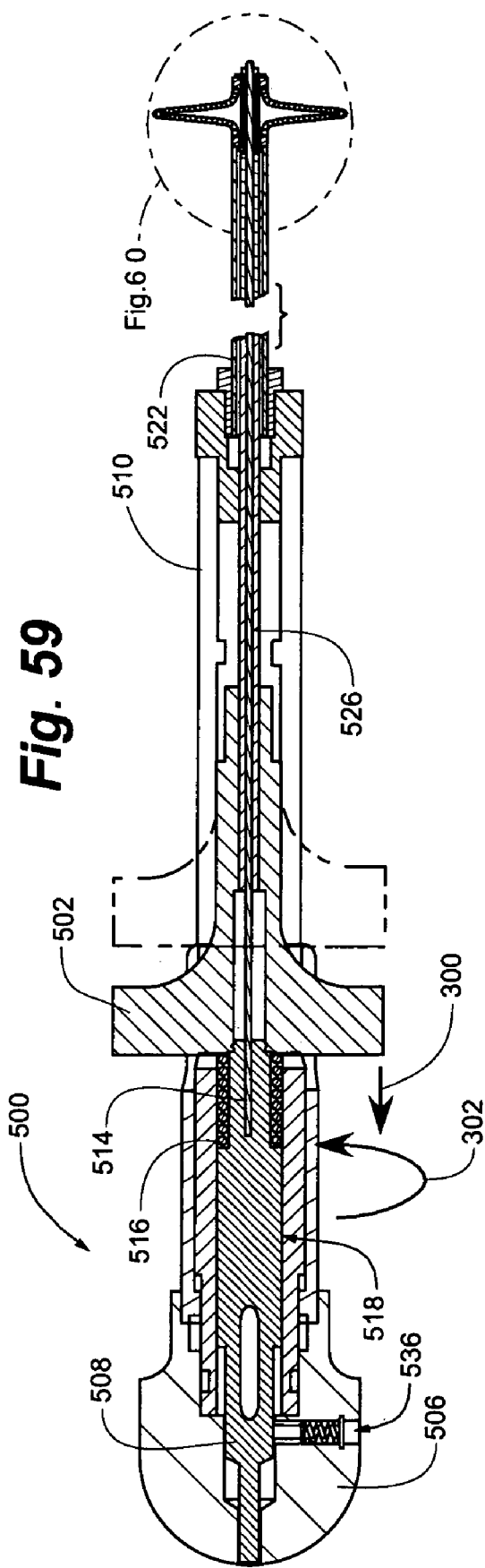

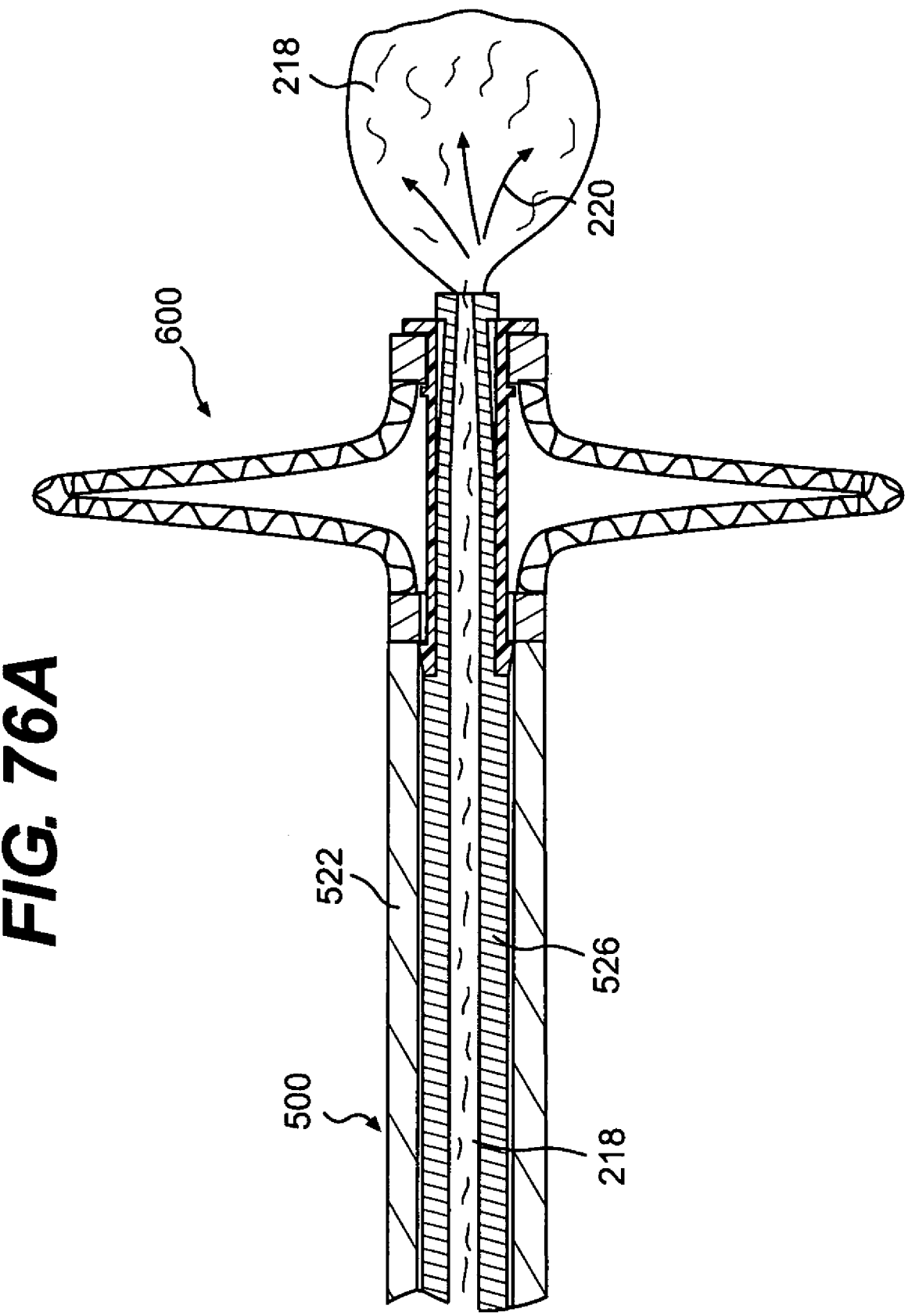

METHOD AND APPARATUS FOR THE TREATMENT OF THE INTERVERTEBRAL DISC ANNULUS

CROSS-REFERENCE TO A RELATED APPLICATIONS

This application is a continuation-in-part of U.S. patent application Ser. No. 10/352,981 filed Jan. 29, 2003 and a continuation-in-part of U.S. patent application Ser. No. 10/327,106 filed Dec. 24, 2002, now U.S. Pat. No. 7,004,970 each of which are continuations-in-part of U.S. patent application Ser. No. 10/133,339 filed Apr. 29, 2002, now U.S. Pat. No. 7,052,516 which is a continuation-in-part of U.S. patent application Ser. No. 09/947,078, filed Sep. 5, 2001, now U.S. Pat. No. 6,592,625, issued Jul. 15, 2003, which is a continuation of U.S. patent application Ser. No. 09/484,706, filed Jan. 18, 2000, now abandoned which claims the benefit of U.S. Provisional Application No. 60/160,710, filed Oct. 20, 1999. This application also claims, through application Ser. No. 10/133,339 the benefit of U.S. Provisional Application No. 60/309,105, filed Jul. 31, 2001. This application is also related to, and claims the benefit of, U.S. patent application Ser. No. 10/075,615, filed on Feb. 15, 2002. All are incorporated herein by reference in their entirety.

FIELD OF THE INVENTION

The invention generally relates to methods and devices for the closure, sealing, repair and/or reconstruction of an intervertebral disc annulus, and accompanying delivery devices and tools, and their methods of use. The repair can be of an aperture in the disc wall, or a weakened or thin portion. The term "aperture" refers to a hole in the annulus that is a result of a surgical incision or dissection into the intervertebral disc annulus, or the consequence of a naturally occurring tear (rent). The invention generally relates to surgical devices and methods for the treatment of intervertebral disc wall repair or reconstruction. The invention further relates to an annular repair device, or stent, for annular disc repair. These stents can be of natural or synthetic materials. The effects of said reconstruction is restoration of disc wall integrity, which may reduce the failure rate (3-21%) of a common surgical procedure (disc fragment removal or discectomy), or advantageously provide a barrier to intradiscal material migration.

BACKGROUND OF THE INVENTION

The spinal column is formed from a number of bony vertebrae, which in their normal state are separated from each other by intervertebral discs. These discs are comprised of the annulus fibrosus, and the nucleus pulposus, both of which are soft tissue. The intervertebral disc acts in the spine as a crucial stabilizer, and as a mechanism for force distribution between adjacent vertebral bodies. Without a competent disc, collapse of the intervertebral disc may occur, contributing to abnormal joint mechanics and premature development of degenerative and/or arthritic changes.

The normal intervertebral disc has an outer ligamentous ring called the annulus surrounding the nucleus pulposus. The annulus binds the adjacent vertebrae together and is constituted of collagen fibers that are attached to the vertebrae and cross each other so that half of the individual fibers will tighten as the vertebrae are rotated in either direction, thus resisting twisting or torsional motion. The nucleus pulposus is constituted of soft tissue, having about 85% water content, which moves about during bending from front to back and from side to side.

The aging process contributes to gradual changes in the intervertebral discs. The annulus loses much of its flexibility and resilience, becoming more dense and solid in composition. The aging annulus may also be marked by the appearance or propagation of cracks or fissures in the annular wall. Similarly, the nucleus desiccates, increasing viscosity and thus losing its fluidity. In combination, these features of the aged intervertebral discs result in less dynamic stress distribution because of the more viscous nucleus pulposus, and less ability to withstand localized stresses by the annulus fibrosus due to its desiccation, loss of flexibility and the presence of fissures. Fissures can also occur due to disease or other pathological conditions. Occasionally fissures may form rents through the annular wall. In these instances, the nucleus pulposus is urged outwardly from the subannular space through a rent, often into the spinal column. Extruded nucleus pulposus can, and often does, mechanically press on the spinal cord or spinal nerve rootlet. This painful condition is clinically referred to as a ruptured or herniated disc.

In the event of annulus rupture, the subannular nucleus pulposus migrates along the path of least resistance forcing the fissure to open further, allowing migration of the nucleus pulposus through the wall of the disc, with resultant nerve compression and leakage of chemicals of inflammation into the space around the adjacent nerve roots supplying the extremities, bladder, bowel and genitalia. The usual effect of nerve compression and inflammation is intolerable back or neck pain, radiating into the extremities, with accompanying numbness, weakness, and in late stages, paralysis and muscle atrophy, and/or bladder and bowel incontinence. Additionally, injury, disease or other degenerative disorders may cause one or more of the intervertebral discs to shrink, collapse, deteriorate or become displaced, herniated, or otherwise damaged and compromised.

Surgical repairs or replacements of displaced or herniated discs are attempted approximately 390,000 times in the USA each year. Historically, there has been no known way to repair or reconstruct the annulus. Instead, surgical procedures to date are designed to relieve symptoms by removing unwanted disc fragments and relieving nerve compression. While results are currently acceptable, they are not optimal. Various authors report 3.1-21% recurrent disc herniation, representing a failure of the primary procedure and requiring re-operation for the same condition. An estimated 10% recurrence rate results in 39,000 re-operations in the United States each year.

An additional method of relieving the symptoms is thermal annuloplasty, involving the heating of sub-annular zones in the non-herniated painful disc, seeking pain relief, but making no claim of reconstruction of the ruptured, discontinuous annulus wall.

Some have also suggested that the repair of a damaged intervertebral disc might include the augmentation of the nucleus pulposus, and various efforts at nucleus pulposus replacement have been reported. The present invention is directed at the repair of the annulus, whether or not a nuclear augmentation is also warranted.

In addition, there has been experimentation in animals to assess various surgical incisions with and without the direct surgical repair of the annulus. These studies were performed on otherwise healthy animals and involved no removal or augmentation of nucleus pulposus. The authors of these experiments conclude that direct repair of the annulus does not influence the healing of the disc.

The present inventors have found, advantageously and contrary to accepted practice, that the annulus tissue may be sutured and that annular healing may be facilitated by reapproximation, reinforcement, and/or support of annular tissue.

Methods and devices for carrying out annular repair and/or reconstruction are a subject of the present invention.

BRIEF SUMMARY OF THE INVENTION

The present inventions provide methods and related devices for reconstruction of the disc wall in cases of displaced, herniated, thinned, ruptured, or otherwise damaged or infirm intervertebral discs. In accordance with the invention, a method is disclosed for intervertebral disc reconstruction for treating a disc having an aperture, weakened or thin portion in the wall of the annulus fibrosis of the intervertebral disc. Repair, reconstruction, sealing, occluding an aperture, weakened or thin portion in the wall of the annulus may prevent or avoid migration of intradiscal material from the subannular space.

The method of the invention includes, in one embodiment, the steps of providing a first delivery tool having a proximal end and a distal end, the distal end carrying a treatment device; providing at least one second delivery tool having a proximal end and a distal end, the distal end carrying a fixation element; introducing the distal end of the first delivery tool at least partially into subannular intervertebral disc space; deploying said treatment device; introducing the distal end of said at least one second delivery tool at lest partially into subannular intervertebral disc space; and deploying at least one fixation device into, or through, the wall of an annulus to hold said treatment device at least partially within the subannular intervertebral disc space; and removing the delivery tools.

A fixation device useful for intervertebral disc reconstruction for treating a disc having an aperture, weakened, or thin portion in the wall of the annulus fibrosis of said intervertebral disc, said device, in one embodiment comprises at least one anchor portion and at least one band.

A treatment device, according to one embodiment, comprises a mesh patch that radially expands in the subannular space.

The invention also comprises delivery tools for delivering fixation devices and treatment devices, as well as kits comprising devices and tools.

The objects and various advantages of the invention will be apparent from the description which follows. In general, the implantable medical treatment devices are placed, positioned, and subsequently affixed in the annulus to reduce re-extrusion of the nucleus or other indtradiscal material through an aperture by: establishing a barrier or otherwise closing or partially closing the aperture; and/or helping to restore the natural integrity of the wall of the annulus; and/or promoting healing of the annulus. Increased integrity and faster and/or more thorough healing of the aperture may reduce future recurrence of herniation of the disc nucleus, or intradiscal material, from the intervertebral disc, and the recurrence of resulting back pain. In addition, it is believed that the repair of the annular tissue could promote enhanced biomechanics and reduce the possibility of intervertebral disc height collapse and segmental instability, thus possibly avoiding back pain after a surgical procedure.

Moreover, the repair of an aperture (after for example, a discectomy procedure) with the reduction of the re-extrusion of the nucleus may also advantageously reduce adhesion formation surrounding the nerve roots. The nuclear material of the disc is toxic to the nerves and is believed to cause increased inflammation surrounding the nerves, which in turn can cause increased scar formation (adhesions or epidural fibrosis) upon healing. Adhesions created around the nerve roots can cause continued back pain. Any reduction in adhesion formation is believed to reduce future recurrence of pain.

The methods and devices of the present inventions may create a mechanical barrier to the extrusion of intradiscal material (i.e., nucleus pulposus, or nuclear augmentation materials) from the disc space, add mechanical integrity to the annulus and the tissue surrounding an aperture, weakened, or thin portion of the wall of the annulus, and promote faster and more complete healing of the aperture, weakened or thin portion Although much of the discussion is directed toward the repair of the intervertebral disc after a surgical procedure, such as discectomy (a surgical procedure performed to remove herniated fragments of the disc nucleus), it is contemplated that the devices of the present invention may be used in other procedures that involve access (whether induced or naturally occurring) through the annulus of the intervertebral disc, or prophylactic application to the annulus. An example of another procedure that could require a repair technique involves the replacement of the nucleus (nucleus replacement) with an implantable nucleus material to replace the functioning of the natural nucleus when it is degenerated. The object of the invention in this case would be similar in that the repair would maintain the replacement nucleus within the disc space.

According to an embodiment of the invention, a sub-annular device can be employed to repair an aperture, degenerated, weakened, or thin portion in an intervertebral disc annulus. The device can be secured in place with one or more fixation elements, such as sutures or anchors which may also be used to re-approximate the tissues surrounding the aperture, degenerated, weakened, or thin portion. The invention, through involvement of the sub-annular space and wall for the repair of the aperture has several advantages. The first advantage of a repair that involves a sub-annular surface derives itself from the physical nature of a circular (or an elliptical) compressed chamber with a radius, like an intervertebral disc. Sealing the inside wall has the inherent advantage of being at a smaller radius of curvature versus the outer wall and thus, according to LaPlace's Law, the patch would be subjected to lower stresses at any given pressure, all else held equal.

Another advantage of utilizing the inner surface to accomplish sealing is that the natural pressure within the disc can enhance the seating of the device against the inner wall of the disc space. Conversely, if the repair is performed on the outer surface of the annulus there is an inherent risk of leakage around the periphery of the device, with the constant exposure to the pressure of the disc.

Another advantage of the present invention in utilizing an inner surface of the annulus is the reduction of the risk of having a portion of the device protruding from the exterior surface of the annulus. Device materials protruding from the exterior of the annulus pose a risk of damaging the nerve root and/or spinal canal which are in close proximity. Damage to these structures can result in continued pain, incontinence, bowel dysfunction and paralysis.

Some embodiments of the present invention may also incorporate the concept of pulling the tissues together that surround the aperture, the inner surface, and the outer surface of the annulus to help close the aperture, increase the integrity of the repair, and promote healing.

An example of the technique and placement of the device according to one embodiment of the invention is as follows:

1. A treatment device is actuated into a delivery configuration by delivery device and passed through an aperture in the wall of the annulus, positioning a treatment device in the subannular disc space, as shown in FIG. 3A-3C.

2. The delivery device is actuated to deploy the treatment device, as shown in FIG. 3D.

3. Holding the treatment device in the deployed configuration, a fixation instrument is employed to introduce one or more fixation elements into, or through, the annulus to secure the treatment device and subsequently removed, as shown in FIGS. 2, 5 and 6.

4. The delivery device is disengaged from the treatment device.

Several devices according to the present invention can be used to practice the above illustrative inventive steps to seal, reconstruct and/or repair the intervertebral disc. In some of the representative devices described herein, there is: a reconfigurable device (note: patch, stent, device, mesh, barrier, and treatment device are here used interchangeably) that has, in use, at least a portion of the device in the sub-annular space of the intervertebral disc annulus; a means to affix the at least a portion of the device to or within at least a portion of the annulus; a means to draw the patch or fixation device into engagement with the annular tissue in tension to thereby help reduce the relative motion of the surfaces of the aperture and/or annulus after fixation, and thus promote healing. Reducing motion of the annular surfaces may provide the optimal environment for healing.

Some of the concepts disclosed hereinbelow accomplish these objectives, as well as may advantageously additionally incorporate design elements to reduce the number of steps (and time), and/or simplify the surgical technique, and/or reduce the risk of causing complications during the repair of the intervertebral disc annulus. In addition, the following devices may become incorporated by the surrounding tissues, or to act as a scaffold in the short-term (3-6 months) for tissue incorporation.

In an exemplary embodiment, one or more mild biodegradable surgical sutures can be placed at about equal distances along the sides of a pathologic aperture in the ruptured disc wall (annulus) or along the sides of a surgical dissection or incision in the annular wall, which may be weakened or thinned. The sutures hold an expandable device to a subannular surface of the annulus.

Sutures are then drawn in tension and secured in such a fashion as to draw the expandable device into engagement with the annular tissue, and also to help effect closure of the aperture, to enhance natural healing and subsequent reconstruction by natural tissue (fibroblasts) crossing the gap now bridged by the device in the disc annulus.

In an exemplary embodiment, the method can be augmented by creating a subannular barrier in and across the aperture by placement of a patch of biocompatible material acting as a bridge or a scaffold, providing a platform for traverse of fibroblasts or other normal cells of repair existing in and around the various layers of the disc annulus.

Such biocompatible materials may be, for example, medical grade biocompatible fabrics or fibers, biodegradable polymeric sheets, or form fitting or non-form fitting fillers for the cavity created by removal of a portion of the disc nucleus pulposus in the course of the disc fragment removal or discectomy. The prosthetic material can be placed in and around the intervertebral space, created by removal of the degenerated disc fragments.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate illustrative embodiments of the invention and, together with the description, serve to explain the principles of the invention.

FIG. 1 shows a primary closure of an opening in the disc annulus.

FIGS. 2A-2B show a primary closure with a stent.

FIGS. 3A-3D show an annulus stent being inserted into and expanded within the disc annulus.

FIGS. 4A-4C shows a perspective view of a further illustrative embodiment of an annulus stent, and collapsed views thereof.

FIGS. 6A-6C show a method of inserting the annulus stent of FIG. 4A into the disc annulus.

FIGS. 14A-14C schematically depict the patch of FIG. 13 being fixated through use of a barbed surgical staple device and a cinch line.

FIGS. 16A-16C schematically depict the stnet/patch of FIG. 15 being fixated through use of a barbed surgical staple device that penetrates the patch/stent and a cinch line.

FIGS. 24A-24B show an illustrative configuration of an anchor band delivery device.

FIG. 47 is a view of the anchor band delivery tool pre-deployment in cross section.

FIG. 48 shows a detail of the distal end of the anchor band (fixation element) delivery tool in cross section.

FIG. 50 is a view of the anchor band delivery tool in cross section during a deployment cycle.

FIG. 51 is a detail pf the distal end of the anchor band delivery tool depicted in FIG. 50.

FIG. 54 is a view of the anchor band delivery tool in cross section during the cutting of the suture tether and release of the anchor band.

FIG. 55 shows a detail of the distal end of the anchor band delivery tool during release of the anchor band.

FIG. 57 depicts an illustrative embodiments of a therapeutic device delivery tool (TDDT)

FIG. 58 shows a detail of the distal end of the threapetutic device delivery tool with a therapeutic device mounted thereon.

FIG. 59 depicts the deployment of a therapeutic device using the TDDT.

FIGS. 76A-76B show a cross section view of the delivery of a flowable material from the distal end of delivery device.

DETAILED DESCRIPTION OF ILLUSTRATIVE EMBODIMENTS OF THE INVENTION

Figure 5A:
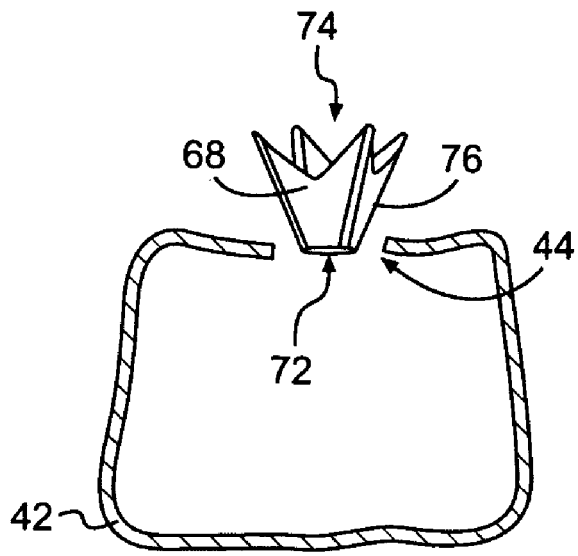
FIGS. 5A-5C show the annulus stent of FIG. 4A being inserted into the disc annulus.

Reference will now be made in detail to selected illustrative embodiments of the invention, with occasional reference to the accompanying drawings. Wherever possible, the same reference numbers will be used throughout the drawings to refer to the same or like parts.

In the surgical repair of an aperture in the annulus, as shown in FIG. 1 and as described in related commonly-assigned U.S. Pat. No. 6,592,625 to Cauthen, a damaged annulus 42 is repaired by use of surgical sutures 40. One or more surgical sutures 40 are placed at about equal distances along the sides of a pathologic aperture 44 in the annulus 42. Reapproximation or closure of the aperture 44 is accomplished by tying the sutures 40 so that the sides of the aperture 44 are drawn together. The reapproximation or closure of the aperture 44 enhances the natural healing and subsequent reconstruction by the natural tissue (e.g., fibroblasts) crossing the now surgically narrowed gap in the annulus 42. Preferably, the surgical sutures 40 are biodegradable, but permanent non-biodegradable may be utilized. In all embodiments where biodegradable materials are indicated, suitable biodegradable materials may include, but are not limited to, biodegradable polyglycolic acid, swine submucosal intestine, collagen, or polylactic acid. Other suitable suturing (and band) materials include, e.g., polymeric materials such as polyethylene terephthalate (PET), polyester (e.g., Dacron™), polypropylene, polyethylene, polycarbonate urethane or metallic material include, e.g., titanium, nickel titanium alloy, stainless steel, surgical steels or any combinations thereof.

Additionally, to repair a weakened or thinned wall of a disc annulus 42, a surgical incision or dissection can be made along the weakened or thinned region of the annulus 42 and one or more surgical sutures 40 can be placed at about equal distances laterally from the incision. Reapproximation or closure of the incision is accomplished by tying the sutures 40 so that the sides of the incision are drawn together. The reapproximation or closure of the incision/dissection enhances the natural healing and subsequent reconstruction by the natural tissue crossing the now surgically narrowed gap in the annulus 42. Preferably, the surgical sutures 40 are biodegradable, but permanent non-biodegradable materials may be utilized.

Where necessary or desirable, the method can be augmented by placing a patch in and across the aperture 44. The patch acts as a bridge in and across the aperture 44, providing a platform for traverse of fibroblasts or other normal cells of repair existing in and around the various layers of the disc annulus 42, prior to closure of the aperture 44. FIGS. 2A-B, for example, show a biocompatible device employed as an annulus stent 10, being placed in and across the aperture 44. The annulus stent 10 acts as a bridge in and across the aperture 44, providing a platform for a traverse of fibroblasts or other normal cells of repair existing in and around the various layers of the disc annulus 42, prior to closure of the aperture 44. In some embodiments the device, stent or patch can act as a scaffold to assist in tissue growth that healingly scars the annulus.

In an illustrative embodiment, the annulus stent 10 is a solid unit, formed from one or more of the flexible resilient biocompatible or bioresorbable materials well know in the art. The selection of appropriate stent materials may be partially predicated on specific stent construction and the relative properties of the material such that, after fixed placement of the stent, the repair may act to enhance the healing process at the aperture by relatively stabilizing the tissue and reducing movement of the tissue surrounding the aperture.

For example, the annulus stent 10 may be made from:

A porous matrix or mesh of biocompatible and bioresorbable fibers acting as a scaffold to regenerate disc tissue and replace annulus fibrosus as disclosed in, for example, U.S. Pat. No. 5,108,438 (Stone) and U.S. Pat. No. 5,258,043 (Stone), a strong network of inert fibers intermingled with a bioresorbable (or bioabsorbable) material which attracts tissue ingrowth as disclosed in, for example, U.S. Pat. No. 4,904,260 (Ray et al.).

a biodegradable substrate as disclosed in, for example, U.S. Pat. No. 5,964,807 (Gan at al.); or an expandable polytetrafluoroethylene (ePTFE), as used for conventional vascular grafts, such as those sold by W.L. Gore and Associates, Inc. under the trademarks GORE-TEX and PRECLUDE, or by Impra, Inc. under the trademark IMPRA.

Furthermore, the annulus, stent 10, may contain hygroscopic material for a controlled limited expansion of the annulus stent 10 to fill the evacuated disc space cavity.

Additionally, the annulus stent 10 may comprise materials to facilitate regeneration of disc tissue, such as bioactive silica-based materials that assist in regeneration of disc tissue as disclosed in U.S. Pat. No. 5,849,331 (Ducheyne, et al.), or other tissue growth factors well known in the art.

Many of the materials disclosed and described above represent embodiments where the device actively promotes the healing process. It is also possible that the selection of alternative materials or treatments may modulate the role in the healing process, and thus promote or prevent healing as may be required. It is also contemplated that these modulating factors could be applied to material substrates of the device as a coating, or similar covering, to evoke a different tissue response than the substrate without the coating.

Materials of the patch could include a metallic material (e.g., NiTi alloy, Stainless steel, Titanium), or a polymeric material (e.g., polypropylene, polyethylene, polyurethane, polycarbonate urethane, Polyetheretherketone (PEEK), polyester, PET, poly olefin copolymer, polypropylene, polyethylene), or a biodegradable or bioresorbable material (e.g., collagen, cellulose, polysaccharide, polyglycolic acid (PGA), a polylevolactic acid (PPLA), a polydioxanone (PDA) or for example a racemic polylactic acid (PDLLA), or a combination of these materials.

In an illustrative method of use, as shown in FIGS. 3A-3D, lateral extensions 20 and 22 of a stent 10 are compressed together for insertion into the aperture 44 of the disc annulus 42. The annulus stent 10 is then inserted into the aperture 44, where the lateral extensions 20, 22 expand. In an expanded configuration, the upper surface 28 can substantially conform to the contour of the inside surface of the disc annulus 42. The upper section 14 is positioned within the aperture 44 so that the annulus stent 10 may be secured to the disc annulus 42, using means well known in the art.

In an alternative method, where the length of the aperture 44 is less than the length of the outside edge 26 of the annulus stent 10, the annulus stent 10 can be inserted laterally into the aperture 44. The lateral extensions 20 and 22 are compressed, and the annulus stent 10 can then be laterally inserted into the aperture 44. The annulus stent 10 can then be rotated inside the disc annulus 42, such that the upper section 14 can be held back through the aperture 44. The lateral extensions 20 and 22 are then allowed to expand, with the upper surface 28 contouring to the inside surface of the disc annulus 42. The upper section 14 can be positioned within, or proximate to, the aperture 44 in the subannular space such that the annulus stent 10 may be secured to the disc annulus, using means well known in the art.

It is anticipated that fibroblasts will engage the fibers of the polymer or fabric of the intervertebral disc stent 10, forming a strong wall duplicating the currently existing condition of healing seen in the normal reparative process.

Figure 5B:
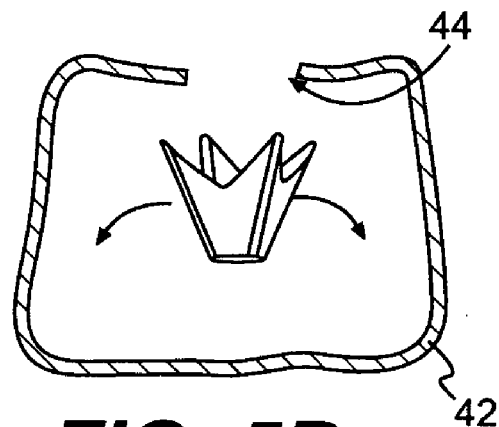
Figure 5C:
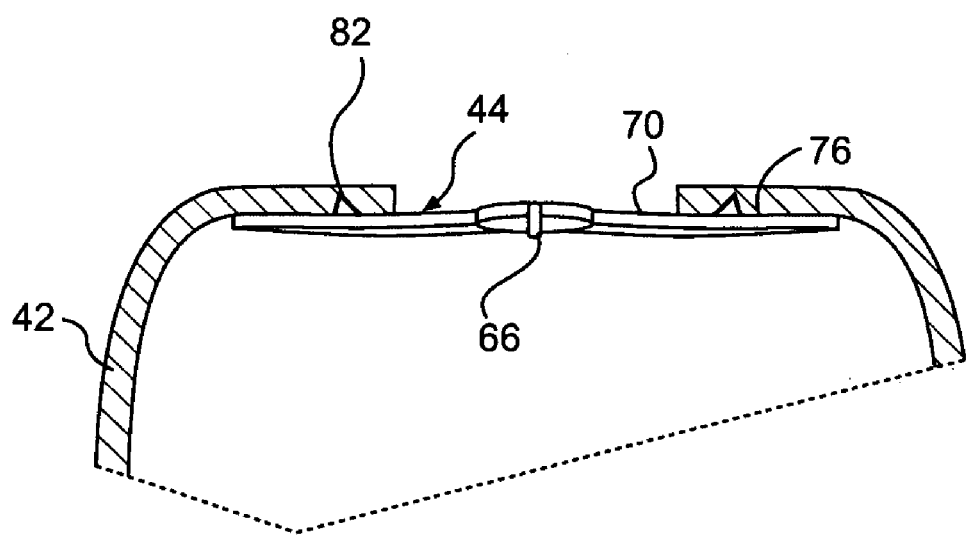

In an alternative embodiment, as shown in FIG. 4A, the annulus stent 10 is substantially umbrella shaped, having a central hub 66 with radially extending struts 67. Each of the struts 67 is joined to the adjacent struts 67 by a webbing material 65, forming a radial extension 76 about the central hub 66. The radial extension 76 has an upper surface 68 and a lower surface 70, where the upper surface 68 contours to the shape of the disc annulus' 42 inner wall when inserted as shown in FIG. 6A-6C, and where the lower surface 70 contours to the shape of the disc annulus' 42 inner wall when inserted as shown in FIG. 5A-5C. The radial extension 76 may be substantially circular, elliptical, or rectangular in plan shape.

As shown in FIGS. 4B and 4C, the struts 67 are formed from flexible material, allowing the radial extension 76 to be collapsed for insertion into aperture 44, then the expand conforming to the shape of the inner wall of disc annulus 42. In the collapsed position, the annulus stent 10 is substantially frustoconical or shuttlecock shaped, and having a first end 72, comprising the central hub 66, and a second end 74.

In an alternative embodiment, the radial extension 76 has a greater thickness at the central hub 66 edge than at the outside edge.

In a method of use, as shown in FIGS. 5A-5C, the radial extension 76 is collapsed together, for insertion into the aperture 44 of the disc annulus 42. The radial extension 76 is folded such the upper surface 68 forms the outer surface of the cylinder. The annulus stent 10 is then inserted into the aperture 44, inserting the leading end 72 though the aperture 44 until the entire annulus stent 10 is within the disc annulus 42. The radial extension 76 is released, expanding within the disc 44. The lower surface 70 of the annulus stent 10 contours to the inner wall of disc annulus 42. The central hub 66 is positioned within the aperture 44 so that the annulus stent 10 may be secured to the disc annulus 42 using means well known in the art.

It is anticipated that fibroblasts will engage the fibers of the polymer or fabric of the annulus stent 10, forming a strong wall duplicating the currently existing condition of healing seen in the normal reparative process.

In an alternative method of use, as shown in FIGS. 6A-6C, the radial extension 76 is collapsed together for insertion into the aperture 44 of the disc annulus 42. The radial extension 76 is folded such that the upper surface 68 forms the outer surface of the stent, for example in a frustoconical configuration as illustrated. The annulus stent 10 is then inserted into the aperture 44, inserting the tail end 74 through the aperture 44 until the entire annulus stent 10 is in the disc. The radial extension 76 is released, expanding within the disc. The upper surface 68 of the annulus stent 10 contours to the disc annulus' 42 inner wall. The central hub 66 is positioned within the aperture 44 so that the annulus stent 10 may be secured to the disc annulus 42, using means well known in the art.

In one illustrative embodiment, the barbs 82 on the upper surface 68 of one or more strut 67 or other feature of the radial extension 76, engage the disc annulus' 42 inner wall, holding the annulus stent 10 in position.

Figure 7:
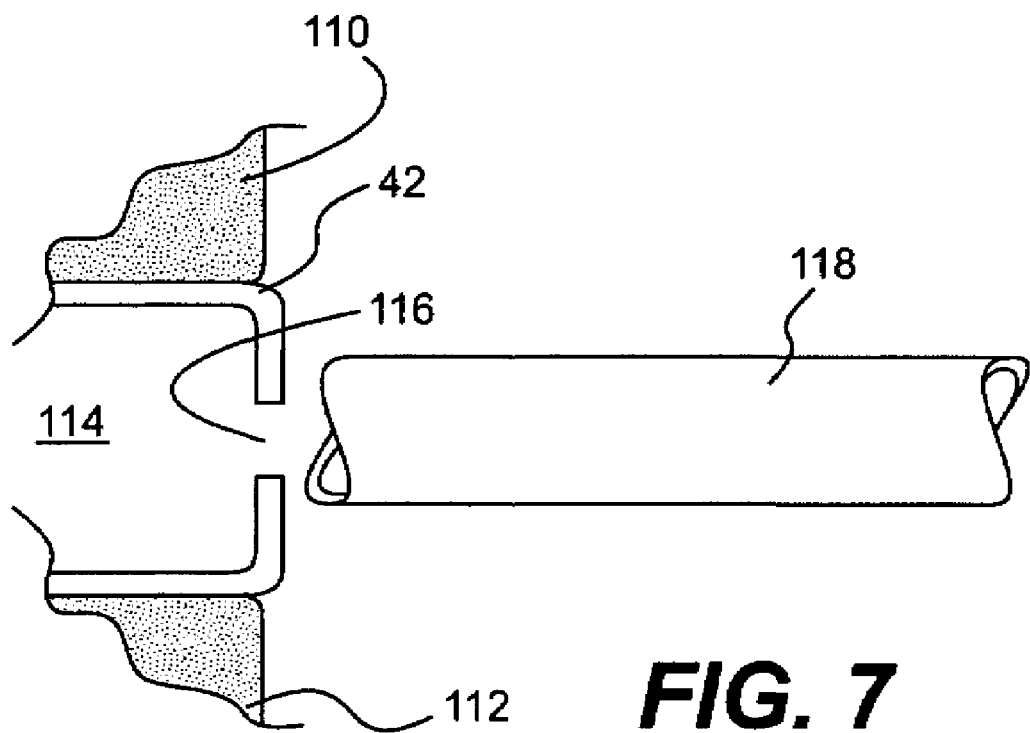
FIG. 7 shows an illustrative embodiment of an introduction device for an annulus stent.

FIG. 7 shows a further aspect of the present invention. According to a further illustrative embodiment, a simplified schematic cross section of a vertebral pair is depicted including an upper vertebral body 110, a lower vertebral body 112 and an intervertebral disc 114. An aperture or rent 116 in the annulus fibrosus (AF) is approached by a tube 118, which is used to deliver a device 120 according to a further aspect of the present invention. The device 120 may be captured by a delivery tool 122 through the use of a ring or other fixation feature 124 mounted on the repair device 120.

Figure 8:
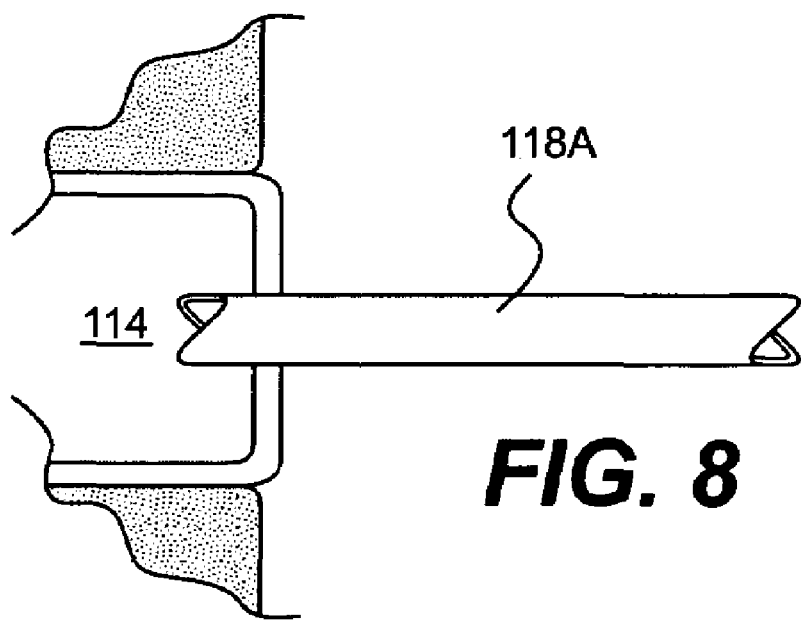
FIG. 8 shows a variation of the device depicted in FIG. 7.

FIG. 8 shows a delivery method similar to that depicted in FIG. 7, with the exception that the tube 118A has a reduced diameter so that it may enter into the sub-annular space of the disc 114 through the aperture or rent.

Figure 9A:
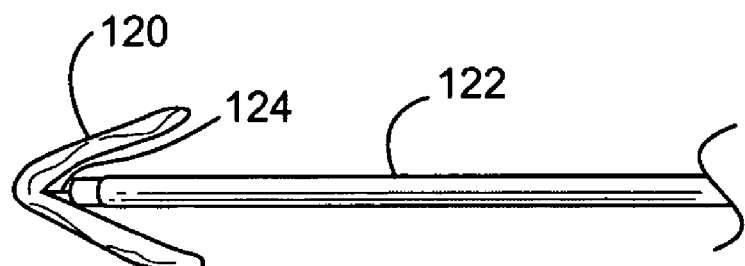
FIGS. 9A-9C show an exemplary introduction tool for use with the devices of FIGS. 7 and 8 with a stent deflected.
Figure 9B:
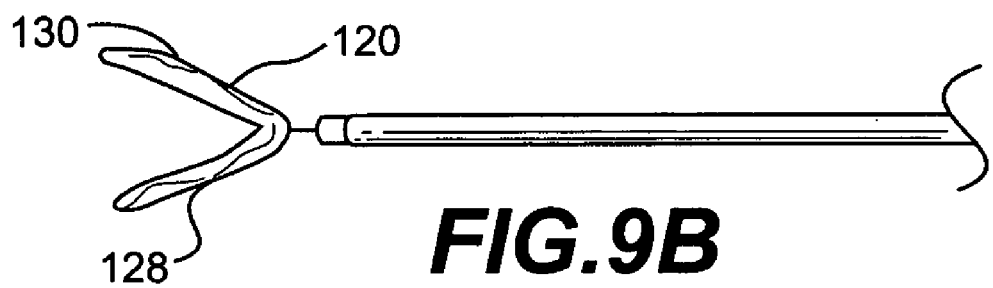
Figure 9C:
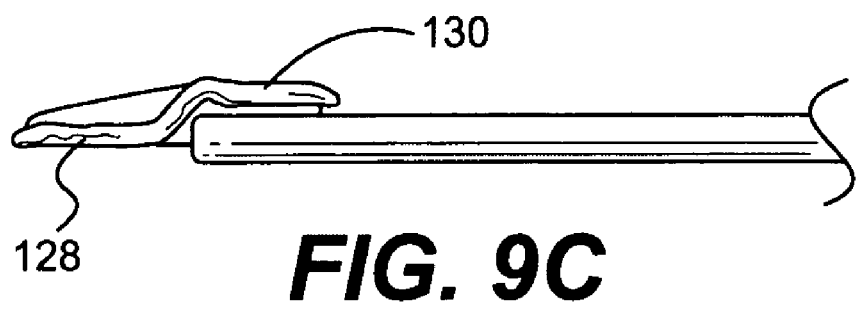

Turning to FIGS. 9A-9C, according to a further aspect of the present invention, the delivery of the device 120 through the delivery tube 118 or 118A may be facilitated by folding the arms or lateral extensions 128, 130 of the device to fit within the lumen of the tube 118 or 118A so that the stent or device 120 is introduced in a collapsed configuration. The device 120 is moved through the lumen of the tubes 118 or 118A through the use of delivery tool 122. FIG. 9B shows the arms deflected in a distal, or forward direction for insertion into the delivery tube 118 or 118A while FIG. 9A shows the arms 128, 130 deflected into a proximal position. FIG. 9C shows the device 120 curled so that one arm 128 is projecting distally, or in a forward direction, and the other arm 130 is projecting proximally, or in a rearward direction. Because the lateral extent of the device is relatively flexible, whether the device is of natural or synthetic material, other collapsible configurations consistent with the intent of this invention are also possible, including twisting, balling, crushing, folding, bending, etc.

Figure 10A:
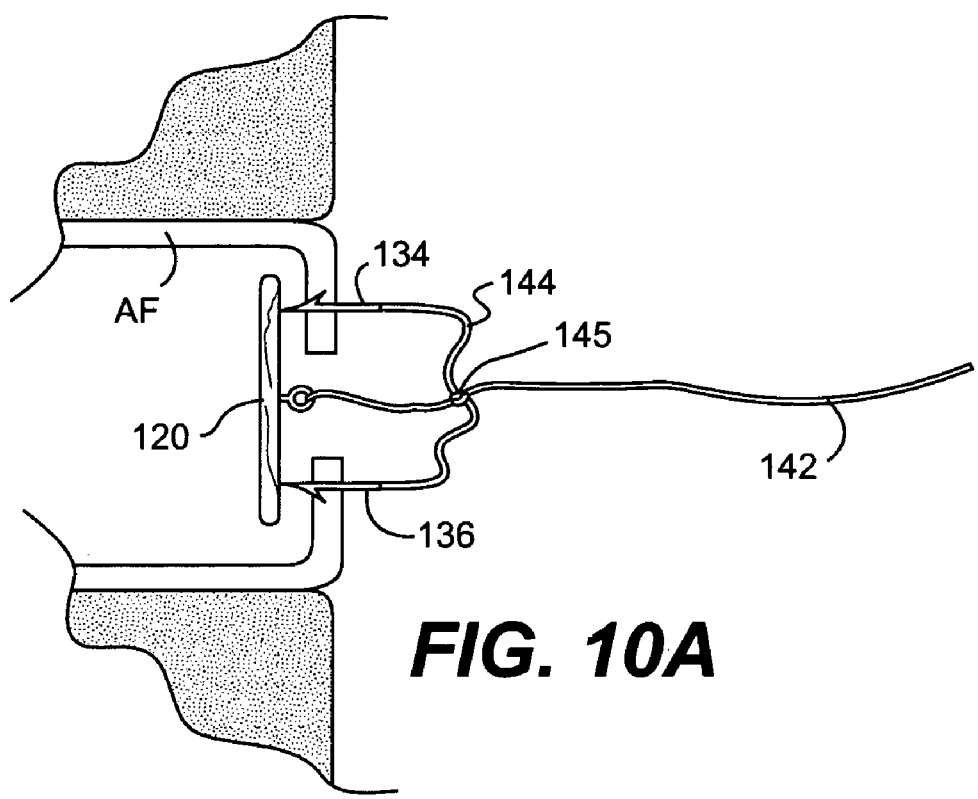
FIGS. 10A-10B show a still further illustrative embodiment of an annulus stent employing secondary barbed fixation devices.

FIG. 10A shows an alternative fixation strategy where a pair of barbs 134 and 136 are plunged into the annulus fibrosus from the exterior of the annulus while the device 120 is retained in the sub-annular space by means of a tether 142. Although there are a wide variety of fixation devices in this particular example, a tether 142 may be knotted 145 with the band 144 holding the barbs 134 and 136 together to fix the device in the sub-annular space. The knot is shown in an uncinched position to clarify the relationship between the tether 142 and the bands 144. Using this approach, the device can be maintained in a subannular position by the barbed bands while the tether knot is cinched, advantageously simultaneously reapproximating the annulus to close the aperture while drawing the device into sealing, bridging engagement with the subannular wall of the annulus fibrosus.

Figure 10B:
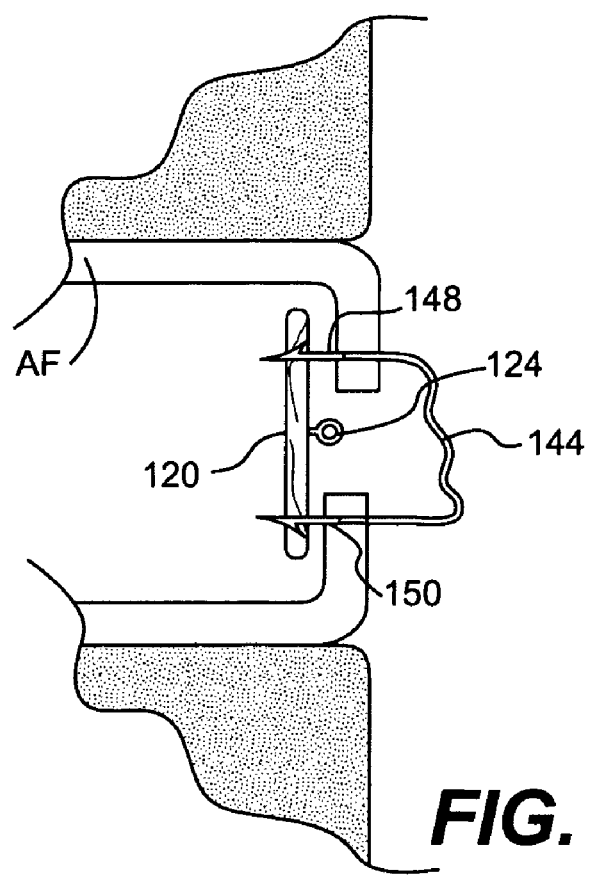

FIG. 10B shows an alternative fixation strategy where the barbs 148 and 150 are sufficiently long that they can pierce the body of the device 120 and extend all the way through the annulus fibrosus into the device 120. In this configuration, the band 144 connecting the barbs 148 and 150 may be tightened to gently restrain and position the device 120 in the subannular space, or tightened with greater force to reapproximate the aperture or rent.

Patches can be folded and expanded in a single plane or in three dimensions. As shown in FIGS. 9A-9C for example, collapsing the patch can be accomplished laterally, whether the device is a single material or composite. Others can collapse in three dimensions, such as those shown in FIGS. 4, 5, 27, 30 and 34. Devices which expand in three dimensions can optionally be packaged in a restraining sheath, jacket, gelatin shell or "gelcap", or a mesh of biosorbable or dissolvable material, that would allow for facile placement and subsequent expansion.

It is understood that there can be a variety of device designs of patches/stents/meshes/devices/treatment devices to accomplish the expansion of a device from a first configuration, to a second configuration to occupy at least a portion of the sub-annular space and reduce re-extrusion of the nucleus, or otherwise facilitate maintaining other intradiscal materials within the disc space. These devices can be constructed of single components or multiple components, with a variety of different materials, whether synthetic, naturally occurring, recombinated (genetically engineered) to achieve various objectives in the delivery, deployment and fixation of a device to repair or reconstruct the annulus. The following device concepts are further discussed for additional embodiments of a device and/or system for the repair of an intervertebral disc annulus. The following descriptions will illustratively depict and describe methods, devices, and tools to deliver a treatment to an intervertebral disc after a, lumbar discectomy procedure; although, it is anticipated that these methods, devices, and tools may be similarly used in a variety of applications. As an example, the embodiments described herein may also advantageously maintain materials within the disc space other than natural disc tissue (nucleus, annulus, cartilage, etc.), such as implants and materials that may be used to replace and/or augment the nucleus pulposus or other parts of disc's tissues. These procedures may be performed to treat, for example, degenerative disc disease. Whether these materials are intended to replace the natural functioning of the nucleus pulposus (i.e., implantable prosthetics or injectable, in-situ curable polymer protein, or the like) or provide a fusion between vertebral bodies (i.e., implantable bony or synthetic prosthetics with materials to facilitate fusion, such as growth factors like bone morphogenic proteins) one skilled in the art would realize that variations to the embodiments described herein may be employed to better address characteristic differences in the various materials and/or implants that could be placed within the subannular space, and that these variations would be within the scope of the invention.

Furthermore, it should be noted that surgeons differ in their techniques and methods in performing an intervention on a spinal disc, and the inventive descriptions and depictions of methods, devices and delivery tools to repair annular tissue could be employed with a variety of surgical techniques; such as, but not limited to: open surgical, microsurgical discectomy (using a magnifying scope or loupes), minimally invasive surgical (through, for example, a METRx™ system available from Medtronic, Inc.), and percutaneous access. Surgeons may also employ a variety of techniques for intra-operative assessment and/or visualization of the procedure, which may include: intra-operative probing, radiography (e.g., C-arm, flat plate), and endoscopy. It is contemplated that the inventive embodiments described are not limited by the various techniques that may be employed by the surgeon.

In addition, the surgical approach to the intervertebral disc throughout the figures and descriptions depict a common approach, with related structures, to a lumbar discectomy; although, it is possible that surgeons may prefer alternative approaches to the intervertebral disc for various applications (for example, different intervertebral disc levels such as the cervical or thoracic region, or for nucleus augmentation), which may include, but is not limited to: posterior-lateral, anterior, anterior-lateral, transforaminal, extra-foraminal, extra-pedicular, axial (i.e., through the vertebral bodies), retroperitoneal, trans psoas (through the Psoas muscle), contralateral. The approach to the intervertebral disc space should not be interpreted to limit the use of the invention for the repair or reconstruction of the an aperture, weakened or thin portion of the annulus, as described herein.

It is also important to note that the boundary in the intervertebral disc space between the annulus fibrosus and the nucleus pulposus as depicted herein may be demarked or otherwise highlighted; however, it is important to recognize that these tissues are not as precisely demarked in human tissues, and may be even less so as the patient ages or evinces degeneration of the intervertebral disc. This demarcation may be especially difficult to discern during an operative procedure, using for example; available surgical tools (i.e., probes), fluoroscopic guidance (x-ray), or visual (endoscope) guidance. However, in general, the layers of the annulus have more structural integrity (and strength) than the nucleus, and this integrity varies from the outer most layers of the annulus being of higher structural integrity than the inner most layers of the annulus.

Moreover, the drawings and descriptions herein are necessarily simplified to depict the operation of the devices and illustrate various steps in the method. In use, the tissues may be manipulated by, and are frequently in contact with, the various tools and devices; however, for clarity of construction and operation, the figures may not show intimate contact between the tissues the tools and the devices.

Figure 11A:
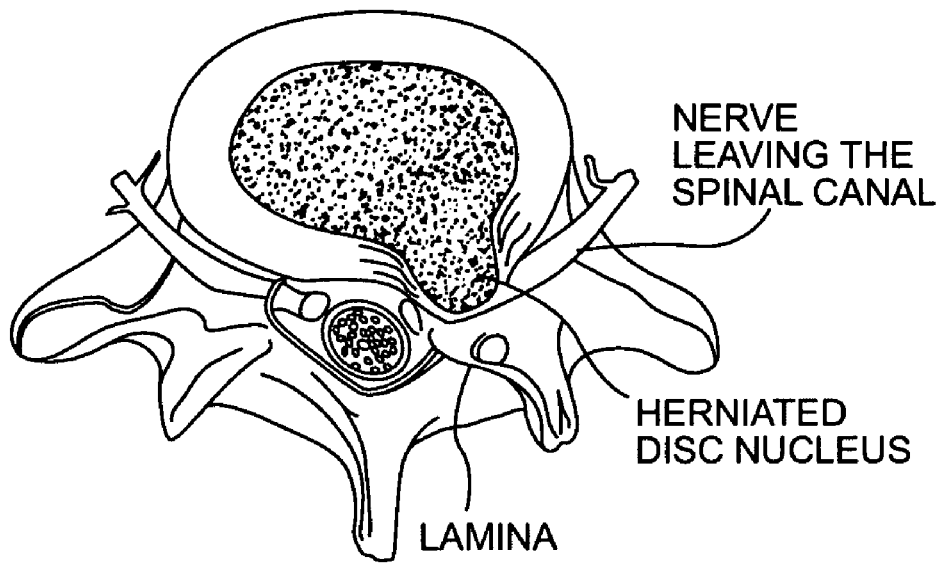
FIG. 11A shows a herniated disc in perspective view.
Figure 11B:
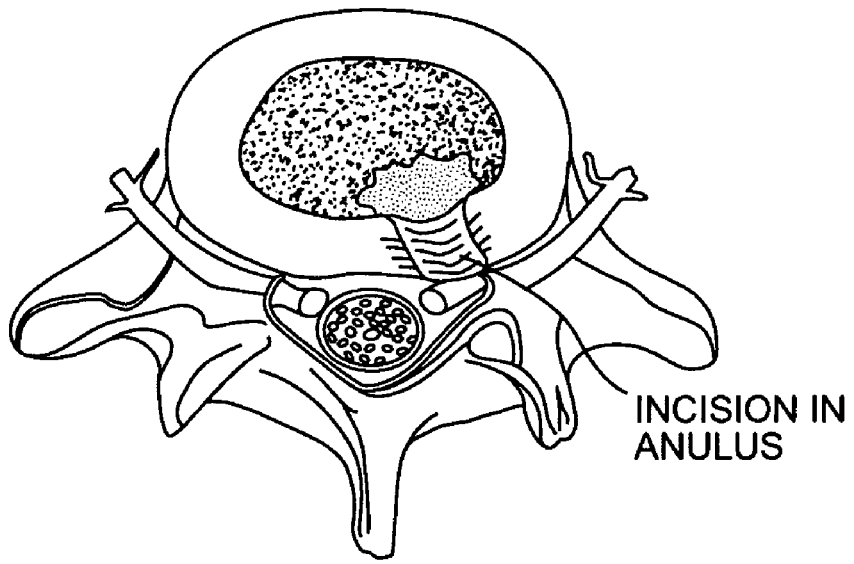
FIG. 11B shows the same disc after discectomy.

As depicted in FIG. 11A, a herniated disc occurs when disc nucleus material emerges from the subannular region and outside of the disc. Herniated disc nucleus material then impinges on nerve tissue, causing pain. A discectomy attempts to relieve pressure on the nerve tissue through surgical removal of disc material, the result usually being an aperture in the disc annulus wall, and usually a void in the subannular space where disc nucleus was removed, as shown in FIG. 11B. FIG. 11B typifies a disc after the discectomy procedure has been performed, as do most of the drawings and descriptions contained herein. However, it should be understood that in order to perform a discectomy procedure, there are a variety of instruments and tools readily available to the surgeon during spine surgery, or other surgical procedures, to obtain the outcome as shown in FIG. 11, or other outcomes intended by the surgeon and the surgical procedure. These tools and instruments may be used to: incise, resect, dissect, remove, manipulate, elevate, retract, probe, cut, curette, measure or otherwise effect a surgical outcome. Tools and instruments that may be used to perform these functions may include: scalpels, Cobb elevators, Kerrison punch, various elevators (straight, angled, for example a Penfield), nerve probe hook, nerve retractor, curettes (angled, straight, ringed), rongeurs (straight or angulated, for example a Peapod), forceps, needle holders, nerve root retractors, scissors. This list is illustrative, but is not intended to be exhaustive or interpreted as limiting. It is anticipated that some of these tools and/or instruments could be used before, during, or after the use of the inventive methods, devices and tools described herein in order to access, probe (e.g., Penfield elevator), prepare (e.g., angled or ringed curette, rongeur, forceps), and/or generally assess (e.g., angled probe) treatment site or facilitate the manipulation (e.g., forceps, needle holder), introduction (e.g., forceps, needle holder, angled probe), or deployment (e.g., forceps, needle holder, angled probe) of the treatment device and/or it's components.

The are a variety of ways to affix a device to the sub-annular wall of the annulus in addition to those discussed hereinabove. The following exemplary embodiments are introduced here to provide inventive illustrations of the types of techniques that can be employed to reduce the time and skill required to affix the patch to the annulus, versus suturing and tying a knot. Discussed hereinabove is the use of sutures, staples and other fixation devices to affix the patch to the annulus. In a simple example, a patch/stent could be compressed, passed through a guide tube such as tubes 18, 18A shown in FIGS. 7 and 8, and expanded within the sub-annular space.

Another fixation means includes the passing of "anchoring bands" into the wall of the annulus, vertebral bodies (superior, inferior, or both), or the Sharpey's Fibers (collagenous fibers between the junction of the annular fibers and vertebral bodies). In the following example of anchors, the barbs or bands are affixed to the annulus/vertebral bodies/Sharpey's fibers. Another element, for example a suture, cinch line, or a staple is utilized to attach the anchor bands to the patch, and thus hold the patch in proximity to the inner wall of the annulus. In addition, these bands may re-approximate the tissues at the aperture.

Figure 12A:
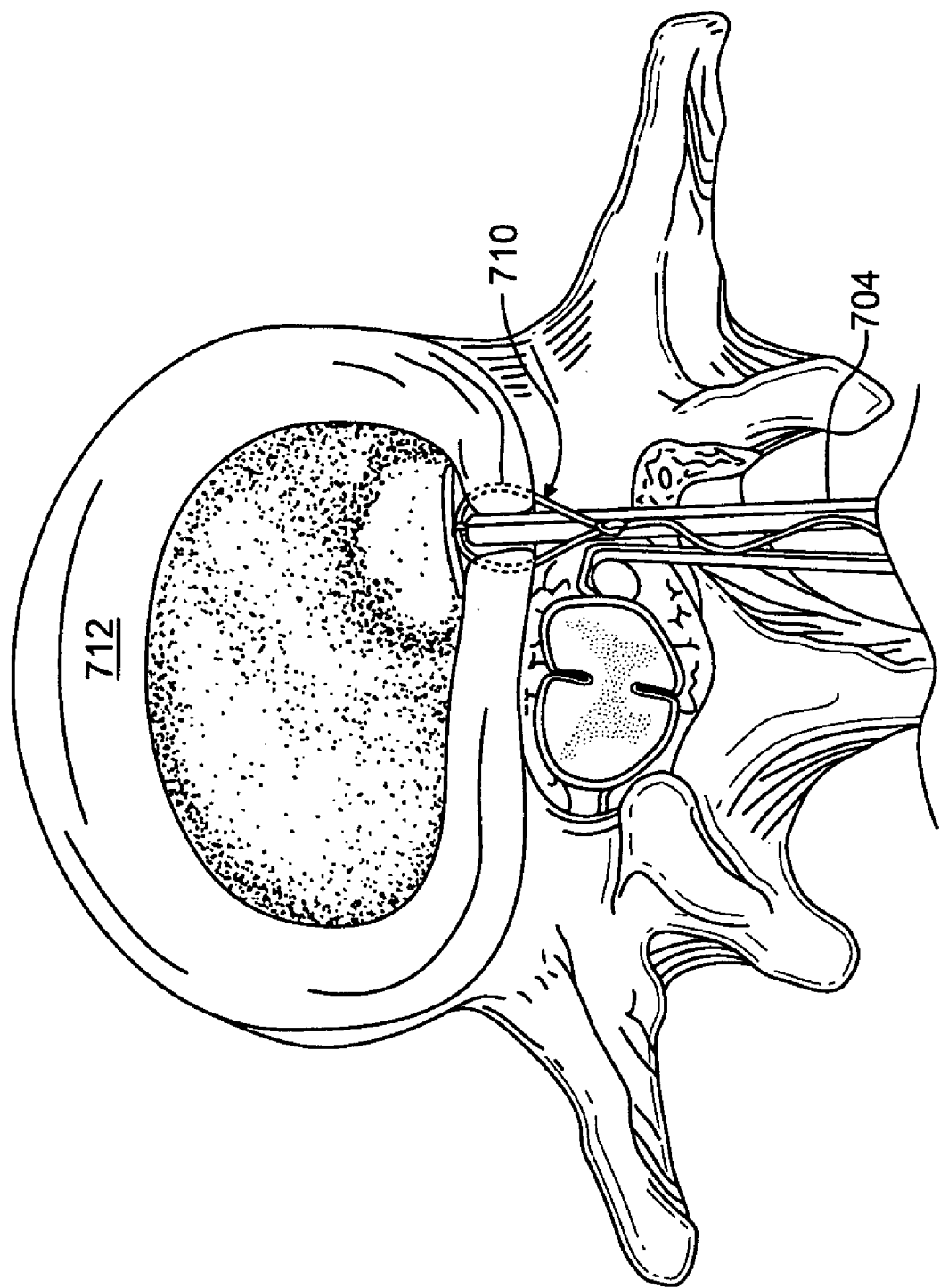
FIGS. 12A-12G show a still further illustrative embodiment of an introduced and expanded annulus stent/patch being fixated and the aperture reapproximated.
Figure 12B:
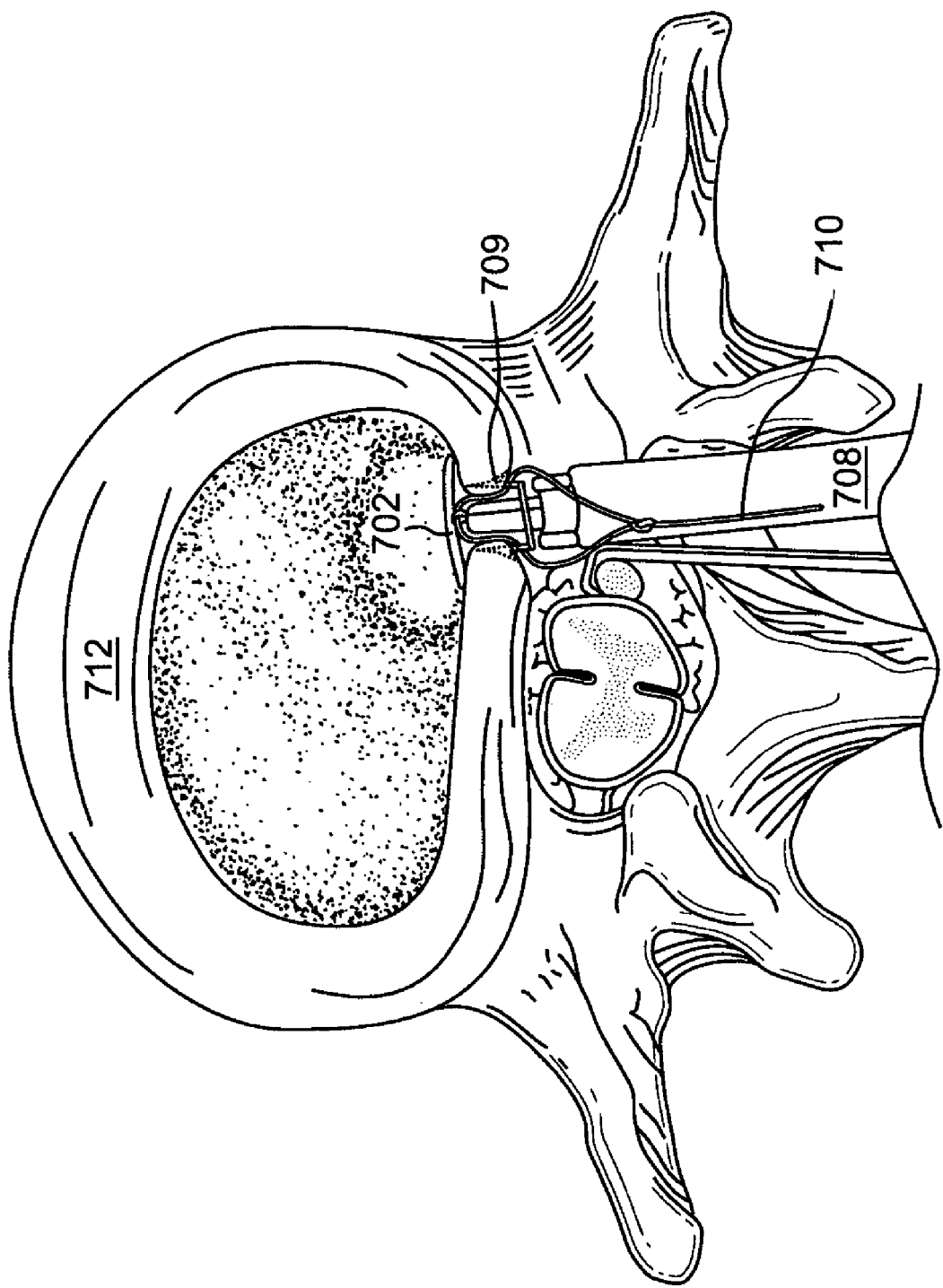
Figure 12D:
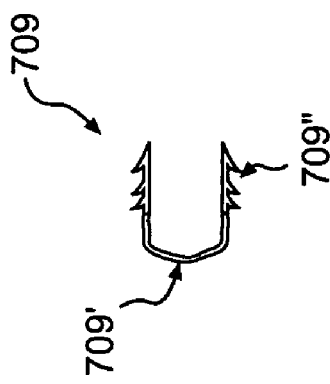
Figure 12C:
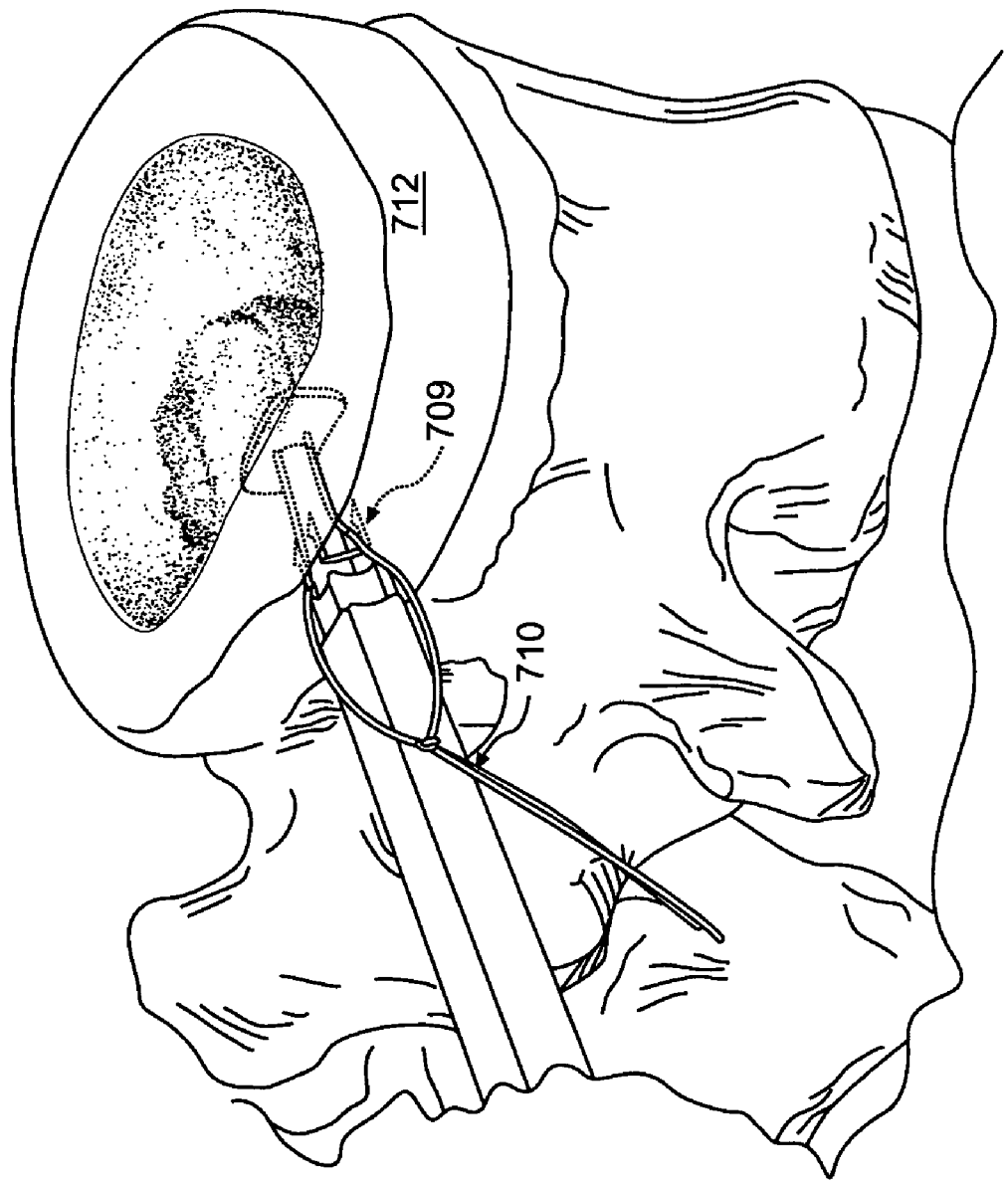
Figure 12E:
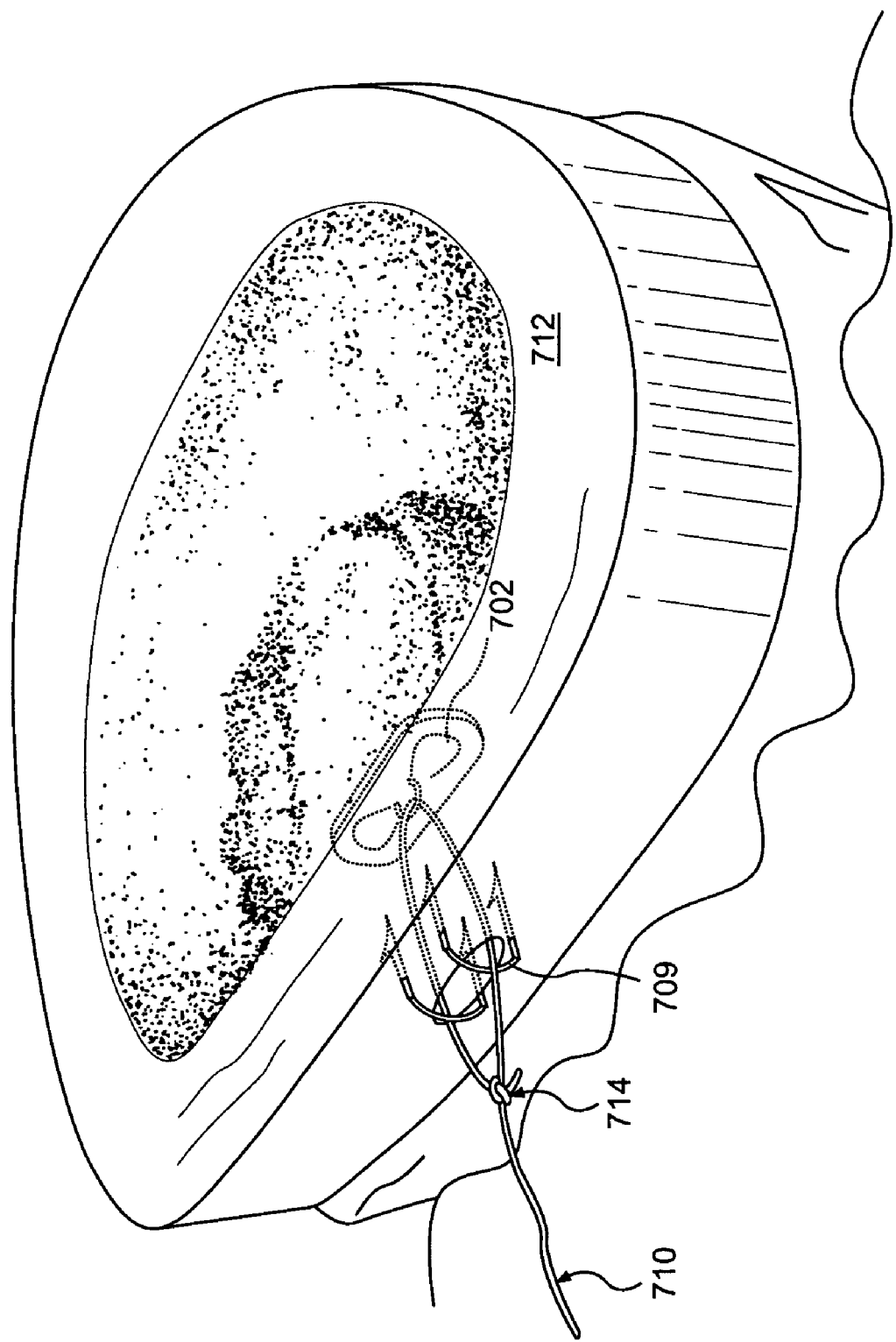
Figure 12F:
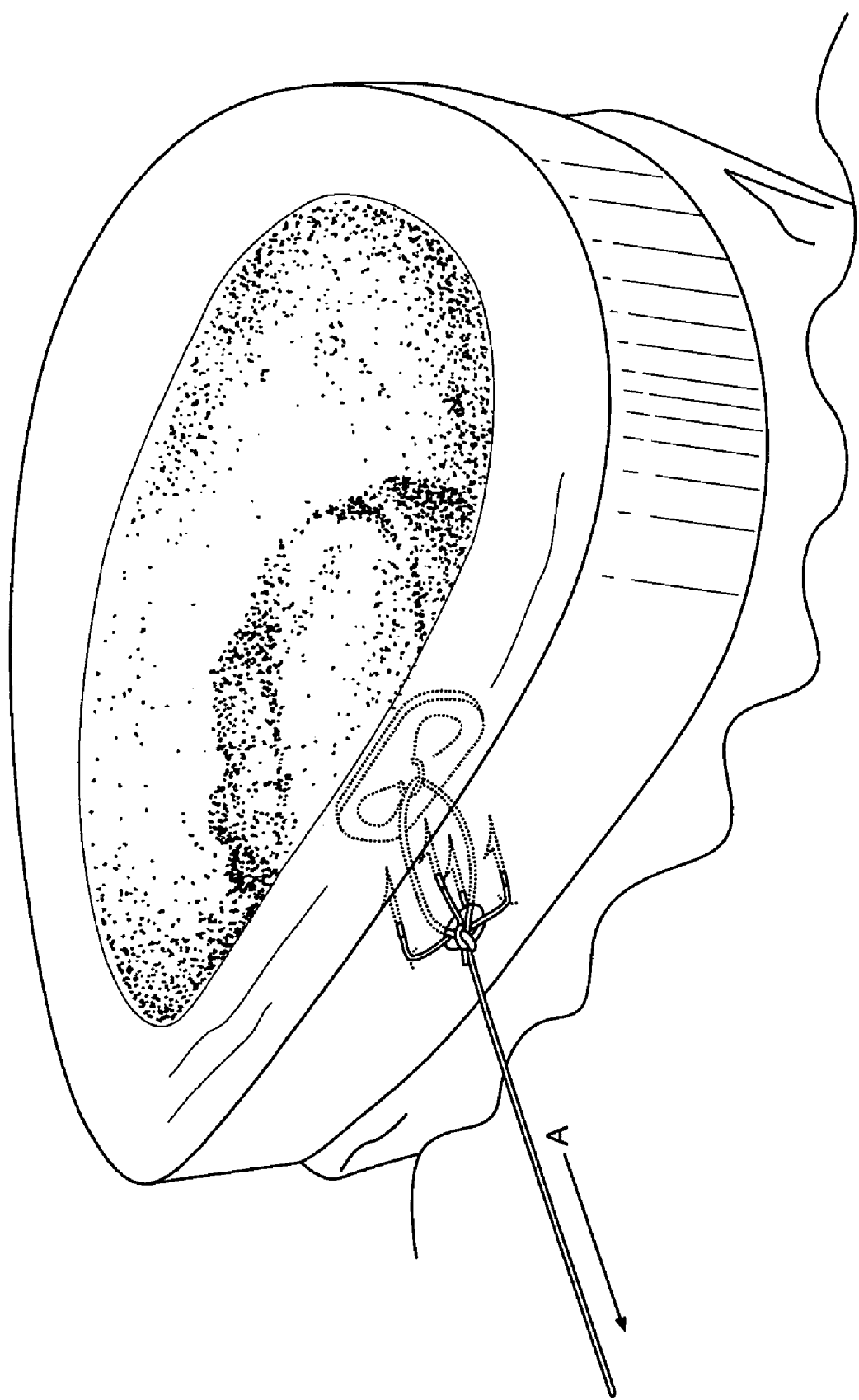
Figure 12G:
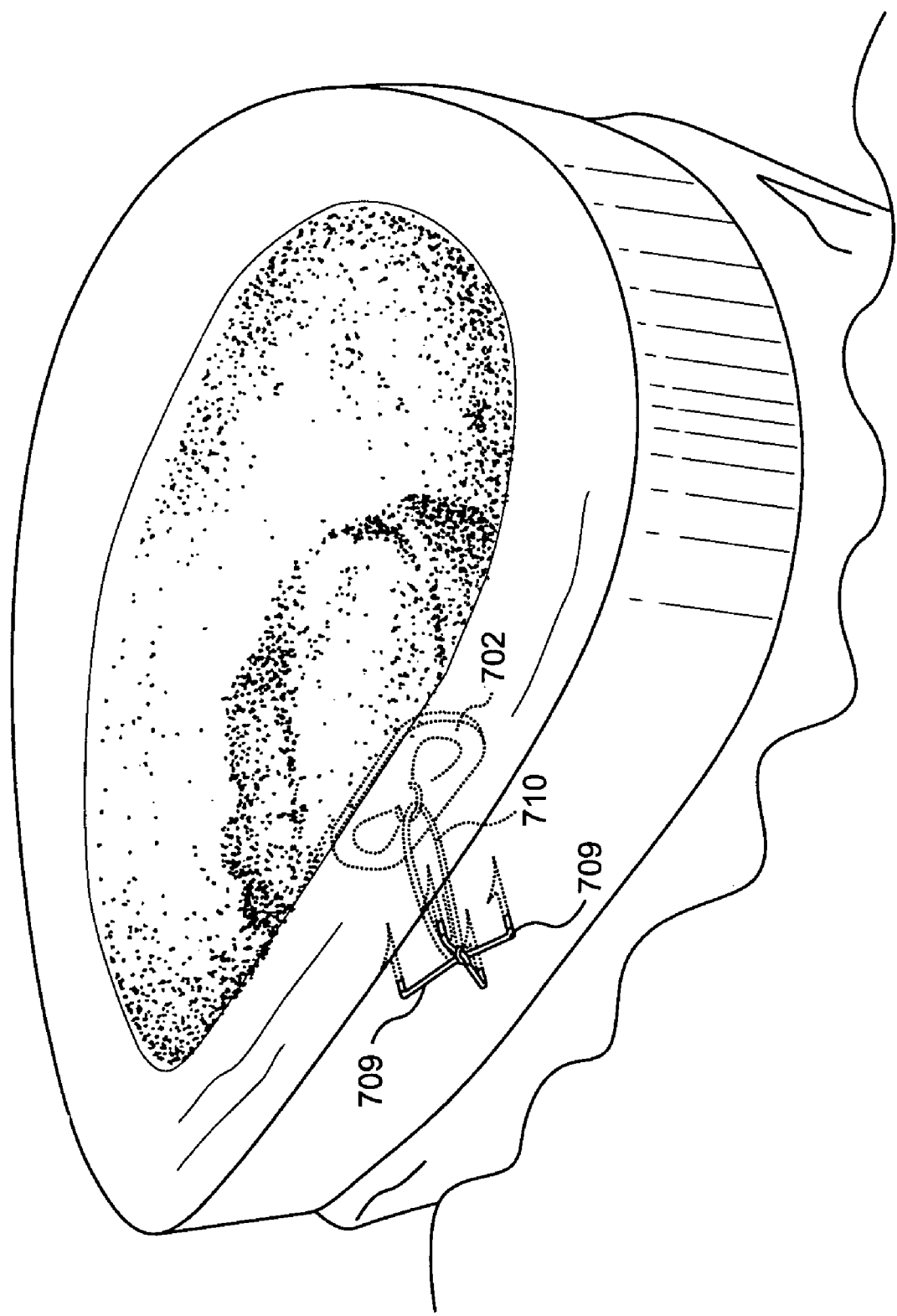
Figure 13A:
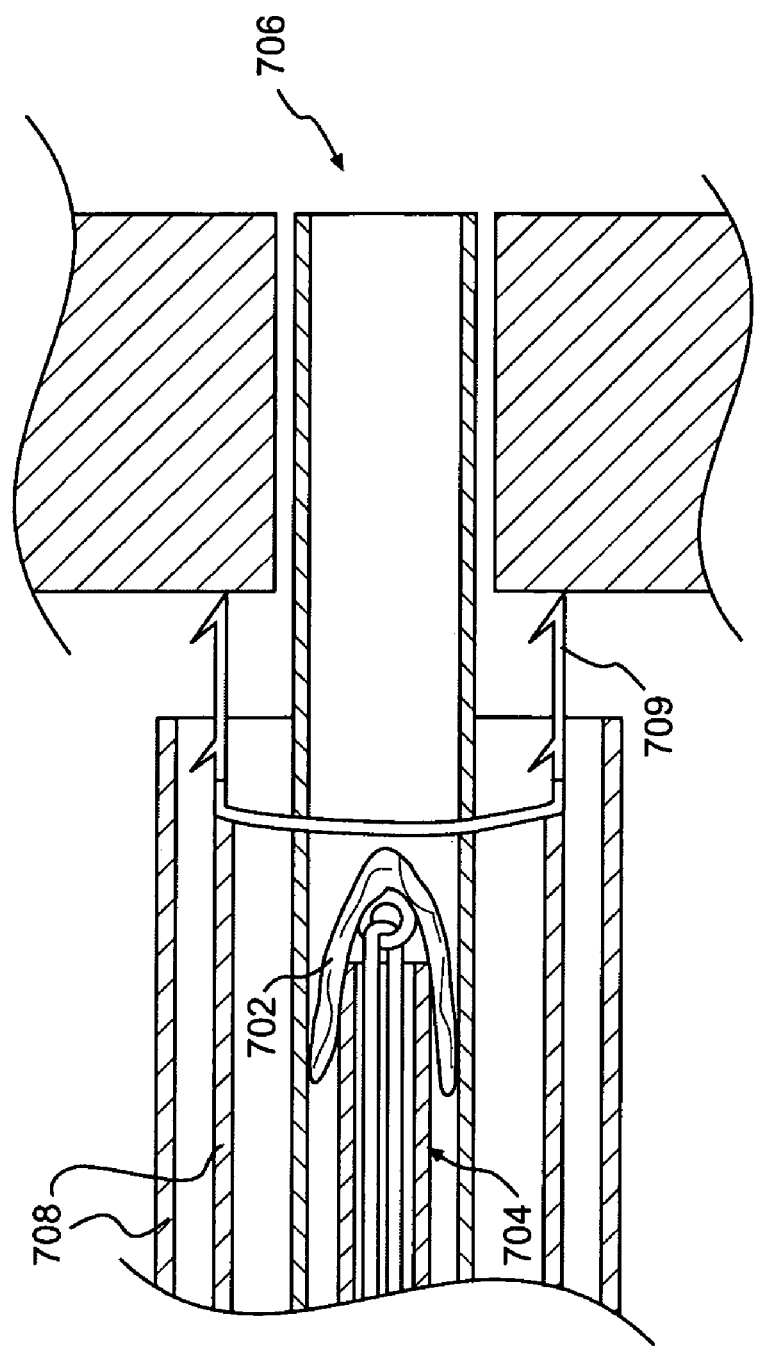
FIGS. 13A-13C schematically depict a still further embodiment of the invention where an expandable stent/patch is tethered in situ using a cinch line.
Figure 13B:
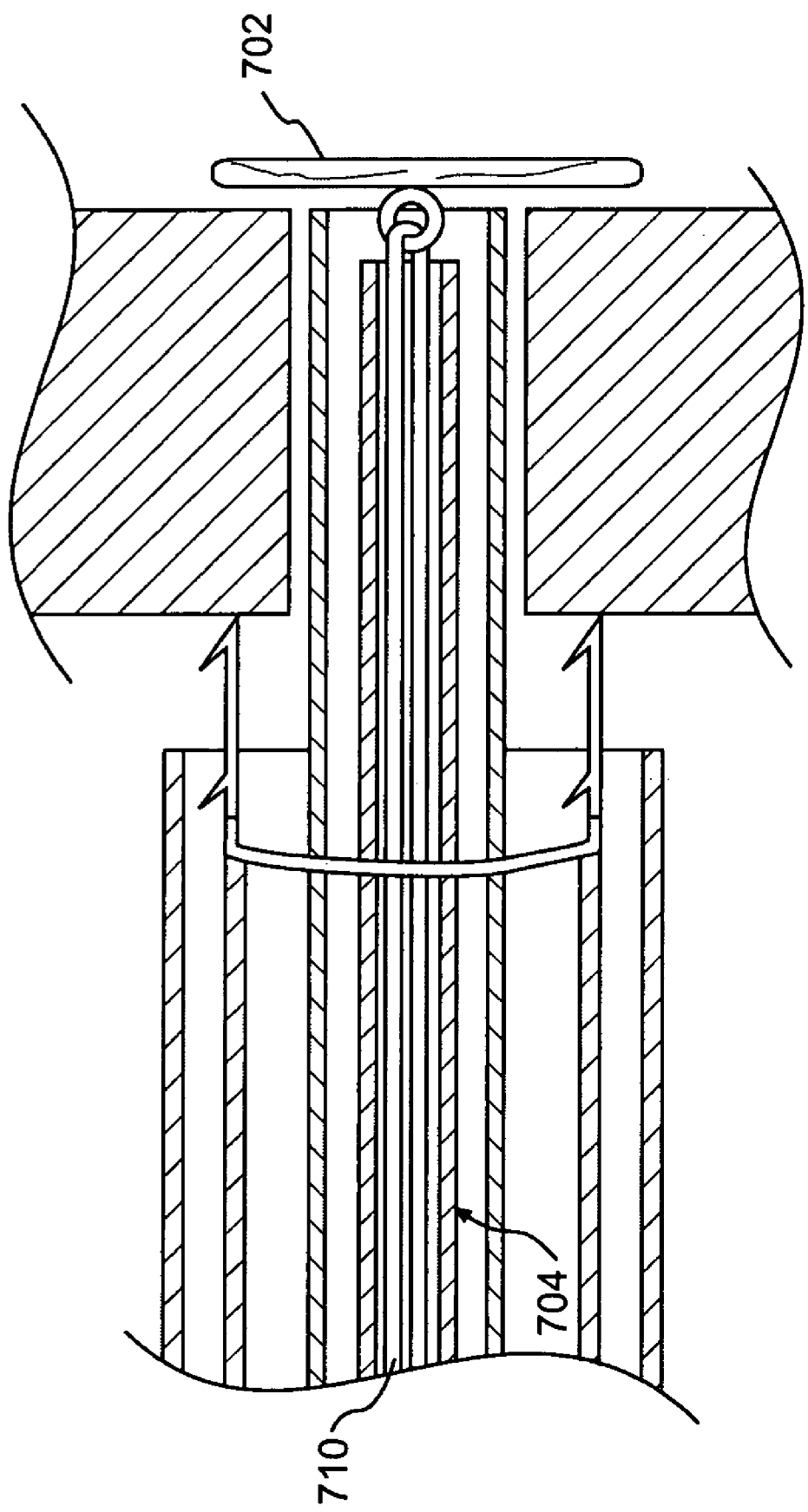
Figure 13C:
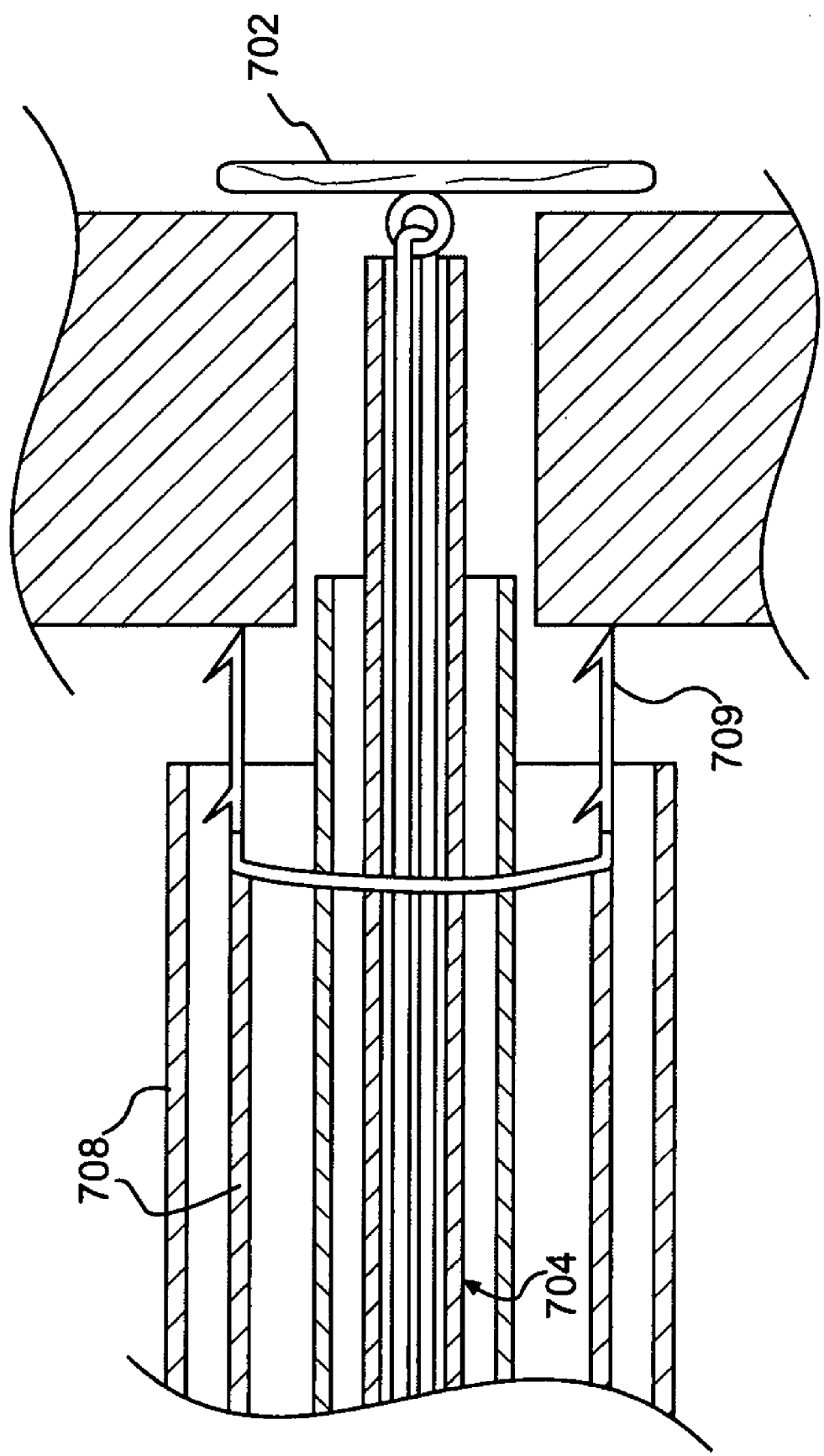
Figure 14A:
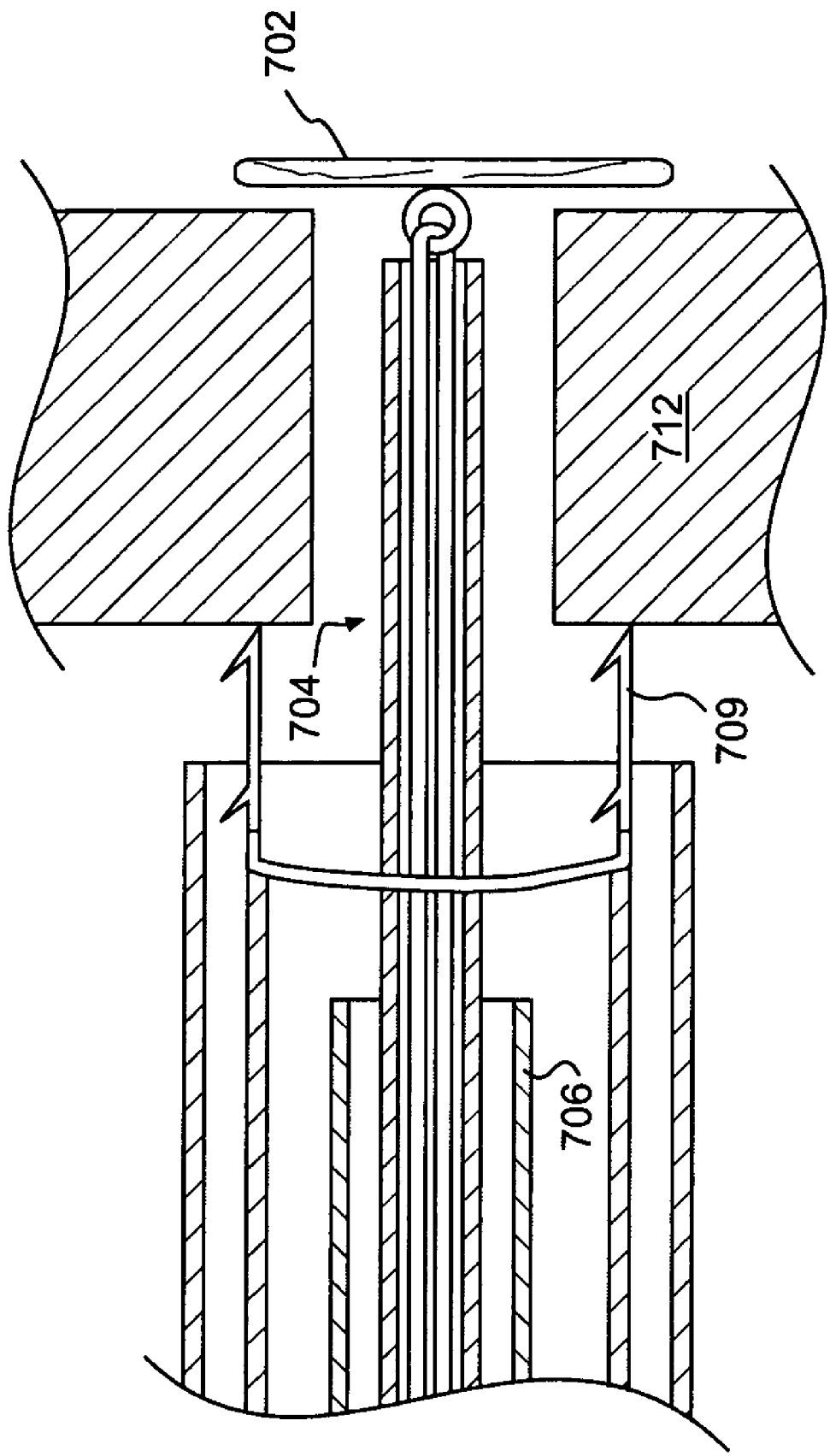

Another example of fixating the device to inner wall of the annulus is further illustrated by FIGS. 12-14. As discussed hereinabove, with reference to FIGS. 7-10, a patch 120 is placed with a delivery tool 122, through the inner lumen of a guide tube 118, into the sub-annular space and then expanded. This step can also be seen in FIGS. 13 and 14, where a patch 702 is folded and passed through a guide tube 706 and is held by a delivery tool 704. Also shown is a anchor band or staple 709 and an anchor band delivery device 708. Within the guide tube, or within the delivery tool, there is a suture line or cinch line 710 that is attached to the center of the patch 702. This can be seen in FIG. 12A with the guide tube 706 removed. As seen in FIGS. 13C and 14A, the guide tube 706 is retracted after the patch 702 has been expanded and deployed. Next, as shown in FIGS. 12 and 14, an anchor band delivery tool 708 is used to deliver one or more "bands" 709 onto the outer surface of the annulus. These are intended to be anchored into the wall of the annulus with barb shapes that do not allow for the barbs to be pulled back through the annulus. The anchor bands resemble a construction of a "staple". The bands could actually be constructed by connecting two barbed elements with, for example, a suture between the two barbed elements.

The barbs and the connection band between the barbs could be constructed of the same material or of different materials. For example, the barbed part of the anchor band could be a biodegradable/bioabsorbable material (such as, for example, collagen, cellulose, polysaccharides, carbohydrates, polyglycolic acid, polylevolactic acid, polydioxanone, racemic polylactic acid) or could be constructed of a metallic or polymeric biocompatible material (e.g., titanium, NiTi alloy, stainless steel, platinum, gold, polyurethane, polycarbonate urethane, polyimide, polyamide, polypropylene, polyethylene, polypropylene, polyester, PET, PEEK). The anchors could also be constructed of a combination of these materials. In addition, the band that connects these barbs can be constructed of materials that are similar to the barbs, or different materials. For example, the connection band could be a biodegradable/bioabsorbable suture, such as Vicryl, or a biocompatible material such as polypropylene, polyethylene, silk, stainless steel, PET. In addition, it is possible that these elements are constructed from multiple materials to accomplish the objective of anchoring into the annulus and providing for a fixation site to draw the tissues together.

Figure 14B:
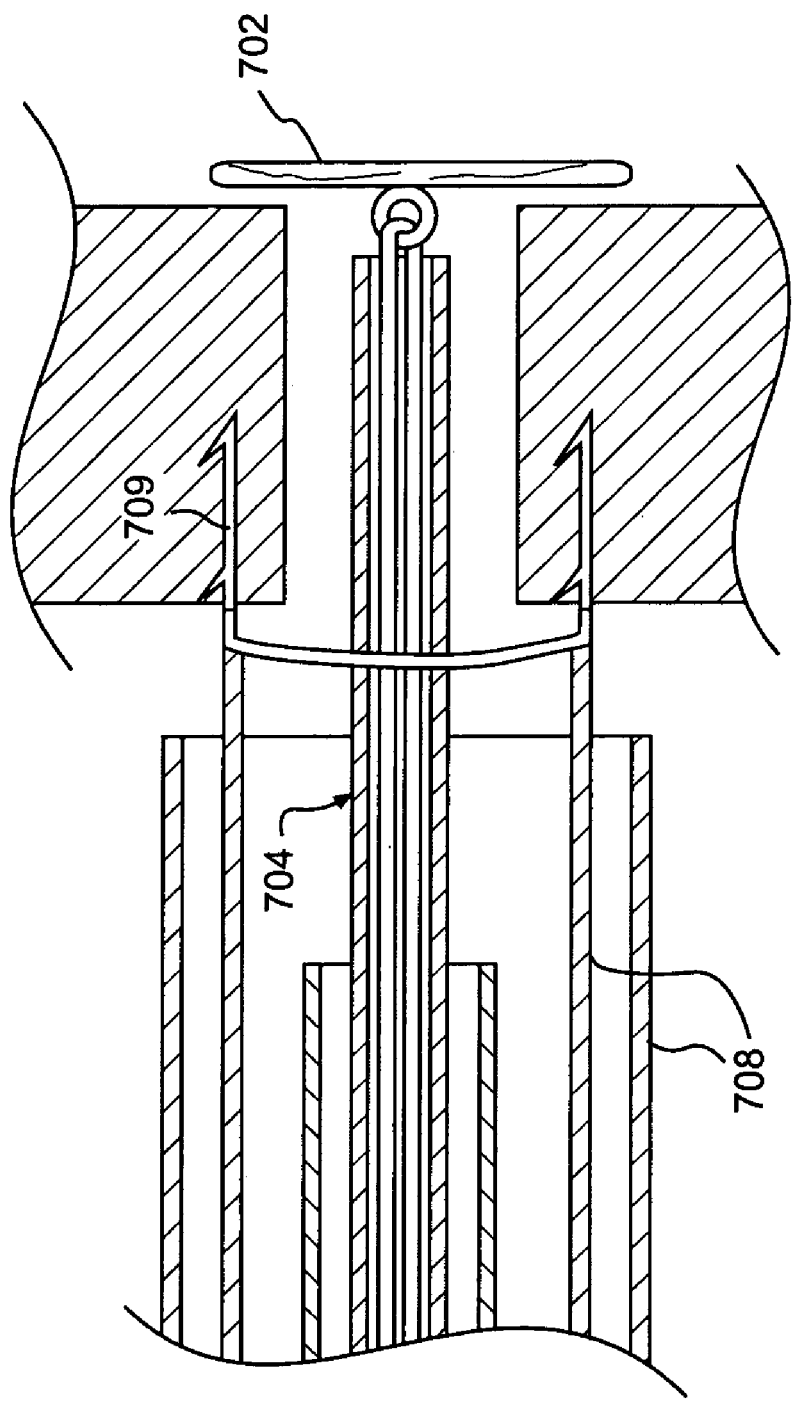

FIGS. 12B and 12C show the placement of the anchor bands 709 into the annulus 712 with the anchor band delivery tool 708. FIGS. 14A and 14B schematically show the placement of the anchor bands 709 into the wall of the annulus 712 and the retraction of the anchor band delivery device 708, with the patch delivery tool 704 still in place. FIG. 12D depicts a representative anchor band 709, having a pair of stainless steel barbs 709" connected by a suture 709'. FIG. 12E shows the patch 702, anchor bands 709, and cinch line or suture 710 with the delivery tools removed, prior to drawing the patch and the tissues of the annulus together. In this embodiment there is a pre-fabricated slip knot 714 on the cinch line, although other locking elements or knots are possible. Suture loops can connect to the barbs directly, as in FIG. 12, or loop to surgical staples, or are placed directly into the annulus. The presence of a pre-fabricated knot on the cinch line makes the process of repairing quicker since there is no need to tie a knot. It also facilitates drawing the tissues together. The use of the cinch line and a pre-fabricated knot can be placed by, for example, an external tube such as a knot pusher. FIG. 12E is similar to FIG. 10 described hereinabove prior to "tying" the knot 714. FIG. 12F shows the drawing of the patch and the annular tissues together by pulling on the suture in the direction "A" indicated by the arrow. In this case, the Knot Pusher has been removed from the cinch line 710. The suture 710 is drawn proximally to draw the patch 702 into engagement with the inner wall of the annulus to seal the aperture from within, as well as draw the walls of the annulus together to reapproximate the annular aperture. FIG. 14C and FIG. 12G show the cinch line suture 710 tied and drawing the annular tissues together, after the excess suture line has been cut. It is also apparent from this device, fixation and delivery system that the outer surfaces of the aperture may be drawn together for re-approximation.

The cinching of the anchor bands and the patch also allows for taking-up the slack that allows for the accommodation of varying sizes. For example, the thickness of the annular wall surrounding the aperture can vary from 1 mm up to 10 mm. Therefore, if the anchor bands have a set length, this design with a cinch line accommodates different dimensions of the thickness of the wall of the annulus by drawing the "slack" of the bands together within the aperture.

Although it has been described here as patch placement that involves two lateral anchor bands with a suture to draw the patch, bands and tissues together, one or two or more bands could be used and two bands is only an example. Furthermore, the anchor bands were placed with the barbs in a superior-inferior fashion. One skilled in the art would recognize that these could be placed at different locations surrounding the aperture, vertebral bodies or into the Sharpey's fibers Although the patch depicted in the example above does not have barbs attached to the patch, it is also possible to have the barbs as described hereinabove to further promote the fixation of the patch to the inner wall of the annulus.

Figure 17:
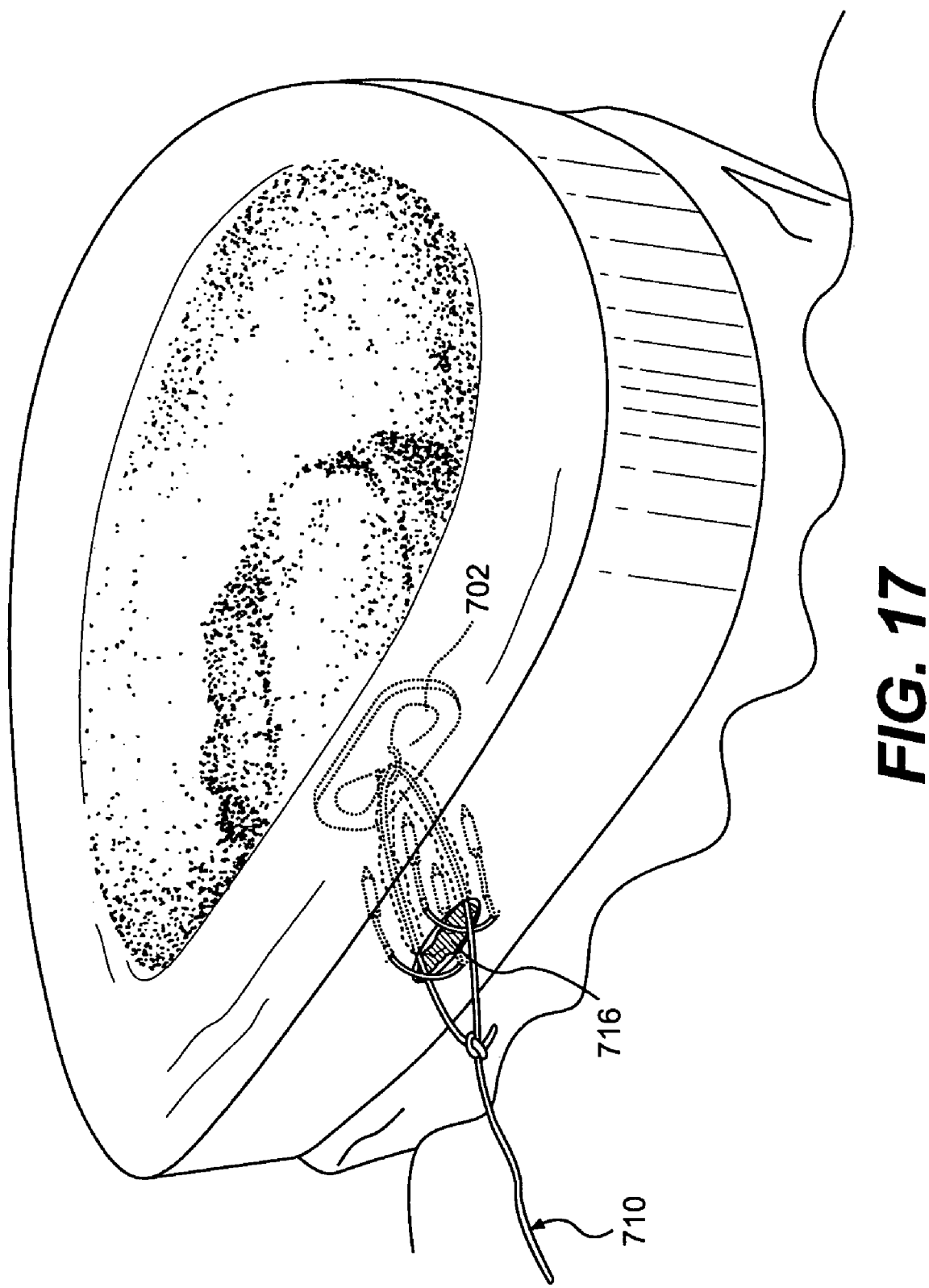
FIG. 17 depicts an exemplary use of filler material within the aperture during placement of a patch/stent tethered by a cinch line.

Finally, although the drawings depict an aperture that lends itself to re-approximating the tissues, it is conceivable that some apertures, whether natural or surgically made, may be relatively large and therefore might require the placement of additional material within the aperture to act as a scaffold for tissue in growth, between the patch on the inner wall of the annulus and the anchor bands located on the outer wall. An example of material to fill the aperture might include autograft para-spinal fascial tissue, xenograft, allograft, or other natural collagenous materials. The filler material could also be of a biocompatible material such as a Dacron (polyester, or PET), polypropylene, polyethylene material. FIG. 17 shows the illustrative filling of an aperture with implant material 716 prior to cinching the suture 710.

Figure 15A:
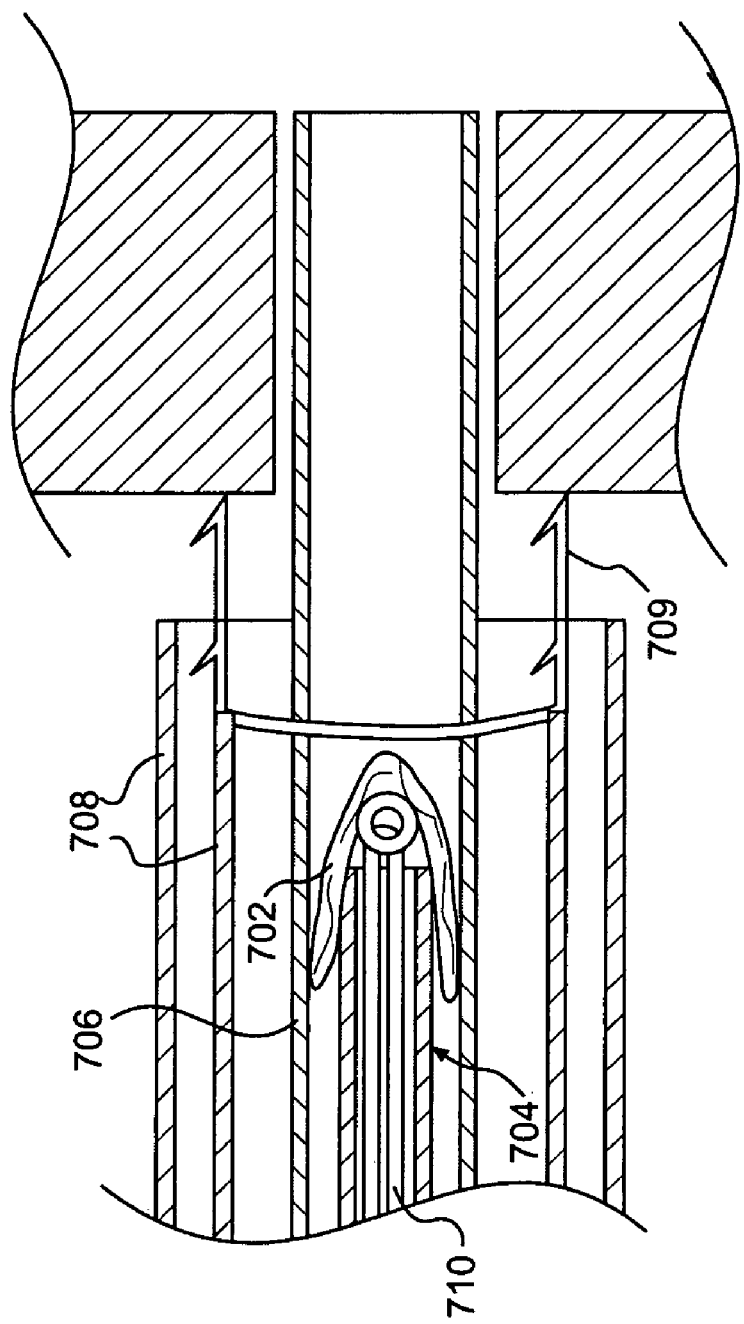
FIGS. 15A-15C schematically depict a still further embodiment of the invention where an expandable stent/patch is tethered in situ using a cinch line.
Figure 15B:
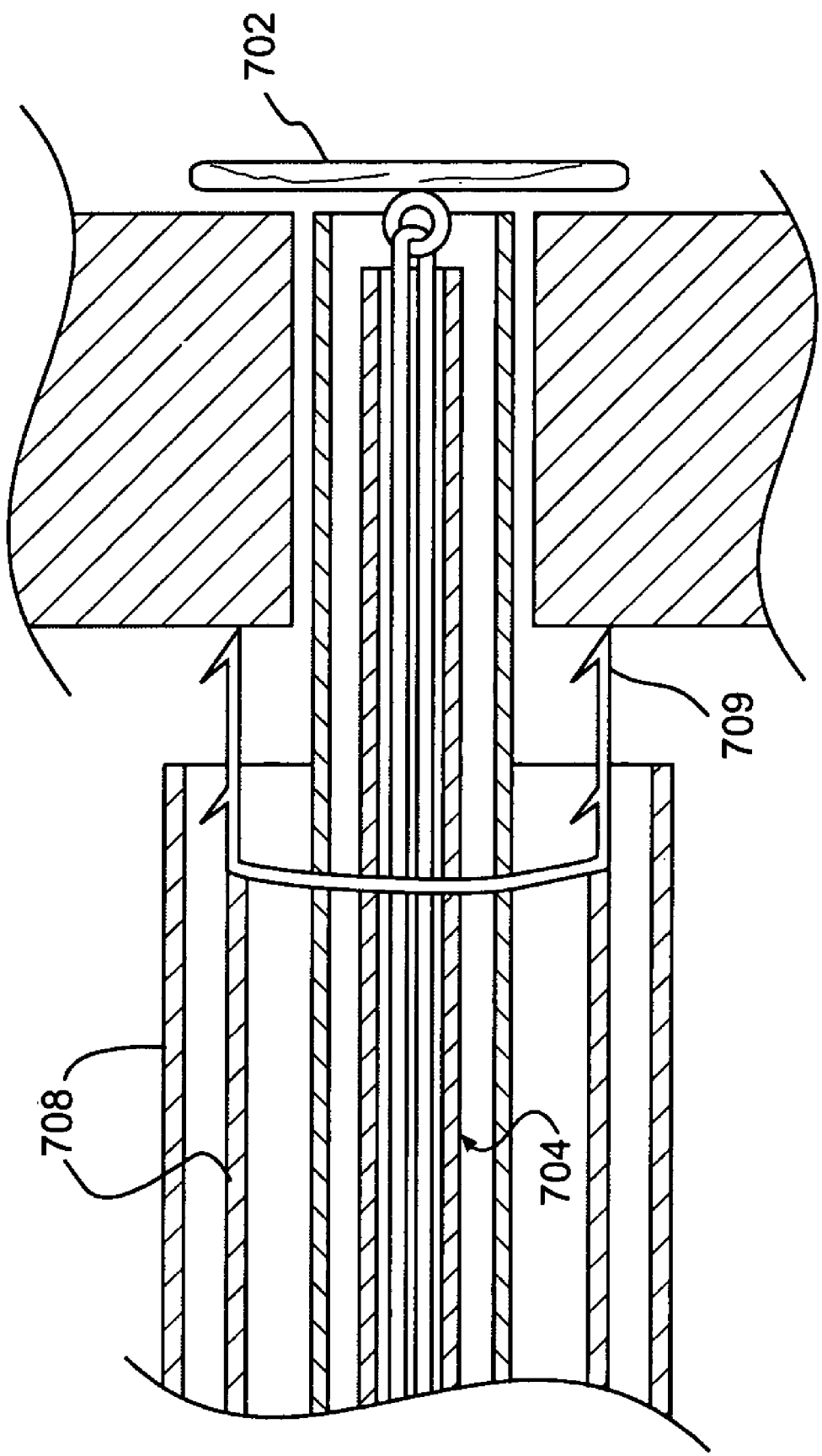
Figure 15C:
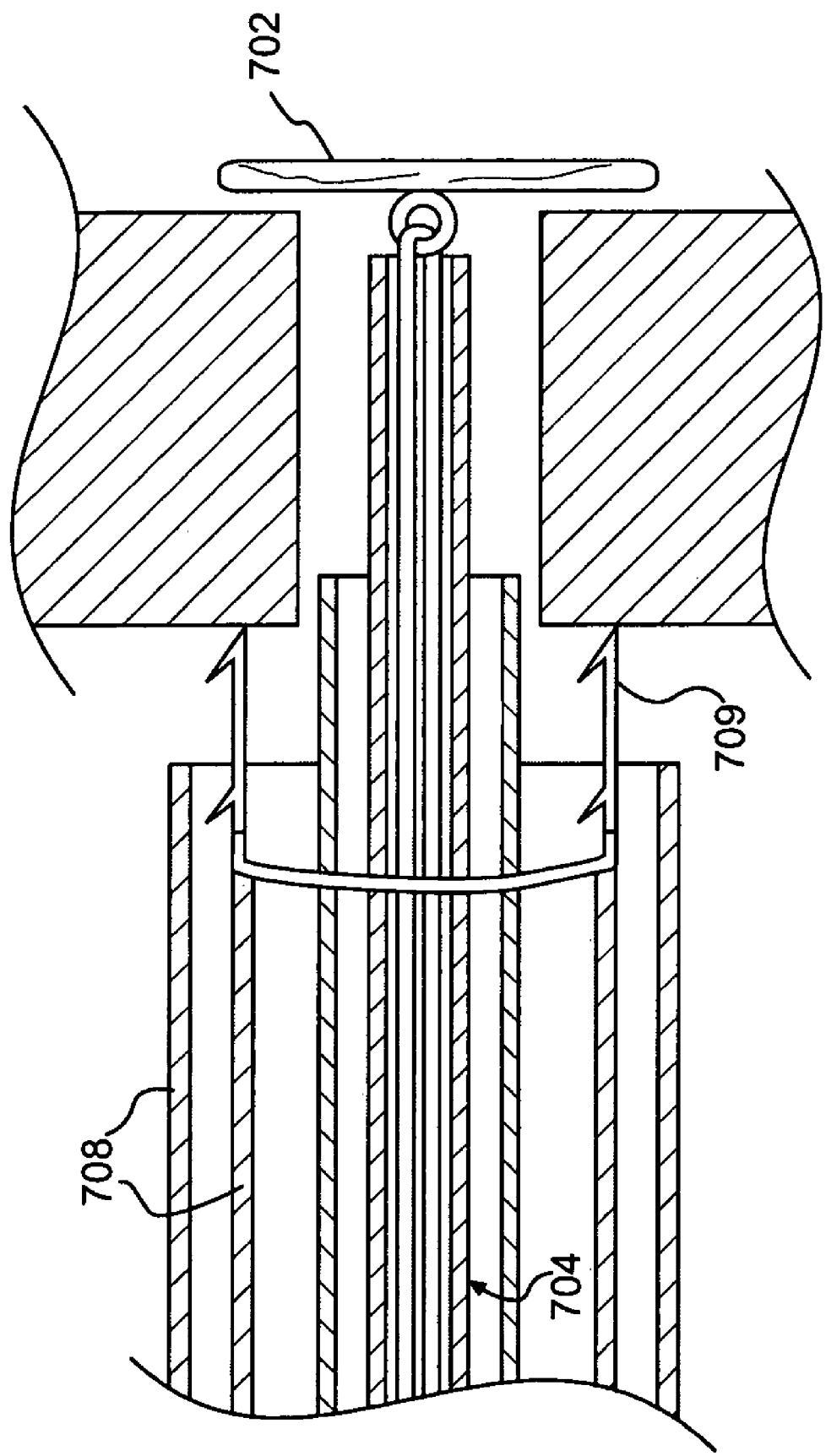
Figure 16A:
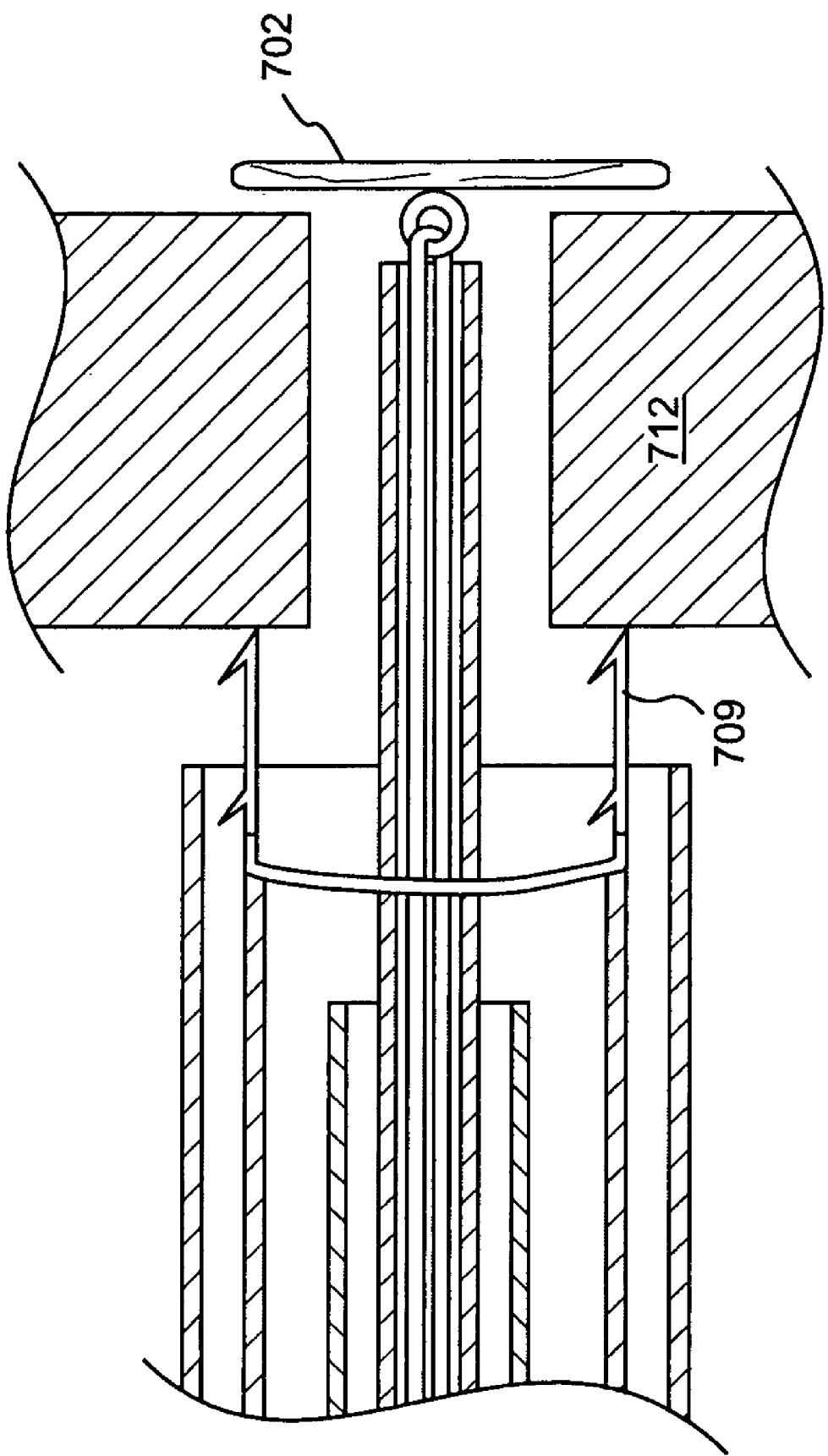
Figure 16B:
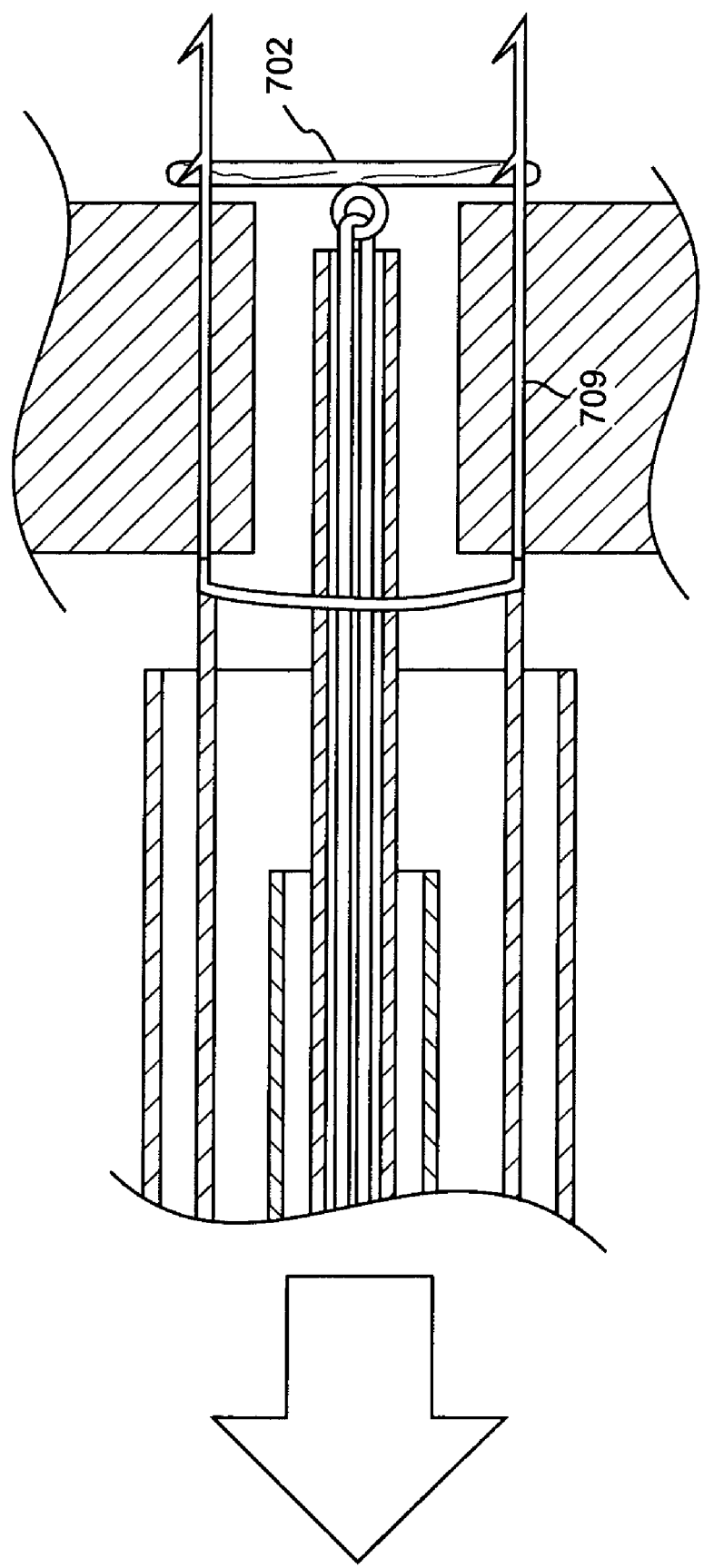

As an alternative embodiment of the present invention, the anchor bands 709 as described previously (anchor bands into annulus) could be sufficiently long enough to pass through the annulus and then through the patch. The barbs in this embodiment have an engaging involvement with the patch. This concept was previously discussed hereinabove in connection with FIG. 10. Further illustration of such a system is schematically shown in FIGS. 15 and 16. Passing the barbs through the patch, in this embodiment, provides additional security and safety by reducing the possibility that the barbs may migrate after implantation. In this application of the invention, the suture cinch line may (FIG. 16C) or may not (FIG. 10B) be used in addition to the anchor bands to draw the tissues together and reduce tissue movement surrounding the aperture.

Figure 18A:
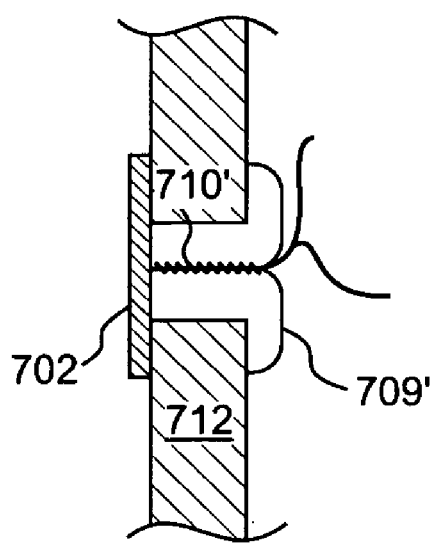
FIGS. 18A-18E show exemplary embodiments of various additional patch/stent fixation techniques.
Figure 18B:
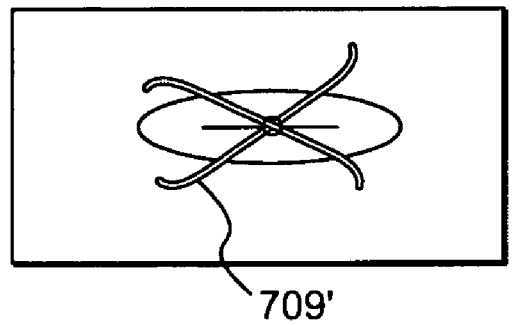
Figure 18C:
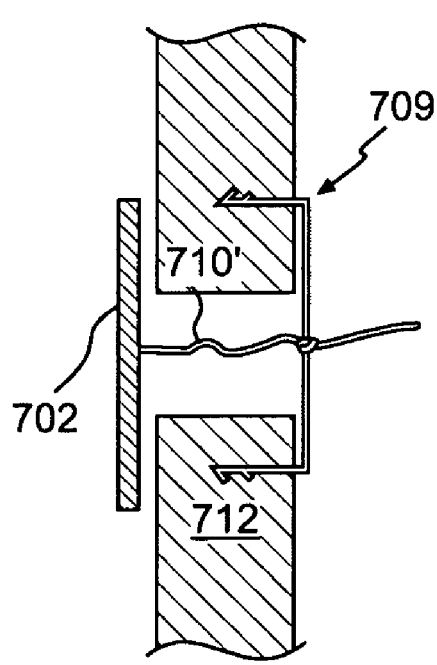
Figure 18D:
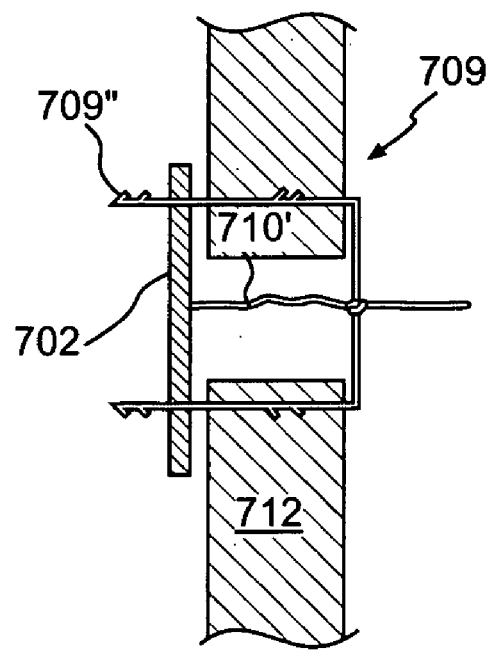
Figure 18E:
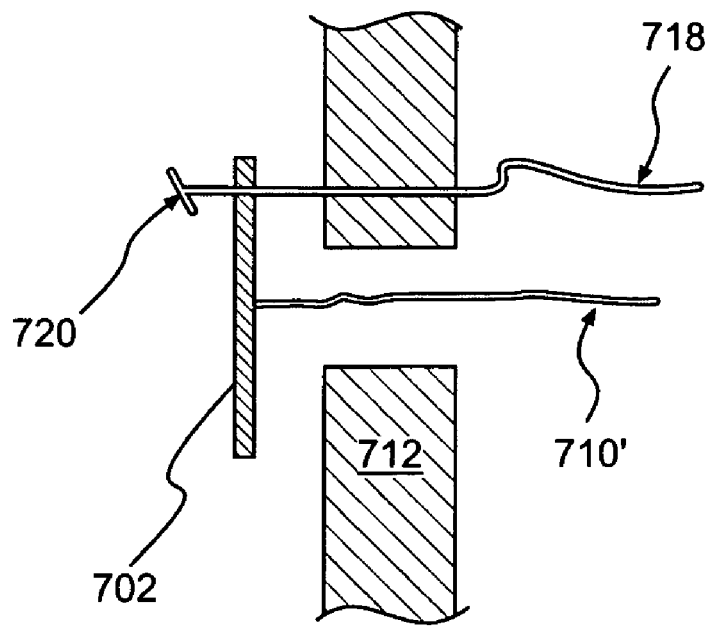

In addition, although the bands shown in FIG. 12 through 16 take the form of a "barb", they could as easily take a form of a simple T-barb 720, as shown in FIG. 18E, or a C-type element wherein the object is to have irrevocable engagement with the patch device 702 after the penetration through the patch. A T-type attachment, when aligned longitudinally with the suture, passes through the patch. The T section then rotates to prevent the suture anchor from being pulled back through the patch. In another embodiment a "C" retainer made of a superelastic material may be attached to the end of the suture band. The C retainer is loaded into a needle wherein it is held straight. The needle is used to pass the C retainer and suture through the patch and deploy the retainer in a second configuration in the shape of a "C".

It is also foreseen within the scope of the invention that there may be patch designs which will accommodate the placement and securement of the anchor to the fabric that covers the frame of the patch. For example, a frame for a patch that is made out of metal such as Nitinol can provide for "windows". The device, covered with a mesh fabric, for example silicone or Dacron, would therefore allow the anchoring barbs to be passed through the "windows" in the frame of the patch. In this case, the barb can be secured to the patch in the fabric covering the frame.

Alternatively, the patch can be secured by passing barbs that engage the lattice of the patch frame. These embodiments of the invention illustrate designs in which the barbs engage with the vertical, horizontal or criss-crossed structures/members of the frame. In this case, the barbs would pass through the mesh or lattice of the frame and they would be unable to pass back out of the structure.

Although this discussion refers to "anchor bands" that are shown to be two anchors connected by a suture, it is also contemplated that single barbs with sutures could be placed and the sutures' ends, at the outer surface of the annulus, are tied after placement through the patch. It is also possible that these "single anchors" could be retained by a suture "pledget" on the outer wall of the annulus to better hold the outer surface, or could include a suture (or band) locking device.

Figure 19:
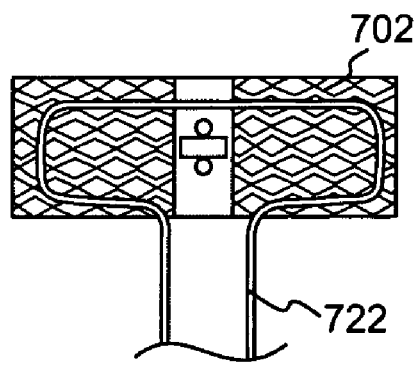
FIG. 19 shows a still further illustrative embodiment of a stent/patch having a frame.

One objective in the designs discussed hereinabove is to provide a way to "pull up the slack" in a system to adjust the length of sutures and for anchor bands. According to the present invention, a technique referred to as the "Lasso Cinch Knot" was developed as a means to draw the anchor bands together with a suture cinch line that is incorporated into the patch design. FIG. 19 gives further description of the use of the Lasso embodiment. In essence, patch and frame constructs are used that incorporate the "barbs through the patch" design. Once the barbs have passed through the patch, an internal lasso 722 is drawn tight around the sutures of the anchor bands and thus draws the extra suture material within the patch. The internal lasso gathers the sutures of the bands, and as the lasso is tightened, it cinches together the sutures of the bands and therefore tightens them and eliminates slack, bringing the patch/stent into closer or tighter engagement with the annulus wall. The patch in FIG. 19 additionally provides for a diamond shape grid pattern, which advantageously provides a grid which will while allowing a probe or similar instrument to pass through with little resistance, provides resistance to a barb or other restraining feature on the instrument. The frame shown can be made from nitinol, and the locking and holding windows shown at the center of the FIG. 19 would allow for rotation about the z-axis during placement. A slipknot technique using, for example a knot pusher, would aid in the loop pulling process by the lasso. The internal loop (lasso) can be tacked to the outside corners of the patch/stent, in order to hold the loop at the outer edges of the patch frame. When cinching the lasso knot, the loop can be pulled free from some or all of its tacked attachment points to the frame, to prevent deformation of the planar shape of the frame when cinching the lasso. As above, the frame can be a composite structure or sandwich formed with some type of mesh fabric. The proximal mesh fabric can be bonded fully to the patch frame, for example through the use of an adhesive, for instance a silicone. Adhesive, advantageously, can fill the interstices of the grid pattern while allowing for easy probe penetration and protection of the suture lines. Protection of the suture lines is advantageous when the lasso is used to pull and bunch a group of band sutures together.

It is also contemplated within the scope of the present invention that sutures or bands 710' can be preattached directly to a stent/patch. As shown in FIG. 18A several separate barbs 709" into the annulus 712 can be directly attached to the patch 702. Each "barb" of FIG. 18A can be independently placed into the annulus after the patch is deployed.

Figure 20A:
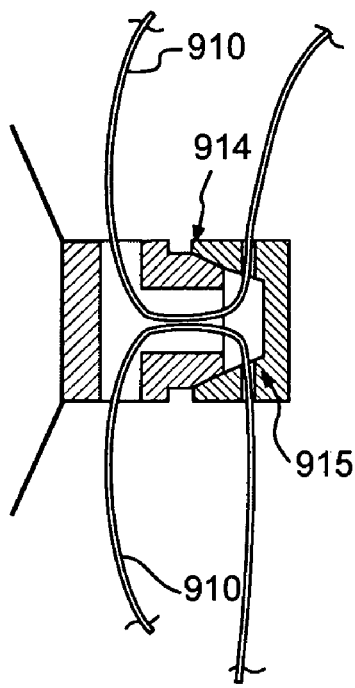
FIGS. 20A-20C show a still further exemplary embodiment of the invention having external fixation anchors.
Figure 20B:
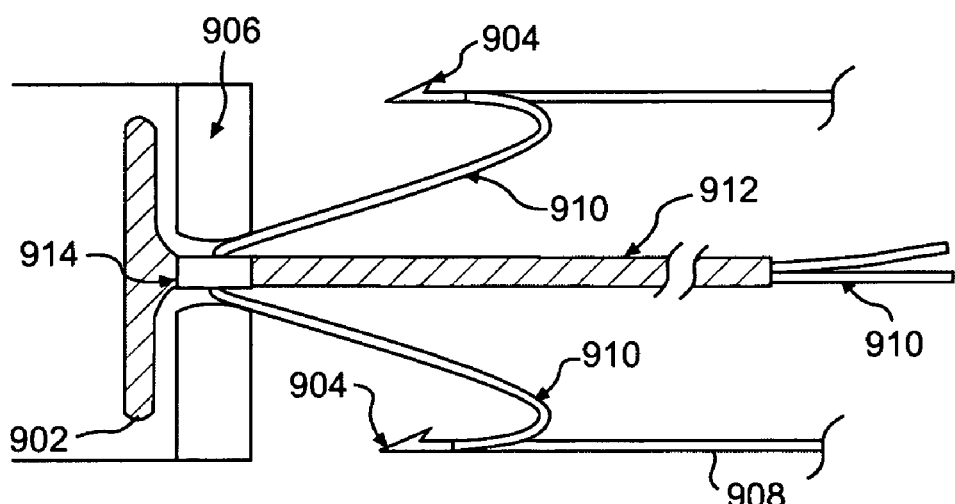
Figure 20C:
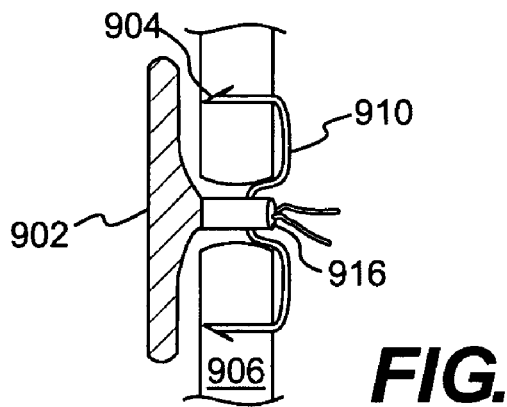

An alternative embodiment for securing a patch 902 and reapproximating a rent or incision is to provide each of the separate barbs with sutures having variable lengths as shown in FIG. 20. Each independent suture barb 904 is placed into the annulus 906 or into the patch 902 with the barb delivery tool 908. After the placement, all of the suture lines 910 are drawn taught, by drawing on the free ends that exit the patch delivery tool 912. A locking element (which may be referred to as a locking clamp, or band locking device, or band retention device) 914 that uses a gasket 915 and threading mechanism within is attached to the patch 902 and is used to tighten the gasket 915 around the distal ends of the sutures 910. The patch delivery tool 912 is removed and the extra suture length is cut. It is also possible that the gasket mechanism could be a press-fit to accommodate the tightening of the sutures to the patch.

Alternatively, the locking mechanism can be as shown in FIG. 21, although in this case the engagement of the locking element 914' takes part on the anchor. Pulling the tether 910 in the direction of arrow B will tighten and lockingly hold in tension to aid in securement and tissue approximation. The adjustable length band between the two anchors allows slack to be taken up between the anchors 916. Two T-type anchors are illustratively shown in this example, but multiple anchors of differing configurations could be used. The locking features can be included on the feature band, as depicted here, and allow for substantially one-way locking engagement with the anchor members. This adjustability advantageously promotes for the accommodation of varying thickness of the annulus from patient to patient. The suture/band slack in this embodiment may be taken up to close the defect in the annulus and/or to shorten the band between anchors for a secondary cinching of multiple tensioned suture bands as described herein.

Figure 22A:
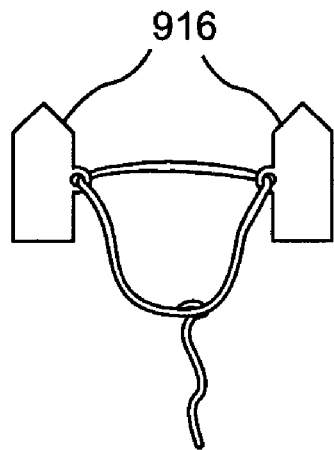
FIGS. 22A-22C show still further embodiments of the invention having external fixation anchors.
Figure 22B:
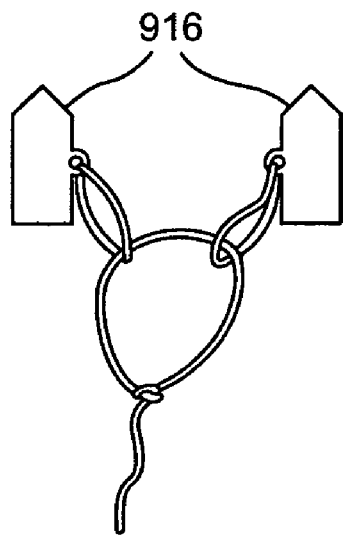
Figure 22C:
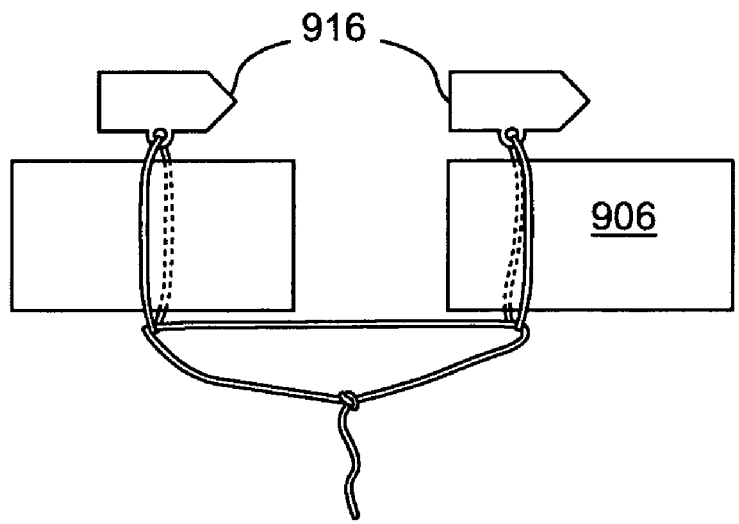

FIG. 22 shows alternative embodiments for tightening "anchoring barbs" with different configurations of sutures and cinch lines. For example in FIG. 58B each independent barb has a looped suture attached to it. Through each of these loops is passed a cinch line, which contains a knot. After placement of the barbs within the annulus, and possibly through the patch, the cinch line draws the loops of the barbs together. The advantage of this embodiment is that it allows for the independent placement of multiple barbs and the ability to draw all of them together.

Although cinch lines have been described as using a knot to "lock" the length of the suture, other mechanisms could also lock the length, as shown in FIG. 21. The locking of the suture length is accomplished through a mechanical element located on the barb which engages with three dimensional elements attached to the suture line which mechanically press fit through the engagement element on the barb, thus locking the length of the suture line into place.

Although the embodiments of FIG. 21 and FIG. 22 depict the use of a single locking mechanism (e.g., knot on cinch line), it is conceivable that various designs could use more than one locking element to achieve the re-approximation and drawing together the tissue surrounding an aperture.

Similarly, an alternative embodiment to cause tension within the device and draw the tissues together after placement of the anchor bands might include an elastic band or band with a spring which one end can be attached to the anchor bands and the other end attached to the patch. Alternatively, the anchor bands might, in and of themselves may be made of an elastic band between the barbs, or may contain a spring element between the barbs. Such an embodiment can be made to resemble a so-called "Bobber Spring." Again, it is contemplated that the elastic or resilient element could be made from a wide variety of metals, polymeric, or biodegradable/bioabsorbable material.

As previously mentioned, the present invention also encompasses delivery devices or tools of the following description. The delivery devices of the present invention are configured to deliver at least one, or a portion thereof, device into (or through) the annulus or other surface or tissue. The delivery tools (or devices) will typically comprise devices or shafts having proximal and distal ends. As referred to herein, the proximal portion of a device or tool or component will generally refer to the portion of the device/tool/component that is located furthest away from the patient (and closest to the surgeon); whereas, the distal portion will generally refer to the portion that is within (in use), or closest to the patient (and therefore furthest away from the surgeon). Although some of the device descriptions may refer to some fixation element embodiments as being "fixation" or "anchor/anchor band/barb", this is done for clarity reasons and should not be misconstrued to suggest that the device is not capable of also performing a treatment and/or a repair.

In addition, the following descriptions of delivery devices/tools are generally intended to be single-use and disposable; however, it is clear that these tools could as easily be constructed to be partially, or wholly, re-usable and re-sterilizable.

Figure 25A:
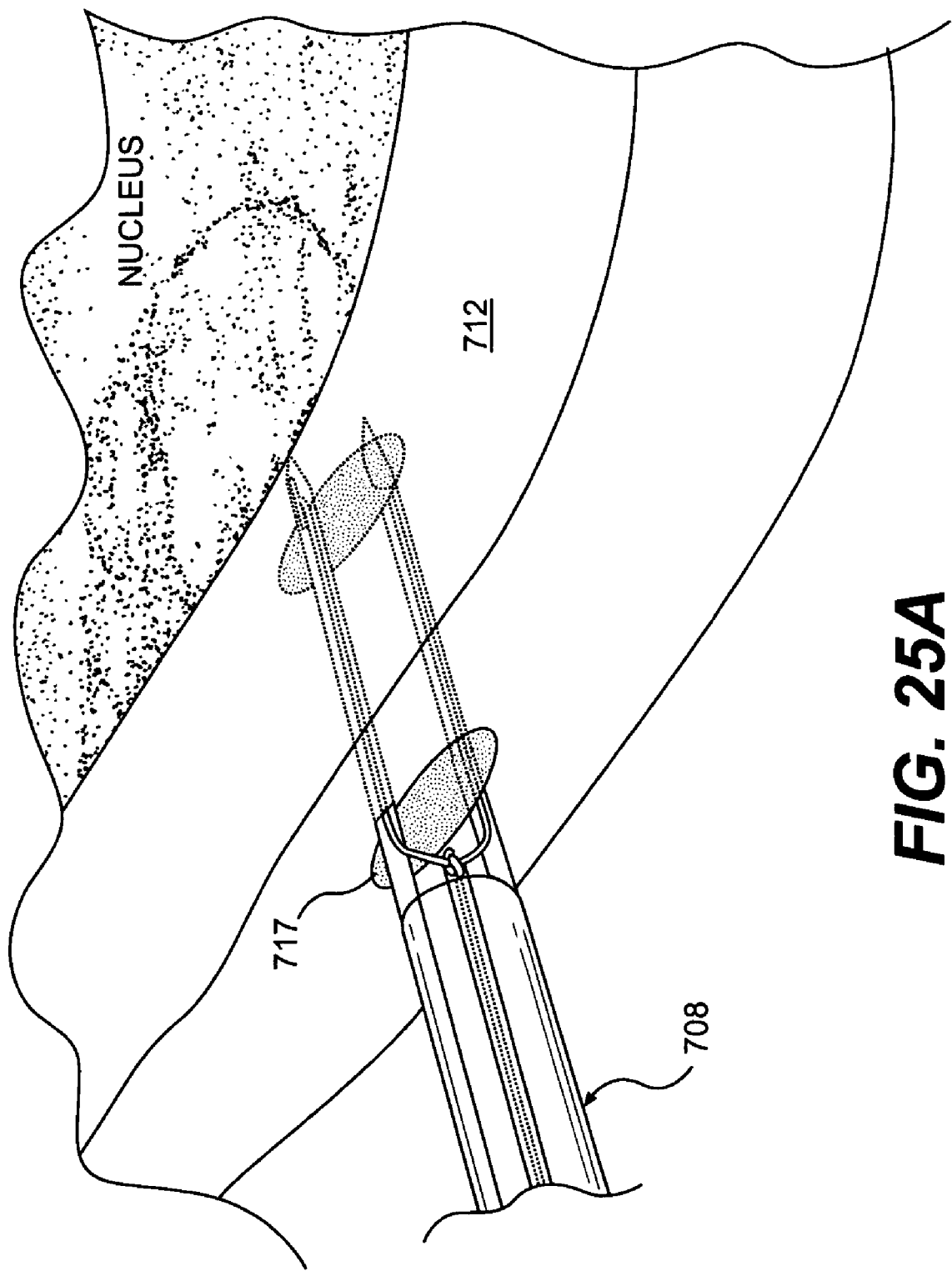
FIGS. 25A-25D show an anchor band delivery device comprising two devices, each with at least one T-anchor (barbs) and band with pre-tied knot and optional knot pusher according to illustrative embodiments of the invention.
Figure 25B:
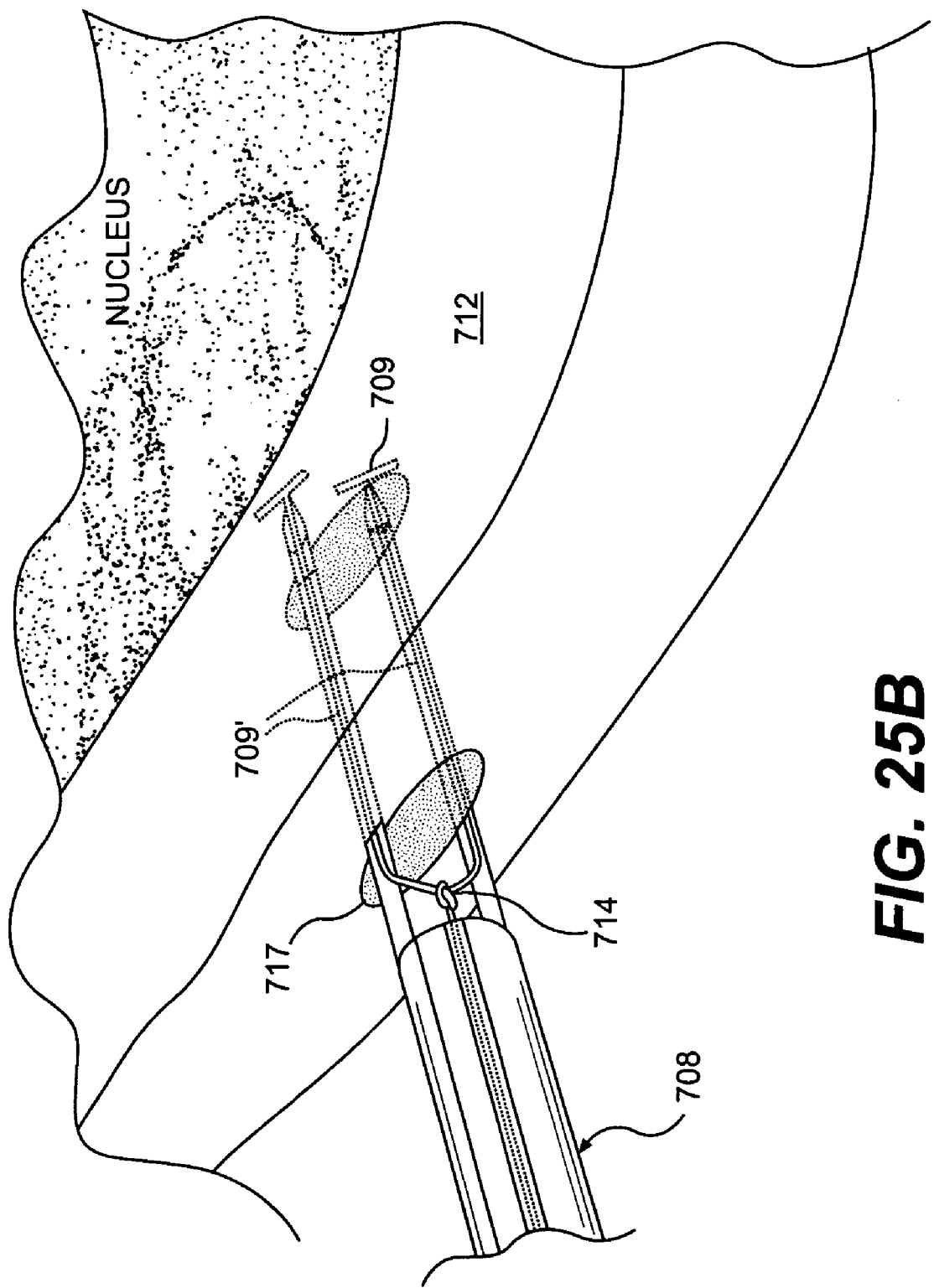
Figure 25C:
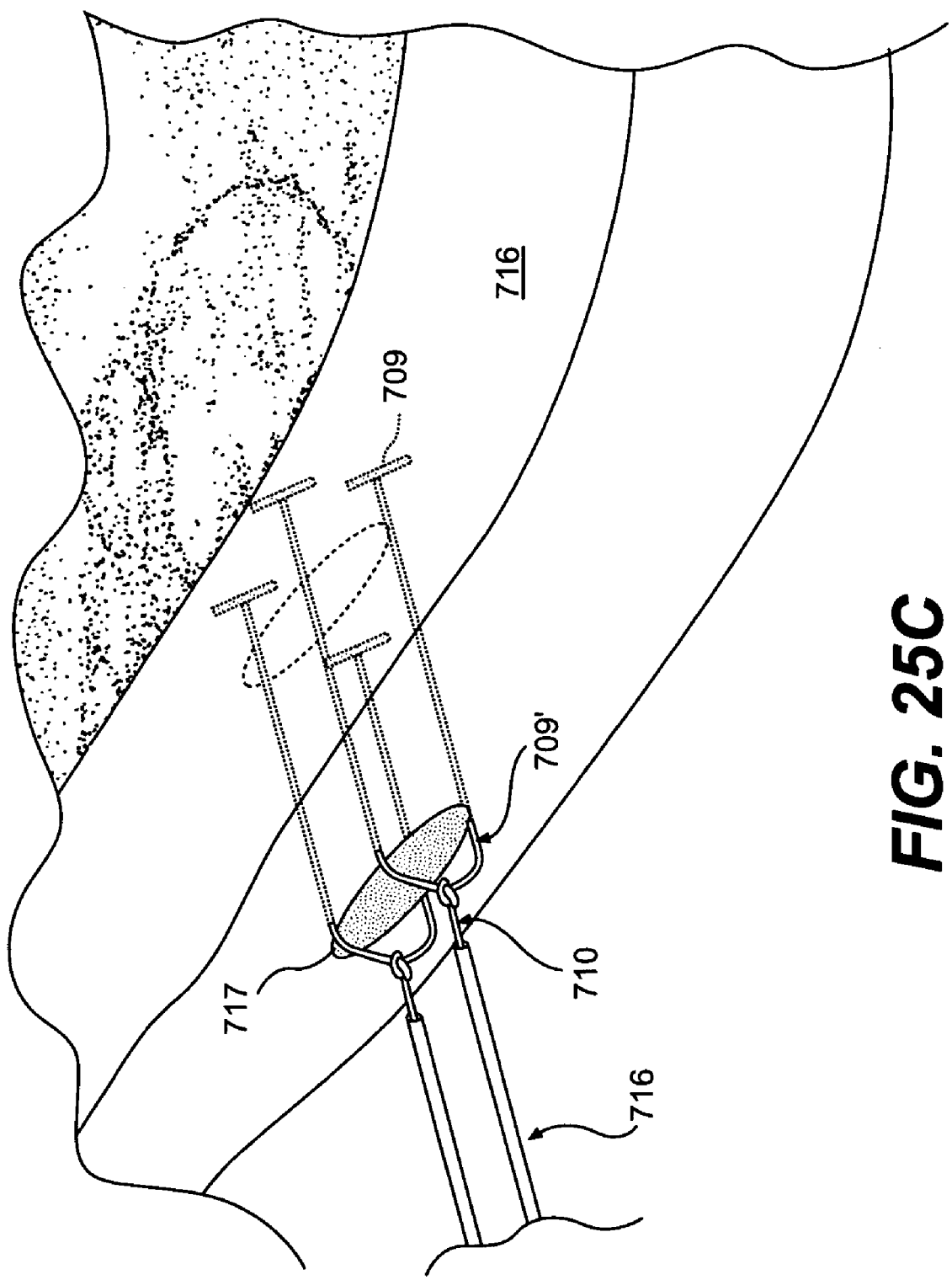
Figure 25D:
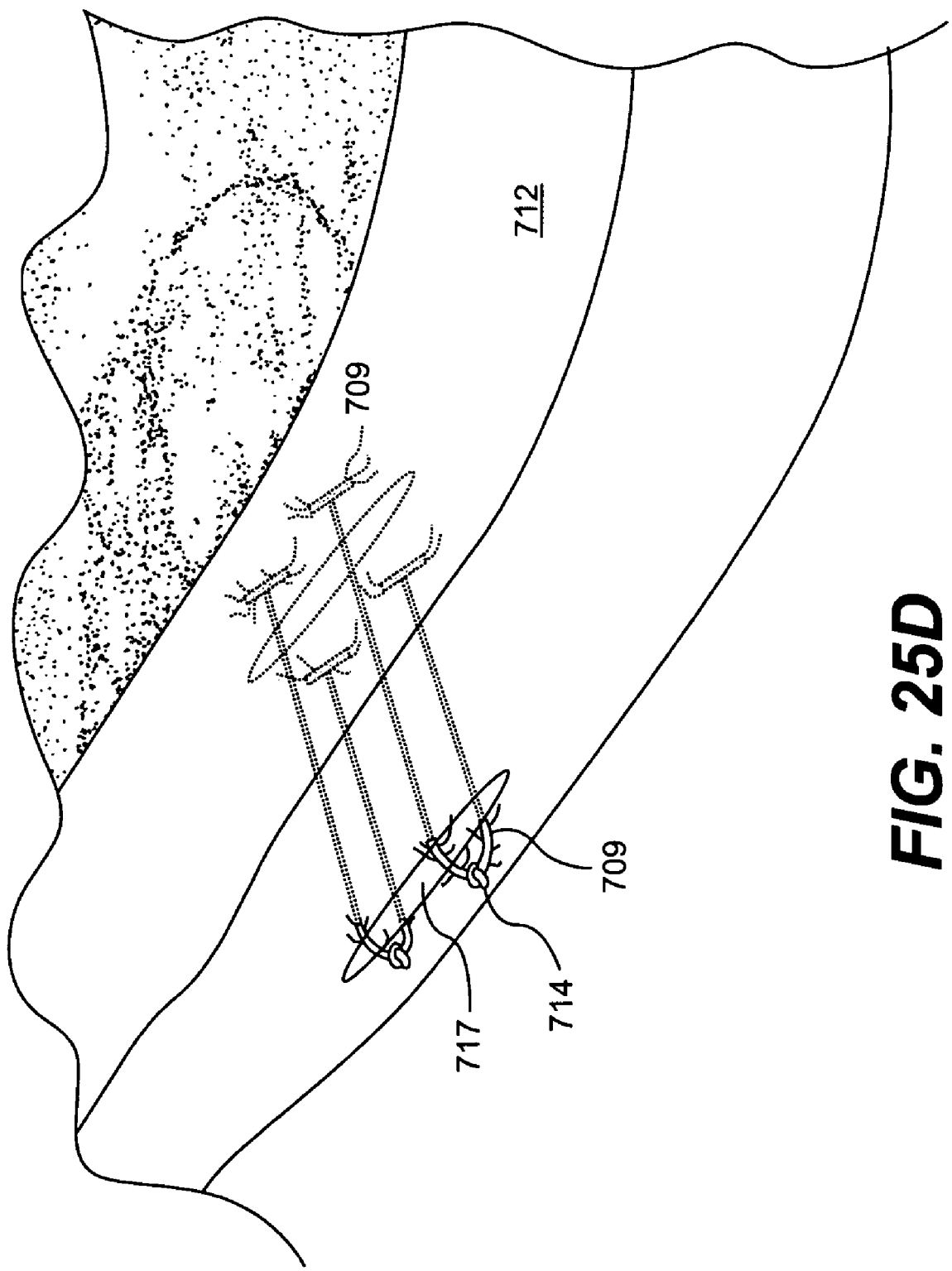
Figure 26:
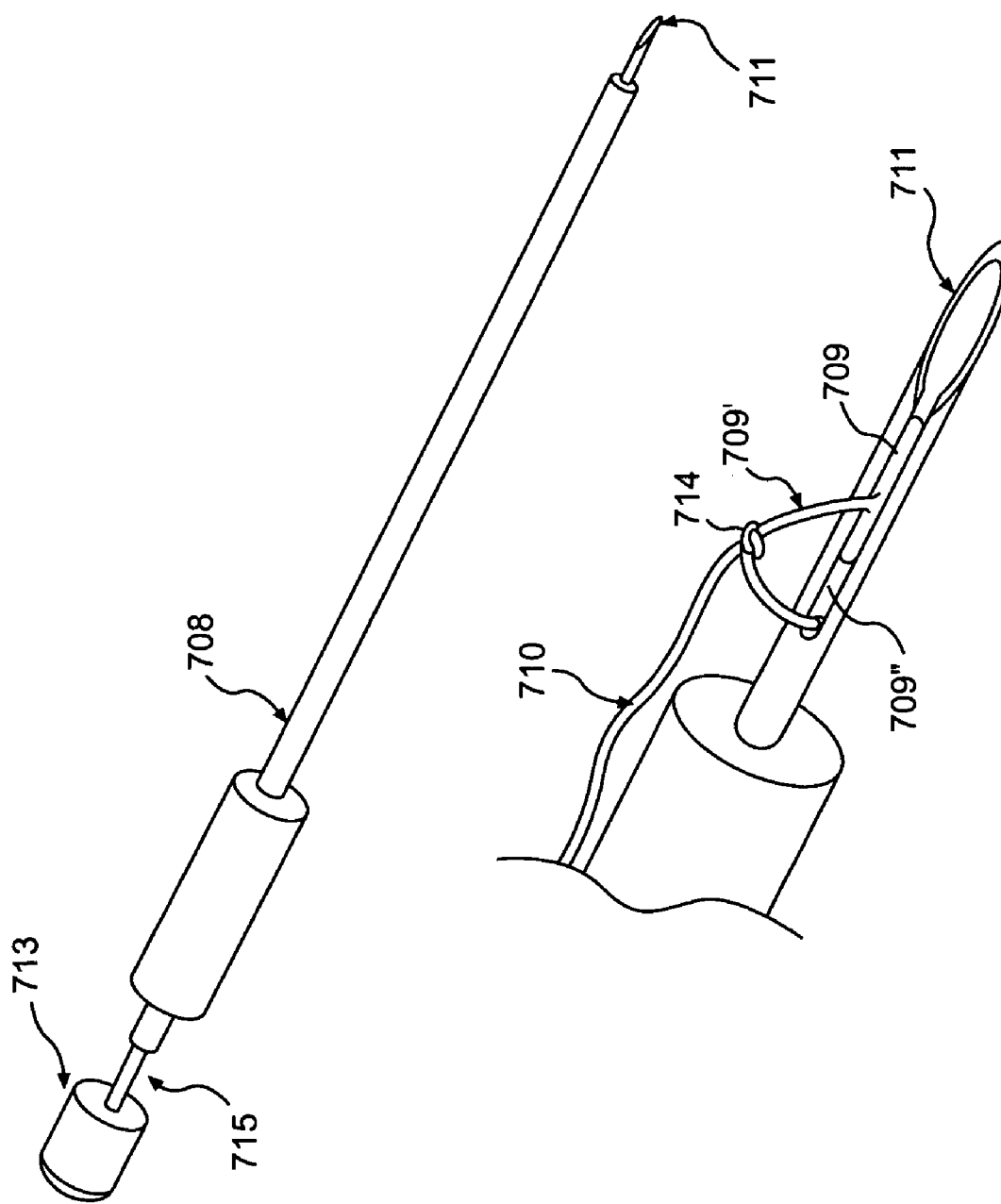
FIG. 26 shows an anchor and band delivery device according to one embodiment of the invention.

An illustrative delivery device as depicted in FIGS. 24-26 may be configured to accommodate and deploy at least one fixation device, such as a barb or T-anchor with one or more associated bands. Advantageously, the distal end of the delivery device will comprise a hollow needle or cannula 711, having a circular, elliptical, triangular, hexagonal or other inner cross sectional area, suitable to accommodate the cross-sectional shape of the fixation device within. The distal point of the cannula 711 is advantageously sharpened, as a needle, to accommodate insertion. The cannula 711 is advantageously cut obliquely as shown in FIG. 26 to form a sharp leading surface or point for ease of insertion. The cannula 711 may contain a cut or groove 718 along its side to accommodate one or more anchors 709 as shown (or barbs, not shown), e.g., in FIG. 24B or 26. In one embodiment, the at least one fixation device (including band and barb or T-anchor), or portion thereof, is disposed within the cannula 711 as shown in FIGS. 24a, 24b, and/or 26. Alternatively, the T-anchor 709 (or barb, not shown), or other fixation device may be hollow and disposed in a manner surrounding the device of the delivery device.

The delivery device 708 will also advantageously contain within it an ejection rod 715. The proximal end of the ejection rod 715 typically will contain an end portion 713 to function as a stopper, e.g., having a diameter larger than the remaining portion of the rod, such as is shown in FIG. 24a. The diameter of the remaining portion of the ejection rod 715 will be small enough for insertion within the shaft of the device 708. Upon insertion of the cannula 711 into the location of choice, the ejection rod is pushed to deliver the fixation device. The delivery device is then removed.

Advantageously, the ejection rod 715 and delivery device may be configured to deliver multiple fixation devices, sequentially or simultaneously. Thus, if multiple fixation devices are contained within the device, the ejection rod 715 and delivery device may be configured such that the rod 715 be pushed a first distance, sufficient to deliver a first fixation device. The device is then removed from the first insertion point and inserted into a second insertion point, where the ejection rod is then pushed a second distance for delivery of a second fixation device, and so-on as desired. For simultaneous delivery of multiple fixation devices, multiple delivery devices may be arranged in parallel (or substantially parallel). The distance between (or among) the delivery devices may be fixed or adjustable, as desired.

The distance the ejection rod 715 is pushed to define a first, second, and subsequent distances may be regulated by feel. Alternatively, the distance can be regulated by the architecture of the device. For example, the shaft and ejection rod may be fitted with a notch-and-groove configuration, respectively. In such configuration, the notch in the outer surface of the ejection rod may be aligned with a groove in the inner surface of the device. The length of the groove defines a first distance. The ejection rod 715 would be then turned or rotated within the device, aligning the notch within the device to a second groove defining a second distance, and so-on. In an alternative embodiment, the ejection rod and anchor portion of the fixation device (e.g., barb or T-anchor) may surround the shaft of the device, as a sleeve surrounds an arm. In such a configuration, the delivery tool would comprise a solid shaft and the ejection rod and fixation device would be at least partially hollow and disposed over the distal portion of the delivery device. Pushing the ejection rod in a proximal to distal direction would deploy the anchor portion of the fixation device.

FIGS. 24A and 24B describe one embodiment of an anchor band delivery device 708 and fixation means. FIG. 24A shows a general drawing of a delivery device. FIG. 24b further depicts the distal end of the delivery device. Anchor band delivery device 708 contains two pointed needles or cannulas 711. Each cannula 711 contains an anchoring T-type anchor 709 (or barb) positioned within the distal end of the cannula 711. A band 709' links the two anchors 709 (or barbs) together and a cinch knot 714 secures the anchors (or barbs). Cinch line 710 is pulled to decrease the length of the band 709' that attaches the anchors 709.

Referring to FIG. 25A, anchor band delivery device 708 is inserted into the annulus 712 sufficiently to engage the inner layers of the annulus 712, and preferably located at the inner wall of the annulus 712. The anchors 709 are ejected from the delivery device by pressing the ejection rod 715 in a fashion to expel the T-anchors 709 (or barbs, not shown) from the device. For example, pressing on the proximal end of ejection rod 715 as shown in FIG. 24A drives the ejection rod 715 in a distal direction, thus expelling the anchor from the device. FIG. 25B shows the anchors 709 (or barbs) after being ejected. FIG. 25C shows a knot pusher 716 attached to the delivery tool 708 that can be used to tighten the knot 714 once the fixation device is secured into the annular tissue. FIG. 25C shows the placement of two anchors 709, or fixation devices (anchors and bands), after they have been delivered to the annulus and before the bands 709 have been tightened. The knot pushers 716 of both devices are still in contact with the knots and the delivery needles have been pulled back, away from the annulus. FIG. 25D shows the final placement of the two anchor bands after drawing together the tissues surrounding the aperture 717, the inner wall of the annulus 712, and/or the outer wall of the annulus; and, after tightening and cutting the knot located on each anchor band. Although this FIG. 25 shows the passage of the bands superior and inferior to the aperture, these bands could also be placed in a multitude of locations to effect desired or equivalent outcomes.

In addition, as previously described, one could use barbs having a multitude of configurations. One could also configure delivery devices to deliver one (as in FIG. 26), two (as in FIG. 24A), or more barbs simultaneously, and according to predetermined or variable distances or patterns. The delivery devices may also be configured to eject one, two, or more barbs sequentially. Further, the barbs could be delivered by a delivery device that does not require a cannula to cover the barb. In such a configuration, the barb may be disposed on the tip or outside of the delivery device's shaft, and removed therefrom upon injection into the desired location of the annulus or other tissue. Bands and knots may be pre-tied to accommodate each configuration, as previously discussed.

For example, although FIGS. 24 and 25A-B depict a device that places two anchors 709 banded together with one device, one could accomplish an equivalent or other desired result with a single device that delivers multiple barbs at the same time.

FIG. 26 shows an alternative delivery device that delivers two or more anchors (or barbs) from a single cannula 711. In this embodiment, a first single anchor 709 is ejected from the cannula 711 by pushing the ejection rod 715 a first distance sufficient to eject the first anchor 709, but insufficient to eject the second. Then the delivery device is removed from the first site and passed into another annular location. The second anchor (or barb), not shown, connected to the first anchor or barb by band, is ejected out of the cannula 711 by pushing the ejection rod 715 an additional distance sufficient to eject the second anchor 709" (or barb) into a second fixation point in the annulus.

Although much of this description has described placement of the anchors into the annulus (or soft tissue) of the disc, one could perform anchoring into other tissues surrounding the aperture, including the bone or Sharpey fibers, it is also contemplated that, given the delivery device construction, a bone drill or similar device may be necessary to facilitate the placement of the delivery device through the bony or similar tissue.

The band 709' connecting the thus implanted anchors (or barbs) advantageously contains a moveable knot 714 between the anchors. Suitable knots include, but are not limited to, the Roeder knot and its functional equivalents, and are advantageously, but not necessarily, pre-tied. After insertion of both anchors 709 (or barbs), the band 709' is advantageously tightened by hand or by pushing on the knot with a knot-pusher or similar device. Although not shown in FIG. 26, the knot pusher may be integral to the delivery device. After drawing together the tissues surrounding the aperture, inner wall, and outer wall of the annulus, the excess suture line can be cut. It is also possible to use a cutting device integral to the delivery device to cut the band after cinching. Although the device shown in FIG. 26 depicts two anchors being delivered from a single device, multiple anchors or barbs could be delivered from the same or a similar type of device. Additionally, a delivered configuration of fixation means may result from the use of a single device to deliver multiple anchors sequentially.

The shaft of the device may be of any convenient length, typically from, e.g., 1 inch to 10 inches. Materials of which to make the delivery device include, but are not limited to: metals, such as stainless steel, nickel, titanium alloy, and titanium; plastics, such as PTFE, polypropylene, PEEK, polyethylene, and polyurethane, acrylic, polycarbonate, engineering plastics; and/or composites.

Advantageously, the shaft of the device will have a cross-sectional shape suitable to accommodate an ejection rod and at least one fixation element, or portion thereof. In one embodiment, at least a portion of the shaft of the device may be hollow, having a circular, elliptical, triangular, trapezoidal or other suitable cross-sectional area sufficient to accommodate an ejection rod.

The delivery device may also contain a handle or raised surface configured to accommodate the shape of surgeon's hands or fingers for easier handling. Such raised or configured portion may be made of the same or different material as the tube or shaft. Suitable materials known in the art include, among others, polymers, such as acrylic polymers, polyurethane, polycarbonate, engineering plastics; and metals, such as stainless steel and titanium.

Much of the previous discussion relates to the use of a patch (or stent) for annular repair and/or reconstruction. In some clinical instances, the method of the invention may be accomplished without the use of a patch, however. For example, a patch may be unnecessary to repair small apertures or apertures of certain shapes, or certain weakened or thin portion(s) of an annulus. The invention therefore also encompasses methods for repairing or reconstructing annular tissue that do not necessarily involve the use of a patch, and to fixation devices and tools useful in carrying out these methods, as exemplified in FIG. 25. Accordingly, an additional embodiment of the invention also provides fixation devices that may be used to reapproximate and hold annular tissue. Such fixation devices, as described herein, may contain an anchor portion and a band portion. The anchor portion serves to fix the fixation device in the annular tissue. The band portion, attached to the anchor portion, serves to draw together annular tissue when tightened and secured. At least one fixation device is placed into, or through, the wall of an annulus surrounding an aperture, weakened, or thin portion of the annulus. The device is then drawn in tension to pull together, wholly or partially, the surrounding annular tissue.

The band and the barbs may be separate elements or comprise one continuous element. Bands and barbs may be made of the same or different materials.

The bands may be string-like, made from suture or similar material, or of any construction or dimension that is amenable to the delivery and engagement of the fixation device. For example, the band may have a width greater than, in some embodiments far greater than, its thickness. The suture material may in some embodiments have a width:height ratio of 1.25:1. In some embodiments, bands may be constructed, wholly or partially, of a mesh tube. Moreover, different segments along the length of the band may have different dimensions and constructions. For example, the band may be constructed of thin material, such as nickel titanium alloy or stainless steel wire, close to the anchor barbs, while the middle portion that spans the aperture may comprise a much wider band made of optionally softer material.

Figure 21A:
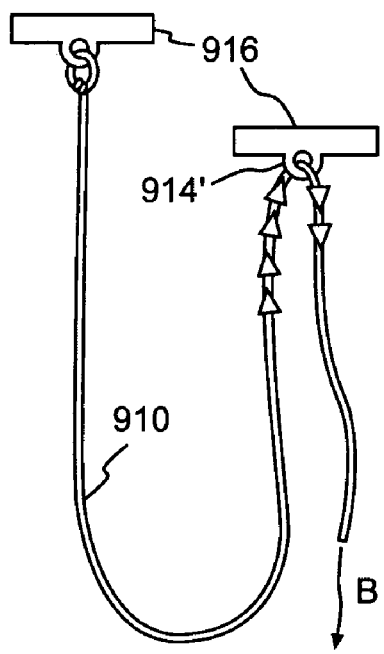
FIGS. 21A-21C show still further embodiments of the invention having external fixation anchors.
Figure 21B:
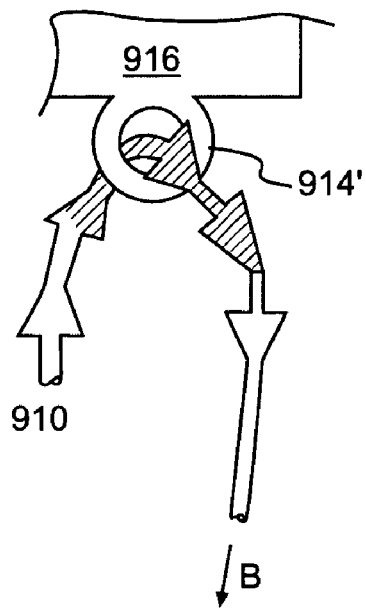
Figure 21C:
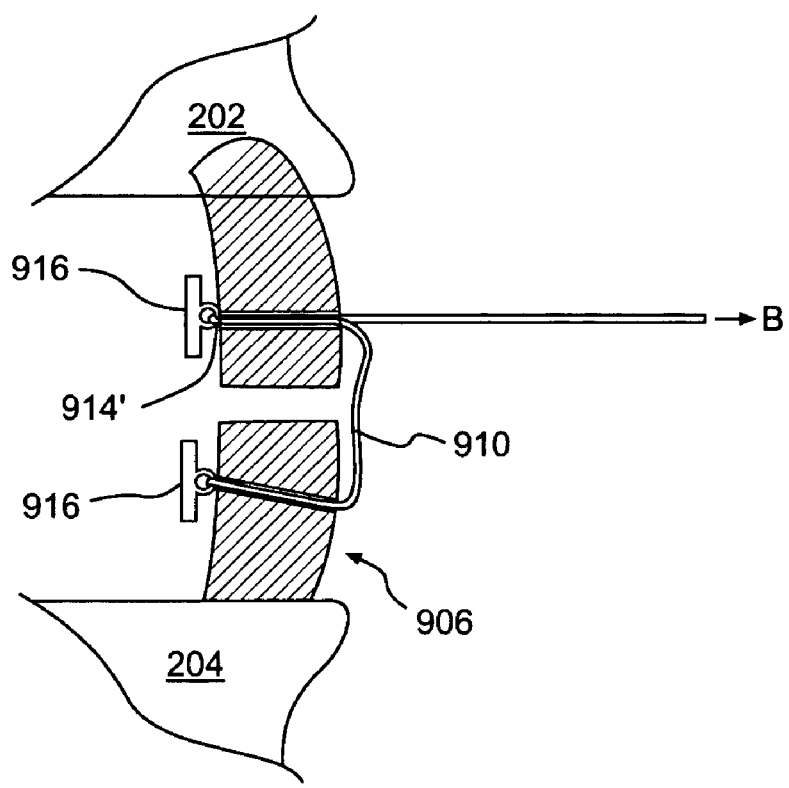
Figure 23:
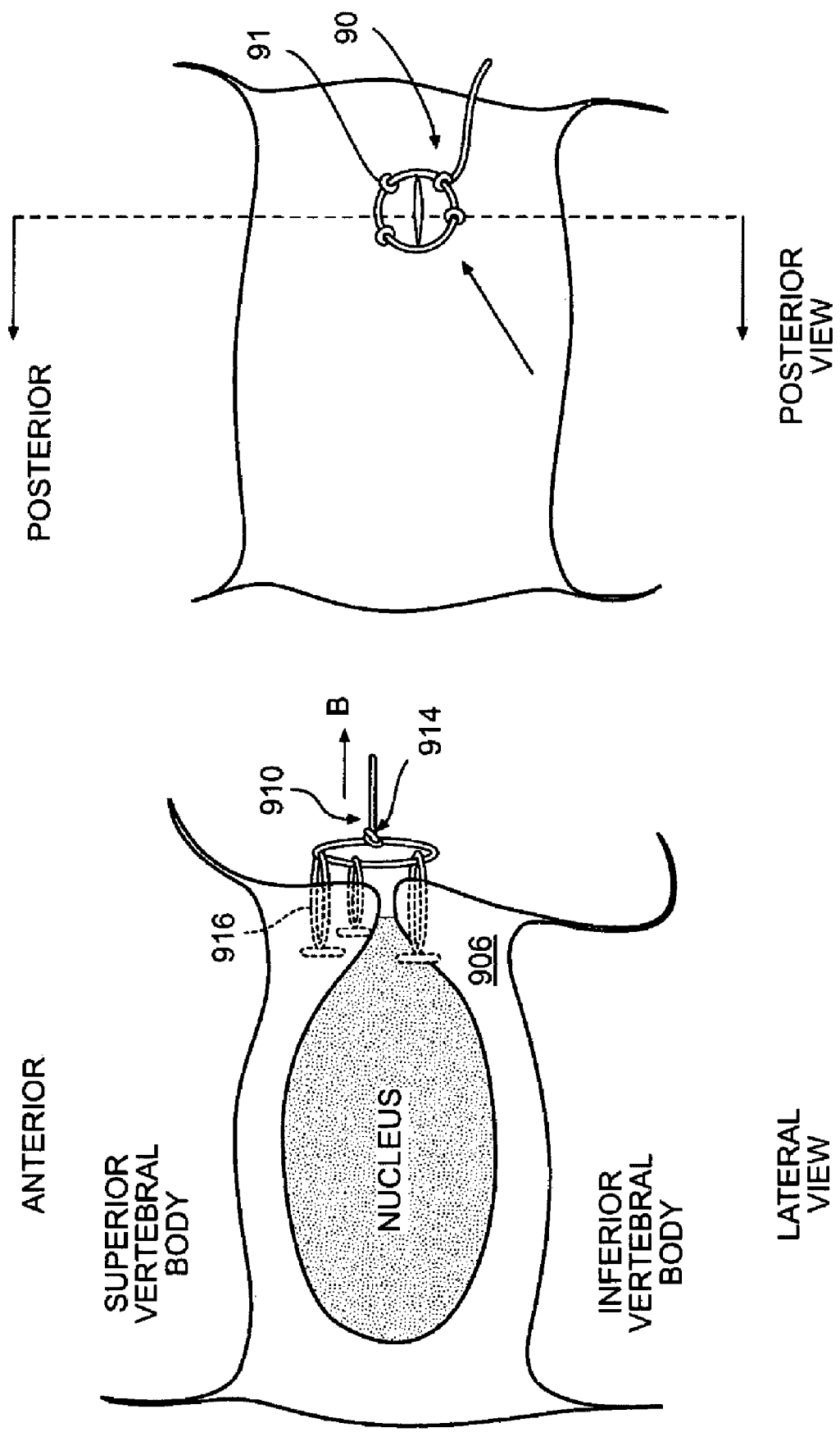
FIG. 23 shows a delivered configuration of fixation means that may result from the use of a single, or multiple, devices to deliver multiple barbs, anchor, or T-anchors sequentially or simultaneously.

FIGS. 21, 22, and 23 show additional examples of embodiments of the invention for repair or reconstruction of the annulus that could be utilized without the additional use of a patch. For instance, in FIGS. 21A-21C, in lieu of (or optionally in addition to) a patch, two anchors are shown having passed through the annulus to the subannular space. By drawing on band 910, the inner and outer walls of the annulus may be drawn together in tension, and may also reapproximate the tissue surrounding the aperture. FIG. 57C shows a single anchor band being placed along an incision or tear in the annulus.

The fixation devices of the invention could be delivered as a pair of barbs attached by a single band, or each barb could be delivered individually Alternatively, multiple barbs (anchors) may be pre-attached to a single or multiple bands for ease and speed of delivery. For example, FIG. 23 shows a fixation device that has multiple anchors 916 (or barbs, not shown) connected together in a configuration similar to FIGS. 22B and 22C, with each anchor 916 being delivered individually into, or through the nucleus or annulus. The anchors, if present, may be shown as in FIG. 23. By drawing on the cinch line, the tissues surrounding the aperture and/or the inner wall of the annulus and/or the outer wall of the annulus are drawn together. Although a knot 914 is shown to affix the suture lines together, other means to lock, fasten clip, retain, or secure the sutures together may also be used.

Figure 78A:
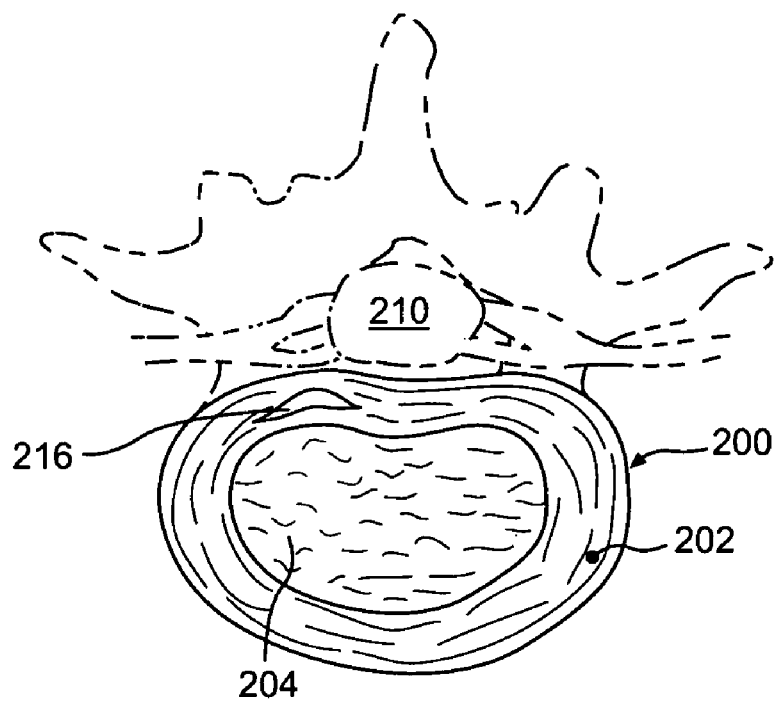
FIGS. 78A-78B depicts an anchor band assembly used to repair a circumferential tear in the annulus.
Figure 78B:
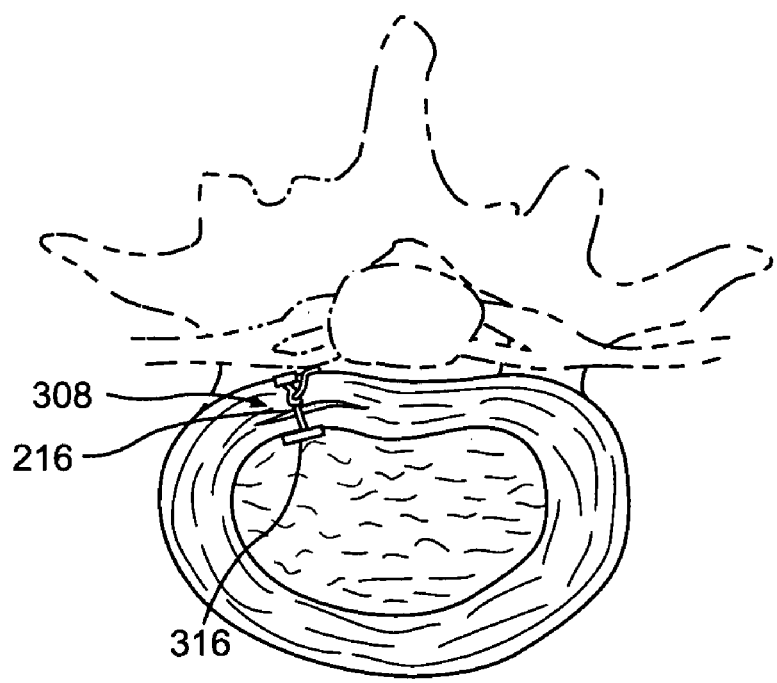

An additional exemplary depiction of fixation devices that may be used to reapproximate and hold annular tissue as previously described in FIGS. 21-23 can be seen, for example, in FIG. 78. In FIG. 78, an anchor band assembly 308 and its complementary delivery tool 400, as exemplarily depicted in FIG. 42 and FIGS. 47-56, are used to repair a damaged, degenerated, weakened, or thin portion in an intervertebral disc annulus having, for example, a circumferential tear 216 compromising the integrity of the annulus. Anchor band assembly 308 may draw in tension the annular tissue surrounding the tear or delamination of the annular laminae, helping to fortify, reconstruct, augment, repair, or otherwise reinforce the annular tissue.

A further exemplary embodiment of the invention in the form of a braided patch 1100 such as depicted in FIGS. 24-32, is a further illustrative embodiment of the present invention that can be deployed into the subannular space to act as a barrier to the extrusion of the nucleus pulposus, or other intradiscal material.

The "patch" 1100 is constructed from a braided tube of filaments 1102. The ends 1104 of the braided tube are heat-sealed to keep the braid from unraveling and the seals also provide structural integrity to the patch when deployed. Although the devices described herein principally utilize heat sealing for forming the ends of the device, there may be a variety of ways to fixate, secure or otherwise form the ends of the device through the addition of other materials to add structure to the filaments, to include, but not limited to, the addition of collars or sleeves, dipping the ends in a material to fixate (i.e., heated polymer, adhesive). These added materials could be metallic or polymeric.

The braided patch 1100 is woven on a braiding machine with multiple filaments 1102 to create the structure. For example, the patch can be woven with 72 polyester filaments in order to create the construct that readily deploys into the annular defect, promotes tissue or matrix ingrowth into the device, and retains an anchor after it has been placed through the wall of the annulus and through the patch. Changing the number of filaments 1102 in the patch, the material of the filaments, the dimension of the filaments (e.g., diameter), as well as the configuration of the filaments (e.g., cross-sectional area), or changing the braid pattern, can create differences in the characteristics of the patch. The braided patch can be made on a standard Steeger braider, or similar type braiding machine, that can handle braiding from anywhere from 16 filaments at a time, to up to 196 filaments. Preferably the patch is braided with between 32 to 144 filaments. In one exemplary embodiment of the present invention, the device is braided with 72 filaments of polyester filaments, with every other braid filament being approximately 0.012" diameter, alternating with yarn (e.g., approximately 64 microfilaments, each approximately 17 microns in diameter, bundled) or alternating with a polyester braid monofilament approximately 0.004" in diameter.

In addition, much of the description herein depicts devices that generally have a tubular form, although it is also anticipated that these devices could be woven on the braider (i.e., by changing the configuration of the braiding mandrel), or reformed in processing (i.e., heat forming) to obtain a patch construct that deviates from a "circular" cross section, in order to obtain different characteristics of the patch pre, during or post deployment to accommodate anatomical, physical, and biological considerations of the patient or the delivery of the implant. These device configurations may include square, rectangular, oblong, symmetrical, non-symmetrical, triangular, "clover leaf", or other cross-sectional constructions that may be partially (i.e., only in a portion of the device body, and/or only in a portion of the device ends), or completely present throughout the device.

The filaments 1102 of the patch can be made of different materials or dimensions, or all of the filaments in a patch can be of like material and dimensions. The filaments can be biocompatible metallic material, such as a stainless steel, a nickel titanium alloy, or other metallic materials. The patch 1100 can also be made from biocompatible polymeric material such as polyethyleneteraphthalate (PET), polyester, polyethylene, polycarbonate urethane, polymethylmethacrylate, or polypropylene, for example. It is also conceivable that the patch can be braided from biodegradable materials, such as polyglycolic acid (PGA), polylactic acid (PLA), collagen (or its derivatives), fibrin (or its derivatives), cellulose (or its derivatives), polysaccharides (or its derivatives) or other biocompatible material that may degrade and/or be re-absorbed by the body over time.

It is also possible to braid the patch 1100 with multiple materials and/or multiple dimensions of the filaments. For example, the patch can be braided with 32 filaments of a polymeric PET material and 32 filaments of polyester yarn material to create a patch that may be optimal for sealing an annulus. The combination of different filament materials, sizes, cross-sectional configuration, number of filaments, and braiding pattern can be used to construct a braided patch that can be delivered into the sub-annular space, while acting as a scaffold to induce healing of the aperture.

Figure 27A:
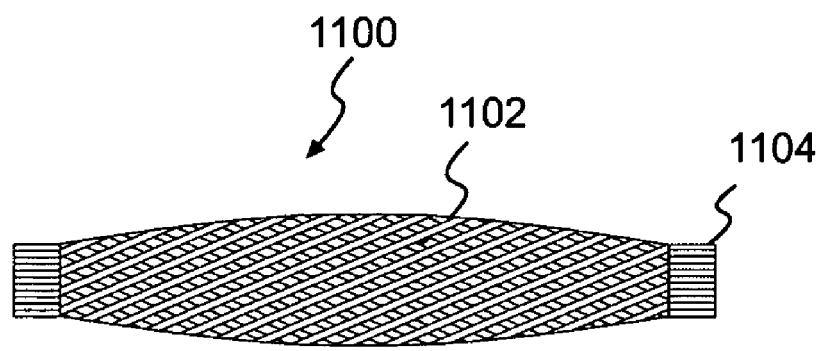
FIGS. 27A-27B show, respectively, a lateral view of a still further exemplary embodiment of the present invention having a braided arrangement in a collapsed configuration and an axial view of the exemplary embodiment in an expanded configuration.
Figure 27B:
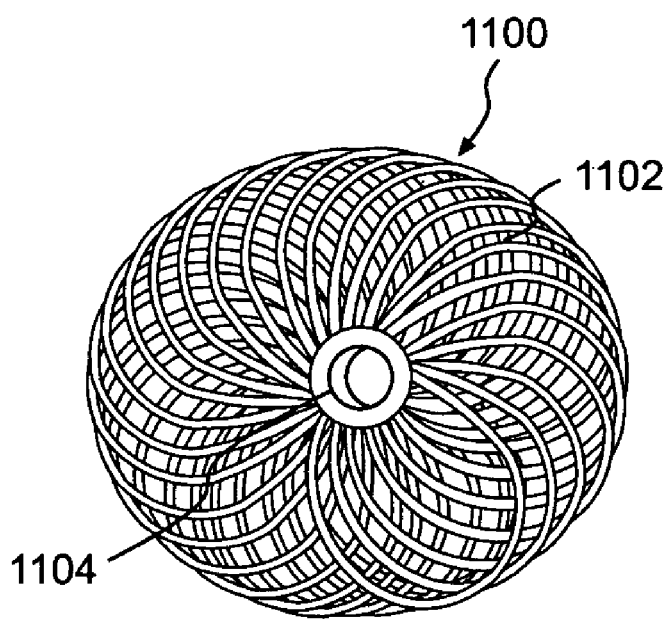
Figure 28:
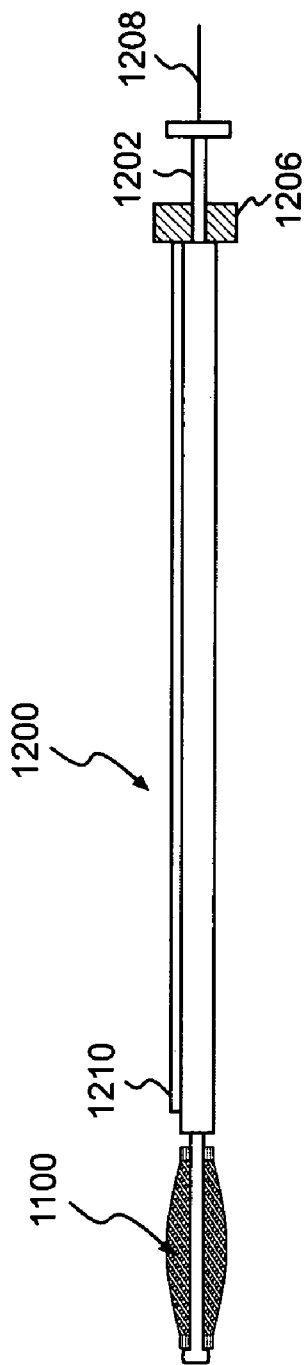
FIG. 28 shows a lateral view of the exemplary embodiment of FIG. 27A in a collapsed configuration mounted on an illustrative delivery device.
Figure 29:
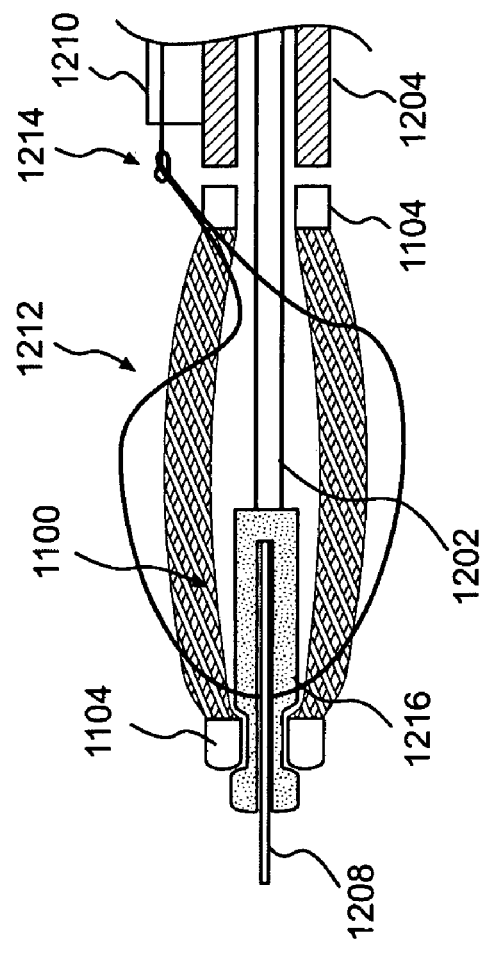
FIG. 29 shows a lateral cutaway view of the exemplary embodiment of FIG. 27A in a collapsed configuration.
Figure 30:
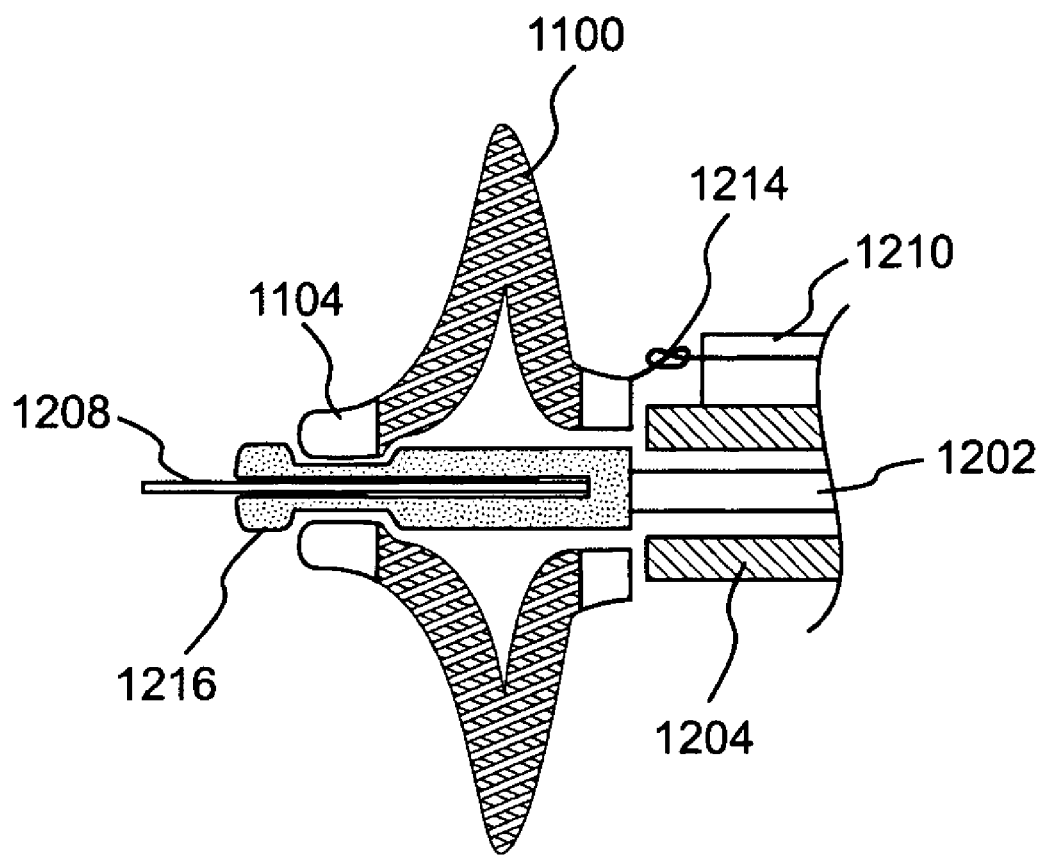
FIG. 30 shows a lateral cutaway view of the exemplary embodiment of FIG. 27B in an expanded configuration.
Figure 31:
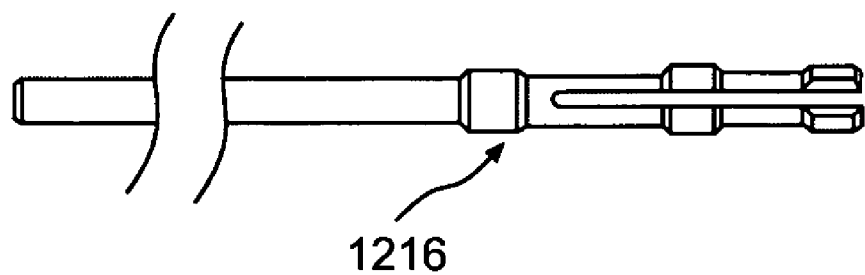
FIG. 31 shows a lateral view of an illustrative delivery member as shown in the exemplary embodiment of FIGS. 29 and 30.

The braided patch has advantages in that it can be placed through an aperture in the wall of the annulus that is relatively small, but then expand to a dimension that is substantially greater than the aperture. For example, it is possible to construct the braided tube to be less than 5 mm in diameter, whereas in its fully deployed state it could be greater than, for example, 20 mm. This is exemplary and is not intended to be construed as limiting in the actual dimensions of the device pre and post deployment Referring to FIG. 28, the non-deployed braided patch 1100 is affixed on the distal end of the patch delivery tool 1200. It is situated in a fashion that is co-axial 1208 with the delivery tool's delivery members, which include inner delivery member 1202. A finger grip 1206 can be formed onto the proximal end of the delivery tool body to assist in manipulation. Further detail of the deployment mechanism can be seen in FIG. 29. The braided patch 1100 is placed on the distal end of the inner delivery member 1202. The heat-set distal cuff 1104 of the patch is situated within a depressed region on the distal region of the inner delivery member 1216. The distal portion of the delivery member 1216 is slotted as shown in FIG. 31, and, in the non-deployed state, contains a co-axial retention member 1208 that acts to press the slotted potions of the inner delivery member apart, and thus securing the distal cuff of the patch 1104 on the distal region of the inner delivery member 1202. The proximal portion of the patch abuts and is in contact with an outer pusher member 1204. In the non-deployed state, the delivery device is passed into the aperture of the annulus. Once inside the annular aperture, the outer pusher member 1204 of the delivery device 1200 is pushed toward the distal end of the device, while the inner delivery member 1202 is pulled proximally. This action of moving these members in such a fashion results in the braided patch expanding perpendicular to tube's axis, as shown in FIGS. 27 and 30.

Once the patch 1100 has been expanded to its fully expanded state, a cinch line 1212 that is connected to the distal and proximal ends of the patch can be tightened and a knot, such as a Roeder knot, can be used to hold the braided patch in its expanded configuration. Although, the device is shown with a cinch knot 1214, it is possible that a locking element may not be needed, depending on the means used to fixate the patch into the annulus. It is possible that no locking means is necessary. It is also possible that alternative locking means can be contemplated to keep the braided patch in its expanded form. A knot pusher 1210 can also be employed to manipulate the knot locking device 1214.

Once the device patch has been expanded into its final configuration in the aperture and subannular space, the retention member 1208 can be removed from the distal portion of the inner member by slidably pulling the proximal end of the retention member in a proximal direction. Removing the retention member relieves the stress holding the distal cuff of the patch in place and allows the patch to be slidably removed from the distal end of the delivery device, and thus deployed into the subannular space.

Figure 32:
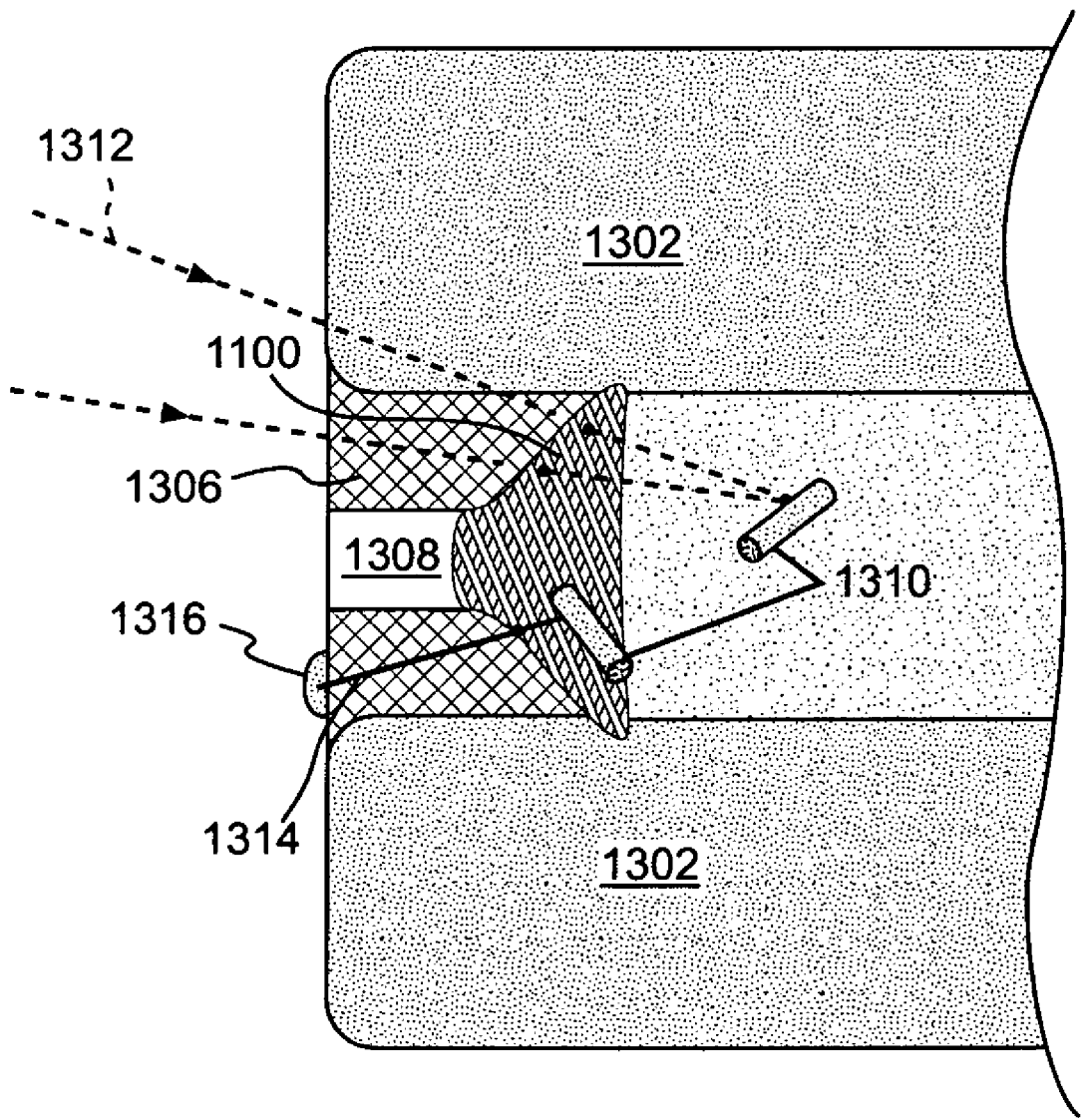
FIG. 32 shows a lateral view of an exemplary embodiment of the invention in an expanded configuration subannularly.

As depicted in FIG. 32, the patch 1100 can be affixed to the inner surface either before or after the deployment of the patch from the delivery device. It is also contemplated that this patch can be affixed to the inner surface of the annulus by the various fixation means described in other parts of this application. For example, anchor bands as shown in FIG. 32 could be used to penetrate the annulus 1306, shown between vertebrae 1302, and the patch to anchor the patch into the sub-annular space. It is also conceivable that single T-anchors 1310 with a band 1314 (e.g., suture) could be delivered through the annulus 1306 and patch 1100 with the portion of the suture on the outer surface of the annulus locked to the outer surface with a knot, pledget, or other locking device 1316. Path 1312 illustrates another possible suture path through the bone of the vertebra to penetrate and hold a T-anchor member 1310 in the patch. It is also conceivable that the patch could be affixed to the inner surface of the annulus through the use of adhesives, such as cyanoacrylate, fibrin glue, polymer protein, polyurethane, compounds that mimic mussel shell adhesive proteins (manufactured by Nerites Corp.), adhesive materials that may be used as adhesives for dural or dermal wound repairs/sealing, or other material used to cure, or adhesively affix the patch in the subannular space in situ. The delivery of these adhesive fixation materials could be delivered through the patch delivery tool, as depicted in FIG. 76 or through the anchor band delivery tool, FIG. 77, or both. FIGS. 76 and 77 are illustratively intended to depict an alternative embodiment (further described below) of the invention in which a nuclear replacement material 218 may be delivered to the intervertebral disc, although they may also exemplify methods and devices to delivery adhesive materials. It is also contemplated that if an adhesive were used to affix the patch to the annulus that an additional membrane material may be added to the patch device to further help restrict fluidic extravasation of the material out of the disc during adhesive delivery, if required. Conversely, the patch construction may be altered to reduce the patch porosity in order to accomplish a similar objective. Furthermore, it is anticipated that materials maybe added to, or changed, on portions the delivery tools to reduce the possibility of the tools being adhesively bonded to the instruments during delivery. For example, cannula 526 in FIG. 76 may be coated with, or be constructed of, PTFE, FEP, polypropylene, polyethylene or other lubriocious materials or coatings. Similarly, portions of delivery device 400 in FIG. 77 may have similar material treatments to accomplish the same objective.

The advantages of the braided design, given the right selection of filament dimension, configuration, material, braid pattern, and number of filaments is that it can be easily delivered to the annular repair site, have the flexibility to take the shape of the annular defect while maintaining the mechanical integrity needed to remain within the disc space upon loading. Another advantage, again with the appropriate selection of material, filament configuration, braiding, dimensional considerations, and multiple filament weaves, is that one can construct a patch that is conducive, in its deployed state, for incorporation of fibrosis and the fibrotic healing of the annular defect. Finally, the patch can be designed so that when it is in its delivered state, it can easily receive one or more anchor bands through the braided filaments while retaining the T-anchor or other similar type fixation device, after passing the fixation device through the patch.

FIGS. 33-41 depict an illustrative method for the deployment of a treatment device into the intervertebral disc 200. As described previously, there are a variety of applications, approaches, techniques, tools, and methods for accessing and performing spinal disc surgery which may be dependent on physician preferences and could be arbitrary. Therefore, the following description and depiction of the method should be considered illustrative and not limiting. In the illustrative scenario which is used in the following descriptions, and with reference to FIG. 33, the disc 200, which is comprised of the annulus fibrosus 202 and the nucleus pulposus 204, is shown in a transverse cross section. The disc 200, as described above, is disposed anatomically between caudal and cephalad vertebral bodies, which a portion of a vertebral body (spinous process 206) seen in FIG. 30. The disc 200 may be accessed for treatment via a surgical incision 208 made in the paramedian region lateral of the spinal canal 210. A microdiscectomy procedure may precede the placement of a treatment device in order to remove disc fragments and to provide a subannular cavity 212. The subannular cavity 212, however, may be preexisting or may be created for the purpose of performing a nuclear augmentation An aperture 214 in the annulus provides a path for the mesh or treatment device delivery tool 500 to place treatment device 600. The treatment device 600 can take the form as described in the embodiments above, or as additionally described below with reference to FIGS. 63-64, as described in commonly-assigned copending U.S. patent application Ser. No. 10/352,981, filed on Jan. 29, 2003 and incorporated herein by reference, or any other appropriate form. Likewise, the anchor band delivery device 400 can take the form as described in the embodiments above, or as additionally described below with reference to FIGS. 47-52, as described in commonly-assigned copending U.S. patent application Ser. No. 10/327, 106, filed on Dec. 24, 2002 and incorporated herein by reference or any other appropriate form.

Figure 33:
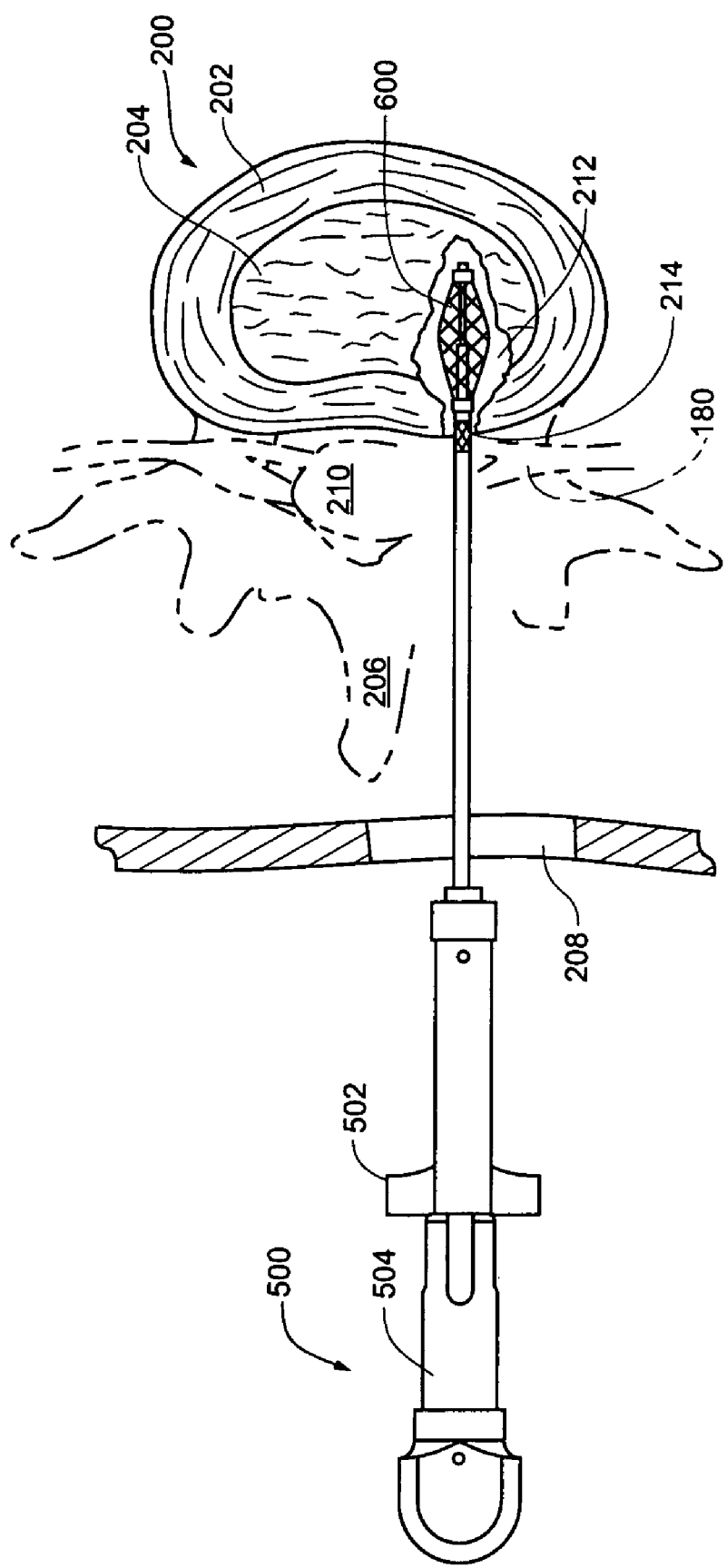
FIG. 33 shows a transverse view of a treatment device mounted on a delivery tool in an unexpanded configuration in the subannular cavity.
Figure 34:
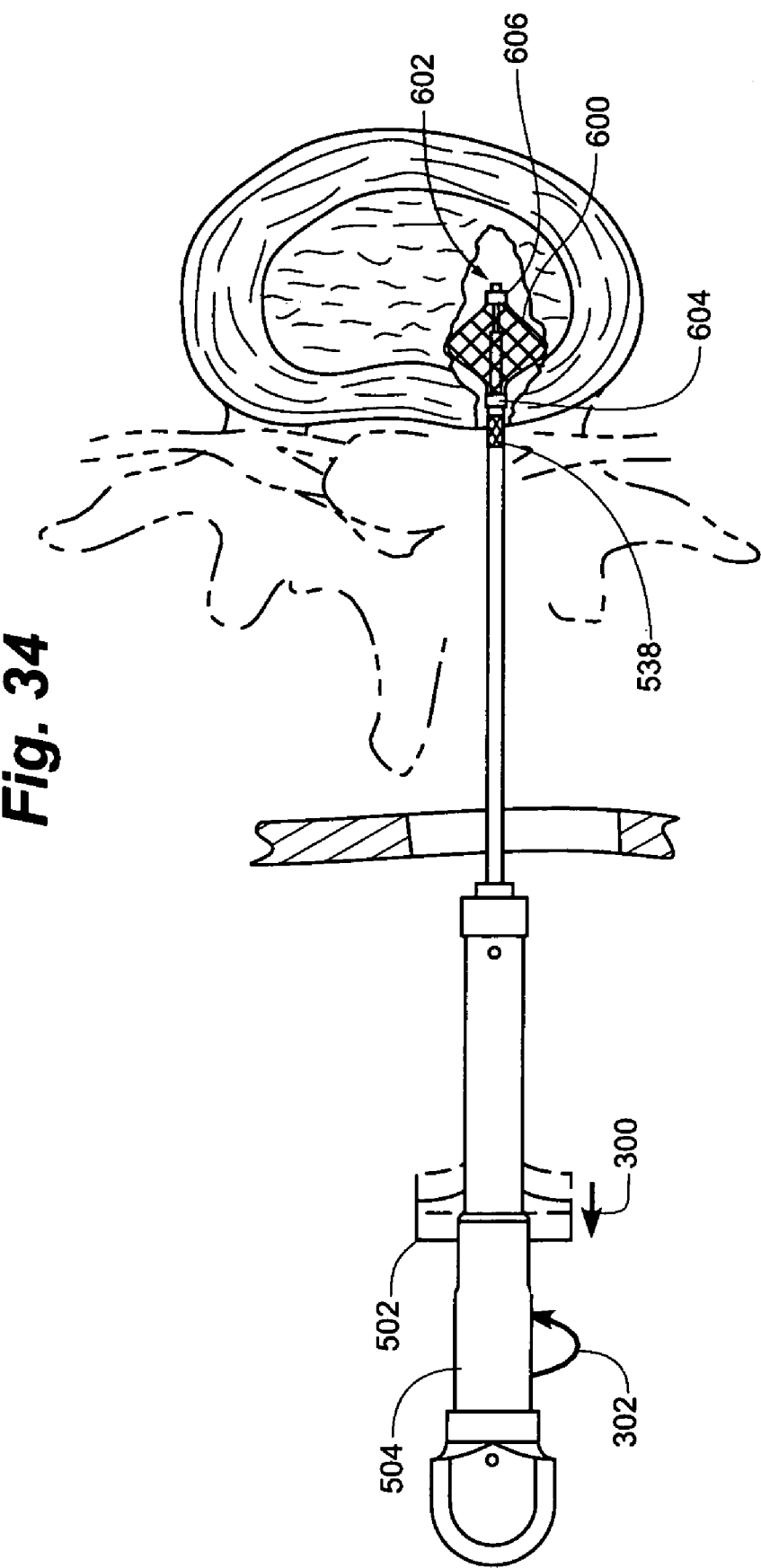
FIG. 34 shows a transverse view of the treatment device being deployed into an expanded configuration in the subannular cavity.
Figure 39:
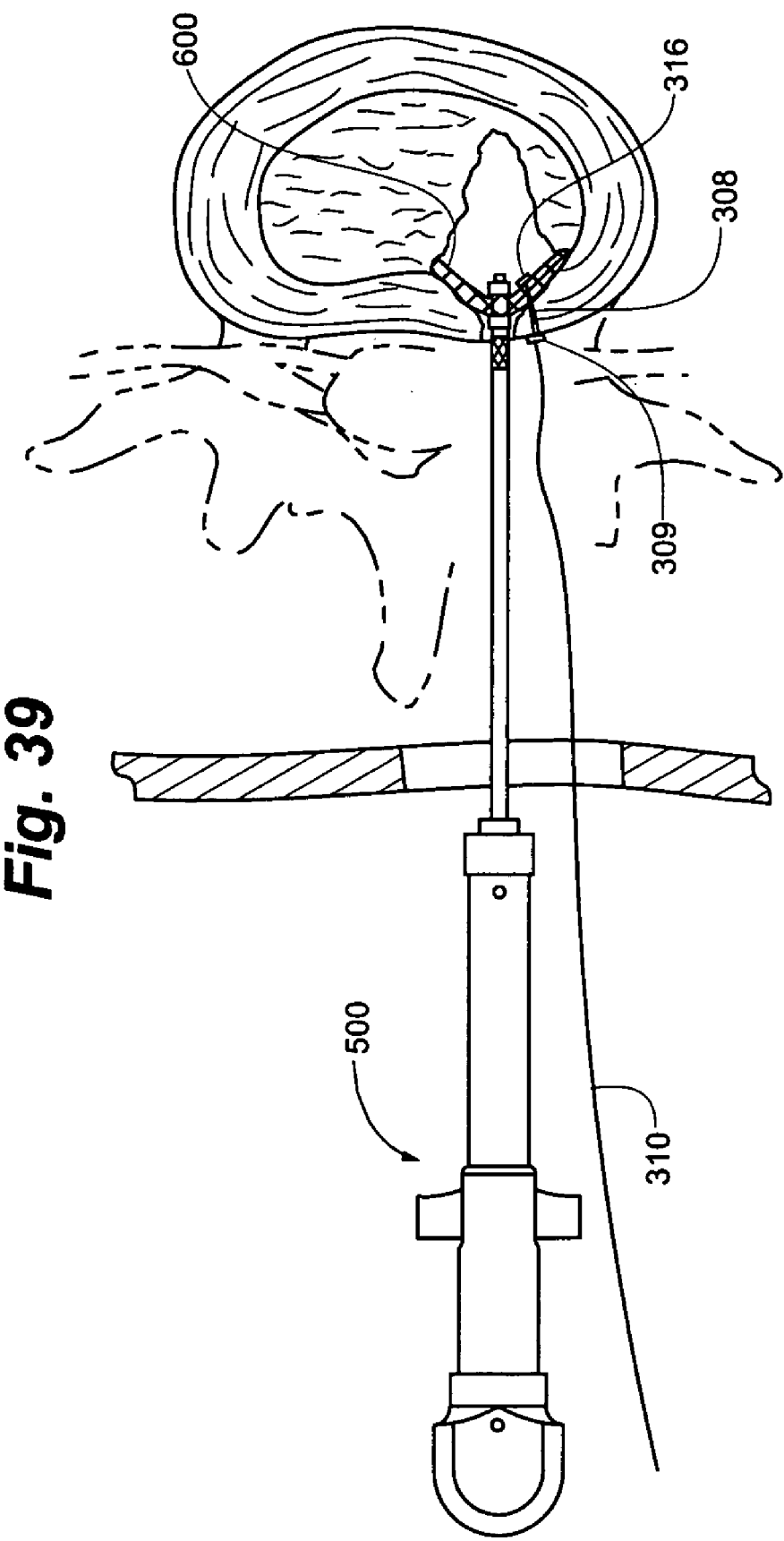
FIG. 39 shows a transverse view of the fixation element after removal of the fixation element delivery tool.

As shown in FIG. 33, a delivery device 500 is introduced through surgical incision 208 to traverse aperture 214 and position treatment device 600 in subannular cavity 212. As depicted, treatment device 600 is in a first configuration sized to permit its passage to the subannular cavity 212. FIG. 39 shows a detail, sagittal view of mesh device 600 mounted on the distal portion 602 of delivery tool 500, introduced to the cavity. Also shown are sections of intervertebral disc tissues. As illustrated, treatment device 600 may have element 608 to latch the mesh device once deployed into its final deployed configuration. If required, there may be a variety of ways to latch, lock or otherwise secure the device in its final configuration, as described previously, or additionally depicted and described below in FIGS. 71A-E below As depicted in FIG. 34, the treatment device delivery tool 500 can be manipulated by, for example, pulling a finger grip 502 in the direction of arrow 300 to deploy treatment device 600 in the subannular cavity 212. As illustrated here, this deployment involves a longitudinal shortening of the treatment device, drawing end 606 toward end 604, resulting in a lateral expansion of the treatment device 600. The pulling of the finger grip 502 may be preceded by the release of a safety lock 504 preventing deployment of the treatment device until intended by the surgeon. As illustrated here, the lock is released through rotation of handle member 504 in the direction of arrow 302. Also shown is a marking 538 on the delivery tool 500 that may visually assist the surgeon in assessing the degree to which the device has been placed in subannular space.

Figure 35:
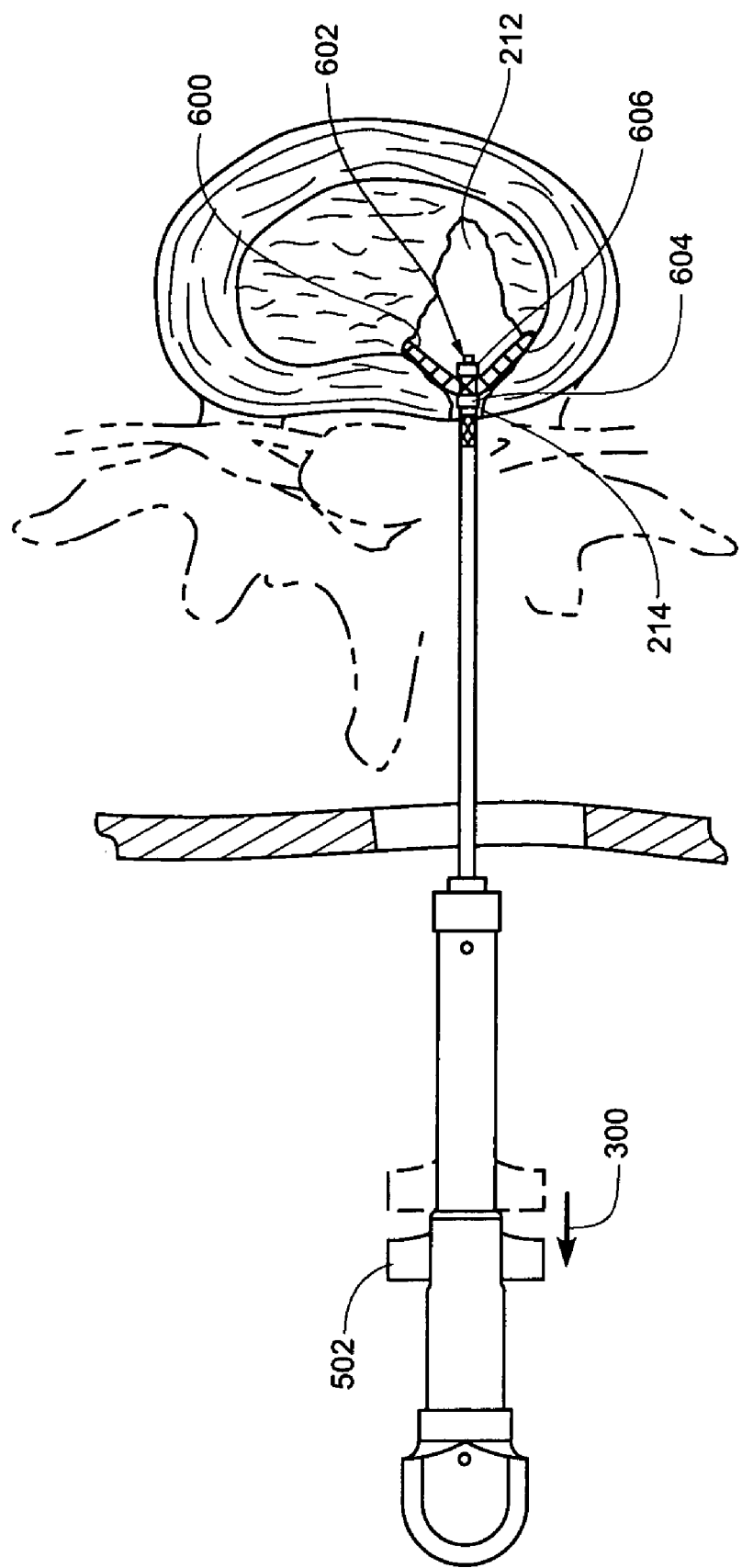
FIG. 35 shows a transverse view of the treatment device fully deployed and adjacent the annular wall.

FIG. 35 shows the finger grip 502 reaching its intended limit, and the concomitant full intended deployment of treatment device 600, where end 606 reaches its intended design position for the deployed configuration of the device 600. In this illustrative depiction, end 606 is pulled adjacent to end 604, and device 600 has reached its maximum intended lateral expansion. As shown, the deployed device 600 may be pulled to internally engage and at least partially conform to the cavity 212. Naturally, the full travel of the finger grip 502 can be determined by the design of the delivery device, or informed by the judgment of the surgeon through visualization, tactile realization, or the like. Once the intended limit has been achieved and the device fully deployed, the delivery device 500 can lock finger pull 502 in place so as to maintain the treatment device 600 in the deployed configuration. It may also be advantageous for the delivery tool 500 to have a perceptible (i.e., audible, tactile, visual) indication that the treatment device has been fully deployed. The mesh/patch delivery tool 500 may be of the type described hereinabove, or as additionally described in FIGS. 57-62 below, or in other sections of this disclosure.

Figure 36:
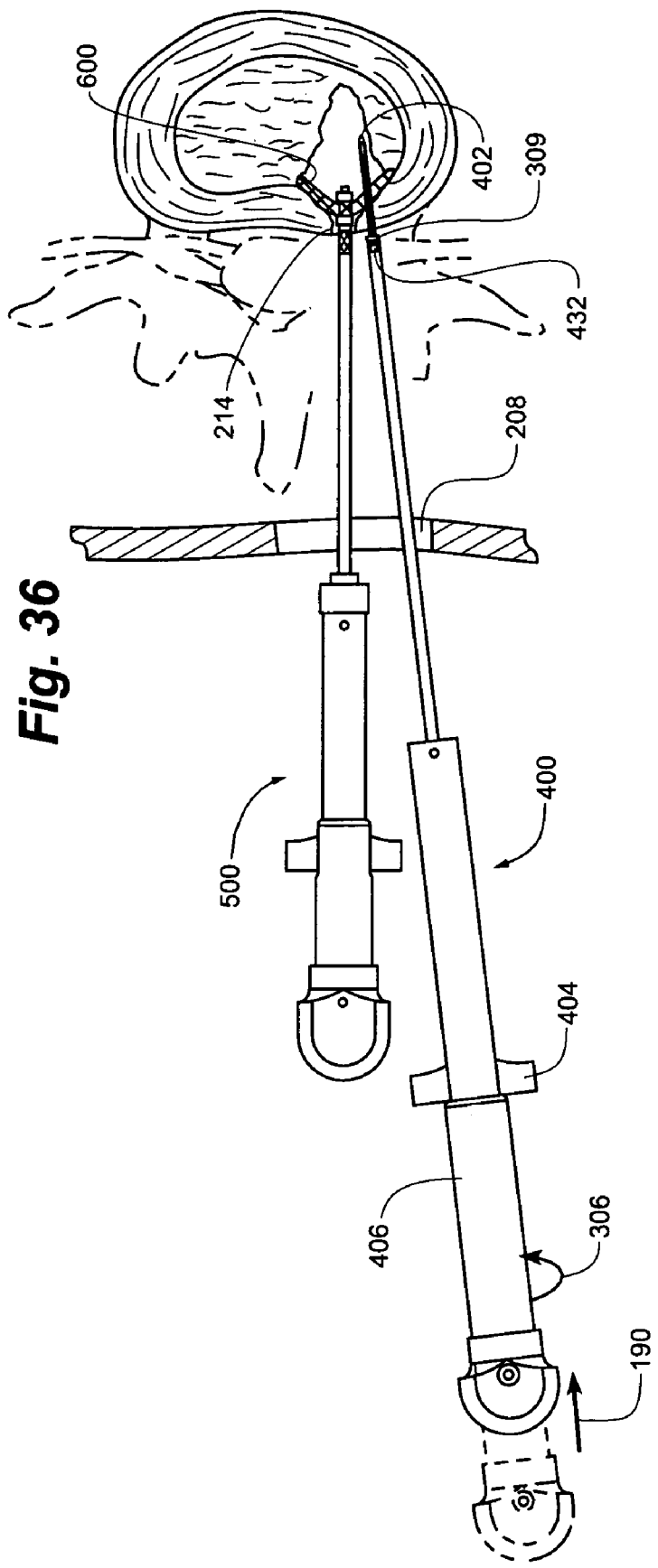
FIG. 36 shows a transverse view of the placement of a fixation element delivery device into the deployed treatment device.
Figure 37:
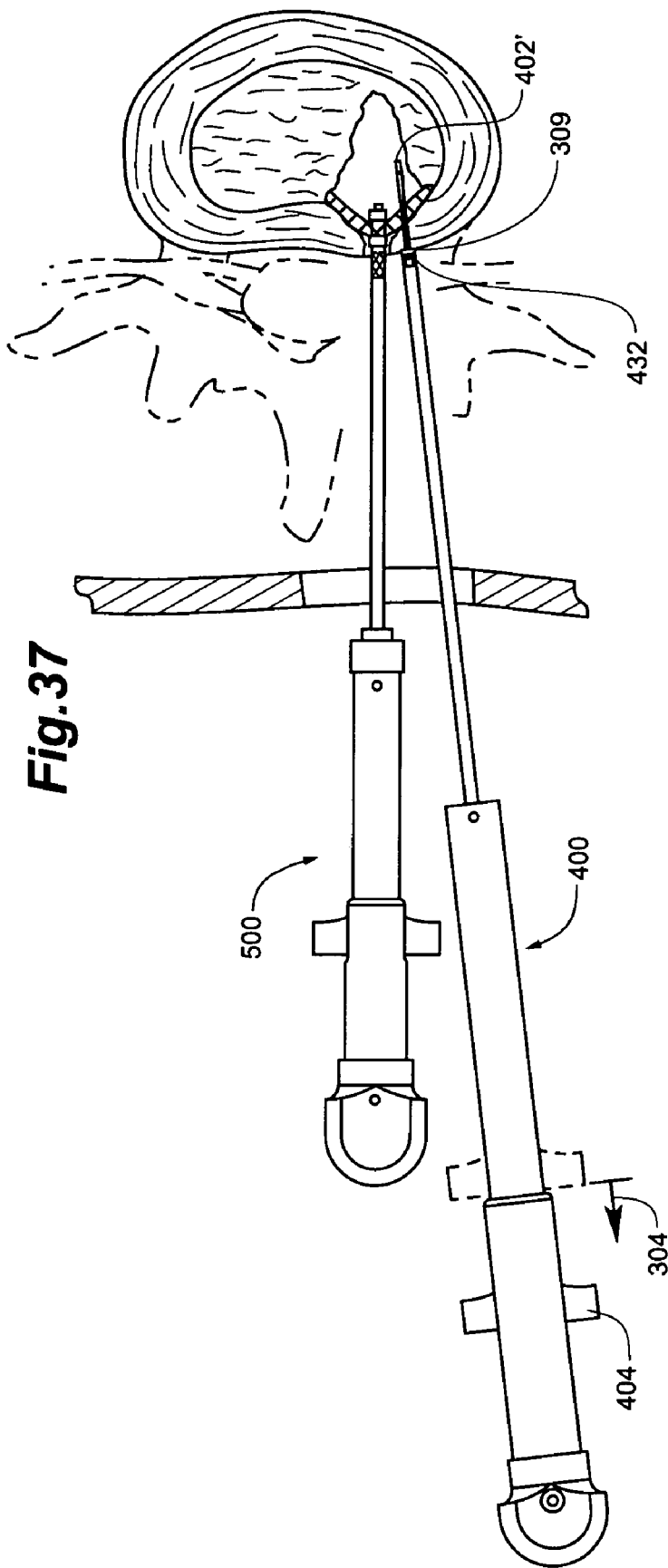
FIG. 37 shows a transverse view of the placement of a fixation element through the treatment device and the annular wall.
Figure 44:
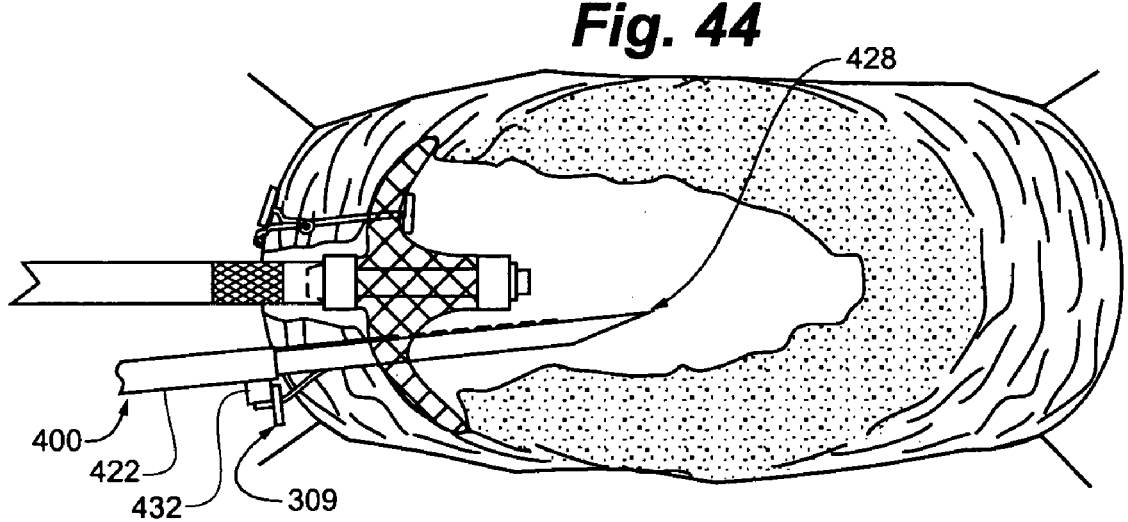
FIG. 44 shows a transverse view of the placement of a fixation element delivery tool through the treatment device and the annular wall.
Figure 45:
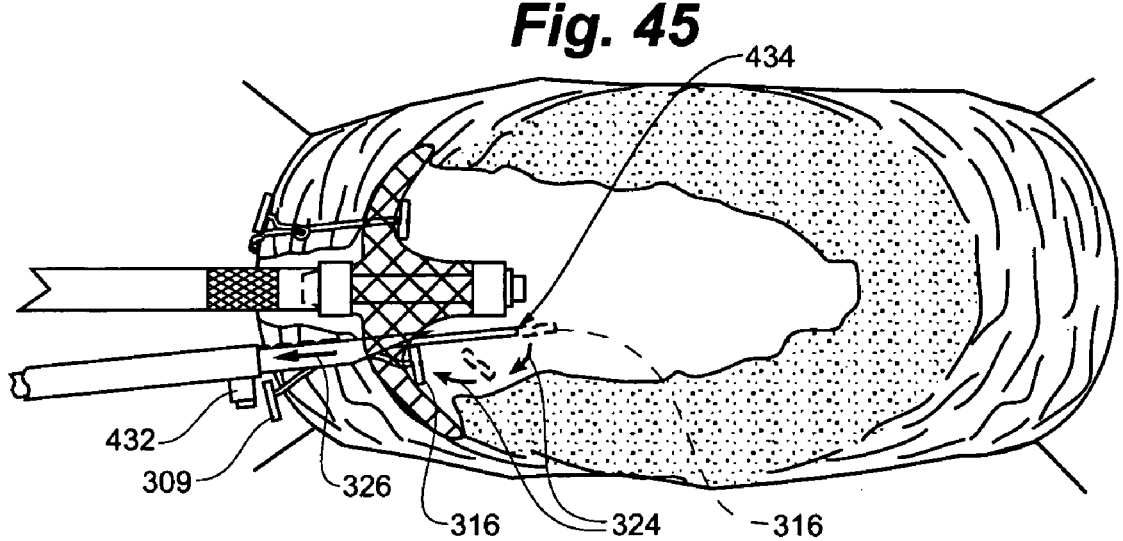
FIG. 45 shows a transverse view of the placement of an additional fixation element through the treatment device and the annular wall.

FIG. 36 next depicts a fixation element or anchor band delivery device 400 introduced through surgical incision 208, where the distal end 402 is passed through the annulus fibrosus 202 adjacent to the aperture 214, and subsequently through treatment device 600, as illustrated by arrow 190. Fixation element delivery tool 400 may have features to provide tactile feedback once the delivery tool has been introduced into tissue to an acceptable extent, for example a feature like tissue-stop 432. As illustrated, delivery device 400 is passed distally until stop 432 and pledget member 309 of the fixation device 308 come in contact with the outer surface of the annulus. Alternatively, and without tissue stop 432 use, pledget member 309 could be of construction to similarly resist, or otherwise visually or tactilely indicate ceasing the passage of delivery device 400 through annular tissue. FIG. 44 shows a detail, sagittal view of a distal end of a fixation element delivery tool 400 introduced into disc tissue and through treatment patch 600. As shown in FIG. 44, one fixation element has been deployed and fixated. FIG. 44 also depicts an exemplary treatment device detection feature 442 on the outer surface of needle cannula 428, as more clearly illustrated in FIG. 48. The patch detection feature 442 on the distal end of needle cannula 428 may advantageously provide perceptible feedback (tactile and/or audible) to the surgeon that the anchor band delivery tool has accessed and penetrated the patch and it is therefore acceptable to deliver the band. Feature 442 is discussed in more detail below. In operation as illustrated in FIG. 36 and in FIG. 37, the delivery device 400 can be manipulated similarly to the treatment device delivery tool. For example, moving finger grip 404 in the direction of arrow 304 will withdraw a portion (for example, the slotted needle cannula 428) of distal end 402 of the device 400 and deploy a fixation element 308, as more described below, in the subannular cavity 212 to secure the treatment device 600. The pulling of the finger grip 404 may be preceded by the release of a safety lock 406 preventing deployment of the fixation element until intended by the surgeon. As illustrated here, the safety 406 is released through rotation of safety 406 in the direction of arrow 306. The fixation element delivery tool 400 may be of the type described hereinabove, or as additionally described in FIGS. 47-56 below, or in other areas of this disclosure FIG. 37 depicts the deployment of a fixation element, 308 into disc tissue following the deployment of FIG. 36. The fixation device may be as described above, for instance a T-anchor, suture, tether, knot, pledget or barb. As illustrated here, the fixation element 308 is a T-anchor with suture bodies, knot, and pledget as more fully described below. During the pulling of finger grip 404 and retraction of slotted needle cannula 428, a knot pusher end 406 of inner cannula 426 is shown holding a proximal portion of the fixation device's 308 slip knot 440, while T-anchor 316 is drawn in tension proximally by tether or suture line 310, to adjust the length of the fixation element 308 to provide the proper tension to securely hold the treatment device 600 in situ. A proximal end of the fixation element, such as a pledget 309, is held or urged into engagement with a bearing surface on the exterior of the annulus. The proximal end of the fixation device can also include a T-anchor or knot or similar tissue locking element. FIG. 48 is a cross sectional view of the distal end of delivery tool 400 as it may be introduced in disc tissue. FIG. 55 shows the distal end of the delivery tool 400 after retraction of the slotted needle cannula 428 and tensioning and drawing T-anchor 316 proximally to a potential final state. The proximal drawing of T-anchor 316 is also illustrated in a detail, sagittal view in FIG. 45, with arrows 324 illustrating motion of the T-anchor. The construction of the locking element 316 is exemplary and is not intended to be limiting of alternative constructions of 316, such as one or more pledgets, knots, barbs or other forms to effect the same function.

Figure 38:
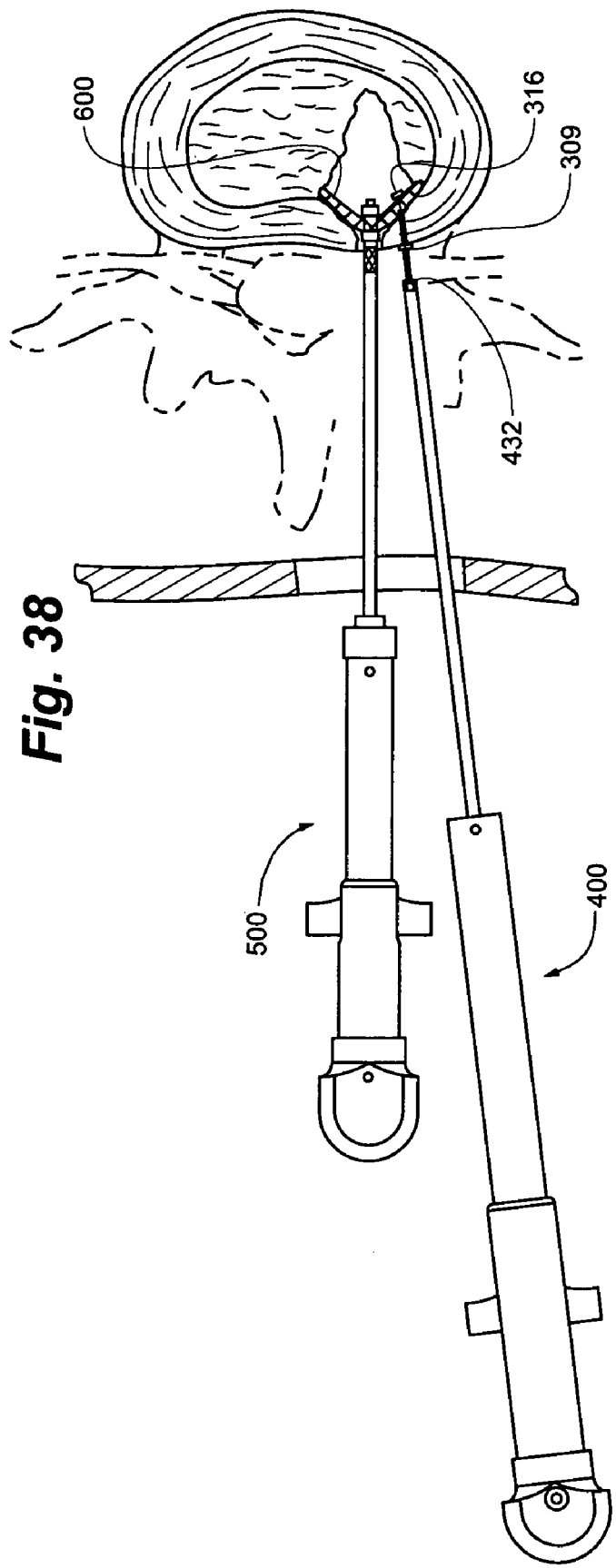
FIG. 38 shows a transverse view of after affixing a fixation element delivered in FIG. 37 and partial removal of the fixation element delivery device.
Figure 40:
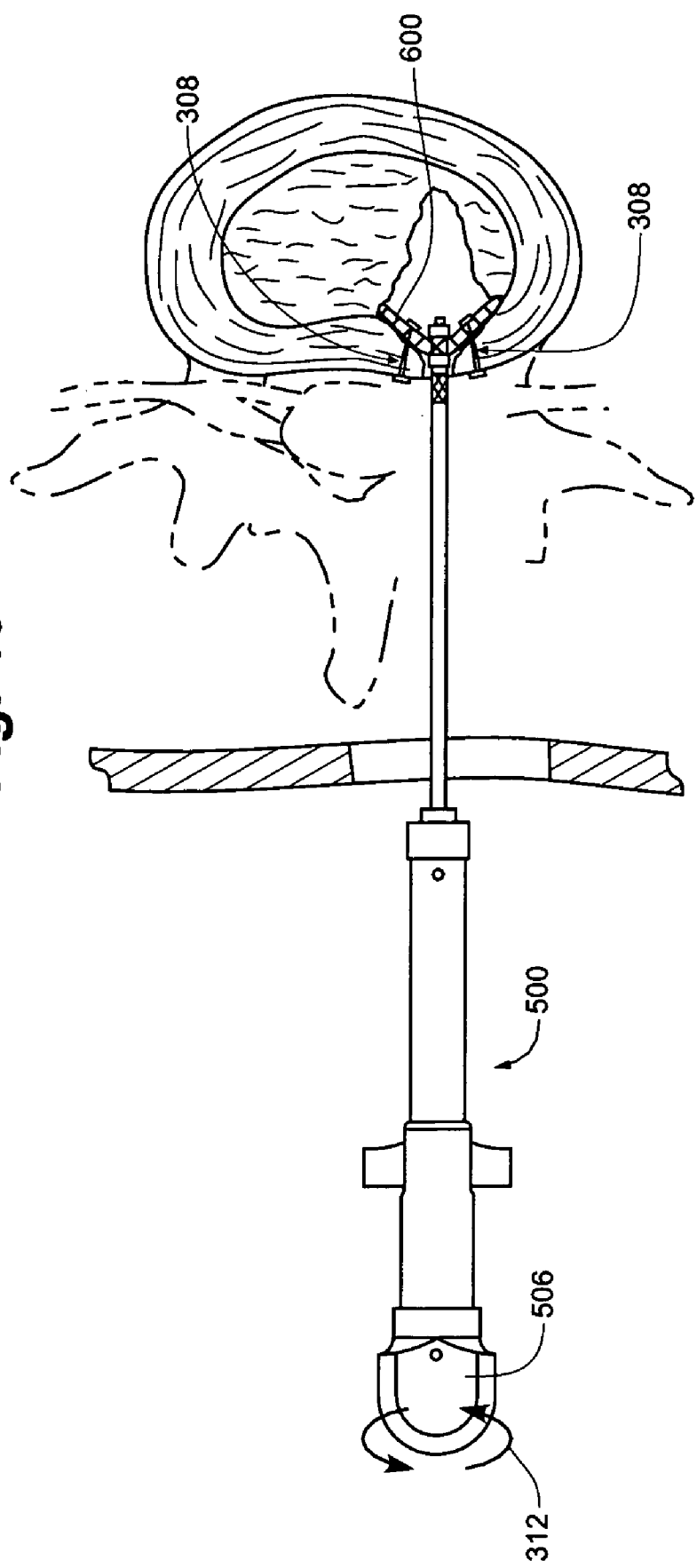
FIG. 40 shows a transverse view of an additional fixation element locked in place on the opposite side of the treatment device.
Figure 41:
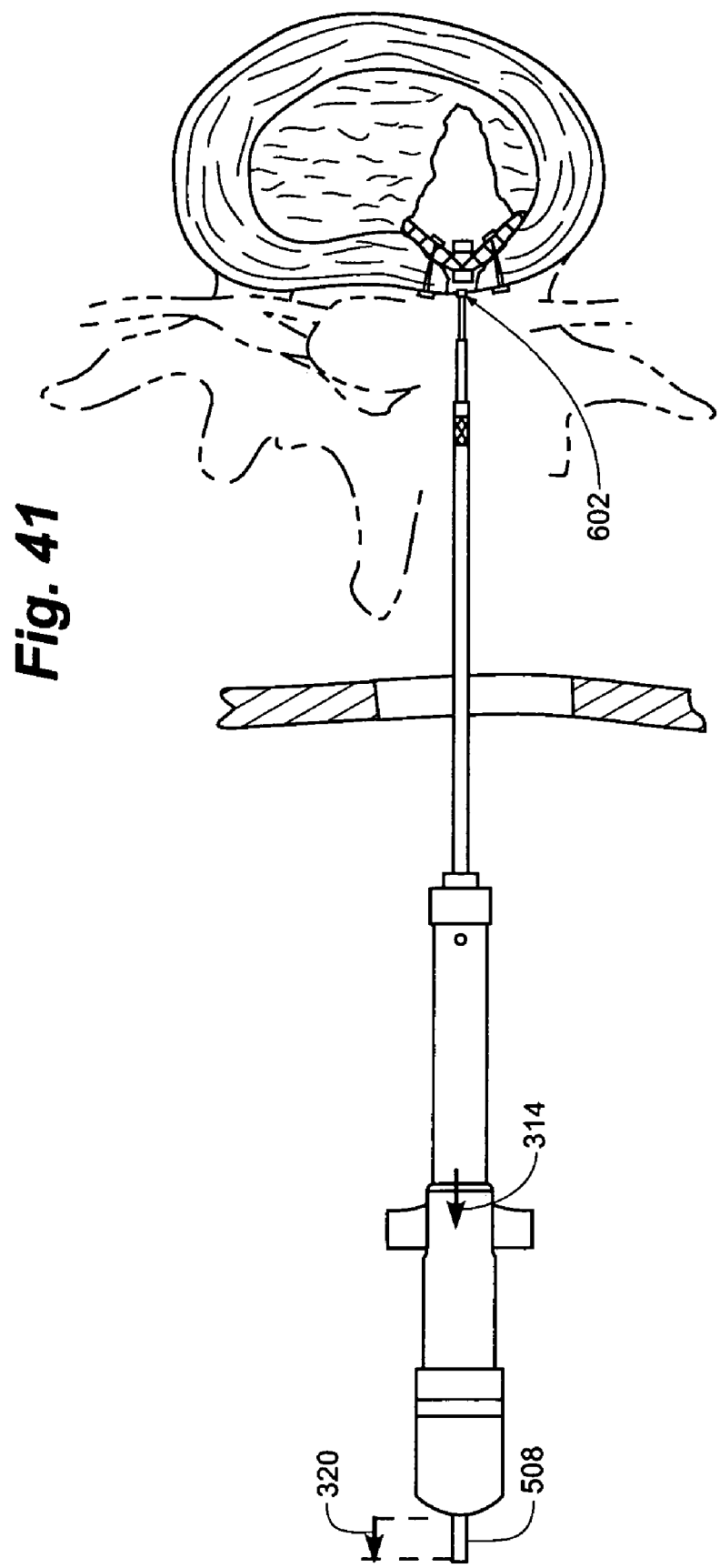
FIG. 41 shows a transverse view of the removal of the treatment device delivery tool.
Figure 42:
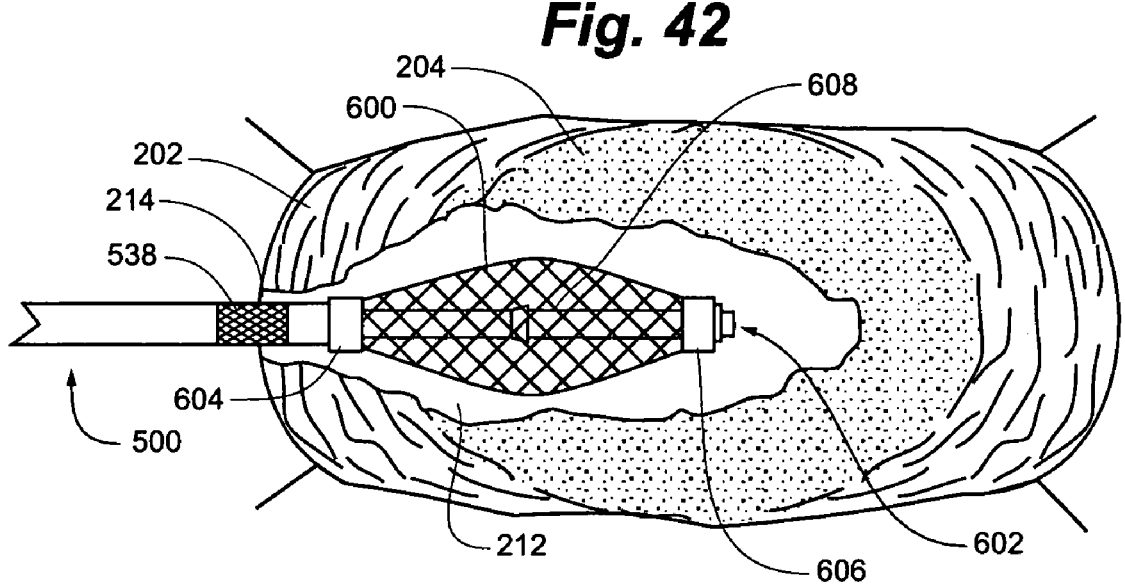
FIG. 42 shows an transverse view of an illustrative embodiment of a treatment device mounted on a delivery tool in an unexpanded configuration in the subannular cavity.
Figure 43:
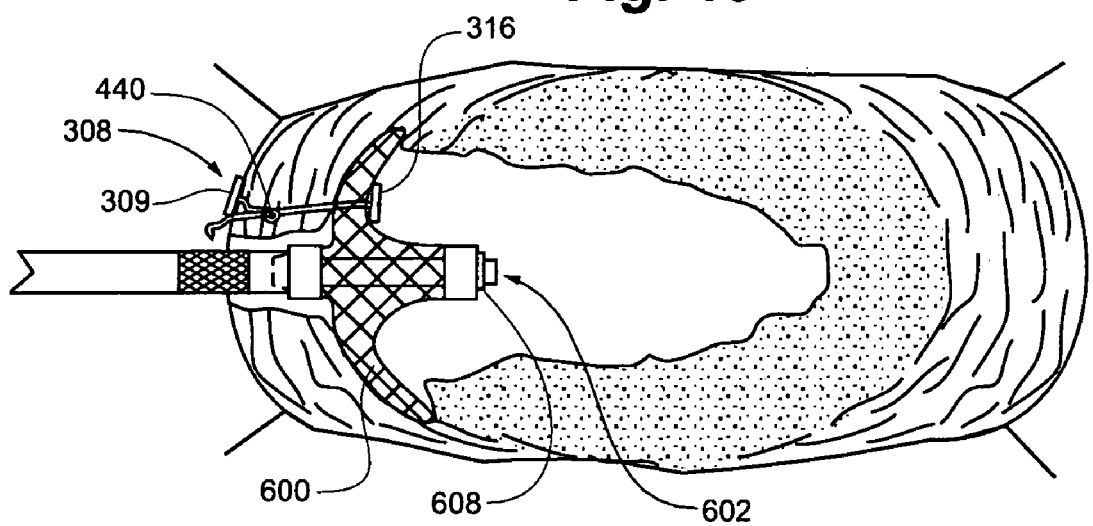
FIG. 43 shows a transverse view of after affixing a fixation element to the treatment device of FIG. 42.
Figure 46:
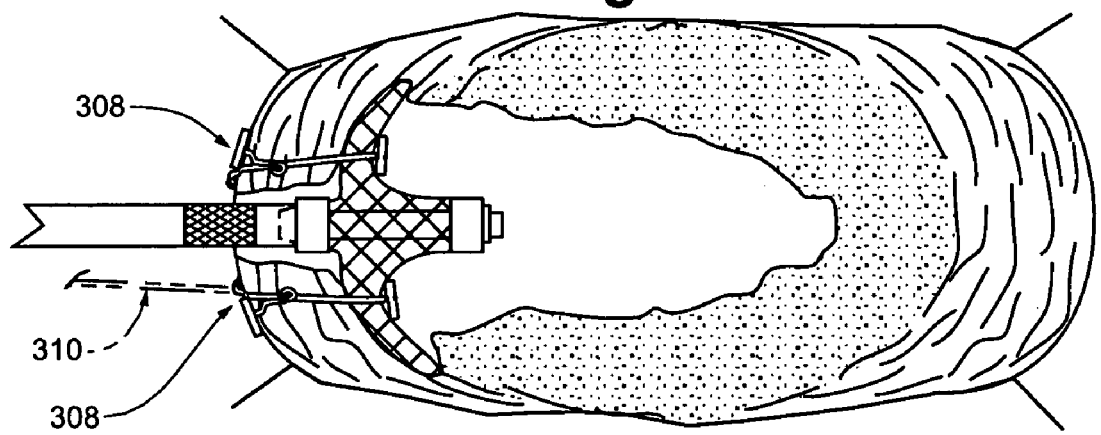
FIG. 46 shows a transverse view after the removal of the fixation element delivery tool.

FIG. 38 shows the partial withdrawal of the fixation element delivery device once the fixation element has been deployed. In the illustrations shown, the final step during the pulling of finger grip 404 proximally results in the release of the fixation element in situ. The release may be accompanied by visual or tactile or auditory confirmation, such as a click. Once released, the fixation element delivery tool can be completely withdrawn as shown in FIG. 39, leaving the suture body 310 of a fixation element extending through the surgical incision 208. The proximal portion of suture body 310 may be cut to a suitable length with readily available surgical tools such as a scalpel or surgical scissors and removed from the surgical site. FIG. 43 shows a detail, sagittal view of a single deployed anchor band assembly 308 with T-anchor 316, pledget 309, slip knot 440 and associated tether components 318 and 310 (after it has been cut in the epi-annular space). Also shown are portions or sections of intervertebral disc tissues. As shown, fixation element 308 is fixedly engaged with the disc tissue and the patch 600. FIG. 40 depicts the treatment device 600 after placement of 2 fixation devices 308, as does FIG. 46 shown in a detail, sagittal view Of course, any number of fixation devices appropriate to secure the treatment device 600 can be used. It is also anticipated that device 600 may be of a construction and design, as described herein, that does not necessitate anchor bands to effect securement of device 600 within the disc space and therefore, illustrations using fixation elements are to be exemplary, and not limiting. Once secured, the treatment device 600 is released from the delivery tool 500. As illustrated here, this is accomplished in a two-step process. First the release mechanism is enabled by rotating knob 506 in the direction of arrows 312. An indicator may then be activated as shown by arrow 320 of indicator 508 in FIG. 41, such as spring-loaded release indicator 508 to notify the surgeon that the treatment device has been released from the delivery tool 500. Accompanying the deployment of indicator 508 is the uncoupling of the treatment device 600 at the distal end 602, as will be described in greater detail below. The delivery tool 500 can then be withdrawn as depicted in the transverse view of FIG. 41, leaving treatment device 600 in situ.

FIGS. 47-53 depict illustrative embodiments of an fixation element delivery tool (or FEDT) as discussed above, which may be referred to alternatively as an anchor band delivery tool (or ABDT). The fixation element 308 is depicted as loaded in the distal end 402 of the ABDT, which will be discussed in greater detail with reference to FIG. 48. The ABDT 400 is comprised of a main body member 410 which may be fixedly attached distally to outer cannula 422, and also to inner cannula 426 at inner cannula anchor 438. Distally, inner cannula 426, as better illustrated in detail in FIG. 48, may comprise a knot pusher (or other means to effect securement of suture tethers 310 and 318 with locking element 440) and T-anchor stand-off 434. Proximally, main body 410 has disposed safety member 406 with an outside diameter telescopically and rotatably received in the inner diameter of a knob 408. Knob 408 and main body member 410 are rigidly attached to one another Slidably disposed within the lumen of the main body member 410 is suture retention block 414, depicted with suture body 310 threaded through its center hole. A spring 316 is also slidably disposed within the lumen of the main body member and can abut either suture retention block 414 or slider member 418. Slider member 418 can be integral with finger grip 404 (not shown) as depicted in FIGS. 36-38. Attached to the proximal end of slider member 418 is a suture cutting blade assembly 420. The blade assembly, as will be discussed in greater detail below, serves to sever the suture body after deployment of the fixation elements as described herein. A slot in the slider member 418 allows the slider member 418 to slide past the outer cannula anchor 426 and, as described previously, 426 may be stationary with respect to main body 410. A slotted needle cannula 428, slidably disposed in the lumen of the outer cannula 422, is secured the distal end of slider member 418 by needle cannula anchor 430, such that the translation of the slider member 418 within main body member 410 concomitantly translates the slotted hypotube 428 within the outer cannula 422.

FIG. 48 is a detailed view of the distal end 402 of the ABDT 400. As described above, the slotted hypotube 428 is slidably received in the outer cannula 422. A tether, consisting of a suture line 318 and a pledget body 309 is located in proximity to an optional tissue stop 432 on the outer cannula 422. It is also possible for pledget 309 to be held by an optional outer cannula pledget holder 433 until release of the anchor band. The suture line 318 is slidably knotted to suture body 310. The distal end of suture body 310 is attached to T-anchor 316, which is held by T-anchor stand-off 434. As described above, T-anchor stand-off 434 and knot pusher 436 may be components of inner cannula 426. In the initial configuration, needle hypotube 428 extends distally of outer cannula 422 and allows the point of slotted hypotube 428 to extend distally of the T-anchor holder 434.

Figure 49:
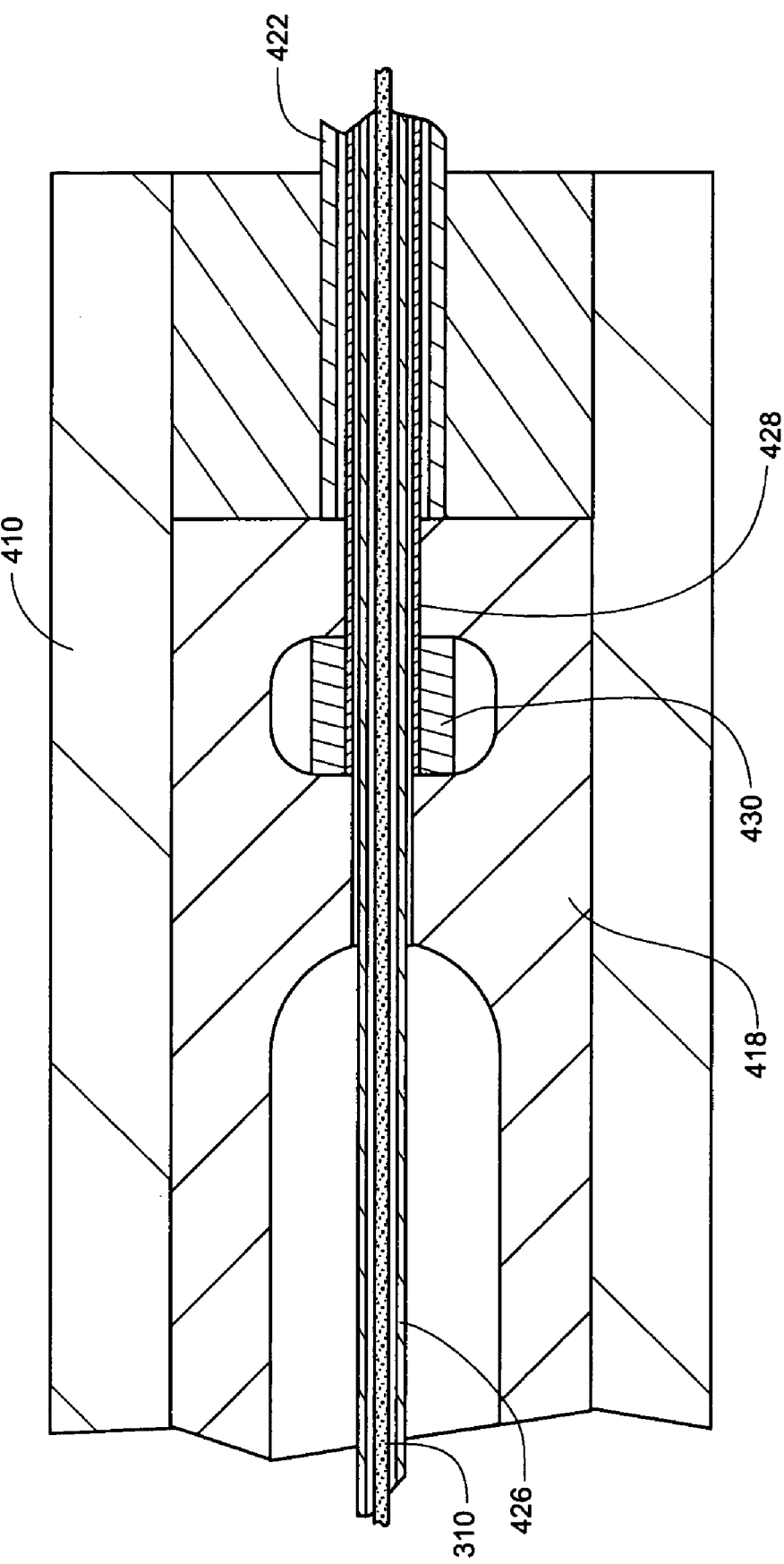
FIG. 49 shows a detail of the slide body and cannula anchor of an exemplary fixation element delivery tool in cross section.
Figure 52:
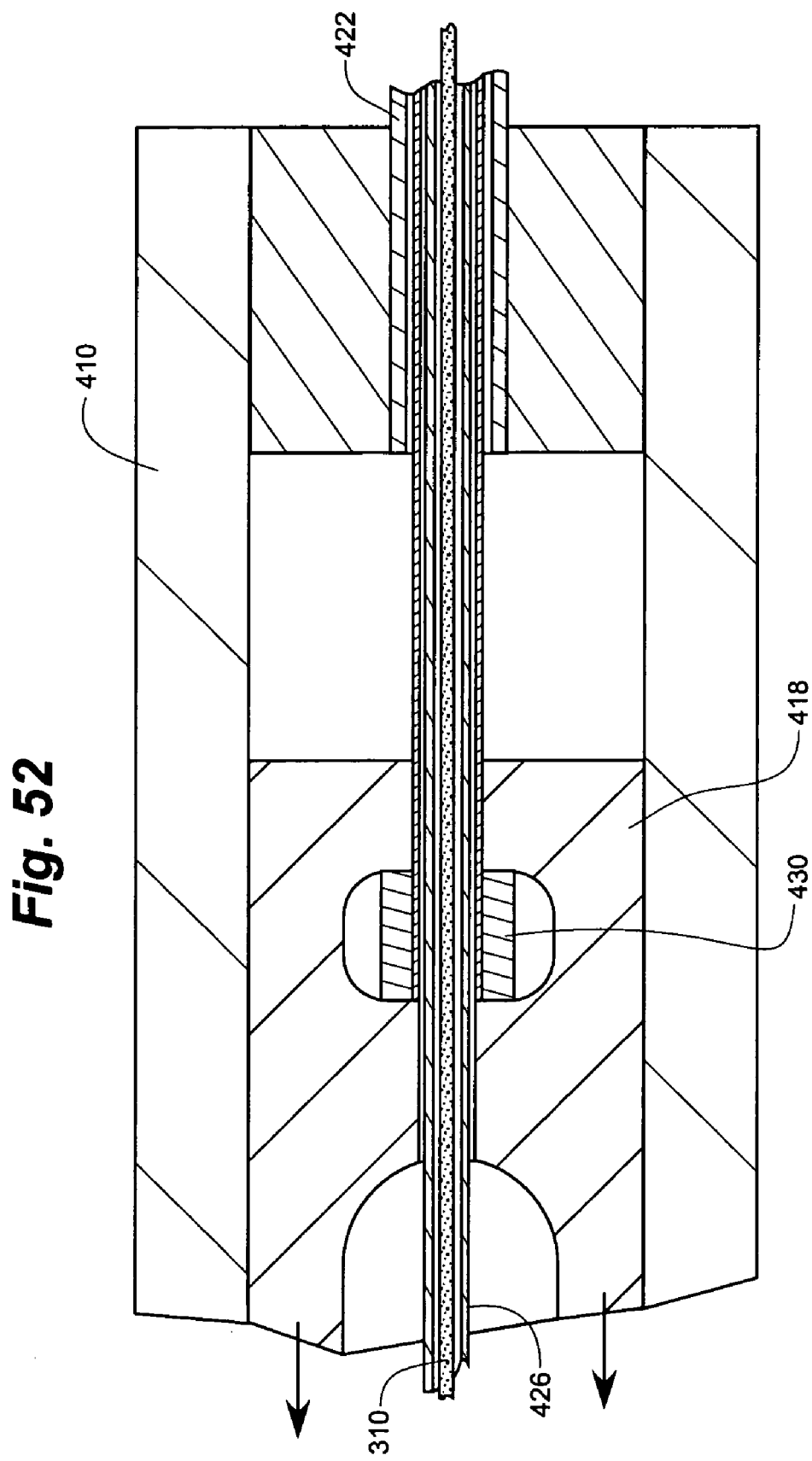
FIG. 52 shows a detail of the slide body and cannula anchor of an exemplary fixation element delivery tool in cross section during a deployment cycle.
Figure 53:
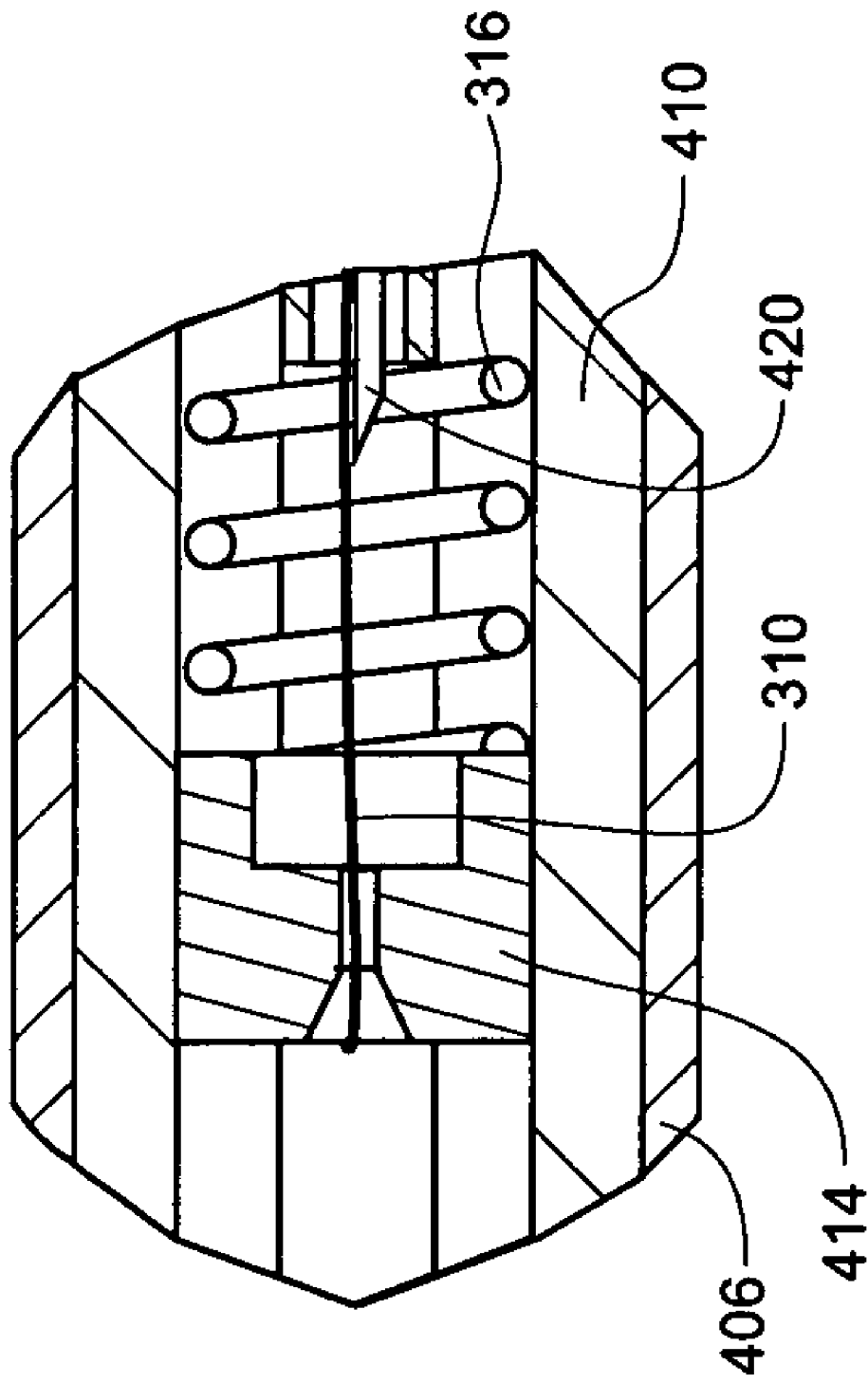
FIG. 53 shows a detail of the suture retention block and blade assembly of the anchor band delivery tool.

FIGS. 47 and 48 depict the ABDT in its initial delivery configuration. The ABDT is locked in this configuration by the distal end of safety 406 engaging the finger grip 404 (not shown) as depicted in FIGS. 36-38. Turning now to FIG. 36, the rotation of handle member 406 in the direction of arrow 306 allows the finger grip 404 (not shown) to engage a slot on safety 406, and permits the surgeon to pull finger grip 404 proximally toward the proximal knob 408. Doing so results in the translation of the slider member 418 proximally, and concomitantly, the proximal translation of the slotted needle cannula 426 (as a result of slotted needle cannula anchor 430) in the direction of arrow 326 (illustrated in FIG. 45). The result, as discussed above, is the unsheathing by the needle 428 of T-anchor 316 held by T-anchor holder 434. The translation of the slide body 418 proximally also urges the spring 416 and suture retention block 414 proximally. The suture retention block 414 is attached to suture body 310, and therefore tension is leveraged onto the suture body 310 to hold it taught and, when appropriate, draw T-anchor 316 from within the delivery tool to a position proximally FIGS. 50 and 51 illustrate the partial deployment of anchor band assembly from ABDT, wherein slotted needle cannula 428 has been partially retracted to expose T-anchor 316. FIG. 49 is a detail, cross sectional view of the distal end of the handle of ABDT 400, illustratively showing the inter-relationships of delivery tool components in the initial configuration and FIG. 52 is a similar detail, cross sectional view showing the inter-relationships after at least a partial deployment of device 400. FIG. 53 is a detail of the suture retention body 414, suture body 310, spring 316 and cutting assembly blade 420, during partial deployment of delivery tool 400, as discussed above.

Figure 56:
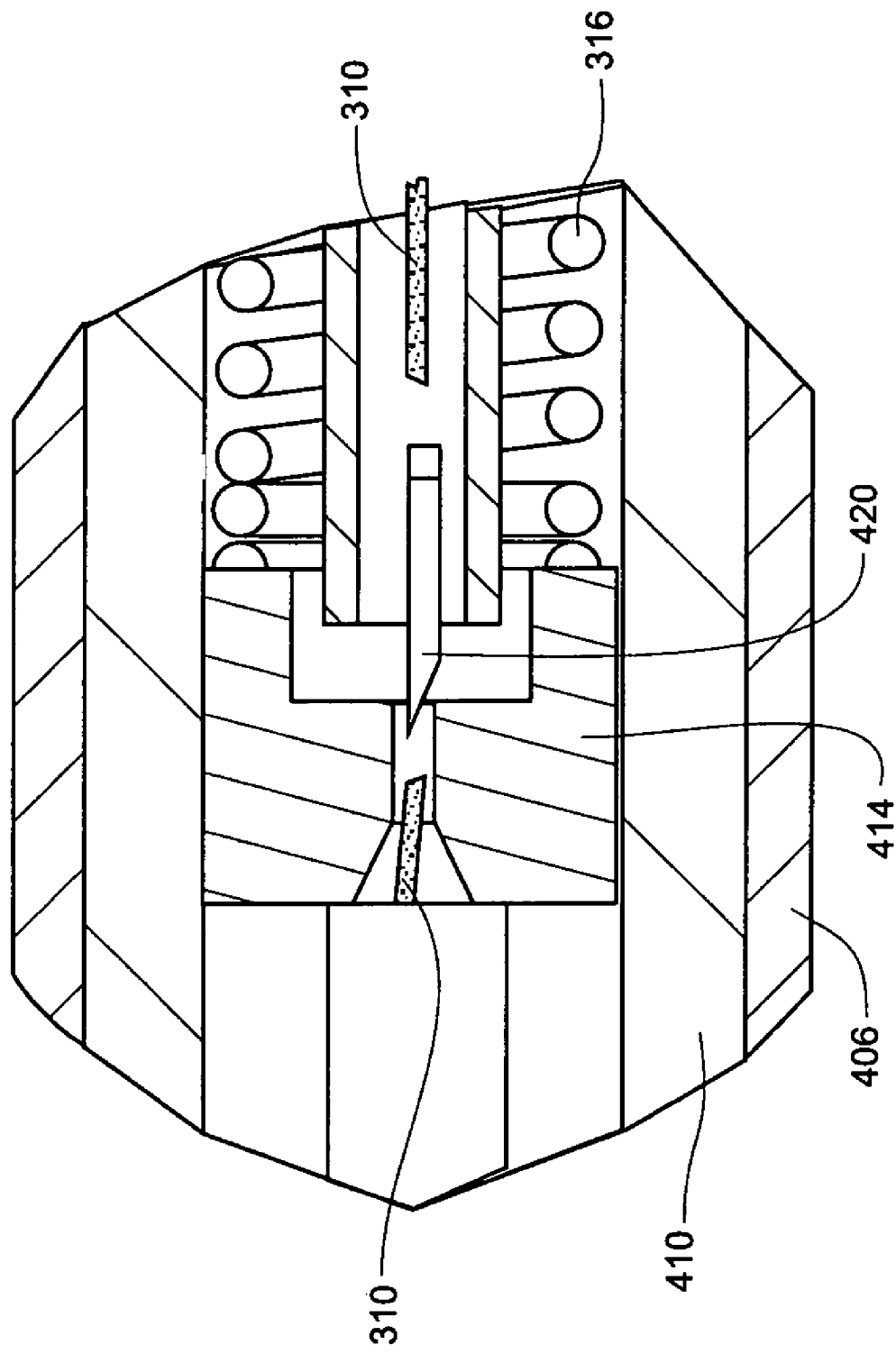
FIG. 56 shows a detail of the shows a detail of the suture retention block and blade assembly of the anchor band delivery tool during the cutting of the tether.

As depicted in FIG. 54 and detail drawings of FIGS. 55 and 56, as slider body 418 continues to slide proximally, in addition to continuing to draw T-anchor as shown in FIG. 55 with arrows, the tether retention block 414 reaches the limit of it's proximal translation (discussed further below), and the slider member engages and compresses spring 316. As the spring is compressed, the blade assembly 420, which is aligned with the hole of suture retention body 414 through which suture body 310 passes, comes into engagement with the suture body 310. FIG. 56 is a detail view of the blade 420 severing the suture body 310. Up to the limit of travel of the suture block 414 and the severing of tether 310, the suture body 310 continues to apply tension to the T-anchor, as shown in greater detail in FIG. 55. With knot pusher holding knot 440, pledget 309, and suture 318 in apposition, and in distally exerted fashion, to the tensioning of suture body 310, anchor band assembly 308 is advantageously cinched into a fixing and/or compressive relationship between ends 309 and 316, as well as any structures (e.g., nucleus, annulus, treatment device) between elements 309 and 316. After severing suture body 310, suture body 310 is still attached, to the anchor band, but has at this point been severed proximally. The suture body 310 will therefore be unthreaded from the interior of the ABDT as the ABDT is withdrawn. As discussed above the suture line 310 may be further cut to length with readily available surgical scissors. Alternatively, a severing mechanism similar to those described herein in the distal portion of tool 400 may be employed to avoid an additional step of trimming the end of body 310.

FIG. 53 is a detail of the suture retention body 414, suture body 310, spring 316 and cutting assembly blade 420, during partial deployment of delivery tool 400, as discussed above Additionally inventive of the anchor band device (and its delivery and deployment tools) is the unique inter-relationship of the slide body, spring, and the tension delivered to the T-anchor and tissue during deployment. For example, T-anchor assembly can be designed to pass through softer, or otherwise more pliable tissues (e.g., nucleus pulposus, softer annular layers) while resisting, under the same tension, passage through tougher tissues and/or substrates (e.g., outer annular layers, treatment device construct). In further illustrative description, tension delivered to the suture line 310 can be limited by the interface between the slide body member 318 and the suture retention block 414, through spring 316 such that tension is exerted on T-anchor body 316 which may sufficiently allow movement of T-anchor 316 through softer tissue, but alternatively requires a greater force to pull T-anchor body through other materials or substrates such as the treatment device 600 or outer layers of the annulus 202. Spring 316 can be designed to sufficiently draw tissues and/or the patch together, while not overloading suture line 310 when the fixation has been effected. Spring 316 may also be advantageously designed to allow blade assembly 420, upon reaching an appropriate loading to effect the delivery, to sever the suture line 310. As illustrative example, but not intended to be limiting, T-anchor body and suture line may be constructed to require approximately 5 pounds of force to draw the T-anchor assembly through nuclear tissue, but substantially greater load to draw T-anchor through annular tissue and/or patch device. Spring may be designed to exert approximately 5 pounds, sufficiently pulling anchor through nuclear tissue, and in proximity to treatment device, as intended. Once sufficient load has been applied to move T-anchor to engage patch, the loading on the suture line is not allowed to substantially increase. Advantageously, additional loading would cause the final compression of spring between suture retention block and blade assembly to sever suture line. Preferably, the severing and the design of the tether elements are such that the ultimate strength of the suture line is greater than the load required to draw T-anchor through soft tissue, or the like, and less than the load inflicted to cause the severing by blade assembly. The description herein is intended to be illustrative and not limiting, in that other device and delivery tools could be derived to employ the inventive embodiments.

FIGS. 57-62 depict illustrative embodiments of a therapeutic device delivery tool (TDDT), or mesh delivery tool (or MDT) as discussed above. The treatment device (or mesh or patch) 600 is depicted as loaded in the distal end of the TDDT 500, which will be discussed in greater detail with reference to FIG. 58. The TDDT 500 is comprised of a main body housing 510 which may be fixedly attached distally to outer cannula 522, which in a lumen thereof slidably receives a holding tube assembly 526. Distally, holding tube 526, as better illustrated in detail in FIG. 58, may comprise a slotted end and accommodate an actuator rod or stylet 514 in an inner lumen. Proximally, main body 510 has disposed thereon safety member 504, and has an outside diameter telescopically and rotatably received in the inner diameter of cap 506. Cap 506 forms part of end cap assembly 524, which also comprises ball plunger assembly 536, which will be described in greater detail below. Slidably disposed within the lumen of the main body member 510 is actuator body assembly 518, which abuts at its distal end, optionally in mating fashion or via detents, against a proximal end of finger grip member 502, which his also slidably disposed in the lumen of main body 510. At the proximal end of the actuator body assembly 518 is formed device release indicator 508, which will be described in greater detail below. A spring 516 is also slidably disposed within the lumen of the main body member and can abut either actuator body assembly 518 or finger grip member 502. The finger grip member can optionally comprise finger members at a distal end, carrying detents to engage with tabs, slots, or other cooperative structure on the inner lumen of main body 510 to lock the finger grip member, aggressively or gently, in the undeployed (unused) or deployed (used) configuration. A holding tube assembly, in the form of a slotted hypotube needle cannula 526, is slidably disposed in the lumen of the outer cannula 522, and is secured to the distal end of actuator body assembly 518, such that the translation of the finger grip member 502 proximally within main body member 510 concomitantly translates the actuator body assembly 518, and thus holding tube assembly 526 within the outer cannula 522.

FIG. 58 is a detailed view of the distal end 602 of the TDDT 500. As described above, the holding tube assembly 526 is slidably received in the outer cannula 522. The TDDT is designed to releasably deploy the treatment device 600 after the distal end 602 is navigated by the surgeon to the intended deployment site. The treatment device 600, shown in cross section and discussed further below, comprises a proximal end, forming a collar or cuff 604, and a distal end, also forming a collar or cuff 606. The proximal end 604 is slidably disposed on holding tube assembly 526, and abuts and is held stationary by outer cannula 522. The distal end of the holding tube assembly 526 can be formed to carry treatment device latch 608. The device latch 608 is formed with a flange or other detent to engage the distal end of treatment device 600, preferable the distalmost end of distal collar 606. The slotted end of holding tube assembly 526 is held radially rigid by actuation rod 514, such that the treatment device 600 is held firmly on the distal end 602 of the TDDT 500.

Figure 60:
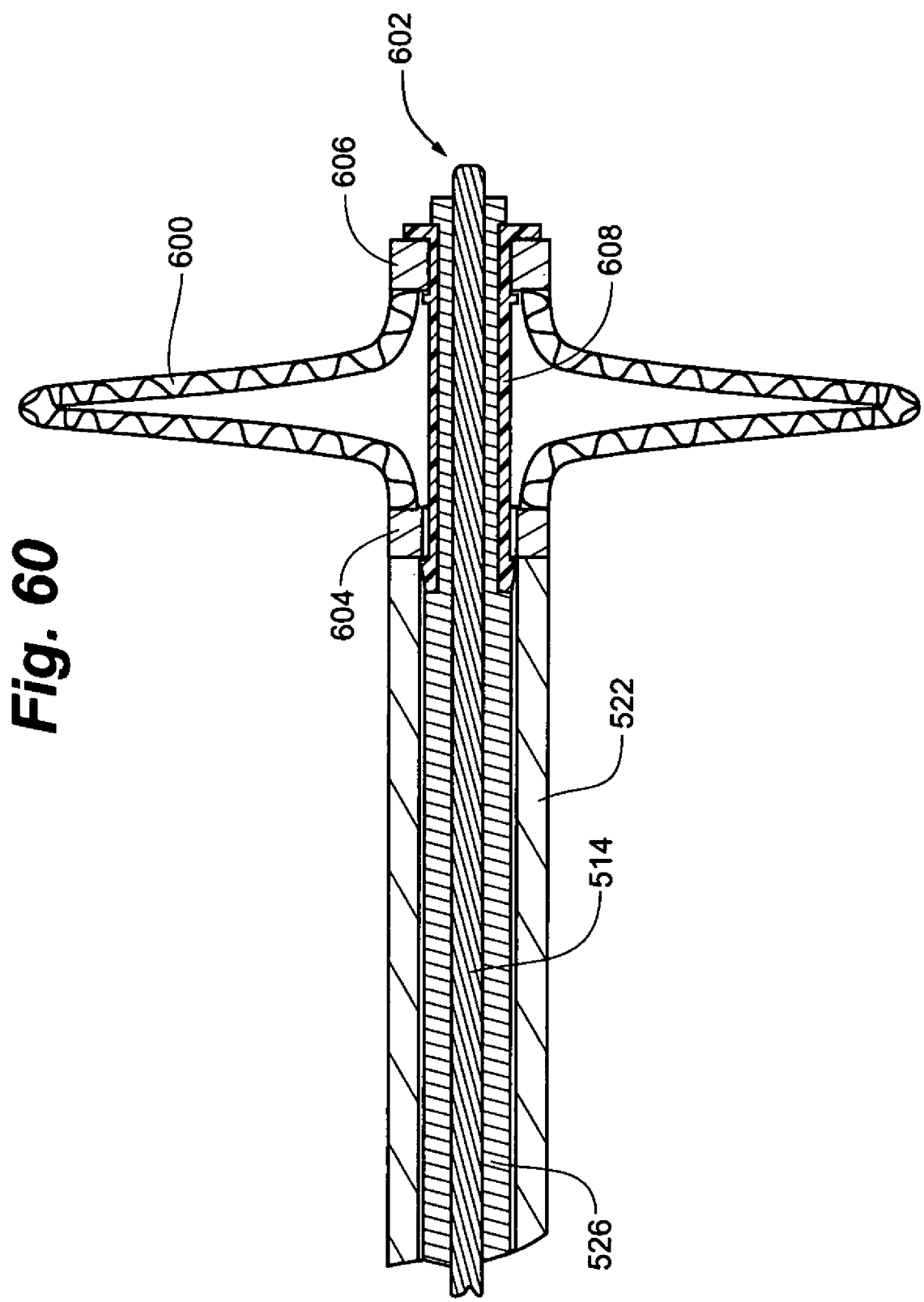
FIG. 60 depicts a detail of the distal end of the TDDT during deployment of a therapeutic device.

FIGS. 57 and 58 depict the TDDT in its initial delivery configuration. The TDDT is locked in this configuration by the distal end of safety 506 engaging the finger grip 502. Turning now to FIG. 59, the rotation of safety 506 in the direction of arrow 302 allows the finger grip 502 to engage a slot on safety 506, and permits the surgeon to pull finger grip 502 proximally in the direction of arrow 300 toward the proximal cap 506. Doing so results in the translation of the slider member 518 proximally, and concomitantly, the proximal translation of the holding tube assembly 526. The result, as further illustrated in FIG. 60, is the movement of the distal end 606 of treatment device 600 moving toward the proximal end 604, resulting in a bulging or lateral expansion of the treatment device 600. The translation of the actuator body assembly 518 proximally also urges the device release indicator 508 proximally, as will be discussed further below.

FIG. 60 depicts the distal end of the TDDT 500 after fully withdrawing the finger grip member 502 proximally, as discussed above. When the finger grip has reached the limit of its intended travel upon being pulled by a surgeon, the treatment device 600 will be in it's deployed configuration. In this configuration, detents on the proximal end of treatment device latch 608 will be poised to engage the proximal end 604 of treatment device 600 to hold it in the deployed state. As illustrated in FIG. 60, the actuation rod 514 can be seen to hold the distal end of the holding tube assembly 526 engaged with the distal end 606 of the treatment device 600, providing for maneuverability or removal until released.

Figure 61:
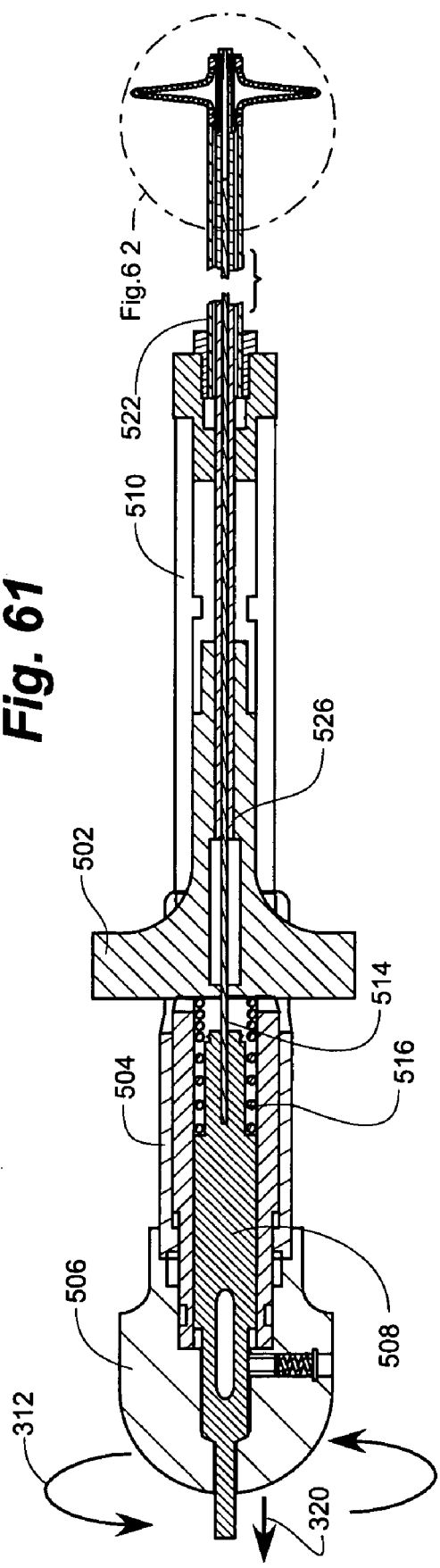
FIG. 61 depicts the TDDT during release of the therapeutic device.
Figure 62:
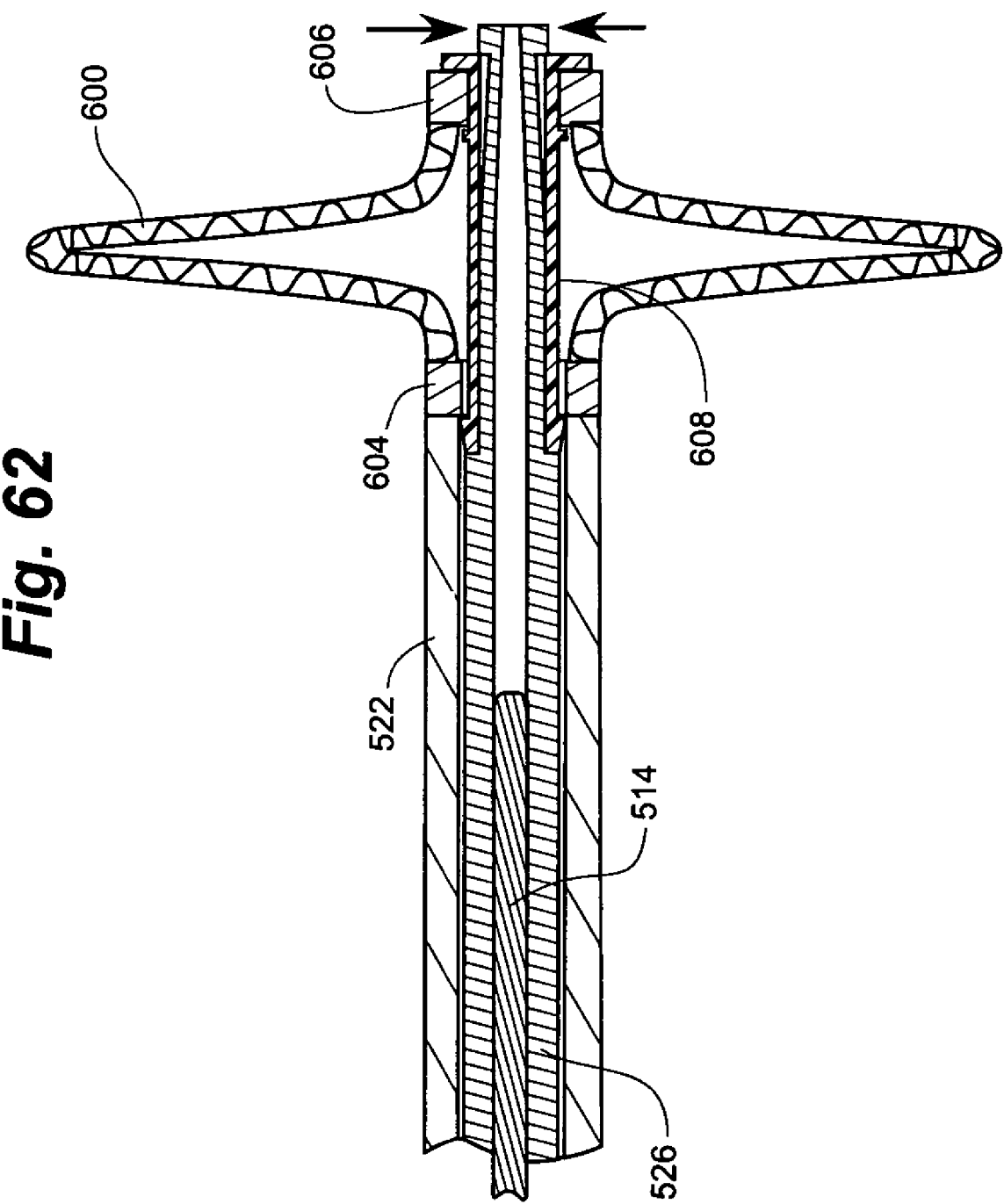
FIG. 62 is a detail view of the distal end of the TDDT during release of the therapeutic device.

FIGS. 61 and 62 illustrate the final deployment of the treatment device 600 just prior to withdrawal of the TDDT. As shown in FIG. 61, the rotation of cap 506 in the direction of arrow 312 releases actuator body assembly 518 from ball plunger 536, permitting its translation proximally under the bias of spring 516. Translation of the actuator body assembly 518 withdraws actuator rod 514 in the proximal direction, which permits the release of the treatment device 600 from the distal end of the TDDT, as further described with reference to FIG. 62. The translation proximally of actuator body assembly 518 permits indicator 508 to emerge from a hole in the cap 506, providing a perceptible indication to the surgeon that the TDDT can be removed and will leave the treatment device in situ. Turning to FIG. 62, the withdrawal of the actuation rod 514 is illustrated, which allows for inward radial compression of the tip of the holding tube assembly 526. Once the distal end of the holding tube assembly 526 is compressed radially inwardly, it can then pass through the inner diameter of the treatment device latch 608, and allow withdrawal of the entire TDDT from the treatment device 600. The final disengagement of the distal end of the outer cannula 522 can advantageously permit the engagement of detents on the treatment device latch 608 to engage the proximal collar 604 of the treatment device 600, locking it in a deployed configuration.

Additionally inventive of the treatment device (and its delivery and deployment tools) is the unique inter-relationship of the actuator body, spring, and the holder tube assembly, allowing the device to be deployed while still holding the device firmly during deployment. The use of the actuator rod to stiffen the distal end of the small diameter outer cannula, and the use of a radially compact treatment device offers additional advantages, such as the ability to pass through softer, or otherwise more pliable tissues (e.g., nucleus pulposus, softer annular layers) while resisting columnar bending during navigation. As an illustrative embodiment, a mesh patch as described in FIGS. 63 and 64 can be employed, but such a device configuration is not intended to be limiting. Other devices that expand radially through linear actuation can also be used.

The spring may be designed to exert approximately 5 pounds, sufficient to provide tactile control while preventing inadvertent release of the treatment device. By requiring actuation of the device in a different direction for release (i.e., rotation of the proximal cap) than that required for initial deployment (i.e., proximal translation of the finger grip), each with tactile, auditory or visually perceptible confirmation, safe an affirmative deployment can be achieved.

Figure 64:
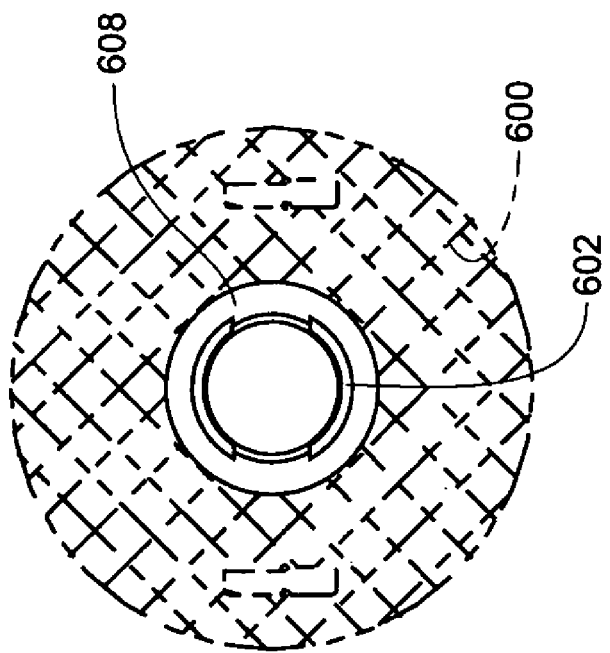
FIG. 64 is a plan view along the axis of an expanded exemplary therapeutic device, showing the disengagement of the TDDT latch.
Figure 63:
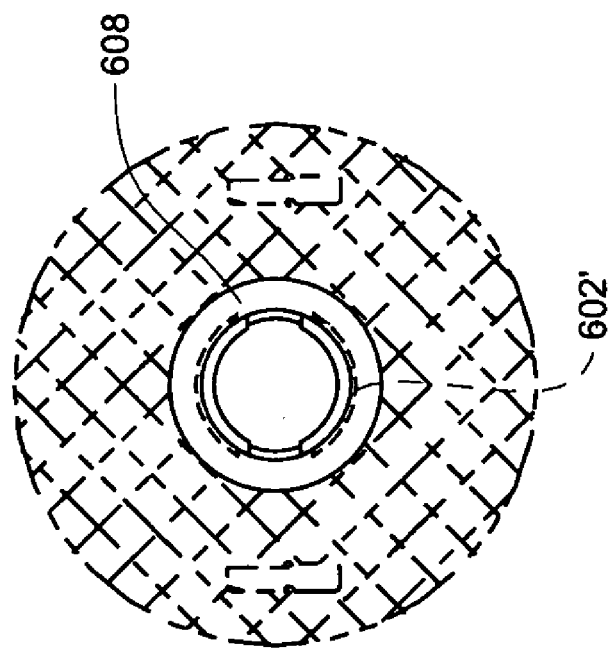
FIG. 63 is a plan view along the axis of an expanded exemplary therapeutic device, showing the engagement of the TDDT latch.

FIGS. 63 and 64 depict anterior views of the distal end 602 of the TDDT and treatment device 600 following deployment. FIG. 63 shows the distal end of holding tube assembly 526 engaging the treatment device latch 608. FIG. 64 shows the distal end of 526' disengaged, following withdrawal of the actuation rod 514 as discussed hereinabove.

Figure 66A:
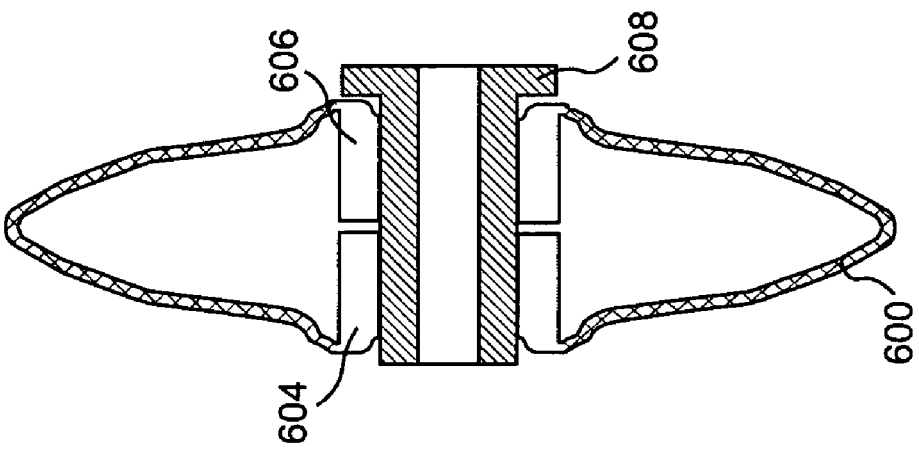
FIGS. 66A-66C depict various configurations of an exemplary therapeutic device.
Figure 66B:
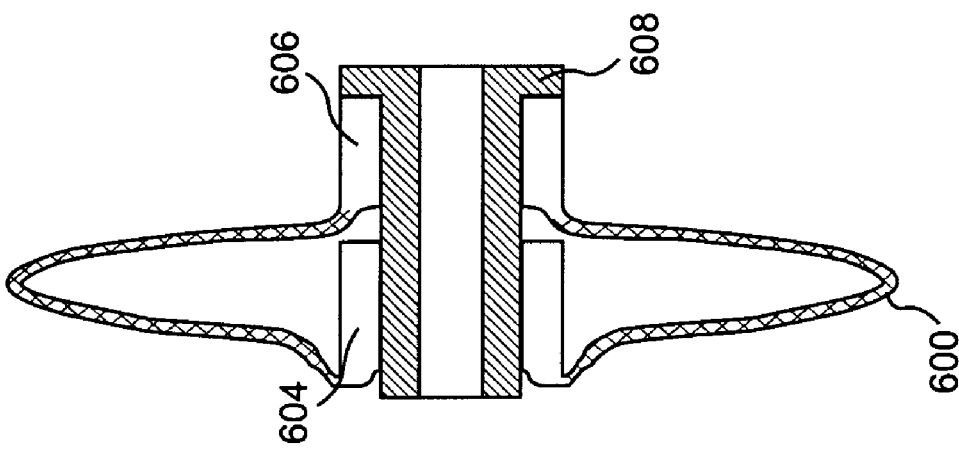
Figure 66C:
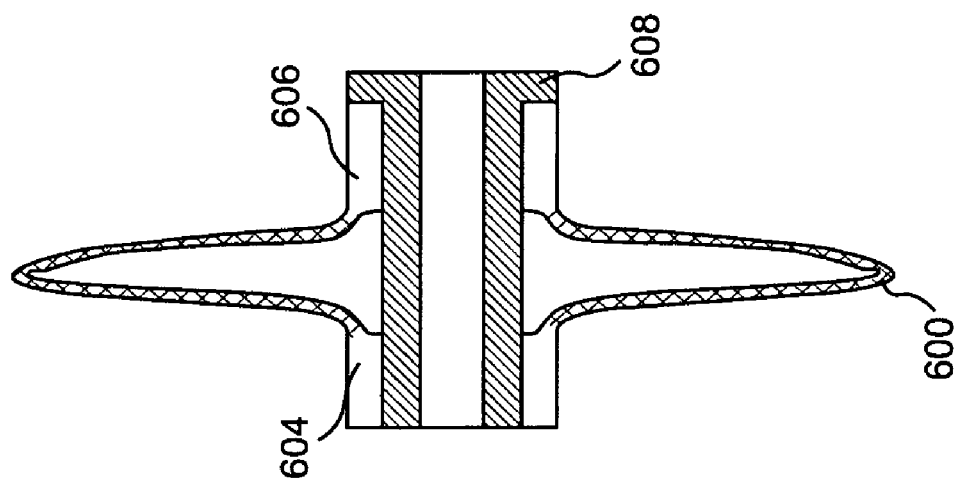

Additional embodiments of treatment device 600 might include constructions that can be "inverted" or "non-inverted" at the either, or both, ends of the device. As illustratively depicted in FIGS. 66A-66C, device 600 is shown in its deployed state, and FIG. 66C may be exemplary of devices described previously wherein distal device portion 606 has a "non-inverted" configuration, shown with distal cuffed portion extending distally, and away, from the body of device 600. Similarly, FIG. 66C reveals a proximal portion 604 of device 600 extending proximally, and away, from the body of device 600. Conversely, FIG. 66B illustratively demonstrates a proximal portion of device 600 in an "inverted" construction, shown with proximal cuffed portion extending distally, and towards, the body of device 600. Advantageously, a deployed configuration with inverted proximal portion of device depicted in FIG. 66 may allow less material of the device to project proximally, in use, and possibly reduce risks of causing injury to elements outside of the disc, including if a device were to expulse from the disc subannular space. FIG. 66A depicts a device construction in which both end portions of the device are "inverted". Changing constructions on ends of the device may also, advantageously, facilitate device 600 deployment and/or device function in the repair of an aperture, weakened, or thin portion in the annulus fibrosus.

Figure 67:
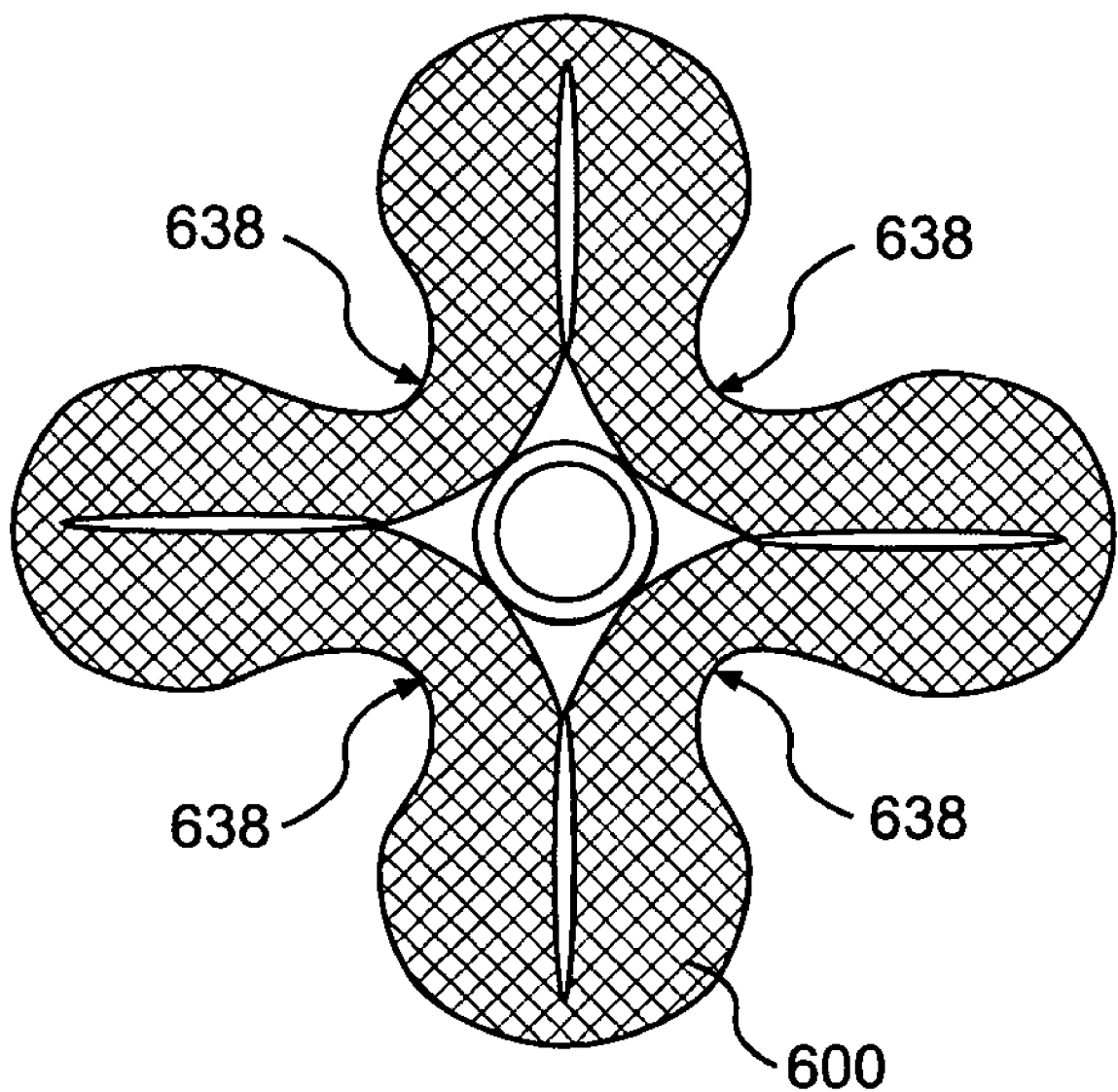
FIG. 67 shows an illustrative embodiment of a pre-set heat formed therapeutic device in cross section through a longitudinal axis.

In alternative embodiment in the construction of device, such as, for example implant 600, devices may be pre-set in a heat forming process to induce the device to have different structural or physical characteristics during the introduction, delivery, deployment, fixation or otherwise use of the device to treat a treatment site. An illustrative example of a pre-set heat forming process is shown in FIG. 67 wherein device 600 is shown in cross section through a longitudinal axis. As shown, device 600 is folded along four axial dimensions in its undeployed state A configuration, such as shown, could, for example, advantageously reduce the radial profile of the device in order to facilitate introduction into the subannular cavity or provide other benefits in the functioning of the device and its delivery. Such a benefit is illustrative, is not intended to limit the many other beneficial effects of altering configurations of devices, or their components as described herein. After deforming the device into a desired configuration, the device may be held in a mold or similar retention apparatus and subjected to a heating process to "heat-set" the material of the device. Naturally, temperature and time duration of heat-setting process are dependent on a device's (and/or components of a device) materials. As an example, but not intending to limit the scope of the invention, if device were comprised of polyethyleneteraphalate (PET) the heat-set process might be accomplished in a temperature range above the material's glass transition temperature (typical glass transition temperatures of various PET's range from approximately 160 degrees Fahrenheit to approximately 180 degrees Fahrenheit) and below the material's melting temperature (typical melting temperatures of various PET's range from approximately 450 degrees Fahrenheit to approximately 550 degrees Fahrenheit)). One skilled in the art would realize that this process is illustrative and will vary depending on the material and the intended characteristics of the device, and therefore should not be limiting in the scope of the invention.

Although FIG. 66A exemplifies a device that is folded along the axis in four equidistant creases, it is clear that the device could be constructed with a single fold or multiple folds, and that four folds is only an example. It is also possible that a single fold or more could be located in a fashion that does not result in a geometrically spaced folds along the axis, for example, a device might have two folds located on generally one side of the device. In addition, it is also possible that one might beneficially construct a configuration in which only a portion of the device has a fold along its longitudinal axis. Further, it is also possible to obtain alternative characteristics of the device by creating one or more circumferential folds (partially, or wholly) along longitudinal axis of a device. It is also possible that the device may have a combination of axial, radial, or otherwise special heat set folds or configurations to beneficially affect the characteristics of the implant.

Figure 68A:
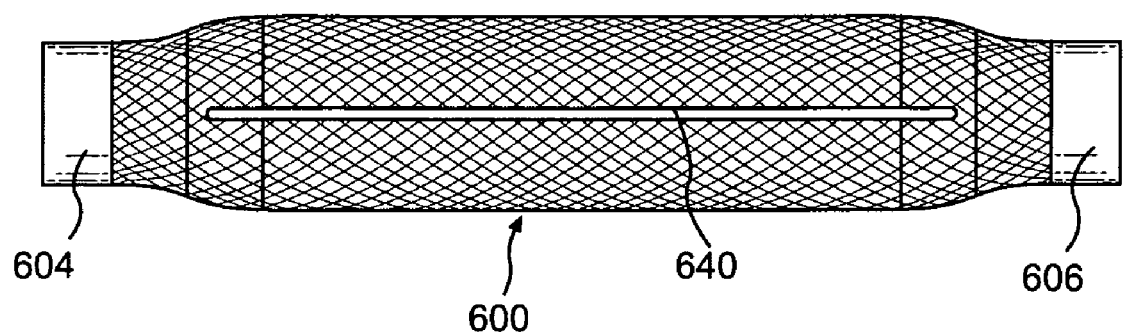
FIGS. 68A-68B show a therapeutic device with a single rib of material affixed to or formed on the device.
Figure 68B:
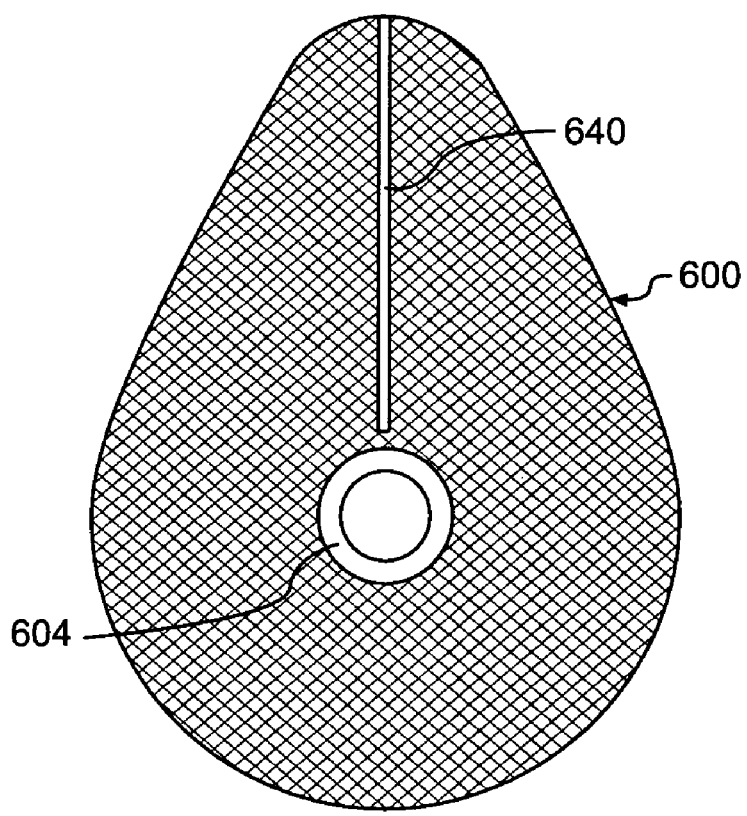
Figure 69A:
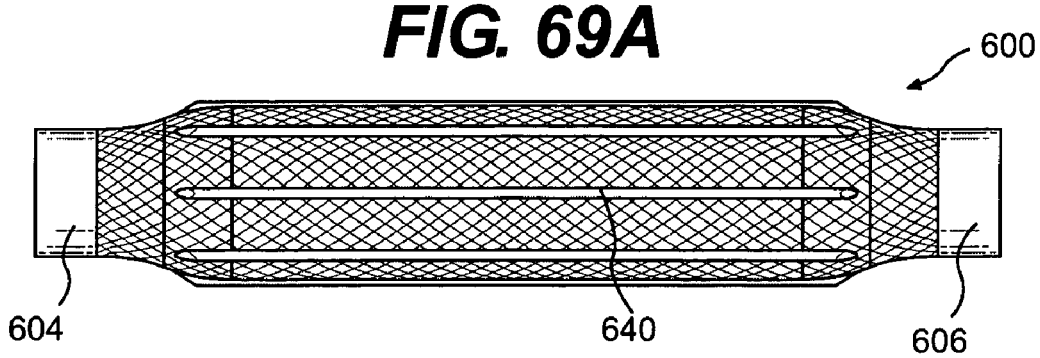
FIGS. 69A-69D show a therapeutic device with multiple ribs of material affixed to or formed on the device.
Figure 69B:
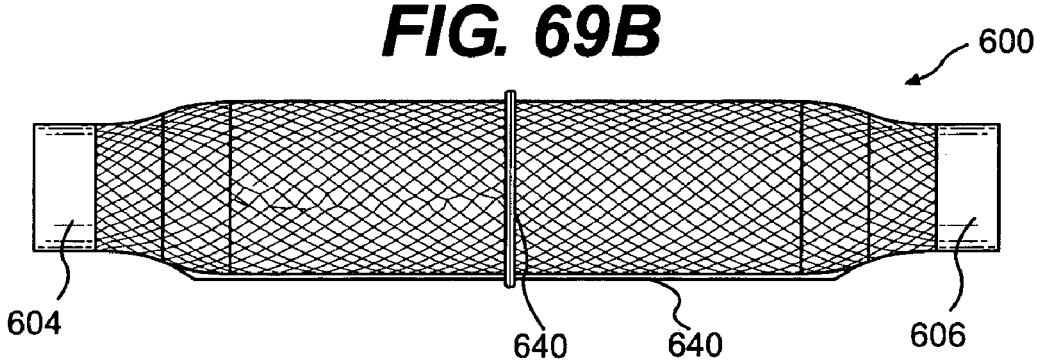
Figure 69C:
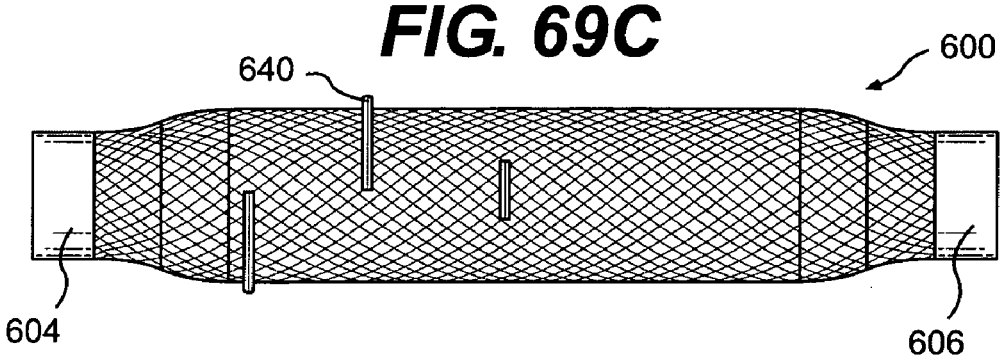
Figure 69D:
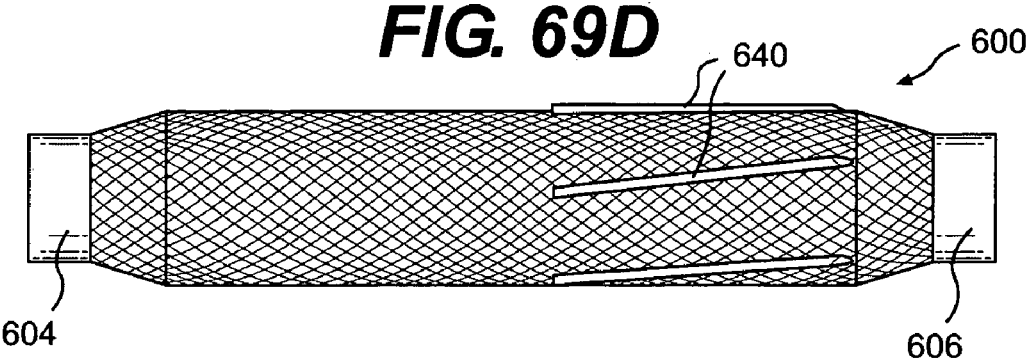

In additional alternative embodiments, it may be possible to perform alternative processes on the implant that may alter the structural or physical characteristics of the device, advantageously inducing the device to evince beneficial characteristics during the introduction, delivery, deployment, fixation or otherwise use of the device to treat a treatment site. For example, it is possible to provide heat to selected regions of a device to heatmelt, heat seal, or otherwise flow and/or fixate various components of a device in selected regions, thus causing the device to have different characteristics during the pre-deployment, deployment or post-deployment of the device. Inclusive in the inventive embodiments are elements that are fixedly attached to at least an element of a device to also effect beneficial characteristic changes of an otherwise unaltered device. The elements may, or may not be of similar materials as the treatment device. FIG. 68A shows a side view of device 600 with a single rib 640 of material affixed to the device, or conversely a rib 640 created by heat setting the material of the device. It should be understood in the description and depictions herein that the rib 640 can be constructed of either form, and the descriptions is intended to be illustrative and not limiting. FIG. 68A exemplifies a single rib 640 element placed along the longitudinal axis of a device 600 having end portions 604 and 606. FIG. 68B shows an expanded configuration of device 600 of FIG. 68A as seen from the proximal portion 604 of device 600. As can be seen, the rib 640 may advantageously change the configuration of a device to induce the device to have different structural or physical characteristics during the introduction, delivery, deployment, fixation or otherwise use of the device to treat a treatment site. Applying heat sealing to a treatment device may be accomplished by a process similar to heat setting, although the temperatures and duration of time of the process would most likely differ. Naturally, temperature and time duration of heat-sealing processes are dependent on a device's (and/or components of a device) materials. As an example, but not intending to limit the scope of the invention, if device were comprised of polyethyleneteraphalate (PET) the heat-seal process might be accomplished in a temperature range slightly below, equal to, or above the material's melting temperature (typical melting temperatures of various PET's range from approximately 450 degrees Fahrenheit to approximately 550 degrees Fahrenheit). One skilled in the art would realize that this process is illustrative and will vary depending on the material and the intended characteristics of the device, and therefore should not be limiting in the scope of the invention. There are a variety of methods that may be used to apply heat-sealing processes, welding, or otherwise melting the material of a device, such as laser, heat iron, RF, and ultrasound. Although FIG. 68 shows as single rib along the device, it is anticipated that the device could have any combination of radial, axial, or otherwise special ribs or rib configurations to beneficially affect the characteristics of the implant, as are further illustrated in FIGS. 69A-D. FIGS. 69A, 69C, 69C, 69D illustrate multiple ribs on device 600. FIG. 69A illustrates ribs aligned a longitudinal dimension of the device. FIG. 69B is exemplary of a circumferential rib, with 69C illustrating partially applied ribs in a circumferential fashion. FIG. 69D is illustrative of ribs that may be applied to a device that are neither circumferential nor longitudinal and illustrative that alternative rib patterns may be employed.

Changing characteristics of the treatment device with various ribbing effects may be performed for a variety of reasons, as an example (and not to be limited in scope of the invention), one might prefer to change the base (e.g., unaltered) characteristics of a device to accomplish, for example, a lower profile of the device while mounted on its delivery tool, or during its deployment. Alternatively, one might want to change the symmetry of the deployed device to open with different configurations to address different anatomical considerations of the treatment site. For example, one might prefer that a deployed device be placed predominantly, more medially of an aperture of a annulus fibrosus. Alternatively, it is possible that one might want to increase the structural integrity of the patch during delivery to provide more radially directed force into soft tissue, for example nuclear tissue, in order to better deliver the device into the intervertebral disc. The drawings and descriptions of ribs and heat sealing elements, and the resulting beneficial outcomes, above and herein are intended to serve as examples to altering the configuration through various processes applied to a device, although, they are only intended to serve as examples, and should not be considered exhaustive of the advantages of changing the characteristics through various heat sealing altering processes, or alternative procedures that apply rib elements to a device.

Heat sealing, in an embodiment of the invention may be used to heat melt, fasten, or otherwise secure the device ends 606 and 604 of the filaments of device 600, as discussed previously. Some of the devices described herein may illustrate end portions as radial (or circular) in cross section. However, heat sealing may advantageously allow end portions of devices to have a multitude of configurations which may address various needs of a device and its delivery tools. For example, end portions of the device may be square, oblong, rectangular, triangular, or multi-sided. Heat sealing may readily be performed by heat sealing and otherwise flowing material of the ends of a device over mandrels having the shape of the intended configurations. The heat sealing method may advantageously facilitate construction of end portions in such a fashion. The various shapes are intended to be exemplary, and not limiting in the scope of the invention. Similarly, it is possible that alternative methods to fixate, secure or otherwise form the ends of the device may also incorporate the different shaped end portions configurations.

Figure 72A:
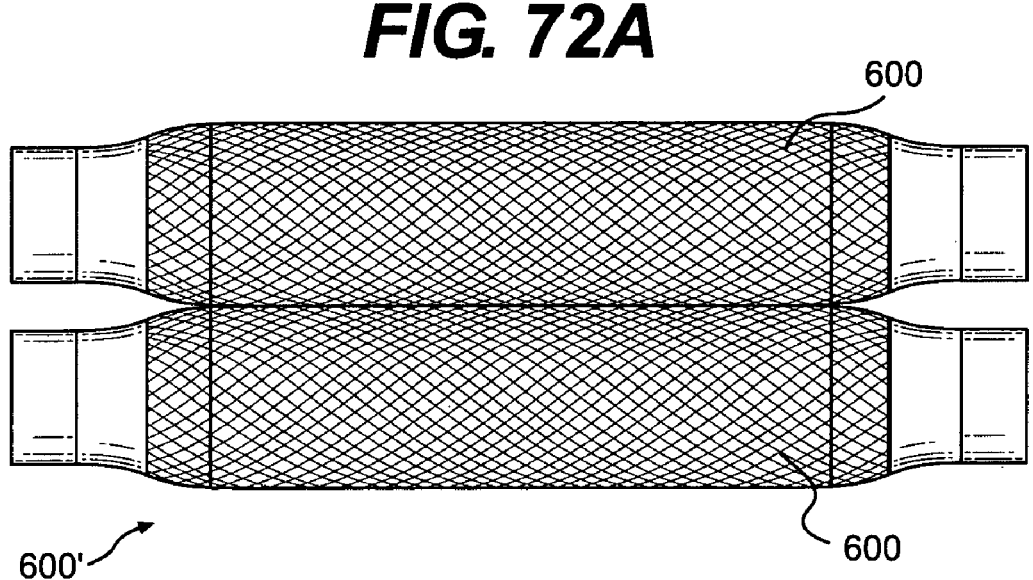
FIGS. 72A-72B show a treatment device constructed of two bodies.
Figure 72B:
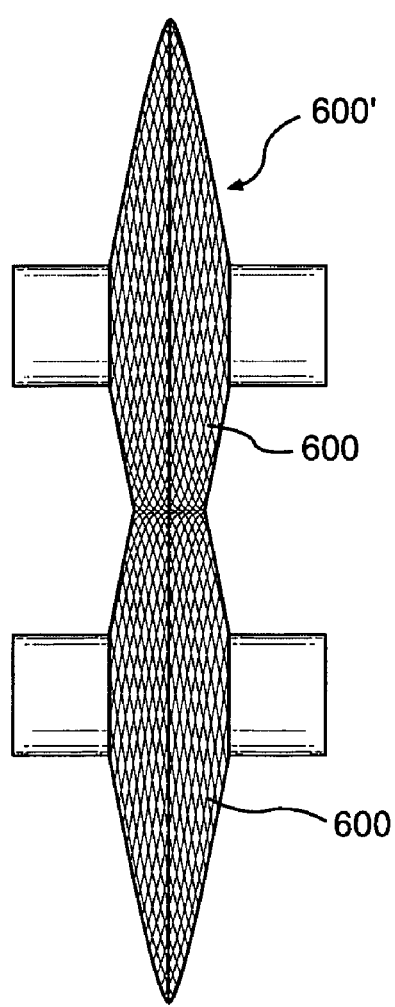
Figure 73A:
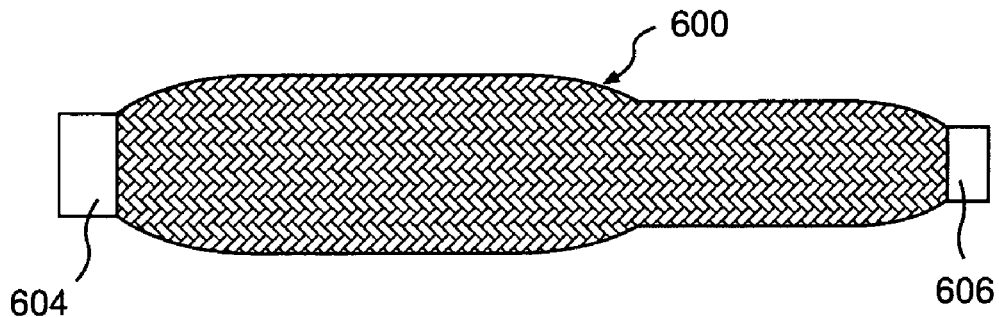
FIGS. 73A-73C show an illustrative example of multiple members forming inner and outer members of a treatment device.
Figure 73B:
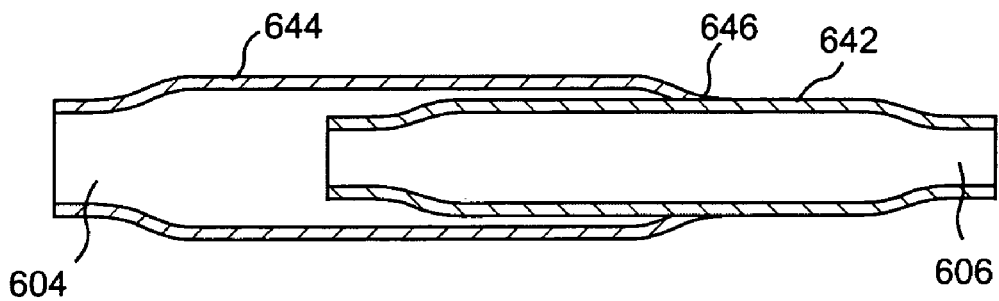
Figure 73C:
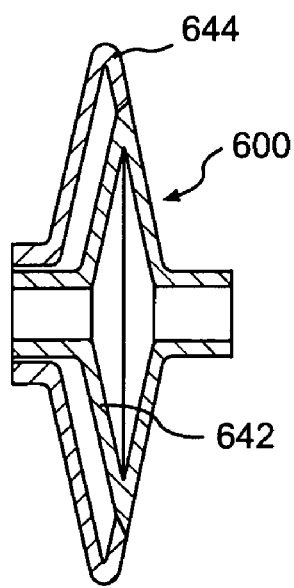

Treatment devices throughout the descriptions and illustrations contained herein may be described as comprising a single braided or woven body like member, However, it is anticipated that treatment devices may contain multiple braided, woven, otherwise patch-like structures, as illustratively shown in FIGS. 72 and 73. FIG. 72A shows a treatment device 600' which may be constructed of two bodies 600, each of which may appear similar to a device shown elsewhere in the description. The form of treatment device 600' may advantageously allow a treatment device to occupy, in use, a dimension which is greater along a plane than another plane, as shown in FIG. 72B were device 600' is depicted in its deployed configuration. In another illustrative example of multiple braided, woven or otherwise patch-like members comprising a treatment device, inner 642 and outer members 644 of braided, woven or patch-like materials are affixed 646 in the form as shown in FIG. 73A-73C. FIG. 73A shows a side view of device 600. FIG. 73B shows a cross sectional view of device 600, comprising inner body 642 and outer body 644. FIG. 73C illustratively depicts a form of device 600 as constructed in FIGS. 73A and 73B in its deployed configuration, advantageously achieving a larger radial profile than device body 642 alone. The devices bodies exemplified in FIGS. 72 and 73 may be affixed through heat sealing, adhesively bonding, sewing, stitching or other various means to attach multiple braided, woven, otherwise patch-like structures together. The use of multiple body members, and any resulting beneficial outcomes, above and herein are intended to serve as examples to altering the construction a treatment device, although, they are only intended to serve as examples, and should not be considered exhaustive of the advantages of employing multiple braided, woven, patch, otherwise mesh-like structures to treatment device.

Figure 74A:
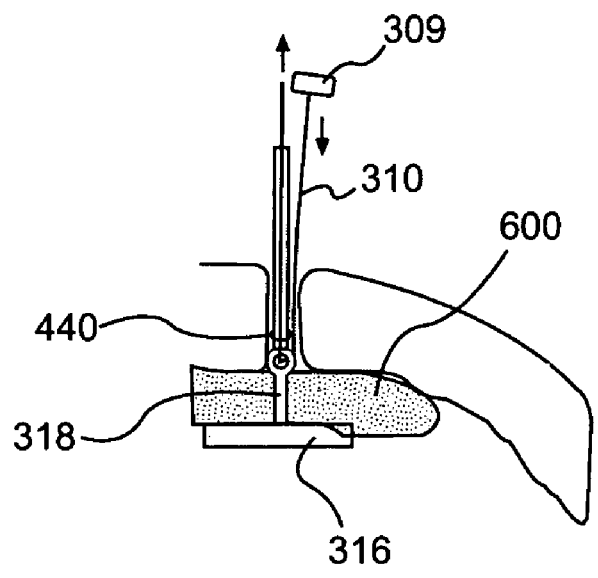
FIGS. 74A-74B show alternative illustrative mechanisms of drawing together locking elements/anchors.
Figure 74B:
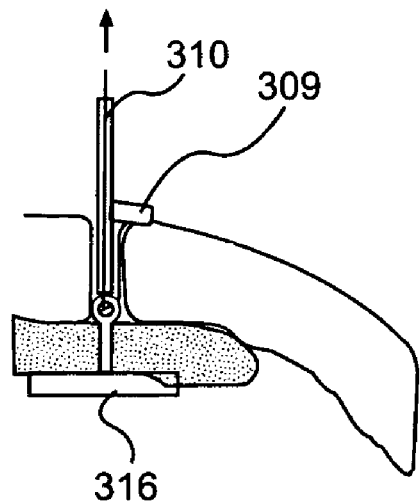
Figure 75A:
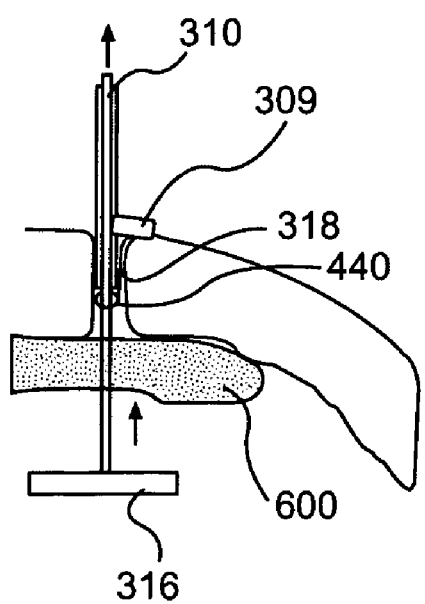
FIGS. 75A-75B show alternative illustrative attachment mechanisms where a pledget element that initially resides on outer annular surface.
Figure 75B:
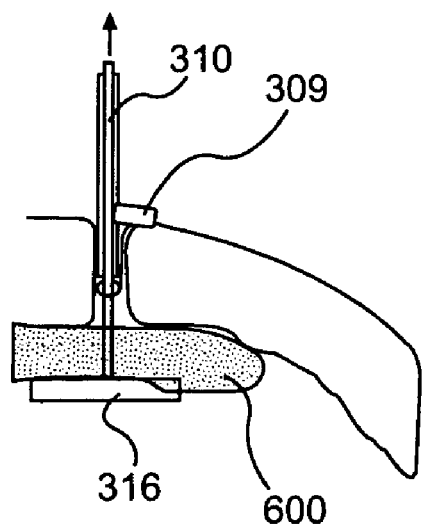

With regards to introduction, delivery, deployment and/or fixation of fixation element 308 as described previously and in particular, with regards to FIGS. 47-56, for example, anchor band assembly 308 and its associated delivery tool 400 may be described as effecting a fixation as shown in FIGS. 75A and B. FIG. 75A shows a pledget element 309 that, initially, may be placed on outer annular surface. As depicted, tether 318 is attached to pledget 309, and pledget and tether are secured to suture line 310 via a slip knot 440, for example During deployment, T-anchor is drawn toward, and engaged with, treatment device 600 as illustrated in FIG. 75B. There may be alternative methods and mechanisms of drawing together locking elements/anchors 309 and 316, as exemplified in FIG. 74. FIG. 74 illustrates a T-anchor member 316 that may be positioned, initially, in proximity of patch 600. As depicted, tether 318 is attached to T-anchor, and T-anchor and tether are secured to suture line 310 via a slip knot 440, for example. During deployment, pledget 309 may be drawn to, and engage with, the surface of outer annulus tissue, as illustrated in FIG. 75B. The description of methods of drawing members together and effecting a fixation of an fixation element with its fixation element delivery tools are intended to be illustrative, and not limiting in the scope of the invention.

Figure 70A:
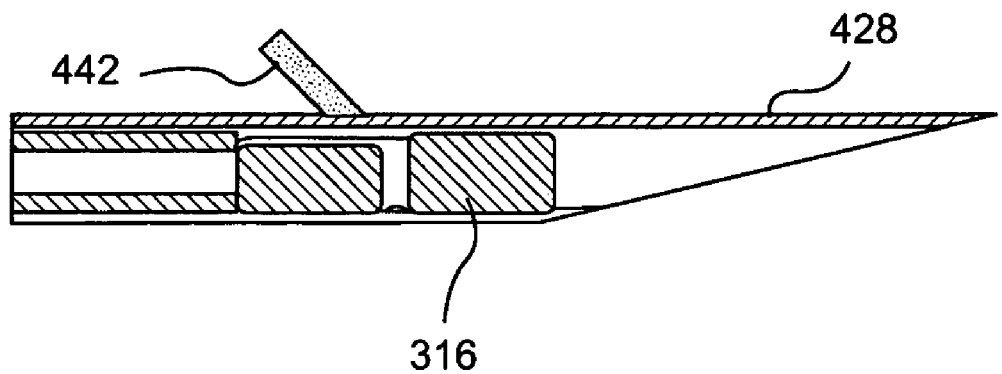
FIGS. 70A-70C illustratively show means that may be attached to the anchor band or anchor band delivery tool for providing perceptible feedback.
Figure 70B:
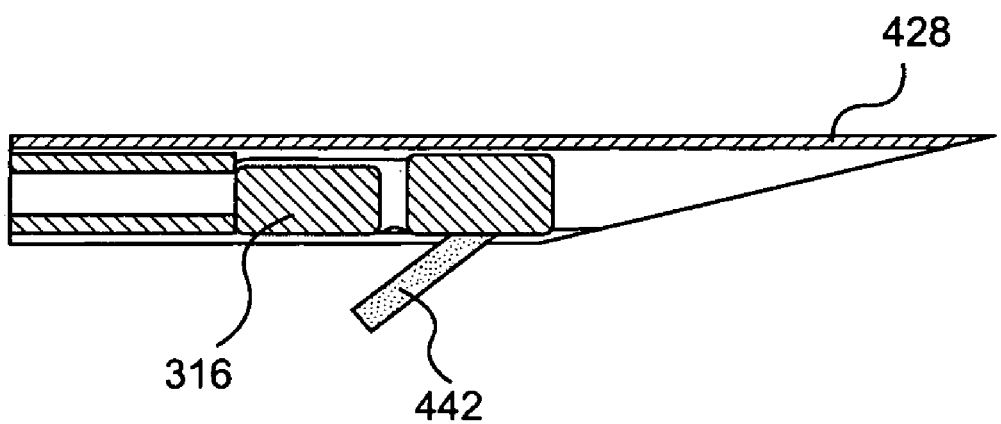
Figure 70C:
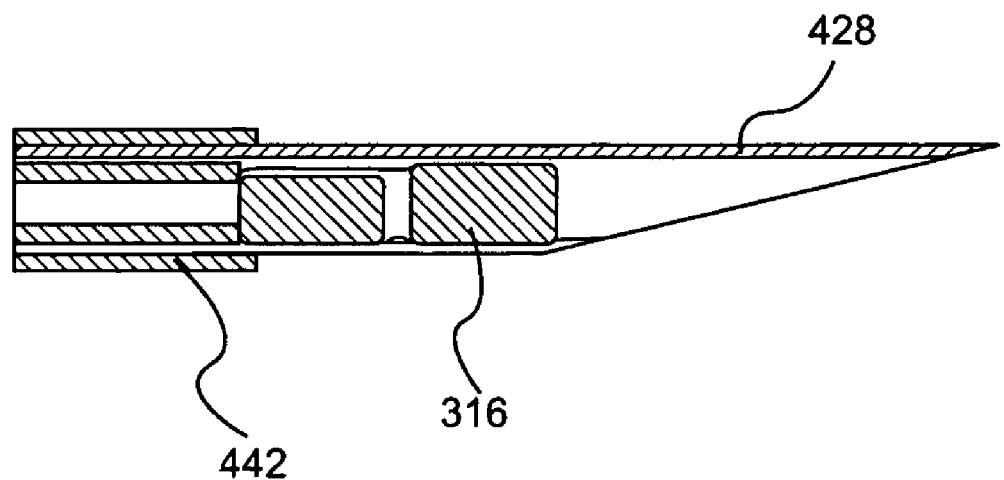

Since the surgeon's visualization of during discectomy procedures is typically limited to the epi-annular space and the aperture at the outside surface of the annulus, any tactile, visual or audible signals to assist, or otherwise enhance, the surgeon's ability to reliably deliver and deploy treatment devices and/or anchor bands may be advantageous. The anchor band delivery tool 400, may have a patch detection feature 442 on the distal end of slotted needle cannula 428 which may provide perceptible feedback (tactile and/or audible) to the surgeon that the anchor band delivery tool has accessed and penetrated the patch and it is therefore acceptable to deliver the band. As shown, detection feature 442 is composed of multiple bands or ribs although the outer surface of needle 428. The movement of the ribs of 442 against the patch structure (e.g., the filaments of treatment device 600) may produce a clicking sound and feel, and the interface of the components of the devices and tools may be optimally designed to enhance such feedback features. One, or multiple, ribs or tabs may be utilized to achieve the perceptible features. The feed back may be perceived on or with the patch and/or patch delivery tool or through the anchor band and/or anchor band delivery tool, or both. FIGS. 70A-70C illustratively shows additional means that may be attached to the anchor band or anchor band delivery tool which might also provide perceptible feedback. These depictions are meant to be illustrative and not limiting in scope of the invention. FIG. 70A shows a tab 442 attached to needle cannula 428 which may be laser cut from the distal end of needle 428. Detection tab 442 may be designed to readily pass through soft tissue and the patch 600 without causing significant disruption, but may be capable due to its design construction to produce tactile and/or audible sensation as it engages the patch lattice or structure. Lateral extent of tab 442 of FIG. 70A may advantageously deflect, or otherwise deform or bend toward the distal end of needle cannula upon removal of the delivery tool so as not to be restricted by the lattice or structure of treatment device 600 upon its removal. Alternatively, detection tab 442 of FIG. 70B is affixed to, or integral with, T-anchor 316. Similarly, detection tab 442 may be designed to readily pass through soft tissue and treatment device 600 without causing significant disruption, but may be capable of producing tactile and/or audible sensation as it engages the patch lattice or structure. In this embodiment, tab 442 advantageously remains with T-anchor 316 after removal of delivery tool 400. Moreover, it is possible to have a detection feature 442 as depicted in FIG. 70C wherein the feature is wholly, or partially, coaxial disposed on the delivery tool and feature 442 may be of a construction that does not readily pass through patch 600, but it is capable of passing through soft tissue of the disc and produce a tactile and/or audible sensation as it engages the patch lattice or structure. Although some of the embodiments illustrate a single tab or rib, it is possible to use more than a single element. Detection features described herein may be of a variety of shapes and affixed to the devices or delivery tools (for example, welding ribs onto the surface of the delivery tool, affixing a flexible filament member to the T-anchor) or be incorporated as an integral component thereof (for example, laser cutting or stamping tabs out of a portion of needle 428, injection molding tabs as part of t-anchor 316). Exemplary materials that could be used to construct the various detection features include, but are not limited to: biocompatible polymeric materials (polyester, polypropylene, polyethylene, polyimides and derivatives thereof (e.g., polyetherimide), polyamide and derivatives thereof (e.g., polyphthalamide), polyketones and derivatives thereof (e.g., PEEK, PAEK, PEKK), PET, polycarbonate, acrylic, polyurethane, polycarbonate urethane, acetates and derivatives thereof (e.g., acetal copolymer), Polysulfones and derivatives thereof (e.g., polyphenylsulfone), or biocompatible metallic materials (stainless steel, nickel titanium, titanium, cobalt chromium, platinum and its alloys, gold and it alloys).

Figure 71C:
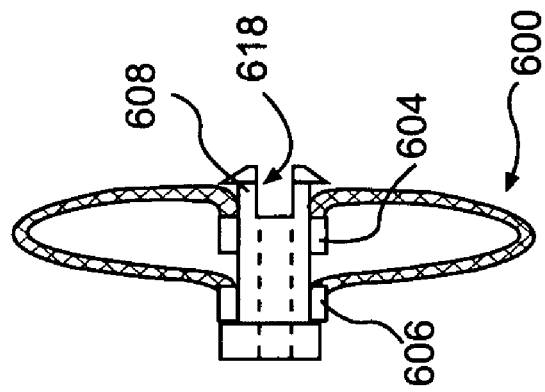
FIG. 71A-71G depict illustrative means for latching, locking or otherwise securing the treatment device in its final configuration.
Figure 71B:
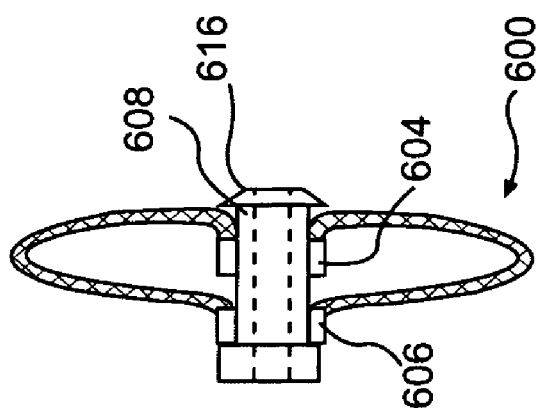
Figure 71A:
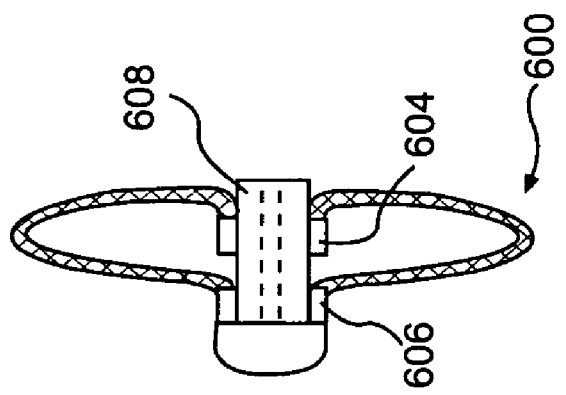
Figure 71F:
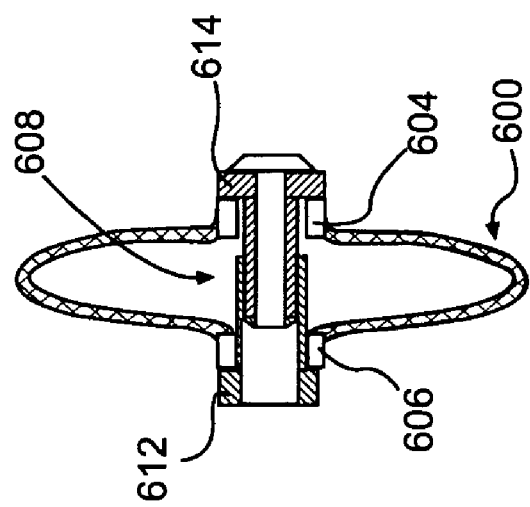
Figure 71E:
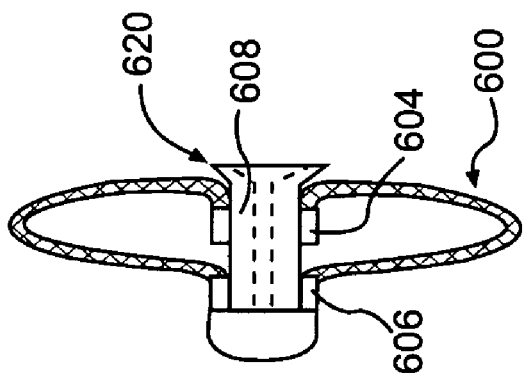
Figure 71D:
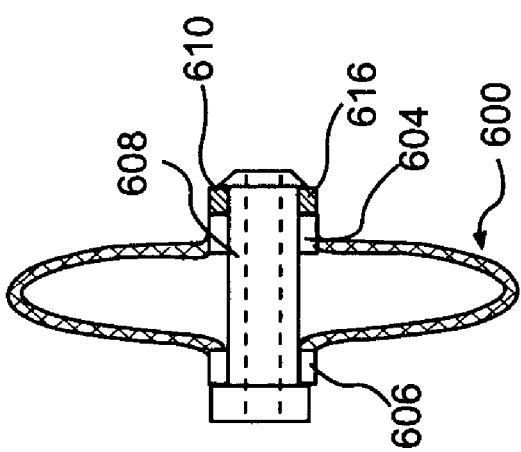
Figure 71G:
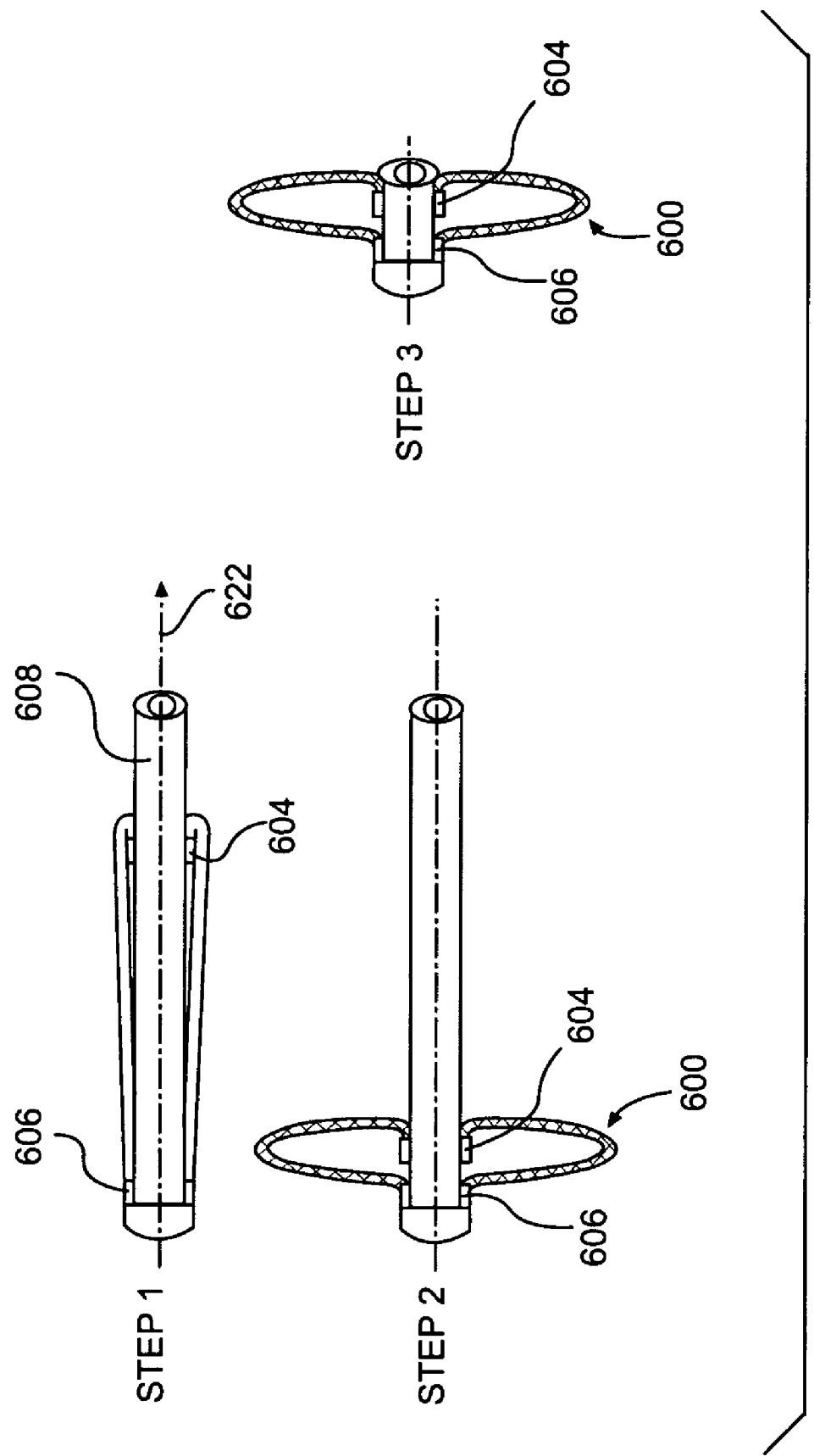

As discussed previously, a patch/stent/mesh/treatment device such as treatment device 600 may have element 608 to facilitate the fixing of the patch or its ends in a final deployed configuration, if required. In one exemplary embodiment as shown in FIGS. 29 and 30, a suture with a knot is used to secure ends together after deployment. There may be a variety of ways to latch, lock or otherwise secure the treatment device in its final configuration, as further depicted in FIG. 71A-G. The drawings and description are intended to be illustrative and not limiting in scope of the invention. It is also anticipated that delivery device tools may need to be altered or otherwise reconfigured in order to accommodate the various latches described. FIG. 71A depicts a latching mechanism that principally involves "press fitting" distal portion/end 606 of treatment device 600 and proximal portion/end 604 of treatment device 600 onto latching element 608. FIG. 71B shows a "barbed" latching element, wherein proximal end 604 passes over the barb to fixate treatment device in its final configuration. FIG. 71C shows an additional slot 618 placed in barbed latch of FIG. 71B to facilitate the flexing of latch 608, to accommodate passing end portion 604 over the proximal end of the latch and latching. FIG. 71D shows an embodiment of a latching device that incorporates a washer 610 to pass over the barbed 616 portion of latch 608 to effect the latching and securing the device in its deployed configuration. In addition, FIG. 71E shows an exemplary embodiment in which a "flared" region 620 is created by the patch delivery tool, or other tool, after the proximal end of the patch 604 has been passed onto the latch. FIG. 71G shows an alternative method and device for latching the patch together incorporating a deformable latching mechanism. In step one of FIG. 71G, inner latching member is drawn out as indicated by the arrow 622 to readily allow mesh proximal end 604 to be slidable moved along the latching member 608. Once patch is advantageously positioned in its final configuration, latch member tension is released, lockingly fixing 604 in closer proximity to distal end 606. Optionally, a latch member cutting tool may be integral to the patch delivery tool to cut latch member 608 to size as shown in step three in FIG. 71G (i.e., resect proximal portion of the latch member in close proximity to proximal end), or if present may be cut with other available tools after delivery of the treatment device.

The latching or securing embodiments described above principally show the locking effected at, around, or near the proximal portion of the treatment device. However, it is equally anticipated that these locking embodiments could be effected on the distal portion of the treatment device, or at both ends simultaneously, as shown in FIG. 71F wherein both ends of the device are drawn together and locked with separate parts of a two part, or multiple piece, locking mechanism 608.

Latching elements could be constructed from various biocompatible materials, such as polymeric materials (for example, polypropylene, polyimide, polyamide, PEEK, polyester, PET polycarbonate urethane, PTFE, polyethylene, engineering plastics), metallic materials (for example, stainless steel, titanium, chromium cobalt alloy, nickel titanium alloy, platinum, gold), bioresorbable of biodegradable materials (for example, material discussed previously for patch or suture materials), natural materials (for example, silk, cotton), or a combination of above materials.

Figure 76B:
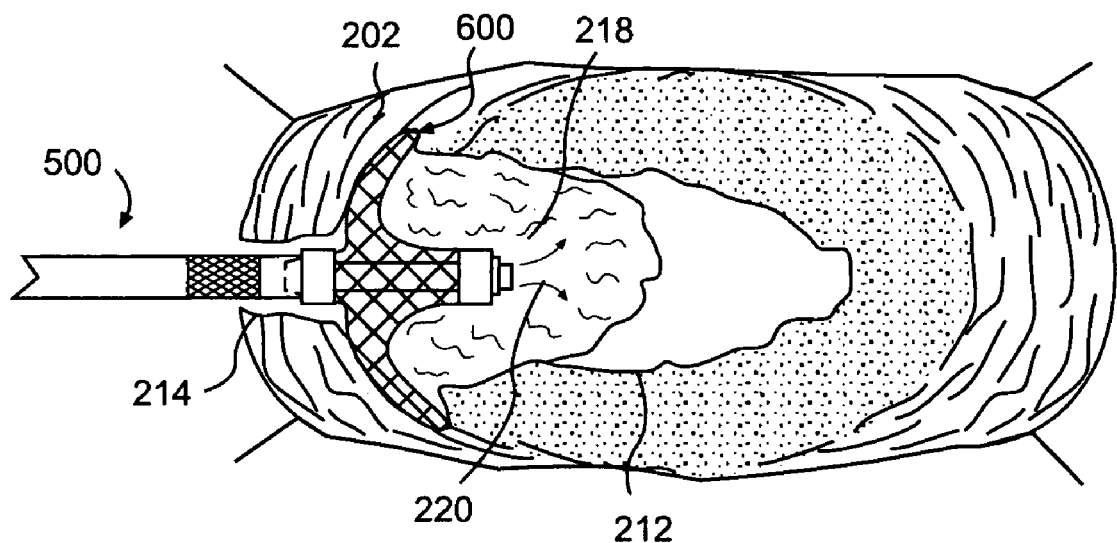
Figure 77:
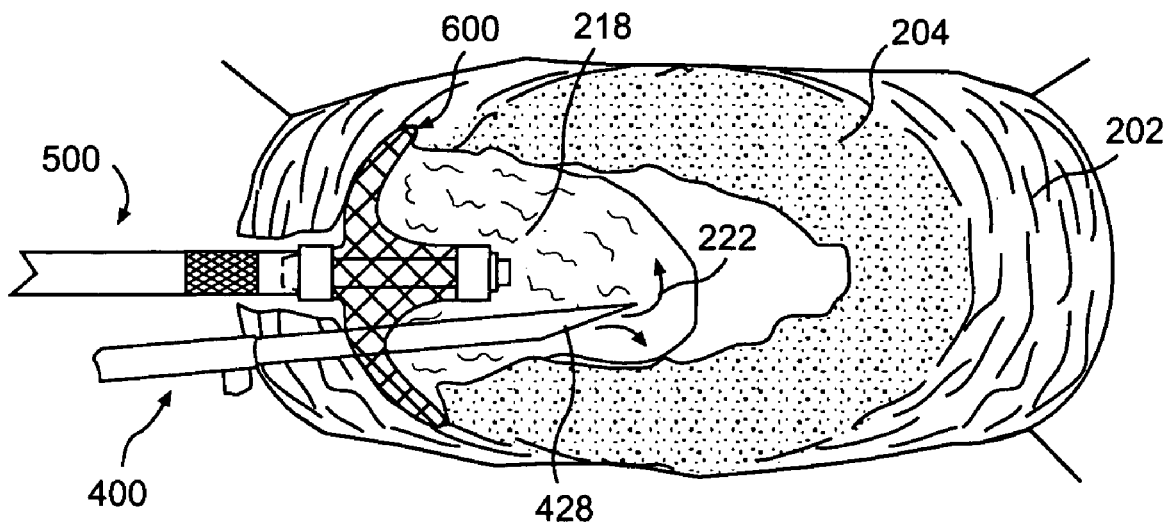
FIG. 77 illustrates an alternative method and device for the introduction of material into the disc space via the fixation element delivery tool.

FIGS. 76 and 77 further illustrate an additional embodiment of the invention wherein the device may be used to repair an aperture within the intervertebral disc in conjunction with a nuclear augmentation procedure. The augmentation of the intervertebral disc nucleus may include partial or complete removal of the disc nucleus and possibly potions of the annulus and other spinal tissues, depending on the design of the implant. The prophylactic and/or therapeutic objective of these nuclear augmentation implants is to help maintain and/or restore the normal or natural function of the spinal disc, as described for example in U.S. Pat. No. 5,976,186 (Bao et al.). The surgical repair of an intervertebral disc may require the removal of the entire disc nucleus being replaced with an implant or a portion of the disc nucleus thereby leaving a void in the intervertebral disc cavity. The volume of nuclear replacement added to the subannular cavity may be less than, equal to, or larger than disc tissue volume removed. The volume of the implant may vary over time, depending on the type of replacement or augmentation device implanted. Although previous embodiments of the invention described herein could be used to contain implant materials within the disc space, FIG. 76 and FIG. 77 illustrate embodiments that may more readily accommodate the introduction of injectable, or otherwise flowable, materials into the disc space. Preferably, the materials would be in situ curable (by way of a number of methods, for example, chemical, thermal, or photoinitiated), although it is not necessary that they are. For example, one could introduce a nucleus augmentation implant comprising small hydrogel particles in an aqueous suspension that could be delivered to the disc space, with the annular repair patch 600 retaining the intradiscal material within the disc space. FIGS. 76B and 77 are depicted with nuclear augmentation material 218 being introduced into the disc space. FIG. 76A shows a cross section view of the delivery of a flowable material 218 from the distal end of delivery device 500 as shown by arrow 220. The nuclear replacement may be introduced through the cannula 526 (as shown in FIG. 58 with rod 514 removed) or another cannula of 500, such as 522. As further illustrated in FIG. 76B, the nuclear augmentation material flows, in use, from the distal end of the delivery tool as shown with arrow 220 and into the intervertebral disc space. FIG. 77 illustrates an alternative method and device for the introduction of material 218 into the disc space via the fixation element delivery tool 400. The nuclear augmentation material is injected and flows from the needle cannula of tool 400 as shown by arrow 222, although, other cannulae of tool 400 might also be advantageously used to deliver material 218, such as cannula 426. As an alternative embodiment, using cannula 426 as a delivery conduit, needle cannula 428 may be advantageously be retracted as described above, prior to, during, or after the delivery of material through conduit 426. In the embodiments described, flowable and/or injectable material is introduced into the disc space and the annular treatment device acts to avoid, restrict or other wise reduce the possibility of the implanted material from extruding or migrating from the subannular space. It is contemplated that one could adapt the delivery tools' construction to accommodate specific characteristics of a variety of augmentation materials, therefore the construction of the delivery tools as depicted are meant to be illustrative, and not limiting.

Flowable, injectable, or otherwise insertable nuclear augmentation materials might include natural or synthetic materials comprising: hydrogels, polymers, polymeric precipitates, polymeric emulsions, collagen, fibrin, polymeric protein compositions, poly vinyl alcohols, polysaccharides, cellulose or any derivations of these materials.

As discussed previously, FIGS. 76 and 77 are illustratively intended to depict the introduction of nuclear replacement material 218 to the intervertebral disc, although they may also exemplify methods and devices to delivery adhesive materials. It is also contemplated that additional membrane material may be added to the treatment device to further help restrict extravasation of material out of the disc during augmentation delivery, if required. Conversely, the treatment device construction may be altered to reduce the mesh porosity in order to accomplish a similar objective. Furthermore, it is anticipated that materials maybe added to, or changed, on portions of the delivery tools to facilitate delivery of the material and removal of the delivery devices after implant introduction. For example, cannula 526 in FIG. 76 may be coated with, or be constructed of, PTFE, FEP, polypropylene, polyethylene or other lubricious materials or coatings. Similarly, portions of delivery device 400 in FIG. 77 may have similar material treatments to accomplish the same objective.

Figure 65:
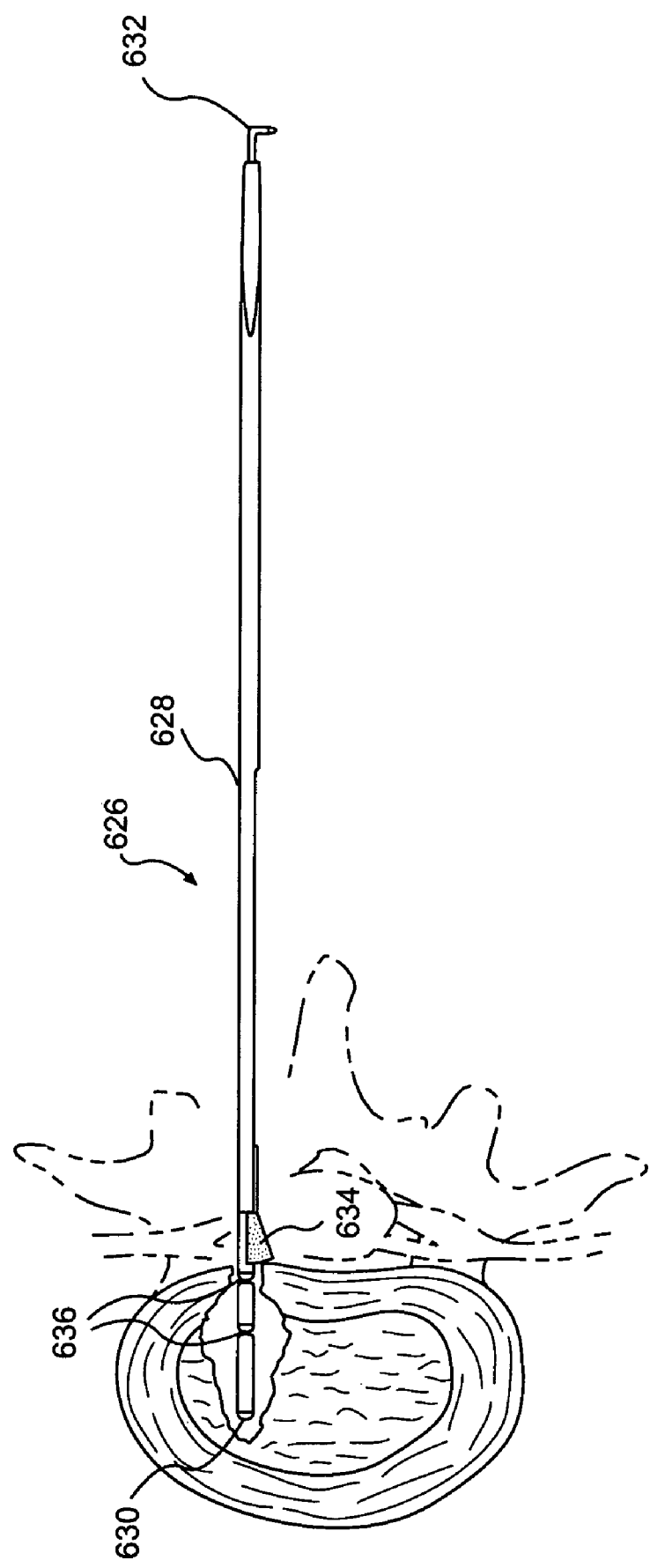
FIG. 65 illustrates an exemplary sizing tool used to assess the treatment site prior to delivery of patch, anchor bands or other treatment devices.

As described above, there are a variety of instruments and tools readily available to the surgeon during spine surgery, or other surgical procedures, to obtain outcomes intended by the surgeon and the surgical procedure. These tools and instruments may be used to: incise, resect, dissect, remove, manipulate, elevate, retract, probe, cut, curette, measure or otherwise effect a surgical outcome. It is anticipated that some of these tools and/or instruments may be used before, during, or after the use of the inventive methods, devices and tools described herein in order to access, prepare, and/or generally assess treatment, treatment site, or facilitate the manipulation, introduction, or deployment of the treatment device and/or it's components. Additional tools and instruments may also be provided to the surgeon to address some of these functions. FIG. 65 illustrates one such tool, wherein sizing tool 626, with handle 628 used for tool manipulation, is placed within the subannular cavity to probe the subannular space and generally assess the treatment site prior to delivery of patch, anchor bands or other treatment devices. Generally the length of the device from the tissue stop 634 to the distal end 630 of tool 626 could allow a physician to measure, or otherwise assess the depth of the cavity and assure sufficient space available as not to cause any untoward events as a result of introduction of the treatment device or its delivery tools.

Additional markers 636, preferably radiographically enhanced, may be placed along distal end of tool to provide indication of the relative components of the treatment device and/or its delivery tools. For example, as shown, two markers may identify where the distal and proximal ends of treatment device may be situated, after deployment, of the patch. This may be performed prior to introduction of treatment device to the cavity. Proximal end may advantageously contain other functional instruments, helping the surgeon to otherwise manipulate, resect, probe and/or assess the cavity or surrounding tissues, such as a angled curette, as shown in FIG. 65. It is anticipated that instrument 626 could be provided as a disposable tool, or a re-sterilizable instrument. The tool may be advantageously constructed of biocompatible metallic materials or polymeric materials, or a combination of both. As an example, the handle and general construction of the instrument may be formed from a polymer such as: polyester, polypropylene, polyethylene, polyimides and derivatives thereof (e.g., polyetherimide), polyamide and derivatives thereof (e.g., polyphthalamide), polyketones and derivatives thereof (e.g., PEEK, PAEK, PEKK), PET, polycarbonate, acrylic, polyurethane, polycarbonate urethane, acetates and derivatives thereof (e.g., acetal copolymer), polysulfones and derivatives thereof (e.g., polyphenylsulfone), or the like, whereas markers 636, tissue stop 634, distal 630 and proximal ends 632 could be made of metallic materials such as stainless steel, platinum iridium alloys, platinum, titanium, gold, or the like. It is also contemplated that the radiographic components could be deposited (e.g., vapor deposition) or affixed (e.g., tubular bands attached circumferentially) onto the instrument 626. The description and depiction of tool is intend to illustrative and not limiting in scope.

Figure 79A:
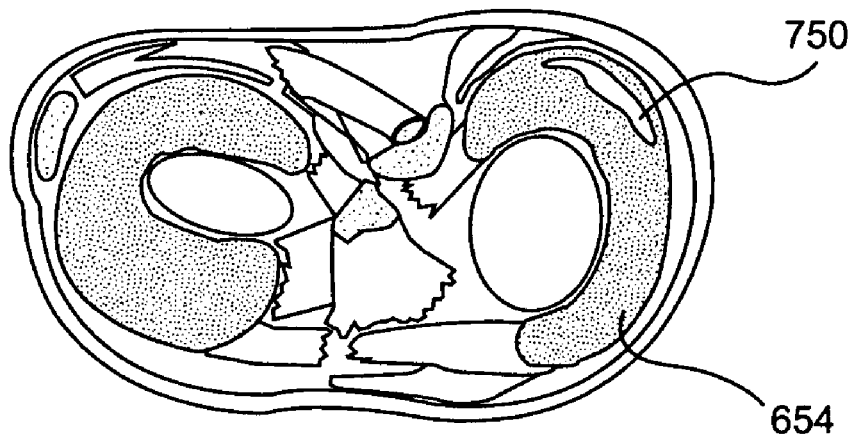
FIG. 79A-79B illustrate illustrative embodiments of the invention used to treat meniscal tissue of the knee.
Figure 79B:
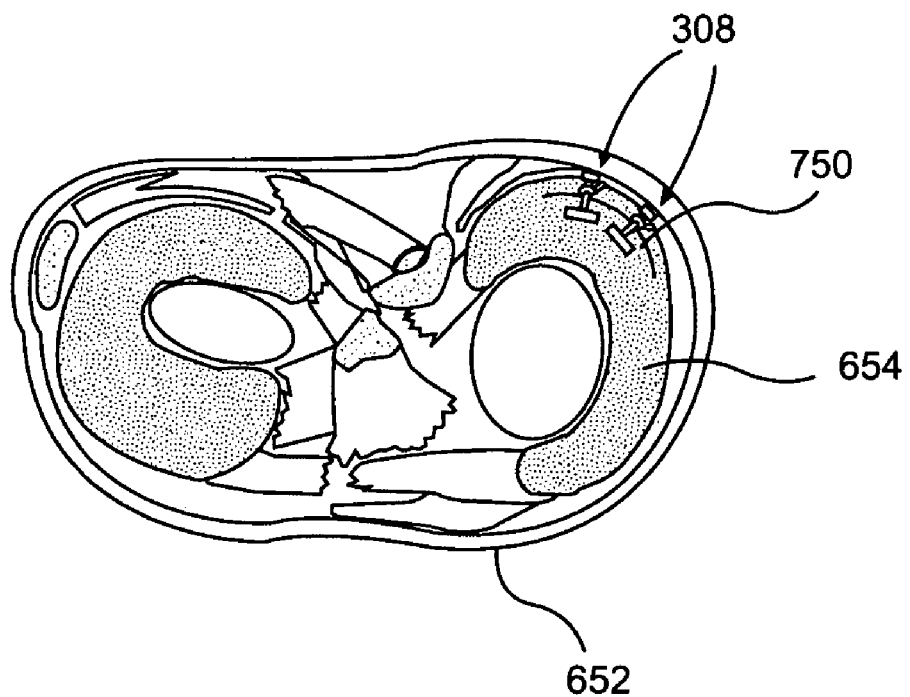

Finally, the description and illustrations described previously may be directed and illustrative of various spinal applications of the invention, it is possible that the inventive methods, devices and delivery tools could be applied to the repair, fixation, augmentation, reinforcement, support or otherwise generally prophylactically or therapeutically treating other tissues. As an example, but not to be limiting the scope of use in other tissues, FIG. 79A-79B illustrate a knee joint in transverse section, containing a meniscus of the knee, anatomically positioned above the Tibia bone 652. The meniscus may be damaged, torn, weakened, delaminated, degenerated, thin or otherwise in need of treatment. Fixation elements and/or treatment devices as described herein, may be deployed within the meniscal tissue to effect a repair as shown in FIG. 79B, for example, with two anchor band assemblies 308 drawing together, and repairing defect 750. It is anticipated within the scope of the invention that methods, devices and/or delivery tools described herein, and their associated materials, may be adapted to accommodate anatomical and physiological characteristics involved in repair of the meniscus.

Figure 80B:
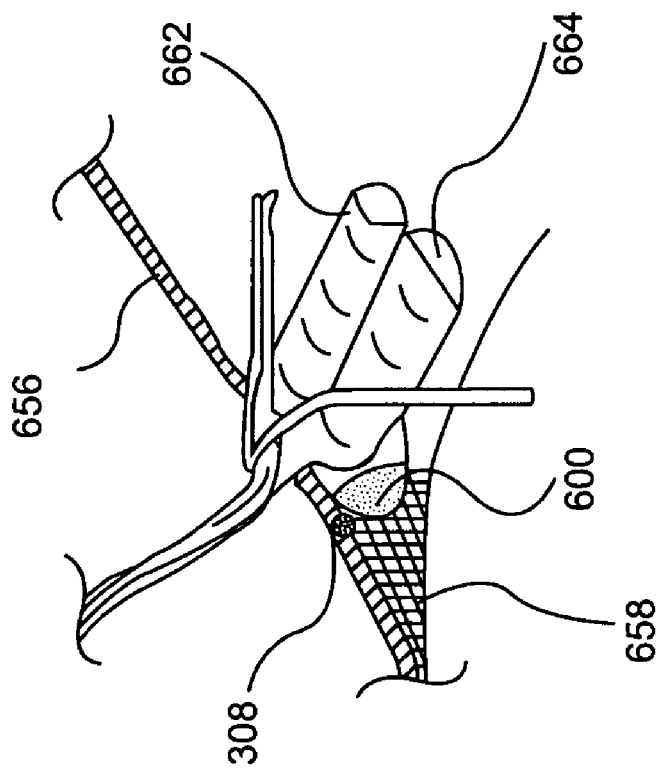
FIGS. 80A-80B illustrate an illustrative general surgical application of the invention for treating hernia.
Figure 80A:
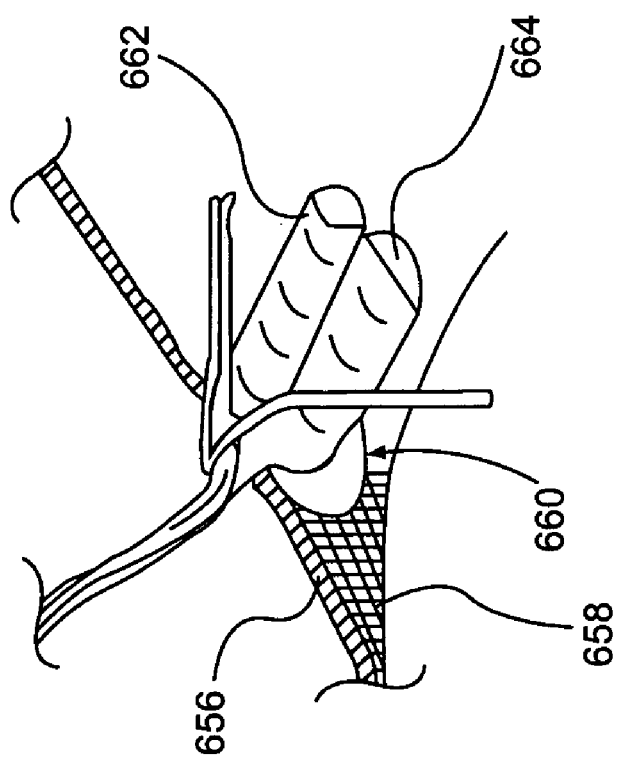

An additional example of using the inventive methods, devices and delivery tools described herein for the repair, fixation, reinforcement, augmentation, support or otherwise generally prophylactically or therapeutically treating other tissues is exemplified in FIGS. 80A-80B. FIG. 80A illustrates a general surgical application wherein the contents of the abdomen may urge the peritoneal cavity to pass out of, or through, the femoral ring 660 in proximity of the Inguinal 656 and Lacunar 658 ligaments, and otherwise present with symptoms associated with a femoral herniation. In FIG. 80A, External Iliac Artery 662 and External Iliac Vein 664 are identified for reference purposes. Treatment devices, as described herein, may be delivered and applied to repair the femoral ring area by placing a treatment device just below the femoral ring, and the associated Inguinal and Lacunar ligaments surrounding the femoral ring area. As illustratively shown in FIG. 80B, once treatment device 600 is deployed, one or more fixation elements 308 may be affixed to the patch and the Lacunar and/or Inguinal ligaments to secure the treatment device, thereby reducing the tendency of the abdominal contents to urge through the femoral along area. It is anticipated within the scope of the invention that methods, devices and/or delivery tools described herein, and their associated materials, may be adapted to accommodate anatomical and physiological characteristics involved in the augmentation, reinforcement, or otherwise reparation of various femoral, inguinal, umbilical, and incisional hernia.

All patents referred to or cited herein are incorporated by reference in their entirety to the extent they are not inconsistent with the explicit teachings of this specification, including; U.S. Pat. No. 5,108,438 (Stone), U.S. Pat. No. 5,258,043 (Stone), U.S. Pat. No. 4,904,260 (Ray et al.), U.S. Pat. No. 5,964,807 (Gan et al.), U.S. Pat. No. 5,849,331 (Ducheyne et al.), U.S. Pat. No. 5,122,154 (Rhodes), U.S. Pat. No. 5,204,106 (Schepers at al.), U.S. Pat. No. 5,888,220 (Felt et al.),U.S. Pat. No. 5,376,120 (Sarver et al.) and U.S. Pat. No. 5,976,186 (Bao et al.).

Various materials know to those skilled in the art can be employed in practicing the present invention. By means of example only, the body portions of the stent could be made of NiTi alloy, plastics including polypropylene and polyethylene, polymethylmethacrylate, stainless steel and other biocompatible metals, chromium cobalt alloy, or collagen. Webbing materials can include silicone, collagen, ePTFE, DACRON, polyester, polypropylene, polyethylene, and other biocompatible materials and can be woven or non-woven. Membranes might be fashioned of silicone, polypropylene, polyester, SURLYN, PEBAX, polyethylene, polyurethane or other biocompatible materials. Inflation fluids for membranes can include gases, liquids, foams, emulsions, and can be or contain bioactive materials and can also be for mechanical, biochemical and medicinal purposes. The stent body, webbing and/or membrane can be drug eluting or bioabsorbable, as known in the medical implant arts.

Further, any of the devices or delivery tools described herein, or portions thereof, could be rendered visible or more visible via fluoroscopy, if desired, through the incorporation of radioopaque materials or markers. Preferably implantable devices are constructed with MRI compatible materials. In particular, devices and/or their components could be wholly or partially radiopaque, as result of, for example: compounding various radiopaque materials (e.g., barium sulphate) into device materials; affixing radiopaque materials to device structures (e.g., bands of platinum, gold, or their derivative alloys); deposition of radiopaque materials onto device structures (e.g., deposition of platinum, gold of their derivative alloys); processing radiopaque materials into device structures (e.g., braiding/weaving platinum or gold wires or its alloy derivatives). One inventive way to achieve radiopacity of a device described herein, for example treatment device 600, is placing one or more radiopaque marker bands onto filaments of braided device 600 before (or possibly after) creating end potions of the device.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

The invention claimed is:

1. A method of treating an aperture in an annulus fibrosus of an intervertebral disc, comprising:
   providing at least one delivery tool having a proximal portion and a distal portion, said distal portion configured to deliver at least one reparative device;
   providing a reparative device, said reparative device comprising at least first and second anchor portions and a flexible connecting assembly connecting said anchor portions, said connecting assembly configured to be shortened and comprising a locking element, the first and second anchor portions being releasably coupled to the distal portion of the delivery tool;

introducing the distal portion of the delivery tool with the reparative device proximate annular tissue to be repaired;

delivering at least a portion of said at least one reparative device into, or through, a portion of the annulus, wherein, upon delivery, such that the first and second anchor portions reside within intervertebral disc tissue, including inserting the first anchor portion and at least a portion of the connecting assembly into or through an outer wall of the annulus fibrosus at a first insertion location proximate the aperture, inserting the second anchor portion and at least a portion of the connecting assembly into or through the outer wall of the annulus fibrosus at a second insertion location proximate the aperture, the second insertion location being separated from the first insertion location such that the aperture is located between the first and second insertion locations, and extending a portion of the connecting assembly across the aperture external to the outer wall of the annulus fibrosus;

actuating said delivery tool, said actuating step causing the release of said reparative device from the delivery tool;

shortening the connecting assembly disposed between the anchor portions so as to draw together, at least partially, annular tissue between the first and second anchor portions thereby at least partially drawing together annular tissue defining the aperture between the first and second insertion locations;

securing said connecting assembly in a shortened configuration with a locking element; and, removing said delivery tool.

2. A method of claim 1, wherein said reparative device is comprised of one or more bands, filaments, lines, wires, tethers or sutures.

3. A method of claim 1, wherein said reparative device comprises biodegradable or bioabsorbable material.

4. A method of claim 1, wherein said reparative device comprises biocompatible material.

5. A method of claim 1, wherein said reparative device comprises material to facilitate regeneration of tissue.

6. A method of claim 5, wherein said material to facilitate regeneration of tissue comprises a growth factor.

7. A method of claim 1, wherein said reparative device comprises polymeric material.

8. A method of claim 1, wherein said anchor portion disposed within the intervertebral disc comprises a t-anchor or barb configuration.

9. A method of claim 1, wherein that the portion of said connecting assembly that is contiguous with said anchor portions is of a smaller girth than a portion of the connecting assembly disposed in between said anchor portions.

10. A method of claim 1, wherein said locking element of said connecting assembly comprises a retainer, clip, or knot.

11. A method of claim 10, wherein said knot is pre-tied.

12. A method of claim 1, wherein multiple reparative devices are used to treat an intervertebral disc.

13. A method of claim 1, wherein said reparative device is used in combination with a treatment device, said treatment device comprising mesh, scaffold, stent, patch, membrane, or tissue reinforcing materials, and wherein said treatment device is delivered to the intervertebral disc with a treatment device delivery tool.

14. A method of claim 13, wherein said treatment device comprises a retention element so as to secure the treatment device in a deployed configuration.

15. A method of claim 13, wherein said treatment device is configured to be attached by compression to a distal portion of the treatment device delivery tool, and capable of being released from the distal portion of the treatment device delivery tool upon relief of said compression.

16. A method of claim 13, wherein said treatment device comprises biodegradable or bioabsorbable material.

17. A method of claim 13, wherein said treatment device comprises biocompatible material.

18. A method of claim 13, wherein said treatment device comprises material to facilitate regeneration of tissue.

19. A method of claim 18, wherein said material to facilitate regeneration of tissue comprises a growth factor.

20. A method of claim 13, wherein said treatment device comprises polymeric material.

21. A method of treating an aperture in an annulus fibrosus of an intervertebral disc, comprising:

providing a delivery tool including first and second needles each having a distal portion;

providing a reparative device including first and second anchor portions and a connecting assembly connecting the anchor portions, the connecting assembly configured to be shortened and including a locking element, the first anchor portion being releasably coupled to the distal portion of the first needle, and the second anchor portion being releasably coupled to the distal portion of the second needle;

inserting the distal portion of the first needle with the first anchor portion coupled thereto into or through an outer wall of the annulus at a first insertion location proximate the aperture in the annulus fibrosus;

inserting the distal portion of the second needle with the second anchor portion coupled thereto into or through the outer wall of the annulus fibrosus at a second insertion location proximate the aperture in the annulus fibrosus, the second insertion location being separated from the first insertion location such that the aperture is located between the first and second insertion locations;

extending a portion of the connecting assembly across the aperture external to the outer wall of the annulus fibrosus;

causing or allowing the first anchor portion to be released from the first needle, and causing or allowing the second anchor portion to be released from the second needle, wherein, upon release, the first and second anchor portions reside within intervertebral disc tissue;

shortening the connecting assembly disposed between anchor portions so as to draw together, at least partially, annular tissue between the first and second insertion locations thereby at least partially drawing together annular tissue defining the aperture between the first and second insertion locations;

securing the connecting assembly in a shortened configuration with the locking element; and, removing the delivery tool.

* * * * *

UNITED STATES PATENT AND TRADEMARK OFFICE
CERTIFICATE OF CORRECTION

PATENT NO.        : 7,615,076 B2                                          Page 1 of 1
APPLICATION NO.   : 11/120750
DATED             : November 10, 2009
INVENTOR(S)       : Cauthen, III et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1137 days.

Signed and Sealed this

Nineteenth Day of October, 2010

David J. Kappos
*Director of the United States Patent and Trademark Office*